US010016617B2

(12) United States Patent
Mason et al.

(10) Patent No.: US 10,016,617 B2
(45) Date of Patent: *Jul. 10, 2018

(54) COMBINATION IMMUNO THERAPY AND RADIOTHERAPY FOR THE TREATMENT OF HER-2-POSITIVE CANCERS

(71) Applicant: THE TRUSTEES OF THE UNIVERSITY OF PENNSYLVANIA, Philadelphia, PA (US)

(72) Inventors: Nicola Mason, Philadelphia, PA (US); Yvonne Paterson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 27 days.

This patent is subject to a terminal disclaimer.

(21) Appl. No.: 14/669,629

(22) Filed: Mar. 26, 2015

(65) Prior Publication Data
US 2015/0196628 A1 Jul. 16, 2015

Related U.S. Application Data

(63) Continuation-in-part of application No. 14/268,436, filed on May 2, 2014, which is a continuation-in-part of application No. 14/189,008, filed on Feb. 25, 2014, now abandoned, which is a continuation-in-part of application No. 13/210,696, filed on Aug. 16, 2011, now Pat. No. 9,017,660, which is a continuation-in-part of application No. 12/945,386, filed on Nov. 12, 2010, now Pat. No. 9,084,747, which is a continuation-in-part of application No. PCT/US2015/017559, filed on Feb. 25, 2015.

(60) Provisional application No. 61/260,277, filed on Nov. 11, 2009, provisional application No. 62/076,411, filed on Nov. 6, 2014.

(51) Int. Cl.
A61N 5/10 (2006.01)
A61K 35/74 (2015.01)
A61K 38/19 (2006.01)
A61K 39/00 (2006.01)

(52) U.S. Cl.
CPC ............... A61N 5/10 (2013.01); A61K 35/74 (2013.01); A61K 38/193 (2013.01); A61K 39/0011 (2013.01); A61K 2039/523 (2013.01); A61K 2039/552 (2013.01); A61K 2039/6037 (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,521,382 A | 6/1985 | Kessick |
| 4,777,239 A | 10/1988 | Schoolnik |
| 4,816,567 A | 3/1989 | Cabilly et al. |
| 5,204,253 A | 4/1993 | Sanford et al. |
| 5,262,177 A | 11/1993 | Brown et al. |
| 5,342,774 A | 8/1994 | Boon et al. |
| 5,580,859 A | 12/1996 | Felgner et al. |
| 5,589,466 A | 12/1996 | Felgner et al. |
| 5,643,599 A | 7/1997 | Lee et al. |
| 5,679,647 A | 10/1997 | Carson et al. |
| 5,681,570 A | 10/1997 | Yang et al. |
| 5,736,524 A | 4/1998 | Content et al. |
| 5,739,118 A | 4/1998 | Carrano et al. |
| 5,804,566 A | 9/1998 | Carson et al. |
| 5,824,538 A | 10/1998 | Branstorm et al. |
| 5,830,702 A | 11/1998 | Portnoy et al. |
| 5,858,682 A | 1/1999 | Gruenwald et al. |
| 5,877,159 A | 3/1999 | Powell et al. |
| 5,922,583 A | 7/1999 | Morsey et al. |
| 5,922,687 A | 7/1999 | Mann et al. |
| 6,004,815 A | 12/1999 | Portnoy et al. |
| 6,015,567 A | 1/2000 | Hudziak et al. |
| 6,017,705 A | 1/2000 | Lurquin et al. |
| 6,051,237 A | 4/2000 | Paterson et al. |
| 6,099,848 A | 8/2000 | Frankel et al. |
| 6,287,556 B1 | 9/2001 | Portnoy et al. |
| 6,306,404 B1 | 10/2001 | LaPosta et al. |
| 6,329,511 B1 | 12/2001 | Vasquez et al. |
| 6,479,258 B1 | 11/2002 | Short |
| 6,500,432 B1 | 12/2002 | Dalemans et al. |
| 6,504,020 B1 | 1/2003 | Frankel et al. |
| 6,521,449 B1 | 2/2003 | Polack et al. |
| 6,565,852 B1 | 5/2003 | Paterson |
| 6,599,502 B2 | 7/2003 | Portnoy et al. |

(Continued)

FOREIGN PATENT DOCUMENTS

CN 1763093 A 4/2006
EP 0902086 3/1999

(Continued)

OTHER PUBLICATIONS

Rongcun et al. (J. Immunol., 163:1037-1044, 1999).*
U.S. Appl. No. 60/490,089, filed Jul. 24, 2003, Thomas W. Dubensky.
Abachin et al., Formation of D-alanyl-lipoteichoic acid is required for adhesion and virulence of Listeria monocytogenes 2002, Mol Microbiol 43:1-14.
Adams et al., 1992, "Cre-lox recombination in *Escherichia coli* cells Mechanistic differences from the in vitro reaction", J. Mol. Biol. 226:661-673.

(Continued)

Primary Examiner — Nelson B Moseley, II
(74) Attorney, Agent, or Firm — Mark S. Cohen; Pearl Cohen Zedek Latzer Baratz LLP

(57) ABSTRACT

This invention provides methods for inducing an immune response against a Her-2/neu antigen-expressing tumor and for treating the same and vaccinating against the same in human and canine subjects using a combination of radiation therapy and a recombinant attenuated *Listeria* strain vaccine.

81 Claims, 30 Drawing Sheets

(56) References Cited

U.S. PATENT DOCUMENTS

| | | |
|---|---|---|
| 6,635,749 B2 | 10/2003 | Frankel et al. |
| 6,740,516 B2 | 5/2004 | Savitzky et al. |
| 6,767,542 B2 | 7/2004 | Paterson et al. |
| 6,773,900 B2 | 8/2004 | Short et al. |
| 6,855,320 B2 | 2/2005 | Paterson et al. |
| 6,991,785 B2 | 1/2006 | Frey, II |
| 7,135,188 B2 | 11/2006 | Paterson |
| 7,375,091 B2 | 5/2008 | Cheever et al. |
| 7,425,449 B2 | 9/2008 | Portnoy et al. |
| 7,488,487 B2 | 2/2009 | Frankel et al. |
| 7,488,802 B2 | 2/2009 | Collins et al. |
| 7,521,051 B2 | 4/2009 | Collins et al. |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,691,393 B2 | 4/2010 | Dubensky et al. |
| 7,700,344 B2 | 4/2010 | Paterson et al. |
| 7,786,288 B2 | 8/2010 | Karp |
| 7,790,177 B2 | 9/2010 | Karp |
| 7,794,728 B2 | 9/2010 | Portnoy et al. |
| 7,794,729 B2 | 9/2010 | Paterson et al. |
| 7,820,180 B2 | 10/2010 | Paterson et al. |
| 7,842,289 B2 | 11/2010 | Dubensky et al. |
| 7,855,064 B2 | 12/2010 | Paterson et al. |
| 7,858,097 B2 | 12/2010 | Paterson et al. |
| 7,871,604 B1 | 1/2011 | Curtiss, III et al. |
| 7,887,822 B2 | 2/2011 | Ferrone et al. |
| 7,935,804 B2 | 5/2011 | Dubensky et al. |
| 8,008,449 B2 | 8/2011 | Korman et al. |
| 8,114,414 B2 | 2/2012 | Paterson |
| 8,168,757 B2 | 5/2012 | Finnefrock et al. |
| 8,287,883 B2 | 10/2012 | Dubensky et al. |
| 8,354,509 B2 | 1/2013 | Carven et al. |
| 8,383,796 B2 | 2/2013 | Korman et al. |
| 8,771,702 B2 | 7/2014 | Paterson et al. |
| 9,012,141 B2 | 4/2015 | Paterson et al. |
| 9,017,660 B2 | 4/2015 | Shahabi et al. |
| 9,226,958 B2 | 1/2016 | Ham, Jr. et al. |
| 2002/0025323 A1 | 2/2002 | Paterson et al. |
| 2002/0136737 A1 | 9/2002 | Frankel et al. |
| 2002/0165172 A1 | 11/2002 | Sallberg et al. |
| 2003/0028206 A1 | 2/2003 | Shiser |
| 2003/0219802 A1 | 11/2003 | Dhaini et al. |
| 2003/0220239 A1 | 11/2003 | Simard et al. |
| 2004/0013685 A1 | 1/2004 | Andersen et al. |
| 2004/0031690 A1 | 1/2004 | Portnoy et al. |
| 2004/0058342 A1 | 3/2004 | Yousef |
| 2004/0228877 A1 | 11/2004 | Dubensky et al. |
| 2005/0048081 A1 | 3/2005 | Frankel |
| 2005/0118184 A1 | 6/2005 | Paterson et al. |
| 2005/0129715 A1 | 6/2005 | Paterson et al. |
| 2005/0281783 A1 | 12/2005 | Kinch et al. |
| 2006/0051380 A1 | 3/2006 | Schulick et al. |
| 2006/0073170 A1 | 4/2006 | Papierok |
| 2006/0093582 A1 | 5/2006 | Paterson et al. |
| 2006/0104991 A1 | 5/2006 | Paterson et al. |
| 2006/0121053 A1 | 6/2006 | Sweeney et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2007/0154953 A1 | 7/2007 | Brunner et al. |
| 2007/0207170 A1 | 9/2007 | Dubensky et al. |
| 2007/0207171 A1 | 9/2007 | Dubensky et al. |
| 2007/0253976 A1 | 11/2007 | Paterson et al. |
| 2007/0264279 A1 | 11/2007 | Paterson et al. |
| 2008/0124354 A1 | 5/2008 | Paterson et al. |
| 2008/0131456 A1 | 6/2008 | Paterson et al. |
| 2008/0213295 A1 | 9/2008 | Cheever et al. |
| 2008/0241069 A1 | 10/2008 | Paterson |
| 2009/0202587 A1 | 8/2009 | Paterson et al. |
| 2009/0143085 A1 | 11/2009 | Lauer et al. |
| 2010/0069344 A1 | 3/2010 | Wang et al. |
| 2010/0189739 A1 | 7/2010 | Frankel et al. |
| 2010/0233212 A1 | 9/2010 | Dubensky |
| 2011/0129499 A1 | 6/2011 | Maciag et al. |
| 2011/0142791 A1 | 6/2011 | Shahabi et al. |
| 2011/0223187 A1 | 9/2011 | Shahabi et al. |
| 2011/0271358 A1 | 11/2011 | Freeman et al. |
| 2012/0014984 A1 | 1/2012 | Shahabi |
| 2012/0135033 A1 | 5/2012 | Wallecha |
| 2014/0186387 A1 | 7/2014 | Lauer et al. |
| 2014/0199258 A1 | 7/2014 | Rothman |
| 2014/0234370 A1 | 8/2014 | Shahabi et al. |
| 2014/0314708 A1 | 10/2014 | Maciag et al. |
| 2015/0297702 A1 | 10/2015 | Shahabi et al. |
| 2015/0366955 A9 | 12/2015 | Shahabi et al. |

FOREIGN PATENT DOCUMENTS

| | | |
|---|---|---|
| EP | 1408048 | 4/2004 |
| WO | WO 1990/012594 | 11/1990 |
| WO | WO 1992/020356 | 11/1992 |
| WO | WO 1993/015212 | 8/1993 |
| WO | WO 1994/017192 | 8/1994 |
| WO | WO 1996/14087 | 5/1996 |
| WO | WO 1996/034631 | 11/1996 |
| WO | WO 1996/34631 | 11/1996 |
| WO | WO 1996/039154 | 12/1996 |
| WO | WO 1997/003211 | 1/1997 |
| WO | WO 1998/004720 | 2/1998 |
| WO | WO 1998/048026 | 10/1998 |
| WO | WO 1999/06544 | 2/1999 |
| WO | WO 1999/007861 | 2/1999 |
| WO | WO 1999/10496 | 3/1999 |
| WO | WO 1999/025376 | 5/1999 |
| WO | WO 2001/27295 | 3/2001 |
| WO | WO 2001/072329 | 10/2001 |
| WO | WO 2001/72329 | 10/2001 |
| WO | WO 2001/079274 | 7/2002 |
| WO | WO 2003/045318 | 6/2003 |
| WO | WO 2003/092600 | 11/2003 |
| WO | WO 2003/102168 | 12/2003 |
| WO | WO 2004/004771 | 1/2004 |
| WO | WO 2004/006837 | 1/2004 |
| WO | WO 2004/056875 | 7/2004 |
| WO | WO 2004/072286 | 8/2004 |
| WO | WO 2005/037233 * | 4/2005 |
| WO | WO 2005/061534 | 7/2005 |
| WO | WO 2005/071088 | 8/2005 |
| WO | WO 2006/017856 | 2/2006 |
| WO | WO 2006/036550 | 4/2006 |
| WO | WO 2007/061848 | 5/2007 |
| WO | WO 2007/103225 | 9/2007 |
| WO | WO 2007/137258 | 11/2007 |
| WO | WO 2008/045148 A2 | 4/2008 |
| WO | WO 2008/109155 | 9/2008 |
| WO | WO 2008/130551 | 10/2008 |
| WO | WO 2008/140812 | 11/2008 |
| WO | WO 2009/110950 | 9/2009 |
| WO | WO 2009/143085 | 11/2009 |
| WO | WO 2009/143167 | 11/2009 |
| WO | WO 2010/011870 | 1/2010 |
| WO | WO 2010/027827 | 3/2010 |
| WO | WO 2010/077634 | 7/2010 |
| WO | WO 2011/060260 A2 | 5/2011 |
| WO | WO 2011/066342 | 6/2011 |
| WO | WO 2011/100754 A1 | 8/2011 |
| WO | WO 2012/12551 | 9/2012 |
| WO | WO 2012/125551 A1 | 9/2012 |
| WO | WO 2013/019906 A1 | 2/2013 |
| WO | WO 2014/100079 | 6/2014 |

OTHER PUBLICATIONS

Ahmadzadeh et al. Tumor antigen-specific CD8 T cells infiltrating the tumor express high levels of PD-1 and are functionally impaired. Blood (2009) 114: 1537-1544.

Alexander et al, Characterization of an Aromatic Amino Acid-Dependent Listeria Monocytogenes Mutant: Attenuation, Persistence, and Ability to Induce Protective Immunity in Mice 1993, Infection and Immunity 10 61 :2245-2248.

Al-Lazikani et al. JMB Standard Conformations for the Canonical Structures of Immunoglobulins., J. Mol. Biol. 273:927-948 (1997).

(56) References Cited

OTHER PUBLICATIONS

Allision et al., 1997, "Cloning and characterization of a Prevotella melaninogenica hemolysin", Infect. Immun. 65(7):2765-71.
Altschul et al. Basic Local Alignment Search Tool Basic Local Alignment Search Tool; J. Mol. Biol. 215:403-410 (1990).
Altschul "Amino Acid Substitution Matrices from an Information Theoretic Perspective", J. Mol. Biol. 219:555-565 (1991).
Altschul et al. A Protein Alignment Scoring System Sensitive at all Evolutionary Distances; J. Mol. Evol. 36:290-300 (1993).
Altschul et al., "Gapped BLAST and PSI-BLAST: a new generation of protein database search programs" (1997) Nucleic Acids Res. 25:3389-3402.
Amersham. Introduction to Glutathione 5-transferase (GST) Gene Fusion System , Pharmacia Biotech; BioDirectory, Piscataway, N.J., ( pp. 384-391) (2001).
An et al., 1996, "A recombinant minigene vaccine containing a nonameric cytotoxic-T -Lymphocyte epitope confers limited protection against Listeria monocytogenes infection", Infect. Immun., vol. 64, No. 5, p. 1685-1693.
Anderson, 1998, "Human gene therapy", Nature, Apr. 30; 392 (6679 Suppl):25-30.
Angelakopoulos et al., "Safety and shedding of an attenuated strain of listeria Monocytogenes with a deletion of actA/plcB in adult volunteers: a dose escalation study of oral innoculation", Infection and Immunity 2002, 70(7): 3592-3601.
Anthony "Precursor Lesions for Liver Cancer in Humans" Cancer Res. (1976) 36:2579-2583.
Attwood et al., "The Babel of Bioinformatics", Science, vol. 290, No. 5491: 471-473, 2000.
Auchtung et al "Regulation of a Bacillus subtilis mobile genetic element by intercellular signaling and the global DNA damage response". Proc Natl Acad Sci USA. Aug. 30, 2005;102 (35):12554-9.
Auerbuch, et al. "Development of a Competitive Index Assay to Evaluate the Virulence of Listeria monocytogenes actA Mutants during Primary and Secondary Infection of Mice" (2001) Infect. Immunity 69:5953-5957.
Awwad, 1989, "Cyclophosphamide-induced immunologically mediated regression of a cyclophosphamide-resistant murine tumor: a consequence of eliminating precursor L3T4+ suppresor T-cells", Cancer Res., 49(7):1649-1654.
Baca et al. "Protein Chemistry and Structure: Antibody Humanization Using Monovalent Phage Display", (1997) J. Biol. Chem. 272:10678-10684.
Baert et al. "Influence of Immunogenicity on the Long-Term Efficacy of Infliximab in Crohn's Disease" (2003) New Engl. J. Med. 348:601-608.
Baloglu et al. "Immune Responses of Mice to Vaccinia Virus Recombinants Expressing Either Listeria Monocytogenes Partial Listeriolysin or Brucella abortus Ribosomal L7/L12 Protein" Vet Microbiol.; 109(1-2) M, Aug. 10, 2005.
Barbas Synthetic Human Antibodies ; Nature Medicine, 1:837-839 (1995).
Bargmann et al. "The neu oncogene encodes an epidermal growth factor receptor-related protein" Nature 319, 226-230, Jan. 16, 1986.
Bear, 1986, "Tumor-specific suppressor T-cells which inhibit the in vitro generation of cytolytic T-cells from immune and early tumor-bearing host spleens", Cancer Res., Apr.; 46(4 Pt 1):1805-12.
Beattie et al. "Cloning and charcterization of T-cell-reactive protein antogens from Listeria monocytogenes", infect. Immune. Sep. 1990, 58(9):2792-803.
Beatty et al., IFN-gamma-dependent inhibition of tumor angiogenesis by tumor-infiltrating CD4+ T cells requires tumor responsiveness to IFN-gamma.J Immunol. Feb. 15, 2001;166(4):2276-82.
Beaucage et al. "Deoxynucleoside Phosphoramidites—A New Class of Key Intermediates for Deoxypolynucleotide Synthesis" Tetra. Lett. 22:1859-1862, (1981).
Becker at al., The changes in the T helper 1 (Th1) and T helper 2 (Th2) cytokine balance 3,4during HIV-1 infection are indicative of an allergic response to viral proteins that may bereversed by Th2 cytokine inhibitors and immune response modifiers—a review and hypothesis; Viruses Genes 28:5-18 (2004).
Belt et al (1991) Efficient cDNA cloning by direct phenotypic correction of a mutant human cell line (HPRT2) using an Epstein-Barr virus-derived cDNA expression vector. Nucleic Acids Res. 19, 4861-4866.
Beniaminovitz et al. "Prevention of Rejection in Cardiac Transplantation by Blockade of the Interleukin-2 Receptor With a Monoclonal Antibody" (2000) New Engl. J. Med. 342:613-619.
Benvegnu, et al. Space Occupying lesions of the liver detected by ultrasonography and their relation to hypatocellular Carcinoma in Cirrhosis; Liver 12:80-83 (1992).
Bernhard et al., 2002, "Vaccination against the HER-2/neu oncogenic protein", Endocrine-Related Cancer, 9:33-44.
Bielecki et al. "Bacillus subtilis expressing a haemolysin gene from Lesteria monocytogenes can grow in mammalian cells", Nature 1990, 354:175-176.
Billaut-Mulot et al. Interleukin-18 modulates immune responses induced by HIV-1 Nef DNA prime/protein boost vaccine; Vaccine 19:95-102 (2000).
Billington et al., 1997, "The Arcanobacterium (Actinomyces) pyogenes hemolysin, pyolysin, is a novel member of the thiol-activated cytolysin family", J. Bacteriol. Oct; 179(19):6100-6.
Bird et al. "An autologous dendritic cell canine mammary tumor hybrid-cell fusion vaccine", Cancer Immunol Immunother. Jan. 2011;60(1):87-97.
Bishop et al. "Adoptive Transfer of Immunity to Listeria Monocytogenes the Influence of In Vitro Stimulationon Lymphocyte Subset Requirements", J. Immunol. 139: 2005-2009 (1987).
Bodmer et al., 1988, "Enhanced recognition of a modified peptide antigen by cytotoxic T cells specific for influenza nucleoprotein", Cell 52:253-258.
Boon et al., 2006, "Human T-cell responses against melanoma" Annu. Rev. Immunol. 24:175-208.
Bourquin et al., 2000, "Myelin oligodendrocyte glycoprotein-DNA vaccination induces antibody-mediated autoaggression in experimental autoimmune encephalomelitis" Eur. J. Immunol. 30:3663-3671.
Bouwer et al. Acquired immunity to an intracellular pathogen: immunologic recognition of L. monocytogenes-infected cells, Immunol. Rev. Aug. 1997; 158:137-46.
Bouwer et al. Cytotoxic-T-lymphocyte responses to epitopes of listeriolysin O and p60 following infection with Listeria monocytogenes, Infect. Immune. Jul. 1996; 64(7):2515-22.
Boyer et al., "DNA prime Listeria boost induces a cellular immune response to SIV antigens in the Rhesus Macaque model that is capable of limited suppression of SIV239 viral replication", Virology. 333: 88-101, 2005.
Brantl et al, "Molecular analysis of the replication region of the conjugative Streptococcus agalactiae plasmid pIP501 in Bacillus subtilis. Comparison with plasmids pAM31 and pSM1 9035" Nucleic Acid Res 18: 4783-4790, 1990.
Brett et al. "Comparison of antigen presentation of influenza A nucleoprotein expressed in attenuated AroA- Salmonella typhimurium with that of live virus", J Immunol. Apr. 1, 1993;150(7):2869-84.
Brockstedt et al, "Listeria-based cancer vaccines that segregate immunogenicity from toxicity" 2004, PNAS, 101:13832-13837.
Bron et al, "Use of the air Gene as a Food-Grade Selection Marker in Lactic Acid Bacteria" 2002, Appl Environ Microbiol, 68: 5663-70.
Bron et al., 2004, "Identification of Lactobacillus plantarum genes that are induced in the gastrointestinal tract of mice", J. Bacteriol. Sep.; 186(17):5721-9.
Brown et al., 1988, "Site-specific integration in Saccharopolyspora erthraea and multisite integration in Streptomyces lividans of actinomycete plasmid pSE101", J. Bacteriology 170: 2287-2295.
Brown et al. "Chemical synthesis and cloning of a tyrosine tRNA gene" 1979, Meth. Enzymol. 68:109-151.
Bruder et al. "Efficient induction of cytotoxic CD8+ T cells against exogenous proteins: establishment and characterization of a T cell

(56) References Cited

OTHER PUBLICATIONS line specific for the membrane protein ActA of Listeria monocytogenes", Eur. J. Immunol. Sep. 1998; 28(9):2630-9.
Bruhn et al., 2005, "Characterization of anti-self CD8 T-cell responses stimulated by recombinant Listeria monocytogenes expressing the melanoma antigen TRP-2", Vaccine, Jul. 21; 23(33):4263-72.
Brundage et al, 1993. Expression and phosphorylation of the Listeria monocytogenes ActA protein in mammalian cells, Proc. Natl. Acad. Sci., USA, 90:11890-11894.
Bubert et al., 1997, "The Listeria monocytogenes iap gene as an indicator gene for the study of PrfA-dependent regulation", Mol. Gen. Genet. Sep.; 256(1):54-62.
Calendar et al., Poster presented at the ISOPOL Meeting 2001, http://64.233.169.104/search?q=cache:mA _uJpQsCrcJ:www.ma.uni-heidelberg.de/inst/imh/download/isopol.doc+Portnoy+Isopol+2001&hl=en&ct=clnk&cd=3&gl=us.
Camilli et al., 1993, "Daul roles of plcA in Listeria monocytogenes pathogenesis", Mol. Microbiol. 8:143-157.
Camilli et al. "Insertional mutagenesis of Listeria monocytogenes with a novel Tn917 derivative that allows direct cloning of DNA flanking transposon insertions", J Bacteriol, Jul. 1990 ;172(7):3738-44.
Camilli et al, 1991, Listeria monocytogenes mutants lacking phosphatidylinositol-specific phospholipase C area virulent, J. Exp. Med., 173:751-754.
Carbone, 1989, "Induction of ovalbumin-specific cytotoxic T cells by in vivo peptide immunization" J. Exp. Med. 169:603-612.
Carbone, 1990, "Class I-restricted processing and presentation of exogenous cell-associated antigen in vivo", J. Exp. Med. 171:377-387.
Carpenter et al. Non-Fc Receptor-Binding Humanized Anti-CD3 Antibodies Induce Apoptosis of Activated Human T Cells; J. Immunol. 165:6205-6213 (2000).
Catic et al. "Introduction of protein or DNA delivered via recombinant *Salmonella typhimurium* into the major histocompatibility complex class I presentation pathway of macrophages", Microbes Infect., Feb. 1999, 1(2):113-21.
Caudy et al., "Fragile X-related protein and VIG associate with the RNA interference machinery" Genes and Development 16: 2491-96.
Cenatiempo, "Prokaryotic gene expression in vitro: transcription-translation coupled systems." 1986, Biochimie 68:505-516.
Chen et al. "Episomal Expression of Truncated Listeriolysin O in LmddA-LLO—E7 Vaccine Enhances Antitumor Efficacy by Preferentially Inducing Expansions of CD4FoxP3_ andCD8 T Cells", Cancer Immunol Res; 2(9) Sep. 2014, pp. 911-922.
Chen, B.J. et al., "PD-L1 Expression Is Characteristic of a Subset of Aggressive B-cell Lymphomas and Virus-Associated Malignancies" Clin Cancer Res 19: 3462-3473 (2013).
Chothia et al. Canonical Structures for the Hypervariable Regions of Immunoglobulins; J Mol. Biol. 196:901-917 (1987).
Chothia et al. Confirmations of immunoglobulin hypervariable Regions; Nature 342:878-883 (1989).
Ciesielski et al. "Therapeutic Effect of a T Helper Cell Supported CTL Response Induced by a Survivin Peptide Vaccine against Murine Cerebral Glioma"; Cancer Immunol Immunother; 57(12): 1827-1835 (2008).
Clackson et al. Making Antibody Fragments Using Phage Display Libraries; Nature 352: 624-628 (1991).
Clark et al., "Clinical use of streptolysin-O to facilitate antisense oligodeoxyribonucleotide delivery for purging autografts in chronic myeloid leukaemia", Bone Marrow Transplantation, vol. 23, No. 12, 1999, pp. 1303/1308.
Clifton et al., "Overcoming cancer immune tolerance and escape", Clinical Cancer Research : An Official Journal of the American Association for Cancer Research 2009, vol. 15, No. 3, pp. 749-751.
Collins et al. "Directional cloning of DNA fragments at a large distance from an initial probe: a circularization method", Proc Natl Acad Sci U S A. Nov. 1984;81(21):6812-6.

Courvalin et al., 1995, "Gene transfer from bacteria to mammalian cells", C R Acad Sci III, Dec; 318(12):1207-12.
Coynault et al. "Virulence and vaccine potential of *Salmonella typhimurium* mutants deficient in the expression of the RpoS (sigma S) regulon", Mol Microbiol. Oct. 1996;22(1):149-60.
Cunto-Amesty et al., 2003, "Strategies in cancer vaccines development", Int. J. Parasitol. 33(5-6):597-613.
Da'Dara et al. Elimination of helminth infection restores HIV-1C vaccine-specific T cellresponses independent of helminth-induced IL-10; Vaccine; 3;28(5)1310-7 (2010).
Dakappagari et al., 2000, "Prevention of mammary tumors with a chimeric HER-2 B-cell epitope peptide vaccine", Cancer Res. Jul. 15; 60(14):3782-9.
Darji et al. The role of the bacterial membrane protein ActA in immunity and protection against Listeria monocytogenes, J. Immunol. Sep. 1, 1998, 161(5):2414-20.
Darji et al. "Antigen-specific T cell receptor antagonism by antigen-presenting cells treated with the hemolysin of Listeria monocytogenes: a noval type of immune escape", Eur. J. Immunol. Jul. 1997; 27(7):1696-703.
Darji et al. T-cell anergy induced by antigen presenting cells treated with the hemolysin of Listeria monocytogenes, Immunol. Lett. Jun. 1, 1997, 57(1-3):33-7.
Darji et al., 1995, "Hyperexpression of listeriolysin in the nonpathogenic species *Listeria innocua* and high yield purification", J. Biotechnol. Dec. 15; 43(3):205-12.
Darji et al., 1995, "Listeriolysin generates a route for the presentation of exogenous antigens by major histocompatibility complex class I", Eur. J. Immunol. Oct.; 25(10):2967-71.
Darji et al., 1997, "Oral somatic transgene vaccination using attenuated *S. typhimurium*" Cell 91:765-775.
Darji et al., 1997, "TAP-dependent major histocompatibility complex class I presentation of soluble proteins using listeriolysin", Eur. J. Immunol. Jun; 27(6):1353-9.
Darji et al., 2003, "Induction of immune responses by attenuated isogenic mutant strains of Listeria monocytoge" Vaccine 1; 21 Suppl. 2:S102-9.
De Boer et al, "A division inhibitor and a topological specificity factor coded for by the minicell locus determine proper placement of the division septum in *E. coli*" 1989, Cell 56:641-649.
De Bruin et al. Selection of high-affinity phage antibodies from phage display libraries; Nature Biotechnol. 17:397-399 (1999).
Decatur et al., "A PEST-Like Sequence in Listeriolysin O Essential for Listeria monocytogenes Pathogenicity", Science 2000, 290:992-995.
Dell'Erba et al., "Immunohistochemical reactivity of anti-melanoma monoclonal antibody 225.28S in Human Breast Cancer Biopsies", Anticancer Res. 2001, vol. 21, No. 2A, pp. 925-930.
Dembo et al. Limit Distribution of Maximal Non-Aligned Two-Sequence Segmental Score Ann. Prob. 22:2022-2039; (1994).
Dermime et al., 2004, "Vaccine and antibody-directed T cell tumour immunotherapy" Biochim Biophys Acta. 1704(1):11-35.
Deshpande et al., 1997, "Isolation of a contact-dependent haemolysin from *Mycobacterium tuberculosis*", J. Med. Microbiol. Mar.; 46(3):233-8.
Dietrich et al., 1998, "Delivery of antigen-encoding plasmid DNA into the cytosol of macrophages by attenuated suicide Listeria monocytogenes" Nature Biotechnology 15:181-185.
Dietrich et al., 2001, "From evil to good: a cytolysin in vaccine development", Trends Microbiol. Jan.; 9(1):23-8.
Disis, "Generation of immunity to the HER-2/neu oncogenic protein in patients with breast and ovarian cancer using a peptide-based vaccine" Clin Cancer Res. 5(6):128-997, Jun. 1999.
Doling et al. Cytotoxic T-lymphocyte epitopes fused to anthrax toxin induce protective antiviral immunity, Infect. Immun. Jul. 1999; 67(7):3290-6.
Dominiecki et al. Tumor sensitivity to IFN-γ is required for successful antigen-specific immunotherapy of a transplantable mouse tumor model for HPV-transformed tumors; Cancer Immunol Immunother ;54(5):477-88 (2005).
Dons et al. "Cloning and characterization of a gene encoding flagellin of Listeria monocytogenes", Mol Microbiol. Oct. 1992;6(20):2919-29.

(56) References Cited

OTHER PUBLICATIONS

Dramsi et al., 1995, "Entry of Listeria monocytogenes into hepatocytes requires expression of inIB, a surface protein of the internalin multigene family", Mol. Microbiol. 16(2):251-61.
Dunn et al., 1991, "Selective radiation resistance of immunologically induced T cells as the basis for irradiation-induced T-cell-mediated regression of immunogenic tumor", J. Leukoc Biol. 49(4):388-396.
Dustoor, "Antitumor activity of listeria monocytogenes on a guinea pig fibrosarcoma", Infection and Immunity, 1979, vol. 23, No. 1, pp. 54-60.
Dzojic et al "Adenovirus-mediated CD40 ligand therapy induces tumor cell apoptosis and systemic immunity in the TRAMP-C2 mouse prostate cancer model" The Prostate 66: 831-838 (2006).
Ebbeson et al. "Rhabdomyolysis, acute renal failure, and compartment syndrome in a child with parainfluenza type 1 infection", The Pediatric Infectious Disease Journal vol. 28, No. 9, Sep. 2009.
Ebert et al., 1990, "Selective immunosuppressive action of a factor produced by colon cancer cells", Cancer Res. 50(19):6158-6161.
Edman et al. A Protein Sequenator; Eur. J. Biochem . 80: 116-132, (1967).
Eisenhauer et al. New response evaluation criteria in solid tumours: Revised RECIST guideline (version 1.1), Eur. J Cancer 45:228-247 (2009).
Emond et al. "A ribosomal DNA fragment of Listeria monocytogenes and its use as a genus-specific probe in an aqueous-phase hybridization assay", Appl Environ Microbiol. Aug. 1993;59(8):2690-7.
Ercolini et al., "Identification and characterization of the immunodominant rat HER-2/neu MHC class I epitope presented by spontaneous mammary tumors from Her-2/neu transgenic mice", Journal of Immunology, 2003, vol. 170, No. 8, pp. 4273-4280.
Everts et al. Selective Intracellular Delivery of Dexamethasone into Activated Endothelial Cells Using an E-Selectin-Directed Immunoconjugate; J. Immunol. 168:883-889 (2002).
Ezzel, 1995, "Cancer Vaccines: An Idea Whose Time Has Come?" J. NIH Res., 7:46-49.
Falk et al., 1991, "Identification of naturally processed viral nonapeptides allows their quantification in infected cells and suggests an allele-specific T cell epitope forecast" J. Exp. Med. 174(2):425-434.
Ferrari et al. "Isolation of an Alanine Racemase Gene from Bacillus subtilis and its Use for Plasmid Maintenance in B. subtilis", Nature Biotechnology 3, 1003-1007.
Finn et al., 2003, "Cancer vaccines: between the idea and the reality" Nature Reviews Immunology 3:630-641.
Flint et al., "Overexpression of the erbB-2 proto-oncogene in canine osteosarcoma cell lines and tumors", Vet. Pathol. 41: 291-296, 2004.
Foote et al. "Antibody Framework Residues Affecting the Conformation of the Hypervariable Loops", J. Mol. Biol. 224:487-499 (1992).
Fouts et al. "Construction and immunogenicity of *Salmonella typhimurium* vaccine vectors that express HIV-1 gp120", Vaccine. Dec. 1995;13(17):1697-705.
Frankel et al. "Induction of cell-mediated immune responses to human immunodeficiency virus type 1 Gag protein by using Listeria monocytogenes as a live vaccine vector", J Immunol. Nov. 15, 1995;155(10):4775-82.
Frey, 1993, "Rat adenocarcinoma 13762 expresses tumor rejection antigens but tumor-bearing animals exhibit tumor-specific immunosuppression", Clin. Immunol. Immunopathol. 69(2):223-233.
Friedman et al., 2000, "Induction of human immunodeficiency virus (HIV)-specific CD8 T-cell responses by Listeria monocytogenes and a hyperattenuated Listeria strain engineered to express HIV antigens" J. Virology 74 9987-9993.
Fu et al., 1990, "Expansion of Immunoregulatory macrophages by granulocyte-macrophage colony-stimulating factor derived from a murine mammary tumor", Cancer Res. 50(2):227-234.
Fuji, 1987, "Significance of suppressor macrophages for immunosurveillance of tumor-bearing mice" J. Natl. Cancer Inst. 78(3):509-517.
Furukawa, 1993, "Nude mouse metastatic models of human stomach cancer constructed using orthotopic implantation of histologically intact tissue" Cancer Res. 53(5):1204-1208.
Gadiot et al., "Overall survival and PD-L1 expression in metastasized malignant melanoma" Cancer 117:2192-2201 (2011).
Galakatos et al. "Biosynthetic alr alanine racemase from *Salmonella typhimurium*: DNA and protein sequence determination", Biochemistry. Jun. 3, 1986;25(11):3255-60.
Galen et al., 2001, "Can a 'flawless' live vector vaccine strain be engineered?", Trends Microbiol. 9(8):372-6.
Gao et al. Overexpression of PD-L1 significantly associates with tumor aggressiveness and postoperative recurrence in human hepatocellular carcinoma. Clinical Cancer Research (2009) 15: 971-979.
Garay-Malpartida et al. Bioinformatics. Jun. 2005;21 Suppl 1 :i169-76.
Genbank Accession No. AF103807, Nov. 1, 1999.
GenBank Acc. No. NC_ 003210, Dec. 17, 2014.
GenBank Accession No. DQ054588, Aug. 21, 2006.
GenBank Accession No. DQ054589, Aug. 21, 2006.
GenBank Accession No. AY878649, Feb. 6, 2005.
GenBank Accession No. U25452, Jul. 16, 2001.
Gentschev et al. "*Salmonella* Strain Secreting Active Listeriolysin Changes Its Intracellular Localization", Infect. Immun., 1995, 63:4202-4205.
Gentschev et al. 1996, "Development of antigen-delivery systems, based on the *Escherichia coli* hemolysin secreatiohn pathway" Gene 179:133-140.
Ghebeh et al. The B7-H1 (PD-L1) T lymphocyte-inhibitory molecule is expressed in breast cancer patients with infiltrating ductal carcinoma: correlation with important high-risk propgnostic factors. Neoplasia (2006) 8: 190-198.
Ghebeh Foxp3+ tregs and B7-H1+/PD-1+ T lymphocytes co-infiltrate the tumor tissues of high-risk breast cancer patients: implication for immunotherapy. BMC Cancer. Feb. 23, 2008;8:57.
Ghosh et al. "Natalizumab for Active Crohn's Disease" (2003) New Engl. J. Med. 348:24-32.
Giannini et al. Morphological Precursors of Hepatocellular Carcinoma: A Morphometrical Analysis; Hepatogastroenterol. 34:95-97 (1987).
Gibellini et al. Extracellular HIV-1 Tat Protein Induces the Rapid Ser 133 Phosphorylation and Activation of CREB Transcription Factor in Both Jurkat Lymphoblastoid T Cells and Primary Peripheral Blood Monoculear Cells; J. Immunol. 160:3891-3898 (1998).
Gilbert et al. Enhanced CD8 T cell immunogenicity and protective efficacyin a mouse malaria model using a recombinant adenoviral vaccine in heterologous prime-boost immunization regimes; Vaccine 20:1039-45 (2002).
Gilman et al. "Isolation of sigma-28-specific promoters from Bacillus subtilis DNA" 1984, Gene 32:11-20.
Gilmore et al., 1989, "A Bacillus cereus cytolytic determinant, cereolysin AB, which comprises the phospholipase C and sphingomyelinase genes: nucleotide sequenc and genetic linkage", J. Bacteriol. Feb.; 171(2):744-53.
Gish et al. Identification of protein coding regions by database similarity search; Nature Genet. 3:266-272 (1993).
Glick (1987). Factors affecting the expression of foreign proteins in *Escherichia coli*, J. Ind. Microbiol. 1:277-282.
Glomski et al., 2002, "The Listeria monocytogenes hemolysin has an acidic pH optimum to compartmentalize activity and pevent damage to infected host cells" J. Cell Biol. Mar. 18; 156(6):1029-38.
Goebel et al., 1993, "Listeria monocytogenes—a model system for studying the pathomechanisms of an intracellular microorganism", Zbl. Bakt. 278:334-347.
Gold et al., "Translational initiation in prokaryotes." 1981, Ann. Rev. Microbiol. 35:365-404.
Gonzalo et al. A heterologous prime-boost regime using DNA and recombinant vaccinia virus expressing the Leishmania infantum P36/LACK antigen protects BALB/c mice from cutaneous leishmaniasis; Vaccine 20:1226-31 (2002).

(56) References Cited

OTHER PUBLICATIONS

Goossens et al., 1992, "Induction of protective CD8+ T lymphocytes by an attenuated Listeria monocytogenes actA mutant" Int. Immunol. Dec.; 4(12):1413-8.
Goossens et al., 1995, "Attenuated Listeria monocytogenes as a live vector for induction of CD8+ T cells in vivo: a study with the nucleoprotein of the lymphocytic choriomeningitis virus", Int. Immunol. May; 7(5):797-805.
Gottesman, (1984). Bacterial regulation: global regulatory networks Annu Rev Genet, Ann. Rev. Genet. 18:415-442.
Gouin et al. "The Listeria monocytogenes InIC protein interferes with innate immune responses by targeting the I B kinase subunit IKK", Proceedings of the National Academy of Sciences, vol. 107, No. 40, Sep. 20, 2010 (Sep. 20, 2010), pp. 17333-17338.
Graham et al. "Candidate AIDS vaccines", N Engl J Med. Nov. 16, 1995;333(20):1331-9.
Gregory et al., 1997, "Internalin B promotes the replication of Listeria monocytogenes in mouse hepatocytes" Infect. Immun. 65(12):5137-41.
Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK.
Gunn et al., "Two Listeria monocytogenes vaccine vectors that express different molecular forms of human papilloma virus-16 E7 induce qualitatively different T cell immunity that correlated with their avility to induce regression of established tumors immortalized by HPV-16", Journal of Immunology, vol. 167, No. 11, 2001, pp. 6471-6479.
Guzman et al. "Attenuated Listeria monocytogenes carrier strains can deliver an Hiv-1 gp120 T helper epitope to MHC class II-restricted human CD4+ T cells", European Journal of Immunology, vol. 28, No. 6, Jun. 1998, pp. 1807-1814.
Hamanishi et al. Programmed cell death 1 ligand 1 and tumor-infiltrating CD8+ T lymphocytes are prognostic factors of human ovarian cancer. Proceeding of the National Academy of Sciences (2007): 104: 3360-3365.
Hancock et al. SIMPLE34: An Improved and Enhanced Implementation for VAX and Sun computers of the SIMPLE algorithm for analysis of clustered repetitive motifs in nucleotide sequences; Comput. Appl. Biosci. 10:67-70 (1994).
Harty et al. "CD8 T lymphocytes specific for the secreted p60 antigen protect against Listeria monocytogenes infection", J. Immunol. May 1, 1995; 154(9):4642-50.
Harty et al. "CD8+ T cells specific for a single nonamer epitope of Listeria monocytogenes are protective in vivo", J Exp Med. Jun. 1, 1992;175(6):1531-8.
Hassan et al., 2004, "Mesothelin: a new target for immunotherapy" Clin. Cancer Res. 10(12 Pt 1):3937-42.
Hauf et al., 1997, "Listeria monocytogenes infection of P388D1 macrophages results in a biphasic NF-kappaB (RelA/p50) activation induced by lipoteichoic acid and Bacterial phospholipases and mediated by IkappaBalpha and IkappaBbeta degradation", Proc. Natl. Acad. Sci. U.S.A. Aug. 19; 94(17):9394-9.
Haynes et al. "Update on the issues of HIV vaccine development", Ann Med. Feb. 1996;28(1):39-41.
Haynes et al. "Scientific and social issues of human immunodeficiency virus vaccine development", Science. May 28, 1993;260(5112):1279-86.
He et al. Humanization and Pharmacokinetics of a Monoclonal Antibody with Specificity for Both E- and P-Selectin; J. Immunol. 160:1029 (1998).
Heinrich et al (Vaccination against prostate cancer using a live tissue factor deficient cell line in Lobund-Wistar rats. Cancer Immunol Immunother 2007;56(5):725-30).
Henikoff et al., "Amino acid substitution matrices from protein blocks" (1992) Proc. Natl. Acad. Sci. USA 89:10915-10919.
Herold et al. "Anti-Cd3 Monoclonal Antibody in New-Onset Type 1 Diabetes Mellitus" (2002) New Engl. J. Med. 346:1692-1698.

Hess et al., 1995, "Listeria monocytogenes p60 supports host cell invasion by and in vivo survival of attenuated *Salmonella typhimurium*" Infect. Immun. May; 63(5):2047-53.
Hess et al., 1996, "*Salmonella typhimurium* aroA- infection in gene-targeted immunodeficient mice: major role of CD4+ TCR-alpha beta cells and IFN-gamma in bacterial clearance independent of intracellular location" J. Immunol. May 1; 156(9):3321-6.
Hess et al., 1996, "Superior efficacy of secreted over somatic antigen display in recombinant *Salmonella* vaccine induced protection against listeriosis" Proc. Nat. Acad. Sci. 93:1458-1463.
Hess et al., 1997, "Protection against murine listeriosis by an attenuated recombinant *Salmonella typhimurium* vaccine strain that secretes the naturally somatic antigen superoxide dismutase", Infect. Immun. Apr.; 65(4):1286-92.
Hess et al, "*Mycobacterium bovis* Bacille Calmette-Guerin strains secreting listeriolysin of Listeria monocytogenes", Proc. Natl. Acad. Sci. U.S.A. Apr. 28, 1988; 95(9):5299-304.
Hess et al. Abstract, "Live antigen carriers as tools for improved anti-tuberculosis vaccines", FEMS Immunol. Med. Microbiol. Feb. 1999; 23(2):165-73.
Higgins et al., Abstract, "Delivery of protein to the cytosol of macrophages using *Escherichia coli* K-12", Mol. Microbiol. Mar. 31, 1999(6):1631-41.
Higgins et al., 1998, "Bacterial delivery of DNA evolves" Nat. Biotechnol. Feb.; 16(2):138-9.
Hiltbold et al. "The presentation of class I and class II epitopes of listeriolysin O is regulated by intracellular localization and by intracelluar spread of Listeria monocytogenes", J. Immunol. Aug. 1, 1996; 157(3):1163-75.
Hiltbold et al. "Mechanisms of processing and presentation of the antigens of Listeria monocytogenes", Infect. Agents Dis. Oct. 1993; 2(5):314-23.
Hino et al. Tumor cell expression of programmed cell death-1 is a prognostic factor for malignant melanoma. Cancer (2010 116(7):1757-66.
Hjortland et al., "Immunotoxin treatment targeted to the higher-molecular weight melanoma-associated antigen prolonging the survival of immunodeficient rats with invasive intracranial human glioblastoma multiforme", J. Neurosurg. 2004, vol. 100, No. 2, pp. 320-327.
Hodgson, 2000, "Generalized transduction of serotype 1/2 and serotype 4b strains of Listeria monocytogenes", Mol. Microbiol. 35(2):312-23.
Hoogenboom et al. "Natural and designer binding sites made by phage display technology", Immunol. Today 21:371-377 (2000).
Hsing et al. "Requirement for Nuclear Factor-kB Activation by a Distinct Subset of CD40-Mediated Effector Functions in B Lymphocytes", J. Immunol. 162:2804-2811 (1999).
Huang et al., 1994, "Role of bone marrow-derived cells in presenting MHC class I-restricted tumor antigens" Science 264:961-965.
Hussain et al., "What is needed for effective antitumor immunotherapy? Lessons learned using Listeria Monocytogenes as a live vector for HPV-associated tumors", Cancer Immunology, Immunotherapy, vol. 54, No. 6, 2005, pp. 577-586.
Hussain et al., "CD4+CD25+ Regulatory T Cells That Secrete TGF and IL-10 Are Preferentially Induced by a Vaccine Vector", 2004, J Immunother 27( 5):339-346.
Ikonomidis et al., 1994, Abstract E-90, Abstracts, 94th General Meeting of the American society for Microbiology, May 23-27.
Ikonomidis et al., "Influenze-specific immunity induced by recombinant Listeria monoctogenese vaccines", Vaccine, vol. 15, No. 4, 1997, pp. 433-440.
Ikonomidis et al. "Delivery of a viral antigen to the class I processing and presentation pathway by Listeria monocytogenes", J Exp Med. Dec. 1, 1994;180(6):2209-18.
Inman et al. PD-L1 (B7-H1) expression by urothelial carcinoma of the bladder and BCG-induced granulomata: associations with localized stage progression. Cancer (2007): 109: 1499-1505.
International Search Report for PCT Application No. PCT/US10/56534 dated Jun. 27, 2011.
International Search Report for PCT Application No. PCT/US12/51187 dated Jan. 23, 2013.

(56) References Cited

OTHER PUBLICATIONS

International Search Report for PCT Application No. PCT/US15/17559 dated Jun. 5, 2015.
International Search Report for PCT Application No. PCT/US15/24048 dated Jul. 30, 2015.
Jensen et al., 1997, "Recombinant Listeria monocytogenes as a live vaccine vehicle and a probe for studying-cell-mediated immunity" Immunological Review 158:147-157.
Jensen, 1997, "Recombinant Listeria monocytogenes vaccination eliminates papillomavirus-induced tumors and prevents papilloma formation from viral DNA", J. Virol. 71(11):8467-8474.
Jiang et al. "Characterization of a mutant Listeria monocytogenes strain expressing green fluorescent protein" Acta. Biochim. Biophys Sin (Shanghai), 37(1): 19-24, (2005).
Johnson et al., "Kabat database and its applications: 30 years after the first variability plot", Nucleic Acids Research, 2000, vol. 28, No. 1, pp. 214-218.
Jones et al. "Characterization of Listeria monocytogenes pathogenesis in a strain expressing perfringolysin O in place of listeriolysin O." (1994) Infect. Immunity 65:5608-5613.
Kabat et al., "Unusual distributions of amino acids in complementarity-determining (hypervariable) segments of heavy and light chains of immunoglobulins and their possible roles in specificity of antibody-combining sites" (1977) J. Biol. Chem. 252:6609-6616.
Kabat "The Structural Basis of Antibody Complementarity", Adv. Prot. Chem. 32:1-75 (1978).
Kaithamana et al. Induction of Experimental Autoimmune Graves' Disease in BALB/c Mice; J. Immunol. 163:5157-5164 (1999).
Karlin et al., "Methods for assessing the statistical significance of molecular sequence features by using general scoring schemes" (1990) Proc. Natl. Acad. Sci. USA 87:2264-2268.
Karlin et al., "Applications and statistics for multiple high-scoring segments in molecular sequences" (1993) Proc. Natl. Acad. Sci. USA 90:5873-5877.
Kaufman et al., "Impact of intracellular location of and antigen display by intracellular bacteria:implications for vaccine development", J. Immunol. Lett. 1999, 65(1-2):81-84.
Kaufmann "Immunity to intracellular bacteria", Annu Rev Immunol. 1993;11:129-63.
Kim et al., "Coexpression of BiP increased antithrombotic hirudin production in recombinant *Saccharomyces cerevisiae*", Journal of Biotechnology, vol. 101, No. 1, pp. 81-87, 2003.
King et. al., "Amplification of a novel v-erbB-related gene in a human mammory carcinoma" (1985). Science 229:974-976.
Knutson et al., "Immunization with a HER-2/neu helper peptide vaccine generates HER-2/neu CD8 T-cell immunity in cancer patients." The Journal of Clinical Investegation, 107:477-484, 2001.
Kocks et al., 1992, "L monocytogenes-induced act in assembly requires the actA gene product", Cell, vol. 68, No. 3, p. 521-531.
Kohler et al, "Expression of the iap gene coding for protein p60 of Listeria monocytogenes is controlled on the posttranscriptional level" J Bacteriol 173: 4668-74, 1991.
Kohler et al. Continuous Cultures of Fused Cells Secreting Antibody of Predefined Specificity; Nature 256: 495 (1975).
Kovacsovics-Bankowski et al., 1993, "Efficient major histocompatibility complex class I peresentation of exogenous antigen upon phagocytosis by macrophages", Proc. Natl. Acad. Sci. USA 90:4942-4946.
Kucera et al., "Prostate Specific Antigen (PSA) in Breat and Ovarian Cancer", Anticancer Res 1997, vol. 17, No. 60, pp. 4735-4737.
Kyte et al., "A simple method for displaying the hydropathic character of a protein", J. Mol. Biol. 157, 105 (1982).
Lampson et al., 1993, "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ", Cancer Research 53:176-182.
Landy, Mechanistic and structural complexity in the site-specific recombination pathways of Int and FLP Current Opinion in Genetics & Development 3:699-707; (1993).

Lasa et al., 1997, "Identification of two regions in the N-terminal domain of ActA involved in the actin comet tail formation by Listeria monocytogenes" EMBO 16(7):1531-40.
Lauer et al., "Characterization of the Attachment Site of Bacteriophage U153 within the Listeria monocytogenes comK Gene" ASM Meeting, Abstract 1999.
Lauer et al., "Systematic mutational analysis of the amino-terminal domain of the Listeria monocytogenes ActA protein reveals novel functions in actin-based motility" Molecular Microbiology 42(5):1163-1177, 2001.
Lauer et al., "Construction, characterization, and use of two LM site-specific phageintegration vectors", 2002 J Bacteliol, 184:4177-4186.
Le Doussal et al. Enhanced In Vivo Targeting of an Asymmetric Bivalent Hapten Antibody Conjugate CocktailsTo Double-Antigen-Positive Mouse B Cells With Monoclonal ; J. Immunol. 146:169-175 (1991).
Leao et al., 1995, "A species-specific nucleotide sequence of *Mycobacterium tuberculosis* encodes a protein that exhibts hemolytic activity when expressed in *Escherichia coli*" Infect. Immun. Nov.; 63(11):4301-6.
Lebrun et al., Aug. 1996, "Internallan must be on the Bacterial Surface to mediate Entry of Listeria monocytogenes into Epilhalial Cells", Molecullar Microbiology 21:579-592.
Lee et al., 1991, "Construction of single-copy integration vectors for *Staphylococcus aureus*", Gene 103:101-5.
Lee et al. Delivery of macromolecules into cytosol using liposomes containig hemolysin from Listeria monocytogenes, J. Biol. Chem., Mar. 29, 1996, 271(13):7249-52.
Lehner et al., 1996, "Processing and delivery of peptides presented by MHC class I molecules", Curr. Opin. Immunol. 8(1):59-67.
Lejeune, 1994, "Nitric oxide involvement in tumor-induced immunosuppression" J. Immunol. 152(10):5077-5083.
Lenz, "Stable integration vector for nutrient broth-based selection of attenuated Listeria monocytogenes strains with recombinant antigen expression" Clin Vaccine Immunol. 15(9):1414-1419. Sep. 2008.
Li et al., "Conditional lethality yields a new vaccine strain of listeria monocytogenes for the induction of cell-mediated immunity", Infection and Immunity, 2005, 73(8): 5065-5073.
Liau et al., 2002, "Tumor immunity within the central nervous system stimulated by recombinant Listeria monocytogenes vaccination", Cancer Res., 62(8):2287-93.
Lieberman et al. "Engineered Listeria monocytogenes as an AIDS vaccine", Vaccine. May 6, 2002;20(15):2007-10.
Lin et al., "Treatment of Established Tumors with a Novel Vaccine that Enhances Major Histocompatibility Class II Presentation of Tumor Antigen", Cancer Res. 1996, 56:21-26.
Lin et al., 2002, "Oral vaccination with recombinant Listeria monocytogenes expressing human papillomavirus type 16 E7 can cause tumor growth in mice to regress" Int. J. Cancer, Dec. 20; 102(6):629-37.
Lingnau et al., 1995, "Expression of the Listeria monocytogenes EGD inlA and inlB genes, whose products mediate bacterial entry into tissue culture cell lines, by PrfA-dependent and independent mechanisms" Infect. Immun. Oct.; 63(10):3896-903.
Lipford et al. "Vaccination with immunodominant peptides encapsulated in Quil A—containing liposomes induces peptide-specific primary CD8+ cytotoxic T cells", Vaccine Jan. 1994; 12(1):73-80.
Lipsky et al. "Infliximab and Methotrexate in the Treatment of Rheumatoid Arthritis" (2000) New Engl. J. Med. 343:1594-1602.
Liu et al. "Randomised, double blind, placebo controlled study of interferon beta-1a in relapsing-remitting multiple sclerosis analysed by area under disability/time curves" (1999) J. Neurol. Neurosurg. Psych. 67:451-456.
Lobocka et al. "Organization and expression of the *Escherichia coli* K-12 dad operon encoding the smaller subunit of D-amino acid dehydrogenase and the catabolic alanine racemase", J Bacteriol. Mar. 1994;176(5):1500-10.
Loeffler et al., 2006, "Comparison of different live vaccine strategies in vivo for delivery of protein antigen or antigen-encoding DNA and mRNA by virulence-attenuated Listeria monocytogenes" Infect. Immun. Jul; 74(7):3946-57.

(56) References Cited

OTHER PUBLICATIONS

Loessner et al., 1995, "Heterogeneous endolysins in Listeria monocytogenes bacteriophages: a new class of enzymes and evidence for conserved holin genes within the siphoviral lysis cassettes", Mol. Microbiol. Jun.; 16(6):1231-41.

Loessner et al., 2000, "Complete nucleotide sequence, molecular analysis and genome structure of bacteriophage A118 of Listeria monocytogenes: implications for phage evolution", Molecular Microbiology 35(2):324-40.

Loessner et al. 1994. Structural proteins and DNA characteristics of 14 Listeria typing bacteriophages. J. Gen. Virol. 75:701-710.

Maciag et al. "The first clinical use of a live-attenuated Listeria monocytogenes vaccine: a Phase I safety study of Lm-LLO-E7 in patients with advanced carcinoma of the cervix", Vaccine. Jun. 19, 2009;27(30):3975-83.

Madden et al. Applications of Network BLAST Server; Meth. Enzymol. 266:131-141 (1996).

Makela et al., Hand book of Experimental Immunology vol. 1, Chapter 3—"Haptens and carriers", pp. 3.1-3.13; 1987.

Manjili et al., 2003, "HSP110-HER2/neu chaperone complex vaccine induces protective immunity against spontaneous mammary tumors in HER-2/neu trangenic mice" J. Immunol. Oct. 15; 171(8):4054-61.

Marks et al. By-passing Immunization Human Antibodies from V-gene Libraries Displayed on Phage; J. Mol. Biol. 222: 581-597 (1991).

Marquis et al., 1997, "Proteolytic pathways of activation and degradation of a bacterial phospholipase C during intracellular infection by Listeria monocytogenes" J. Cell Biol. 137:1381-1392.

Marquis et al. "Intracytoplasmic growth and virulence of Listeria monocytogenes auxotrophic mutants", Infect Immun. Sep. 1993;61(9):3756-60.

Martin et al., 1986, "Nucleotide sequence of the tetM tetracycline resistance determinant of the streptococcal conjugative shuttle transposon Tn1545", Nucleic Acid Res. 14:7047-7058.

Marx et al., 2002, "Broad-host-range cre-lox system for antibiotic marker recycling in gramnegativ bacteria" Biotechniques, Nov.; 33(5):1062-7.

Mata et al. "Evaluation of a recombinant Listeria monocytogenes expressing an HIV protein that protects mice against viral challenge", Vaccine 19:1435-45, 2001.

Mata et al. Th1 T.cell responses to HIV·1 Gag protein delivered by Listeria monocytogenes vaccine are similar to those induced by endogenous listerial antigen's; J. Immunol 163:1449-1456. (1999).

Mata (1997). A hexameric phosphorothioate oligonucleotide telomerase inhibitor arrests growth of Burkitt's lymphoma cells in vitro and in vivo. Toxicol. Appi. Pharmacol. 144:189-197.

Mazda et al. (1997) Extremely efficient gene transfection into lympho-hematopoietic cell lines by Epstein-Barr virus-based vectors. J. Immunol. Methods 204, 143-151.

Mazzaccaro et al. "Major histocompatibility class I presentation of soluble antigen facilitated by Mycobacterium tuberculosis infection", Proc. Natl. Acad. Sci. U.S.A. Oct. 15, 1996; 93(21):11786-91.

McLaughlan et al., 1998, "Molecular characterization of an autolytic amidase of Listeria monocytogenes EGD", Microbiology, May; 144(Pt 5):1359-67.

Mendez et al. Functional Transplant of Megabase Humanimmunoglobulin Loci Recapitulates Human Antibody Response in Mice; Nature Genetics 15:146-156 (1997).

Mengaud et al., 1988, "Expression in *Escherichia coli* and sequence analysis of the listeriolysin O determinant of listeria monocytogenes", Infect. Immun., vol. 56, No. 4, 766-772.

Mengaud et al., "Transcriptional mapping and nucleotide sequence of the Listeria monocytogenes hlyA region reveal structural features that may be involved in regulation" Infect. Immun. 1989 57, 3695-3701.

Menne, et al. "A comparison of signal sequence prediction methods using a test set of signal peptides" (2000) Bioinformatics 16: 741-742.

Merrifield et al., "Solid phase peptide synthesis. 1. The synthesis of a tetrapeptide" J. Am. Chem. Soc., 85:2149-2156 (1963).

Meyaard et al. "LAIR-1, a Novel Inhibitory Receptor Expressed on Human Mononuclear Leukocytes" (1997) Immunity 7:283-290.

Mikayama et al. "Molecular cloning and functional expression of a cDNA encoding gycosylation-inhibiting factor", Nov. 1993, Pro Natl. Acad. Sci., USA, vol. 90:10056-10060.

Milgrom et al. "Treatment of Allergic Asthma With Monoclonal Anti-Ige Antibody" (1999) New Engl. J. Med. 341:1966-1973.

Miller et al, "Targeted vectors for gene therapy" 1995, FASEB J., 9:190-199.

Milligan (1993) "Current concepts in antisense drug design", J. Med. Chem. 36:1923-1937; Antisense Research and Applications (1993, CRC Press).

Mkrtichyan et al. "Anti-PD-1 antibody significantly increases therapeutic efficacy of Listeria monocytogenes (Lm)-LLO immunotherapy", Journal for ImmunoTherapy of Cancer 2013, 1:15.

Mlynarova et al., 2002, "The promiscuity of heterospecific lox sites increases dramatically in the presence of palindromic DNA", Gene, Aug. 21; 296(1-2):129-37.

Mollet et al., 1993, "Directed genomic integratoin, gene replacement, and integrative gene expression in *Streptococcus thermophilus*" J. Bacteriology 175:4315-4324.

Moriishi et al., 1998, "Sequence analysis of the actA gene of Listeria monocytogenes isolated from human", Microbiol. Immunol., vol. 42, No. 2, p. 129-132.

Nagai et al, 1991 Isolation and partial characterization of major protein antigens in the culture fluid of *Mycobacterium tuberculosis*. Infect Immun. Jan. 1991;59(1):372-82.

Nakanuma, et al. Anatomic and molecular pathology of intrahepatic cholangiocarcinoma, J. Hepatobiliary Pancreat. Surg. 10:265-281 (2003).

Narang et al. (1979). Improved Phosphotriester Method for the Synthesis of Gene Fragments, Meth. Enzymol. 68: 90-99.

Naruishi et al (Adenoviral vector-mediated RTVP-1 gene-modified tumor cell-based vaccine suppresses the development of experimental prostate cancer. Cancer Gene Ther. Jul. 2006;13(7):658-63).

Naz et al "Novel human prostate-specific cDNA: molecular cloning, expression, and immunobiology of the recombinant protein" Biochem Biophys Res Commun. 297:1075-84, 2002.

Ngo et al., 1994, "The Protein Folding Problem and Tertiary Structure Prediction", pp. 492-495.

Nielsen, (1999). Peptide nucleic acids as therapeutic agents Current Opin Struct Biol 9:353-57.

Nikodinovic et al., A second generation snp-derived *Escherichia coli-Streptomyces* shuttle expression vector that is generally transferable by conjugation. Plasmid. Nov. 2006;56(3):223-7.

Nitcheu-Tefit et al. "Listeriolysin O Expressed in a Bacterial Vaccine Suppresses CD4_CD25high Regulatory T Cell Function In Vivo", J Immunol. Aug. 1, 2007;179(3):1532-41.

Nomi et al. Clinical significance and therapeutic potential of the programmed death-1 ligand/programmed death-1 pathway in human pancreatic cancer. Clinical Cancer Research (2007);13:2151-2157.

Noriega et al. "Engineered deltaguaB-A deltavirG Shigella flexneri 2a strain CVD 1205: construction, safety, immunogenicity, and potential efficacy as a mucosal vaccine", Infect Immun. Aug. 1996;64(8):3055-61.

Ochsenbein et al., 1999, "A comparison of T cell memory against the same antigen induced by virus versus intracellular bacteria" Proc. Natl. Acad Sci U.S.A. Aug. 3; 96(16):9293-8.

Offit et al. "Addressing Parents' Concerns: Do Multiple Vaccines Overwhelm or Weaken the Infant's Immune System?", Pediatrics vol. 109 No. 1 Jan. 2002.

Ogasawara et al a strategy for making synthetic peptide vaccines Proc. Nati. Acad. Sci. USA vol. 89, pp. 8995-8999, Oct. 1992.

Ohigashi et al. Clinical significance of programmed death-1 ligand-1 and programmed death-1 ligand 2 expression in human esophageal cancer. Clin. Cancer Research (2005): 11:2947-2953.

O'Riordan et al. Listeria Intracellular Growth and Virulence Require Host-Derived Lipoic Acid, Science 302: 462-464(2003).

(56) References Cited

OTHER PUBLICATIONS

Oscarsson et al., 1996, "Induction of haemolytic activity in *Escherichia coli* by the slyA gene product" Mol. Microbiol. Apr.; 20(1):191-9.
Ostrand-Rosenberg "Myeloid-derived suppressor cells: linking inflammation and cancer", J Immunol. Apr. 15, 2009;182(8):4499-506.
Paglia et al., 1997, "The defined attenuated Listeria monocytogenes delta mp12 mutant is an effective oral vaccine carrier to trigger a long-lasting immune response against a mouse fibrosarcoma" Eur. J. Immunol. 27:1570-1575.
Palmeros et al., 2000, "A family of removable cassettes designed to obtain antibiotic-resistance-free genomic modifications of *Escherichia coli* and other bacteria" Gene, Apr. 18; 247(1-2):255-64.
Pamer et al. "Precise prediction of a dominant class I MHC-restricted epitope of Listeria monocytogenes", Nature. Oct. 31, 1991;353(6347):852-5.
Pan et al., "Regression of Established Tumors in Mice Mediated by the Oral Administration of a Recombinant Listeria monocytogenes Vaccine", Cancer Res., 1995, 55:4776-4779.
Pan et al., 1995, "A recombinant Listeria monocytogenes vaccine expressing a model tumour antigen protects mice against lethal tumour cell challenge and causes regression of established tumours" Nature Med. 1:471-477.
Parida et al., 1998, "Internalin B is essential for adhesion and mediates the invasion of Listeria monocytogenes into human endothelial cells" Mol. Microbiol. Apr.; 28(1):81-93.
Parsa et al., "Engineering bacterial vectors for delivery of genes and proteins to antigen-presenting cells", Molecular Pharmaceutics, vol. 4, No. 1, 2007, pp. 4-17.
Passos et al. Recombinant Leishmania Antigens for Serodiagnosis of Visceral Leishmaniasis Clinical and Diagnostic Laboratory Immunology, Oct. 2005, p. 1164-1167, vol. 12, No. 10.
Paterson et al., "Listeria-based vaccines for cancer treatment", Current Opinion in Molecular Therapeutics, vol. 7, No. 5, 2005, pp. 454-460.
Paterson, "Rational approaches to immune regulation", Immunologic Research, 2003; 27/2-3:451-462.
Paterson et al. "Recombinant Listeria monocytogenes cancer vaccines", Curr Opin Immunol. Oct. 1996;8(5):664-9.
Paul et al., 1989, "Fundamental Immunology", Second Edition, Raven Press, 987-988.
Paul et al. Frequent associations between CTI and T-Helper epitopes in HIV-1 genomes and 12, 13 implications for multi-epitope vaccine designs. BMC Microbiology 10:1-16 (2010).
Paul et al. An IL-4 Receptor Region Containing an Insulin Receptor Motif Is Important for IL+Mediated IRS-1 Phosphorylation and Cell Growth, Cell 76 241-251 (1994).
Pawelek et al. "Tumor-targeted *Salmonella* as a novel anticancer vector", Cancer Res. Oct. 15, 1997;57(20):4537-44.
Peng et al. "Adjuvant properties of listeriolysin O in a DNA vaccine strategy", Cancer Immunol Immunother, Jun. 2007;56(6):797-806.
Penichet et al., 2001, "Antibody-cytokine fusion proteins for the therapy of cancer" J. Immunological Methods 248:91-101.
Peters et al. "Tailoring host immune responses to Listeria by manipulation of virulence genes—the interface between innate and acquired immunity", FEMS Immunol Med Microbiol. Apr. 1, 2003;35(3):243-53.
Peters et al. The Induction of HIV Gag-Specific CD8+ T Cells in the Spleen and Gut-Associated Lymphoid Tissue by Parenteral or Mucosal monocytogenes HIV Gag Immunization with Recombinant Listeria; J Immunol; 170:5176-5187 ( 2003).
Peters et al. "Enhancing the immunogenicity of bioengineered Listeria monocytogenes by passaging through live animal hosts", Vaccine. 21.:1187-94. (2003).
Pfeifer et al., 1993, "Phagocytic processing of bacterial antigens for class I MHC presentation to T cells" Nature, Jan. 28; 361(6410):359-62.
Portielji et al. IL-12: a promising adjuvant for cancer vaccination, Cancer Immunol. Immunother. 52:133-144 (2003).
Portnoy et al. "Molecular determinants of Listeria monocytogenes pathogenesis", Infect Immun. Apr. 1992;60(4):1263-7.
Presta "Selection, design, and engineering of therapeutic antibodies" (2005) J. Allergy Clin. Immunol. 116:731.
Pucci et al, "*Staphylococcus haemolyticus* Contains Two D-Glutamic Acid Biosynthetic Activities, a Glutamate Racemase and a D-Amino Acid Transaminase" 1995, J Bacteriol. 177: 336-342.
Pupa et al., 2001, "Prevention of spontaneous neu-expressing mammary tumor development in mice transgenic for rat proto-neu by DNA vaccination" Gene Ther. Jan.; 8(1):75-9.
Purchio et al. "Methods in Enzymology: Methods for molecular cloning in eukaryotic cells", (2003).
Quenee et al., 2005, "Combined sacB-based negative selection and cre-lox antibiotic marker recycling for efficient gene deletion in pseudomonas aeruginosa", Biotechniques, Jan.; 38(1):63-7.
Raveneau et al., 1992, "Reduced virulence of a Listeria monocytogenes phospholipase-deficient mutant obtained by transposon insertion into the zinc metalloproteas gene" Infect. Immune., 60:916-921.
Realini et al., "Proposed roles in protein-protein association and presentation of peptides by MHC Class I receptors", FEBS Lett., 1994, 348:109-113.
Rechsteiner et al (PEST sequences and regulation by proteolysis. Trends Biochem Sci 1996; 21(7) :267-71.
Reiter et al., 1989, "Transfer RNA genes frequently serve as integration sites for porkaryotic genetic elements", Nucleic Acids Research 17(5):1907-14.
Renard et al., "HER-2 DNA and protein vaccines containing potent Th cell epitopes induce distinct protective and therapeutic antitumor responses in HER-2 transgenic mice", The Journal of Immunology, 171(3):1588-1595, 2003.
Repique, 1992, "Immunosuppression derived from human B-lymphoblastoid and melanoma cell lines" Cancer Invest. 10(3):201-208.
Riegler. Preneoplastic Conditions of the Liver; Seminars in Gastrointestinal Disease vol. 7, No. 2:pp. 74-87 (1996).
Riera et al. Evaluation of a latex agglutination test (KAtex) for detection of Leishmania antigen in urine of patients with HIV-Leishmania coinfection: value in diagnosis and post-treatment follow-up. Eur J Clin Microbiol Infect Dis. Dec;23 (12):899-904 (2004).
Robinson et al. "New Hope for an Aids Vaccine", Nat. Rev. Immunol. 2:239-50 (2002).
Rocken et al. "Pathalogy and Pathogenesis of Hepatocellular", Digestive Diseases 19:269-278 (2001).
Roden et al., 2004, "Vaccination to prevent and treat cervical cancer", Hum. Pathol. 35(8):971-82.
Rogers et al. "Amino acid sequences common to rapidly degraded proteins: the PEST hypothesis", Science 1986; 234(4774):364-8.
Rothman et. al. "The use of living listeria monocytogenes as an active immunotherapy for the treatment of cancer", Emerging Cancer Therapy: Microbial Approaches and Biotechnological Tools, Edited by Arsénio M. Fialho and Ananda M. Chakrabarty Copyright © 2010 John Wiley & Sons, Inc.
Rubin et al. "Cloning, sequence determination, and regulation of the ribonucleotide reductase subunits from Plasmodium falciparum: a target for antimalarial therapy", Proc Natl Acad Sci U S A. Oct. 15, 1993;90(20):9280-4.
Russmann et al., 1998, "Delivery of epitopes by the *Salmonella* type III secretion system for vaccine system for vaccine development", Science, Jul. 24; 281(5376):565-8.
Safley et al., "Role of listeriolysin-O (LLO) in the T lymphocyte response to infection with Listeria monocytogenes. Identification of T cell epitopes of LLO" J. Immunology 146(10):3604-3616; May 1991.
Sambrook et al. "Molecular cloning: a laboratory manual", Cold Spring Harbor Laboratory Press, New York 2 (2001).
Samstag (1996). Synthesis and properties of new antisense oligodeoxynucleotides containing benzylphosphonate linkages. Antisense Nucleic Acid Drug Dev. 6:153-156.

(56) References Cited

OTHER PUBLICATIONS

Schafer et al. "Induction of a cellular immune response to a foreign antigen by a recombinant Listeria monocytogenes vaccine", J Immunol. Jul. 1, 1992 ;149(1):53-9.
Scheirlinck et al., 1989, "Integration and expression of alpha-amylase and endoglucanase genes in the Lactobacillus plantarum chromosome", Appl. Environ Microbiol. 55(9):2130-7.
Scher et al., (2008) "Design and End Points of Clinical Trials for Patients With Progressive Prostate Cancer and Castrate Levels of Testosterone: Recommendations of the Prostate Cancer Clinical Trials Working Group" J. Clin. Oncol. 26(7):1148-159.
Schmidt et al., 1995, "Molecular Analysis of the Plasmid-Encoded Hemolysin of Escherichia coli O157:H7 Strain EDL 933", Infection and Immunity, 63(3):1055-1061.
Schneider et al. Induction of CD8+ T cells using heterologous prime-boost immunisation strategies, Immunol.Rev. 170:29-38 (1999).
Schnupf et al., "Phosphorylation, ubiquitination and degradation of listeriolysic O in mammalian cells: role of the PEST-like sequence" Cellular microbiology 8(2):353-364, 2006.
Schnupf et al. "ListeriolysinO: a phagosome-specific lysine", Microbes & Infect. 2007, 9:1176-1187.
Scortti et al., 2007, "The PrfA virulence regulon", Microbes Infect. Aug.; 9(10):1196-207.
Scott, P. et al. Amino Acid Sequences Common to Rapidly Degraded Proteins: The PEST Hypothesis; Immunol. Today vol. 234 364-348.,(1991).
Seavey "A novel human Her-2/neu chimeric molecule expressed by Listeria monocytogenes can elicit potent HLA-A2 restricted CD8-positive T cell responses and impact the growth and spread of Her-2/neu-positive breast tumors" Clin Cancer Res. 15(3):924-32, Feb. 1, 2009.
Sehgal I et al "Prostate cancer cells show elevated urokinase receptor in a mouse model of metastasis" Cancer Cell Int. Aug. 23, 2006;6:21.
Sewell et al., "Recombinant Listeria Vaccines Containing PEST Sequences are potent immune adjuvants for the tumor-associates antigen human pappilomavirus-16 E7", Cancer Research, American Association for Cancer Research, vol. 64, No. 24, 2004, pp. 8821-8825.
Sewell et al. Regression of HPV-Positive Tumors Treated with a New Listeria monocytogenes Vaccine Arch Otolaryngol., Head Neck Surg., Jan. 2004, vol. 130, pp. 92-97.
Shahabi et al. "A live, attenuated Listeria-based immunotherapeutic for the treatment of breast cancer", 2009 ASCO Breast cancer Symposium, Oct. 8, 2009, abstract.
Shahabi et al. "Development of a live and highly attenuated Listeria monocytogenes-based vaccine for the treatment of Her2/neu-overexpressing cancers in human", Cancer Gene Therapy, vol. 18, No. 1, Jan. 1, 2011, pp. 53-62.
Shahabi et al., "Development of a Listeria monocytogenes based vaccine against prostate cancer" Cancer Immunol Immunother (2008) 57:1301-1313.
Shahabi et al., "Live, attenuated strains of Listeria and *Salmonella* as vaccine vectors in cancer treatment", Bioeng. Bugs, 2010, vol. 1, No. 4, pp. 235-243.
Sharpe et al. "The function of programmed cell death 1 and its ligands in regulating autoimmunity and infection", Nature Immunology ; 8:239-245 (2007).
Shaw et al. "Complete nucleotide sequence of macrolide-lincosamide-streptogramin B-resistance transposon Tn917 in *Streptococcus faecalis*", J Bacteriol. Nov. 1985; 164(2):782-96.
Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.
Shen et al., 1998, "Compartmentalization of bacterial antigens: diffrential effects on priming of CD8 T cells and protective immunity" Cell., Feb. 20; 92(4):535-45.
Shetron-Rama et al., 2002, "Intracellular induction of Listeria monocytogenes actA expression" Infect. Immun. 70:1087-1096.

Shimauchi et al. Augmented expression of programmed death-1 in both neoplasmatic and nonneoplastic CD4+ T-cells in adult T-cell Leukemia/ Lymphoma. Int. J. Cancer (2007): 121:2585-2590.
Shimizu et al., 1994, "Effects of CD4+ and CD8+ T cells in tumor-bearing mice on antibody production" Cancer Immunol. Immunother 38(4):272-276.
Shiver et al., Replication-incompetent adenoviral vaccine vector elicits effective antiimmunode ® ciency-virus immunity, Nature 415: 331-5 (2002).
Sin et al. DNA Priming—Protein Boosting Enhances Both Antigen-Specific Antibody and Th1-Type Cellular Immune Responses in a Murine Herpes Simplex Virus-2 gD Vaccine Model, DNA Cell Biol. 18:771-9 (1999).
Singh et al. "Immunoediting sculpts tumor epitopes during immunotherapy", Cancer Res.67(5):1887-92. Mar. 1, 2007.
Singh et al., "Fusion to Listeriolysin O and Delivery by Listeria monocytogenes Enhances the Immunogenicity of HER-2/neu and Reveals Subdominant Epitopes in the FVB/N Mouse", The Journal of Immunology 2005, vol. 175, No. 6, pp. 3663-3673.
Singh et al. "Cancer immunotherapy using recombinant Listeria monocytogenes: transition from bench to clinic", Hum Vaccin. May 2011;7(5):497-505.
Sirard et al., 1997, "Intrtracytoplasmic delivery of Lidteriolysin O by vaccinal strain of Bacillus anthracis induces CD8-mediated protection against listeria monocytogenes", J. Immunology, vol. 159, p. 4435-4443.
Sizemore et al. "Attenuated Shigella as a DNA delivery vehicle for DNA-mediated immunization", Science. Oct. 13, 1995;270(5234):299-302.
Skoble, et al. "Three Regions within ActA Promote Arp2/3 Complex-mediated Actin Nucleation and Listeria monocytogenes Motility" 2000, J. Cell Biol. 150: 527-538.
Skolnick et al. "Form genes to protein structure and function: novel applications of computational approaches in the genomic era", Jan. 2000, Trends in Biotech., 18(1):34-39.
Slamon et al. "Use of Chemotherapy Plus a Monoclonal Antibody Against Her2 for Metastatic Breast Cancer That Overexpresses Her2" 2001, New Engl. J. Med. 344:783-792.
Slifka et al., 1996, "Antiviral cytotoxic T-cell memory by vaccination with recombinant Listeria monocytogenes" J. Virol. 70(5):2902-10.
Smith et al., 1995, "The two distinct phospholipases C of Listeria monocytogenes have overlapping roles in escape from a vacuole and cell-to-cell spread", Infect. Immun. 63:4231-4237.
Smith et al., Sep. 1995, "Asymmetric Distribution of the Listeria monocytogenes ActA Protein is Required and Sufficient to Direct Actin-Based Motility", Molecular Microbiology 17:945-951.
Smith et al., Biochimie. 1992. Use of a new integrational vector to investigate comparement-specific expression of the Bacillus subtilis spoIIM gene; 74 (7-8) p. 705-711.
Souders et al., 2006, "In vivo bactofection: listeriacan function as a DNA-cancer vaccine" DNA Cell Biol. Mar.; 25(3):142-51.
Soussi et al., "Effect of intragastric and intraperitoneal immunization with attenuated and wild-type LACK-expressing Listeria monocytogenes on control murine Leishmania major infection", Vaccine, vol. 20, No. 21-22, 2002, pp. 2702-2712.
Soussi et al., "Listeria monocytogenes as a short lived delivery system for the induction of type 1 cell-mediated immunity againdt the p36/LACK antigen of Leishmania major", Infection and Immunity, vol. 68, No. 3, 2000, pp. 1498-1506.
Strauss-Soukup, "Effects of Neutralization Pattern and Stereochemistry on DNA Bending by Methylphosphonate Substitutions", 1997, Biochemistry 36:8692-8698.
Strych et al, "Mutant Analysis Shows that Alanine Racemases from Pseudomonas aeruginosa and *Escherichia coli* Are Dimeric" 2002, J. Bacteriol. 184:4321-4325.
Stahl et al., 1984, "Replacement of the Bacillus subtilisin structural gene with an in vitro-derived deletion mutation", J. Bacteriol. 158:411-418.
States et al. Improved Sensitivity of Nucleic Acid Database Searches Using Application-Specific Scoring Matrices, Methods 3:66-70 (1991).

(56) References Cited

OTHER PUBLICATIONS

Stitz et al., 1990, "Characterization and immunological properties of influenza A virus nucleoprotein (NP): cell-associated NP isolated from infected cells or viral NP expressed by vaccinia recombinant virus do not confer protection" J. Gen. Virol., 71(Pt 5):1169-1179.
Strungnell et al., 1990, "Stable expression of forgein antigens from the chromosome of *Salmonella typhimurium* vaccine strains", Gene 88:57-63.
Strych et al. "Characterization of the alanine racemases from two mycobacteria", FEMS Microbiol Lett. Mar. 15, 2001;196(2):93-8.
Stryer et al., "Levels of structure in protein architecture", Biochemistry, Third Edition, W H Freeman Company, New York, pp. 31-33, 1998.
Su et al., "Relevance of Hepatic Preneoplasia for Human Hepatocarcinogenesis" (2003) Toxicol. Pathol. 31:126-133.
Sun et al. "Isolation of Listeria monocytogenes small-plaque mutants defective for intracellular growth and cell-to-cell spread", Infect Immun. Nov. 1990;58(11):3770-8.
Supplementary European Search Report for European Application No. 10830785.1 dated Dec. 10, 2013.
Supplementary European Search Report for European Application No. 12824212.0 dated Jun. 3, 2015.
Szalay et al. "Presentation of Listeria monocytogenes antigenes by major histocompatibility complex class I molecules to CD8 cytotoxic T lymphocytes independent of listeriolysin secretion and virulence", Eur. J. Immunol. Jul. 1994; 24(7):1471-7.
Tanabe et al., "Induction of Protective T Cells against Listeria monocytogenes in Mice by Immunization with a Listeriolysin O-Negative Avirulent Strain of Bacteria and Liposome-Encapsulated Listeriolysin O", Infect. Immun., 1999, 67(2):568-575.
Tang et al., "Protein Chemistry and Structure: Use of a Peptide Mimotope to Guide the Humanization of MRK-16, an Anti-P-glycoprotein Monoclonal Antibody", 1999 J. Biol. Chem. 274:27371-27378.
Tanghe "Improved Immunogenicity and Protective Efficacy of a Tuberculosis DNA Vaccine Encoding Ag85 by Protein Boosting" Infect. Immun. 69:3041-7 (2001).
Tanizawa et al. "The primary structure of thermostable D-amino acid aminotransferase from a thermophilic *Bacillus* species and its correlation with L-amino acid aminotransferases", J Biol Chem. Feb. 15, 1989;264(5):2450-4.
Tanizawa et al. "Thermostable alanine racemase from Bacillus stearothermophilus: DNA and protein sequence determination and secondary structure prediction", Biochemistry. Feb. 23, 1988;27(4):1311-6.
Taube et al., Lesions Supports an Adaptive Resistance Mechanism of Immune Escape, Sci Transl Med 4, 127ra37 (2012).
Tauch et al, "The alanine racemase gene alr is an alternative to antibiotic resistance genes in cloning systems for industrial Corynebacterium glutamicum strains" 2002, J. Biotechnol 99:79-91.
Teitelbaum et al. "Mycobacterial infection of macrophages results in membrane-permeable phagosomes", Proc. Natl. Acad. Sci. U.S. A, Dec. 21, 1999, 96(26):15190-5.
Terracciano et al. "Cytogenetic alterations in liver cell tumors as detected by Comparitive Genomic Hybridization", Pathologica 95:71-82 (2003).
Thomas-Kaskel et al (Vaccination of advanced prostate cancer patients with PSCA and PSA peptide-loaded dendritic cells induces DTH responses that correlate with superior overall survival. Int J Cancer. Nov. 15, 2006;119(10):2428-34).
Thompson et al. "Pathogenicity and immunogenicity of a Listeria monocytogenes strain that requires D-alanine for growth", Infect Immun. Aug. 1998;66(8):3552-61.
Thompson et al., "Costimulatory B7-H1 in renal cell carcinoma patients: Indicator of tumor aggressiveness and potential therapeutic target" PNAS 101 (49); 17174-17179 (2004).
Thompson et al., "Overall Survival and PD-L1 Expression in Metastasized Malignant Melanoma" Cancer Res. 66:3381-3385 (2006).
Thompson et al. "PD-1 is expressed by tumor infiltrating cells and is associated with poor outcome for patients with renal carcinoma" Clinical Cancer Research (2007) 15: 1757-1761.
Tilney et al., 1989, "Actin filaments and the growth, movement, and spread of the intracellular bacterial parasite, *Listeria monocytogenes*" J. Cell Biol., Oct.; 109(4 Pt 1):1597-608.
Toplian et al., "Safety, Activity, and Immune Correlates of Anti—PD-1 Antibody in Cancer" New Eng. J Med. 366 (26): 2443-2454 (2012).
Triglia et al. "A procedure for in vitro amplification of DNA segments that lie outside the boundaries of known sequences", Nucleic Acids Res. Aug. 25, 1988;16(16):8186.
Uenaka et al (T cell immunomonitoring and tumor responses in patients immunized with a complex of cholesterol-bearing hydrophobized pullulan (CHP) and NY-ESO-1 protein. Cancer Immun. Apr. 19, 2007;7:9).
Ulmanen et al, "Transcription and Translation of Foreign Genes in Bacillus subtilis by the Aid of a Secretion Vector" 1985. J. Bacteriol. 162:176-182.
Vasil et al., 1982, "Cloning of a phosphate-regulated hemolysin gene (phospholipase C) from Pseudomonas aeruginosa" J. Bacteriol. Oct.; 152(1):431-40.
Vaughan et al. Human Antibodies with Sub-nanomolar Affinities Isolated from a Large Non-immunized Phage Display Library, Nature Biotechnol. 14:309-314 (1996).
Vazquez et al. Differential regulation of Ia expression and antigen presentation by listeriolysin-producing versus non-producing strains of Listeria monocytogenes, J. Leukoc Biol. May 1996; 59(5):683-90.
Vazquez-Boland et al., 1992, "Nucleotide sequence of the lecithinase operon of Listeria monocytogenes and possible role of lecithinase in cell-to-cell spread" Infect. Immun. 60:219-230.
Verch et al., Listeria monocytogenes-Based Antibiotic Resistance Gene-Free Antigen Delivery System Applicable to Other Bacterial Vectors and DNA Vaccines. Infect Immun, 2004. 72(11):6418-25.
Verma et al., 1995, "Delivery of class I and class II MHC-restricted T-cell epitopes of listeriolysin of listeria monocytogenes by attenuated *Salmonella*", Vacine, vol. 13, No. 2, p. 142-150.
Villanueva et al. "Listeriolysin is processed efficiently into an MHC class I-associated epitope in Listeria monocytogenes-infected cells", J. Immunol. Dec. 1, 1995; 155(11):5227-33.
Vines et al. "Identfication and characterization of nucleotide sequence difference in three virulence-associate genes of listeria monocytogenes strains representing clinically important serotypes", Current Microbiology, May 1998, vol. 36, No. 5, pp. 309-318.
Von Heijne. Patterns of Amino Acids near Signal-Sequence Cleavage Sites Eur. J. Biochem. 133:17-21 (1983).
Von Heijne, "A new method for predicting signal sequence cleavage sites" (1986) Nucleic Acids Res. 14:4683-4690.
Walker et al., 1994, "Tumor growth Alters T cell and macrophage production of and responsiveness to granulocyte-macrophage colony-stimulating factor: partial dysregulation through interleukin-10" Cell Immunol. 154(1):342-357.
Wallecha et al. "Construction and characterization of an attenuated Listeria monocytogenes strain for clinical use in cancer immunotherapy" Clin Vaccine Immunol. 16(1):96-103, Jan. 2009.
Wallecha et al., "Multiple effector mechanisms induced by recombinant listeria monocytogenes anticancer immunotherapeutics", Advances in Applied Microbiology, vol. 66, 2009, pp. 1-27.
Ward et al, 1986. Construction and characterisation of a series of multi-copy promoter-probe plasmid vectors for Streptomyces using the aminoglycoside.
Wasserman et al. "Catabolic alanine racemase from *Salmonella typhimurium*: DNA sequence, enzyme purification, and characterization", Biochemistry. Oct. 23, 1984;23(22):5182-7.
Watson et al., 1991, "Splenic macrophages from tumor-bearing mice co-expressing MAC-1 and MAC-2 antigen exert immunoregulatory functions via two distinct mechanisms" J. Leukoc Biol. 49(2):126-138.
Weber, "Assessing Tumor Response to Therapy" Nucl. Med. 50:1 S-10S (2009).

(56) References Cited

OTHER PUBLICATIONS

Wei et al., 2005, "Listeria monocytogenes phosphatidylinositol-specific phospholipase C has evolved for virulence by greatly reduced activity on GPI anchors" Proc. Natl. Acad. Sci. U.S.A. 102:12927-12931.
Weidt et al., 1994, "CD8+ T lymphocyte-mediated antiviral immunity in mice as a result of injection of recombinant viral proteins", J. Immunol. Sep. 15; 153(6):2554-61.
Weiskirch "Listeria monocytogenes: a potent vaccine vector for neoplastic and infectious disease" Immunol. Rev., vol. 158, Aug. 1997, p. 159-169.
Welch et al., Jul. 3, 1998, "Interaction of Human Arp2/3 Complex and the Listeria monocytogenes ActA Protein in Actin Filament Nucleation" Science 281:105-108; pa-998020.
Wilson et al. "Transient expression of bacterial gene fragments in eukaryotic cells: implications for CD8(+) T cell epitope analaysis", J. Immunol. Methods, Feb. 3, 2000; 234 (1-2):137-47.
Wipke et al. "Variable binding affinities of listeriolysin O peptides for the H-2Kd class I molecule", Eur J Immunol. Aug. 1993;23(8):2005-10.
Wirth et al, "Highly efficient protoplast transformation system for *Streptococcus faecalis* and a new *Escherichia coli -S. faecalis* shuttle vector", J Bacteriol, 165: 831, 1986.
Wolff et. al. "Direct Gene Transfer into Mouse Muscle in Vivo", Science 247:1465(1990).
Wood et al. "Cancer immunotherapy using Listeria monocytogenes and listerial virulence factors" Immunol Res. ; 42(1-3):233-45. (2008).
Wootton et al. Statistics of Local Complexity in Amino Acid Sequences and Sequence Databases, Comput. Chem. 17:149-163 (1993).
Wright et al. "Lymphoid/Neuronal Cell Surface OX2 Glycoprotein Recognizes a Novel Receptor on Macrophages Implicated in the Control of Their Function", (2000) Immunity 13:233-242.
Wu et al., "Engineering an itracellular pathway for major histrocompatibility complex class II presentation of antigens", Proc. Natl. Acad. Sci. USA, 1995, 92:11671-5.
Yakamoto et al. "Listeriolysin O derived from Listeria monocytogenes inhibits the effector phase of an experimental allergic rhinitis induced by ovalbumin in mice", Clin Exp Immunol. Jun. 2006;1 44(3):475-84.
Yang et al. "A Randomized Trial of Bevacizumab, an Anti—Vascular Endothelial Growth Factor Antibody, for Metastatic Renal Cancer" (2003) New Engl. J. Med. 349:427-434.
Young et al., 1992, "Tumor-derived cytokines induce bone marrow suppressor cells that mediate immunosuppression through transforming growth factor beta", Cancer Immunol. Immunother. 35(1)1 4-18.
Young et al., 1995, "Holins: form and function in bacteriophage lysis" FEMS Microbiol Rev., Aug., 17 (1-2):191-205.
Zhang et al., 1993, "Functional replacement of the hemolysin A transport signal by a different primary sequence", Proc. Natl. Acad. Sci. U.S.A May 1; 90(9):4211-5.
Zhang et al., "PowerBLAST: A New Network BLAST Application for Interactive or Automated Sequence Analysis and Annotation " (1997) Genome Res. 7:649-656.
Zhao et al. "Pathogenicity and immunogenicity of a vaccine strain of Listeria monocytogenes that relies on a suicide plasmid to supply an essential gene product", Infect Immun. Sep. 2005;73(9):5789-98.
Supplementary European Search Report for European Application No. 13761946.6 dated Sep. 8, 2015.
Yamamoto, K., et al. "Listeriolysin O derived from Listeria monocytogenes inhibits the effector phase of an experimental allergic rhinitis induced by ovalbumin in mice." Clinical & Experimental Immunology 144.3 (2006): 475-484.
Ahmed et al. "Immunotherapy for osteosarcoma: genetic modification of T cells overcomes low levels of tumor antigen expression", Mol Ther. Oct. 2009;17(10):1779-87.
Barry et al (1992) "Pathogenicity and immunogenicity of Listeria monocytogenes smallplaque mutants defective for intracellular growth and cell-ta-cell spread." Infection mutants defective for intracellular growth and cell-ta-cell spread. Infection and Immunity 60 (4): 1625-32.
Bast. et al (1975) "Antitumor activity of bacterial infection. II. effect of Listeria. monocytogenes on growth of a guinea pig hepatoma." J Natl. Cancer Inst., 54(3): 757-761.
Beatly, Dissertation Abstracts International, 2000, 61/10B: 5224 Abstract Only.
Beattie IA, Swaminathan B, Ziegler HK, Cloning and charcterization of T-cell-reactive protein antogens from Listeria monocytogenes, infect. Immune. Sep. 1990, 58(9):2792-803.
Brasseur, et al (1992) "Human gene MAGE-1, which codes for a tumor-rejection antigen, is expressed by some breast tumors." Int. J Cancer 52(5):839-841.
Braun et al. "INLB: An Invasion Protein of Listeria Monocytogenes With a Novel Type of Surface Association", Mol Microbiol. Jul. 1997;25(2):285-94.
Burnham, Clyde M. "Bad bugs: good for cancer therapy?." Drug discovery today 8.2 (2003): 54-55.
Chamberlain, et al (2000) "Innovations and strategies for the development of anticancer vaccines." Expert Opinion on Pharmacotherapy. 1(4): 603-614.
Coussens, et al (1985)"Tyrosine Kinase Receptor with Extensive Homology to EGF Receptor Shares Chromosomal Location with neu Oncogene." Science. vol. 230, 1132-1139.
De Las Mulas "Oncogene HER-2 in canine mammary gland carcinomas: an immunohistochemical and chromogenic in situ hybridization study", Breast Cancer Res Treat. Aug. 2003;80(3):363-7.
De Maria et al. "Spontaneous feline mammary carcinoma is a model of HER2 overexpressing poor prognosis human breast cancer", Cancer Res. Feb. 1, 2005;65(3):907-12.
Disis, et al (1996) Peptide-Based, but Not Whole Protein, Vaccines Elicit Immunity to HER-2/neu, an Oncogenic Self Protein. The Journal of Immunology, vol. 156,3151-3158.
European Search Report for European Application No. 14190388.0 dated Mar. 2, 2015.
European Search Report for European Application No. 14195065.9 dated Mar. 12, 2015.
European Search Report for European Application No. 15182979.3 dated Oct. 26, 2015.
Glaser et al. "Comparative genomics of *Listeria* species", Science. Oct. 26, 2001;294(5543):849-52.
Gunn, George R., Christian Peters, and Yvonne Paterson. "Listeriolysin—a useful cytolysin." Trends in microbiology 9.4 (2001): 161-162.
Gunn, Dissertation Abstracts International, 2001, 62/5B: 2244 Abstract Only.
Harty, John T., Laurel L. Lenz, and Michael J. Bevan. "Primary and secondary immune responses to Listeria monocytogenes." Current opinion in immunology 8.4 (1996): 526-530.
Hu, Paul Q., et al. "*Escherichia coli* expressing recombinant antigen and listeriolysin O stimulate class I-restricted CD8+ T cells following uptake by human APC." The Journal of Immunology 172.3 (2004): 1595-1601.
International Search Report for PCT Application No. PCT/US15/40855 dated Dec. 18, 2015.
International Search Report for PCT Application No. PCT/US15/040911 dated Nov. 2, 2015.
International Search Report of Application No. PCT/US07/06292 dated Jun. 17, 2008.
International Search Reports of Application No. PCT/US07/10635 dated Sep. 11, 2008.
International Search Reports of Application No. PCT/US08/03067 dated Aug. 29, 2008.
Kerksiek, Kristen M., and Eric G. Pamer. "T cell responses to bacterial infection." Current opinion in immunology 11.4 (1999): 400-405.
Lamikanra, Abigail, et al. "Regression of established human papillomavirus type 16 (HPV-16) immortalized tumors in vivo by vaccinia viruses expressing different forms of HPV-16 E7 correlates with enhanced CD8+ T-cell responses that home to the tumor site." Journal of virology 75.20 (2001): 9654-9664.

(56) References Cited

OTHER PUBLICATIONS

Lara-Tejero, Maria, and Eric G. Pamer. "T cell responses to Listeria monocytogenes." Current opinion in microbiology 7.1 (2004): 45-50.
Ma et al. "Expression of HER 2 in Human Osteosarcoma", Sci. Tech. Engng. vol. 11 No. 13 May 2011, 1671 1815( 2011), pp. 3045-3048.
Mandal, Manas, and Kyung-Dall Lee. "Listeriolysin O-liposome-mediated cytosolic delivery of macromolecule antigen in vivo: enhancement of antigen-specific cytotoxic T lymphocyte frequency, activity, and tumor protection." Biochimica et Biophysica Acta (BBA)-Biomembranes 1563.1 (2002): 7-17.
Mitchell et al. "Avoidance of autophagy mediated by PlcA or ActA is required for Listeria monocytogenes growth in macrophages", Infect Immun. May 2015;83(5):2175-84.
Office Action dated Jun. 14, 2016 for Japanese Application No. 2014-526219.
Pan, Zhen-Kun, Larry M. Weiskirch, and Yvonne Paterson. "Regression of established B16F10 melanoma with a recombinant Listeria monocytogenes vaccine." Cancer research 59.20 (1999): 5264-5269.
Peng, Xiaohui, S. Farzana Hussain, and Yvonne Paterson. "The ability of two Listeria monocytogenes vaccines targeting human papillomavirus-16 E7 to induce an antitumor response correlates with myeloid dendritic cell function." The Journal of Immunology 172.10 (2004): 6030-6038.
Radford, K. J., et al. "A recombinant E. coli vaccine to promote MHC class I-dependent antigen presentation: application to cancer immunotherapy." Gene therapy 9.21 (2002): 1455-1463.
Radford, Kristen J., et al. "Recombinant E. coli efficiently delivers antigen and maturation signals to human dendritic cells: presentation of MART1 to CD8+ T cells." International journal of cancer 105.6 (2003): 811-819.
Scardino, et al (2002) "HER-2/neu and hTERT Cryptic Epitopes as Novel Targets for Broad Spectrum Tumor Immunotherapy." The Journal of Immunology, vol. 168,5900-5906.
Shen, Hao, Cristina M. Tato, and Xin Fan. "Listeria monocytogenes as a probe to study cell-mediated immunity." Current opinion in immunology 10.4 (1998): 450-458.
Starks et al., 2004, "Listeria monocytogenes as a vaccine vector: virulence attenuation or existing antivector immunity does not diminish therapeutic efficacy", J. Immunology 173:420-427.
Wada, Takuro "Development of Cancer Vaccine Therapy for Bone and Soft Tissue Sarcomas", J. Jpn. Orthop. Assoc. 78(8) 2004, p. S950.
Zwickey HL, Potter TA, "Peptide epitopes from noncytosolic Listeria monocytogenes can be presented by major histocompatibility complex class I molecules", Infect. Immun. May 1996; 64(5):1870-2.
Zwickey HL, Potter TA, Antigen secreted from noncytosolic Listeria monocytogenes is processed by the classical MHC class I processing pathway, J. Immunol. Jun. 1, 1999; 162(11):6341-50.
Baumhoer et a. "Aberrant expression of the human epidermal growth factor receptor 2 oncogene is not a common feature in osteosarcoma" Human pathology. Jun. 30, 2011;42(6):859-66.
Kawashima et al. "Identification of HLA-A3-restricted cytotoxic T lymphocyte epitopes from carcinoembryonic antigen and HER-2/neu by primary in vitro immunization with peptide-pulsed dendritic cells" Cancer Res. Jan. 15, 1999;59(2):431-5.
Kumar et al. "Prognostic and predictive value of c-erbB2 overexpression in osteogenic sarcoma" Journal of cancer research and therapeutics. Jan. 1, 2006;2(1):20.
Li et al. "A meta-analysis on the association of HER-2 overexpression with prognosis in human osteosarcoma" European journal of cancer care. May 1, 2010;19(3):313-6.
Yalçin et al. "C-erbB-2 expression and prognostic significance in osteosarcoma" Pediatric blood & cancer. Aug. 1, 2008;51(2):222-7.

\* cited by examiner

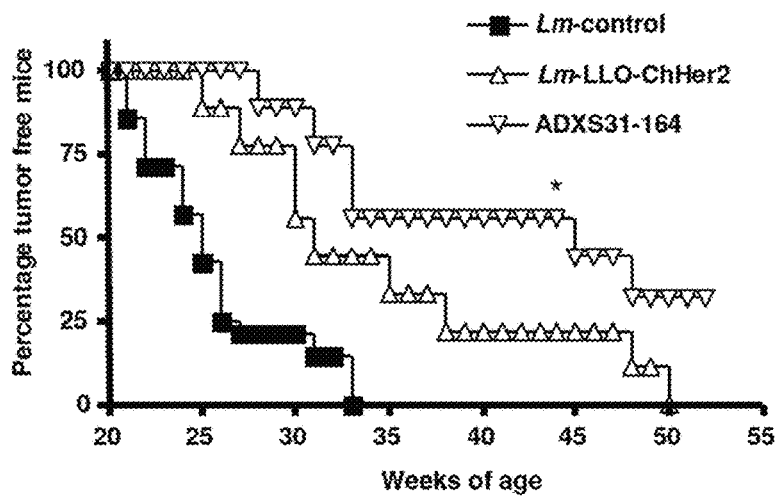
Figure 3
Spleens
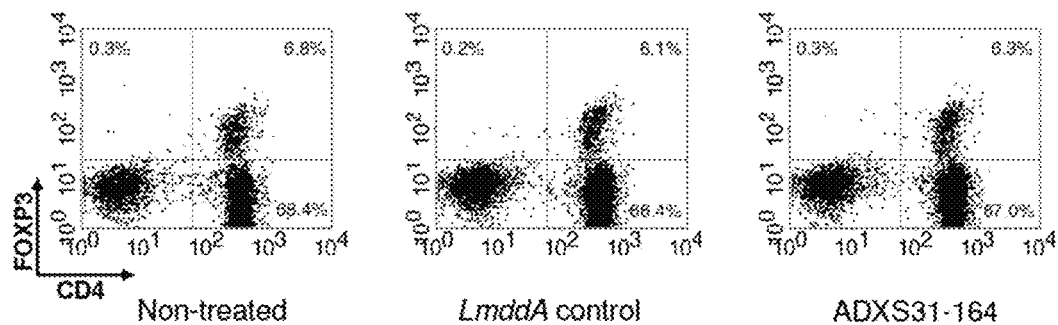
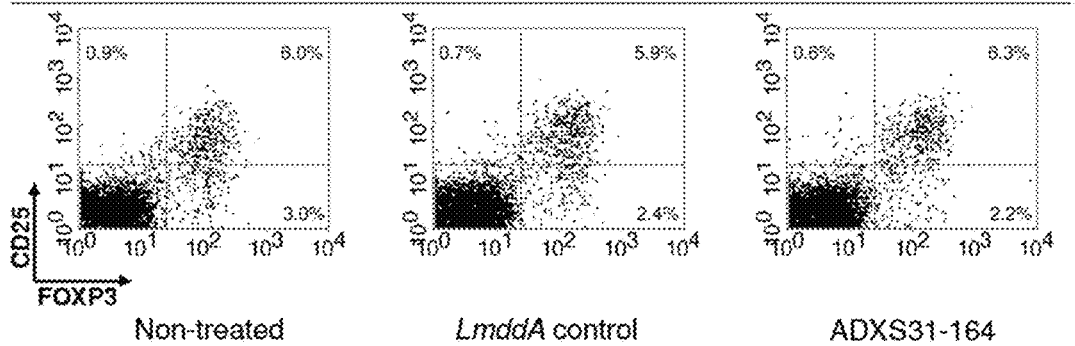
Figure 4

A.
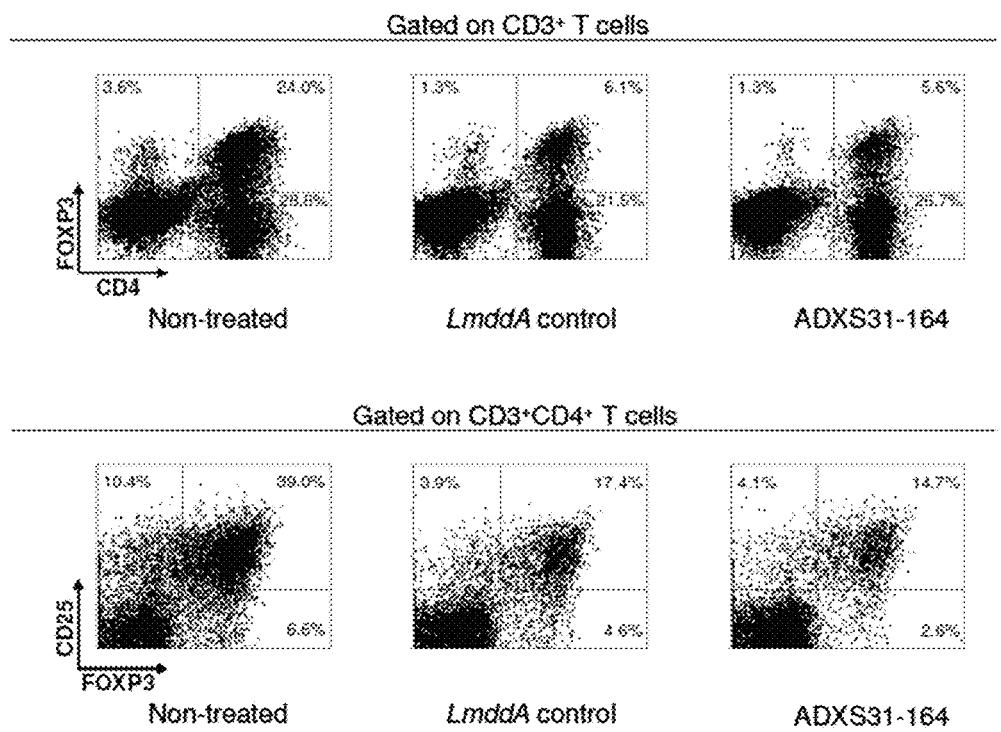
B.
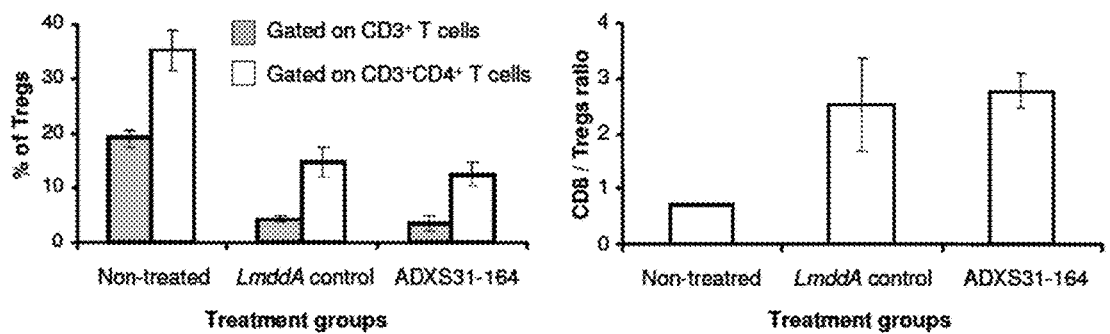
Figure 5

A.
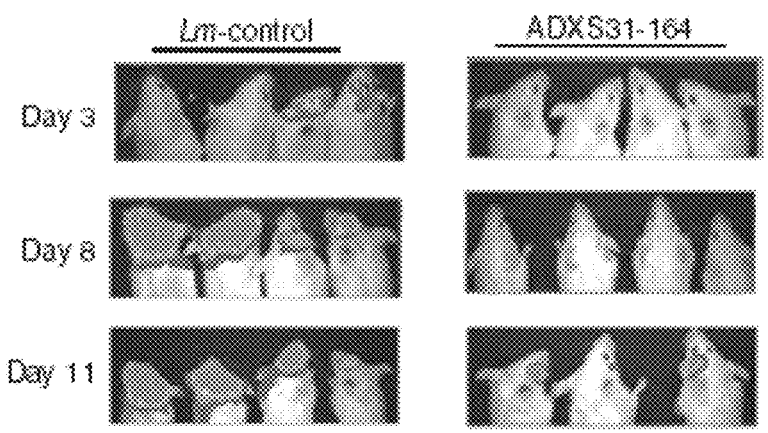
B.
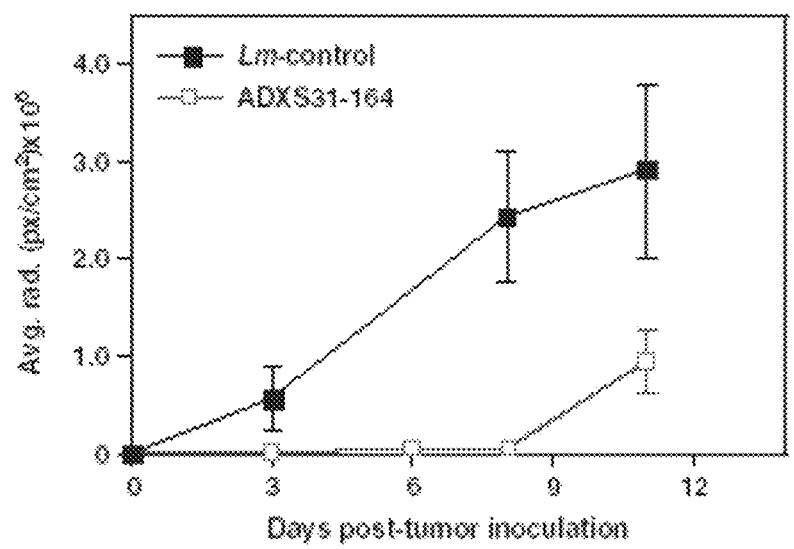
C.
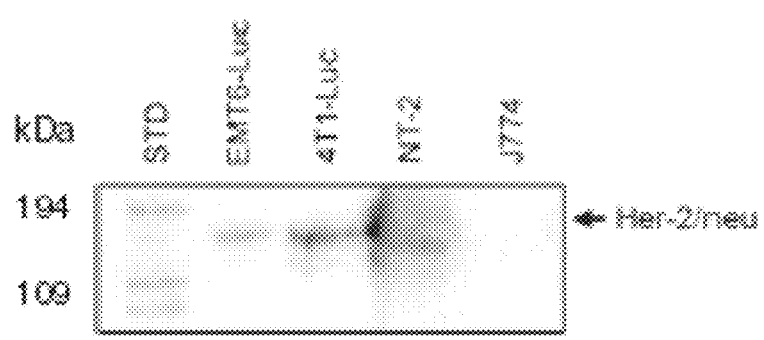
Figure 6

| AGE | BREED | SEX | TUMOR LOCATION | SUBTYPE | GRADE | HER2 SCORE | DOSE | OVERALL SURVIVAL (days) |
|---|---|---|---|---|---|---|---|---|
| 12.5 | American Pit Bull | FS | Proximal humerus | Osteoblastic | II | 2 | 2 x 10^8 | 738 |
| 11.5 | Mixbreed | FS | Distal radius | Osteoblastic | I | 5 | 2 x 10^8 | 267 |
| 9 | Labrador | MC | Proximal humerus | Fibroblastic | II | 7.5 | 2 x 10^8 | 1007+ |
| 6 | Mixbreed | FS | Distal tibia | Osteoblastic | I | 4.5 | 5 x 10^8 | 973+ |
| 7 | Rottweiler | MC | Distal ulnar | Osteoblastic | III | 2.25 | 5 x 10^8 | 955+ |
| 4.5 | English Bulldog | MC | Proximal humerus | Osteoblastic | I | 4 | 5 x 10^8 | 346 |
| 6 | OES | MC | Distal femur | Osteoblastic | II | 1.5 | 1 x 10^9 | 774+ |
| 9 | Greyhound | MC | Proximal humerus | Osteoblastic | II | 5 | 1 x 10^9 | 444 |
| 8 | Golden Retriever | MC | Distal ulnar | Fibroblastic | I | 3 | 1 x 10^9 | 518+ |
| 2 | Labrador | FS | Proximal tibia | Fibroblastic | I | 4.5 | 1 x 10^9 | 468+ |
| 7.5 | Cavalier King Charles | FS | Proximal tibia | Osteoblastic | II | 7.5 | 1 x 10^9 | 469+ |
| 6.5 | Golden Retriever | FS | Distal radius | Osteoblastic | I | 4.5 | 1 x 10^9 | 460+ |
| 10 | Greyhound | MC | Distal femur | Osteoblastic | II | 2 | 1 x 10^9 | 276 |
| 5.5 | Labrador | MC | Distal femur | Osteoblastic | I | 9 | 1 x 10^9 | 342+ |
| 9 | Golden Retriever | FS | Distal femur | Osteoblastic | I | 6 | 1 x 10^9 | 366+ |
| 6.6 | Great Dane | MC | Distal radius | Osteoblastic | II | 7.5 | 3 x 10^9 | 259 |
| 7 | Mixbreed | MC | Proximal humerus | Osteoblastic | II | 9 | 3 x 10^9 | 375+ |
| 6.5 | Rottweiler | FS | Proximal humerus | Osteoblastic | II | 6 | 3 x 10^9 | 362+ |

Figure 7

A 
B 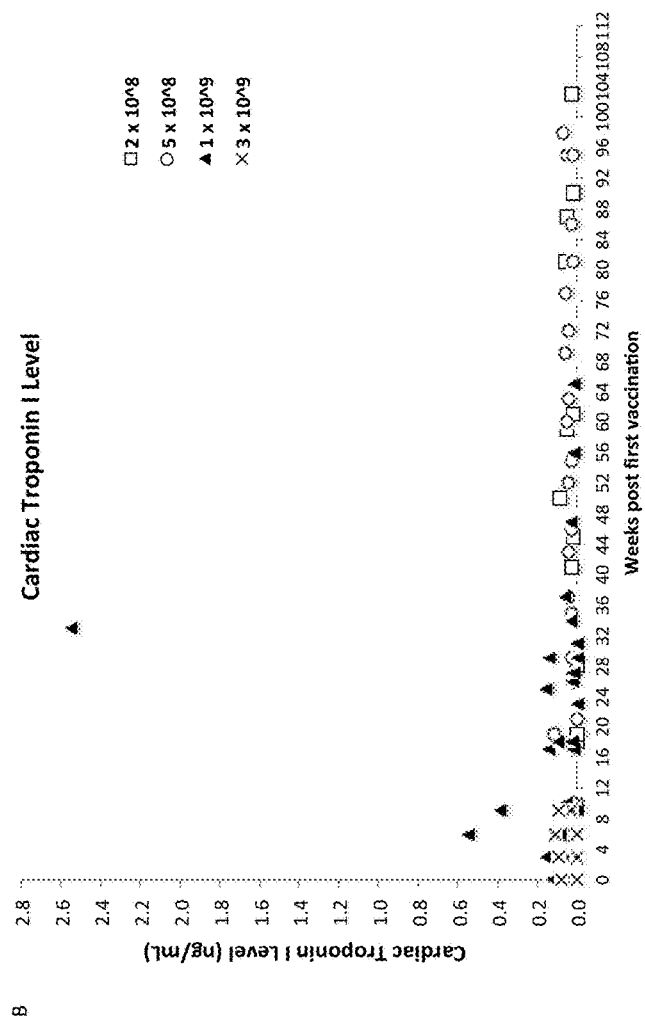
Figure 8

| Number of Dogs with Treatment Related Adverse Events | | | | | | |
|---|---|---|---|---|---|---|
| ADXS31-164 dose | | $2 \times 10^8$ | $5 \times 10^8$ | $1 \times 10^9$ | $3 \times 10^9$ | Total |
| Number of dogs recruited | | 3 | 3 | 11 | 6 | 23 |
| *General Disorders* | | | | | | |
| Pyrexia (T>103) | Grade 1 | 2 | 1 | 5 | 5 | 13 |
| Fatigue | Grade 1 | 1 | 0 | 7 | 2 | 10 |
| Nausea | Grade 1 | 1 | 2 | 10 | 2 | 15 |
| | Grade 2 | 1 | 0 | 0 | 0 | 1 |
| Vomiting | Grade 1 | 1 | 2 | 9 | 3 | 15 |
| | Grade 2 | 2 | 0 | 0 | 3 | 5 |
| *Cardiovascular abnormalities* | | | | | | |
| Arrhythmias | Grade 1 | 0 | 1 | 0 | 0 | 1 |
| | Grade 2 | 0 | 0 | 0 | 1 | 1 |
| Tachycardia | Grade 1 | 0 | 0 | 2 | 1 | 3 |
| | Grade 2 | 0 | 0 | 0 | 1 | 1 |
| Hyoptension | | 0 | 0 | 0 | 0 | 0 |
| Hypertension | Grade 1 | 2 | 3 | 8 | 5 | 18 |
| *Hematological parameters* | | | | | | |
| Thrombocytopenia | Grade 1 | 2 | 2 | 6 | 3 | 13 |
| | Grade 2 | 0 | 0 | 2 | 1 | 3 |
| *Biochemical Parameters (increases)* | | | | | | |
| γ-GT | Grade 1 | 0 | 2 | 1 | 0 | 3 |
| ALKP | Grade 1 | 0 | 1 | 6 | 1 | 8 |
| | Grade 2 | 0 | 0 | 0 | 1 | 1 |
| | Grade 3 | 1 | 0 | 0 | 0 | 1 |
| ALT | Grade 1 | 1 | 1 | 3 | 0 | 5 |
| | Grade 2 | 0 | 0 | 0 | 1 | 1 |
| | Grade 3 | 1 | 0 | 0 | 0 | 1 |
| AST | Grade 1 | 1 | 1 | 4 | 2 | 8 |
| | Grade 2 | 0 | 0 | 2 | 0 | 2 |
| | Grade 3 | 0 | 0 | 1 | 0 | 1 |
| BUN | | 0 | 0 | 0 | 0 | 0 |
| CREA | | 0 | 0 | 0 | 0 | 0 |
| Cardiac Troponin I | Grade 1 | 0 | 0 | 1 | 1 | 2 |

Figure 13A

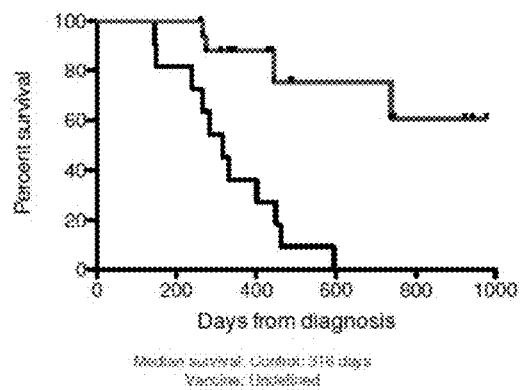

Figure 13B

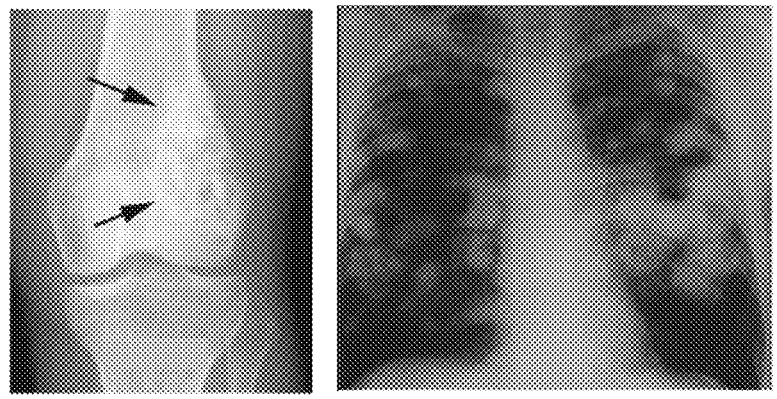
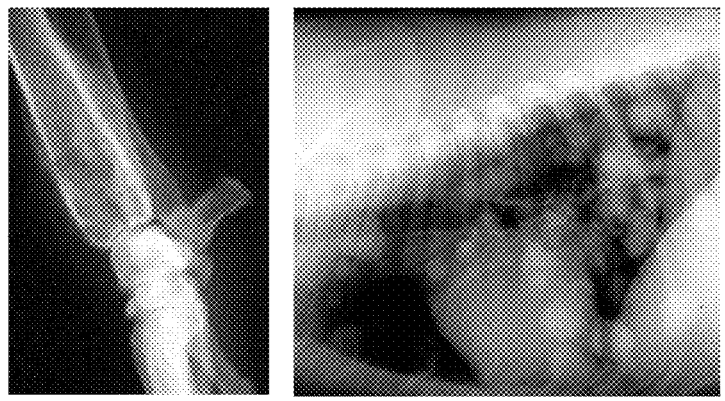
Figure 14
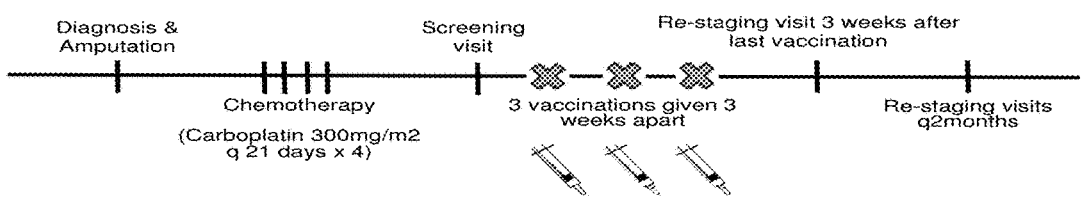
Figure 15

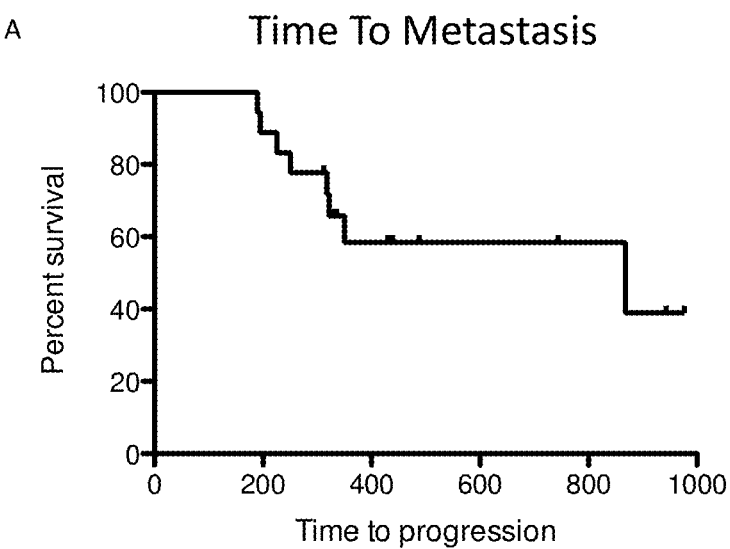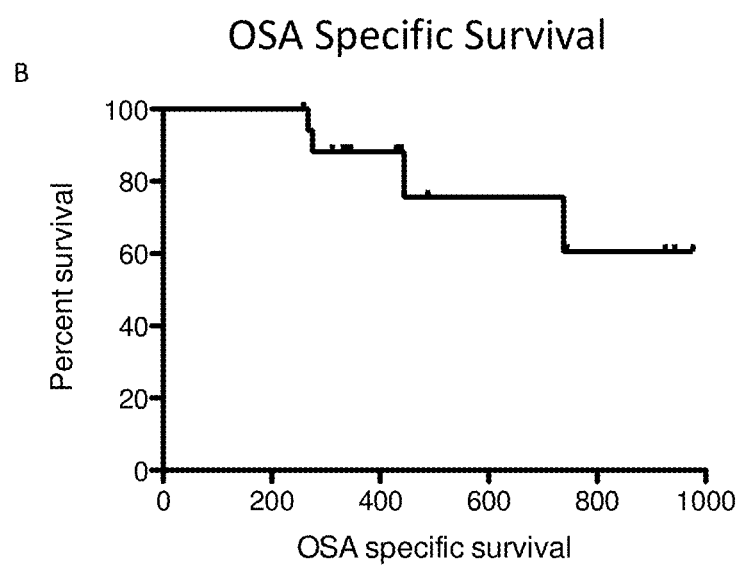
Figure 21

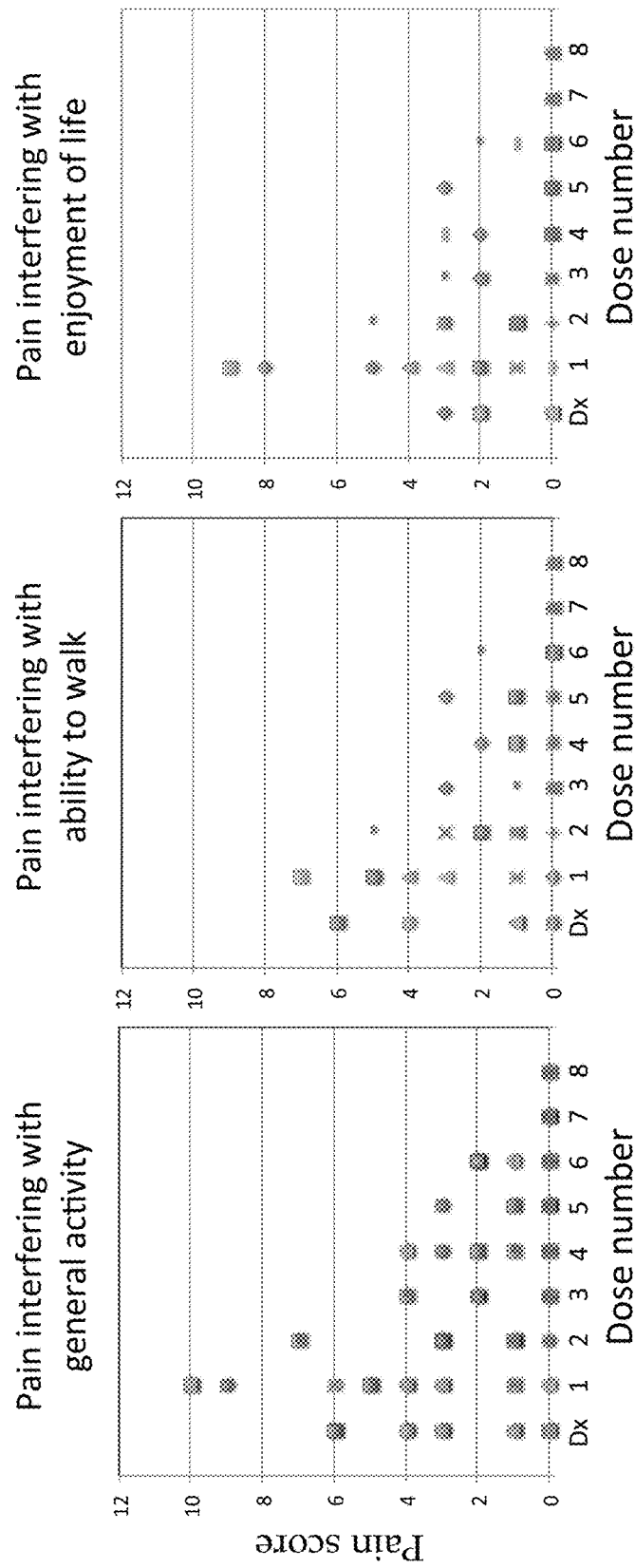

FIG. 31

SEQUENCE LISTING

```
<160> NUMBER OF SEQ ID NOS: 74

<210> SEQ ID NO 1
<211> LENGTH: 1263
<212> TYPE: DNA
<213> ORGANISM: Artificial Sequence
<220> FEATURE:
<223> OTHER INFORMATION: Her-2 chimeric protein

<400> SEQUENCE: 1
gagacccacc tggacatgct ccgccacctc taccagggct gccaggtggt gcagggaaac      60
ctggaactca cctacctgcc caccaatgcc agcctgtcct tcctgcagga tatccaggag     120
gtgcagggct acgtgctcat cgctcacaac caagtgaggc aggtcccact gcagaggctg     180
cggattgtgc gaggcaccca gctctttgag gacaactatg ccctggccgt gctagacaat     240
ggagacccgc tgaacaatac caccccgtc acaggggcct cccaggagg cctgcgggag      300 ctgcagcttc gaagcctcac agagatcttg aaaggagggg tcttgatcca gcggaacccc     360
cagctctgct accaggacac gattttgtgg aagaatatcc aggagtttgc tggctgcaag     420
```

```
aagatctttg ggagcctggc atttctgccg gagagctttg atggggaccc agcctccaac    480
actgccccgc tccagccaga gcagctccaa gtgtttgaga ctctggaaga gatcacaggt    540
tacctataca tctcagcatg gccggacagc ctgcctgacc tcagcgtctt ccagaacctg    600
caagtaatcc ggggacgaat tctgcacaat ggcgcctact cgctgaccct gcaagggctg    660
ggcatcagct ggctggggct cgctcactg agggaactgg gcagtggact ggccctcatc     720
caccataaca cccacctctg cttcgtgcac acggtgccct gggaccagct ctttcggaac    780
ccgcaccaag ctctgctcca cactgccaac cggccagagg acgagtgtgt gggcgagggc    840
ctggcctgcc accagctgtg cgcccgaggg cagcagaaga tccggaagta cacgatgcgg    900
agactgctgc aggaaacgga gctggtggag ccgctgacac tagcggagc gatgcccaac     960 caggcgcaga tgcggatcct gaaagagacg gagctgagga aggtgaaggt gcttggatct    1020
ggcgcttttg gcacagtcta agggcatc tggatccctg atggggagaa tgtgaaaatt      1080
ccagtggcca tcaaagtgtt gagggaaaac acatccccca aagccaacaa agaaatctta    1140
gacgaagcat acgtgatggc tggtgtgggc tccccatatg tctcccgcct tctgggcatc    1200
tgcctgacat ccacggtgca gctggtgaca cagcttatgc cctatggctg cctcttagac    1260
taa                                                                  1263
```

<210> SEQ ID NO 2
<211> LENGTH: 420
<212> TYPE: PRT
<213> ORGANISM: Artificial Sequence
<220> FEATURE:
<223> OTHER INFORMATION: Her-2 chimeric protein

<400> SEQUENCE: 2

```
Glu Thr His Leu Asp Met Leu Arg His Leu Tyr Gln Gly Cys Gln Val
 1               5                  10                  15

Val Gln Gly Asn Leu Glu Leu Thr Tyr Leu Pro Thr Asn Ala Ser Leu
                20                  25                  30

Ser Phe Leu Gln Asp Ile Gln Glu Val Gln Gly Tyr Val Leu Ile Ala
            35                  40                  45

His Asn Gln Val Arg Gln Val Pro Leu Gln Arg Leu Arg Ile Val Arg
        50                  55                  60

Gly Thr Gln Leu Phe Glu Asp Asn Tyr Ala Leu Ala Val Leu Asp Asn
 65                  70                  75                  80

Gly Asp Pro Leu Asn Asn Thr Thr Pro Val Thr Gly Ala Ser Pro Gly
                85                  90                  95

Gly Leu Arg Glu Leu Gln Leu Arg Ser Leu Thr Glu Ile Leu Lys Gly
            100                 105                 110

Gly Val Leu Ile Gln Arg Asn Pro Gln Leu Cys Tyr Gln Asp Thr Ile
        115                 120                 125

Leu Trp Lys Asn Ile Gln Glu Phe Ala Gly Cys Lys Lys Ile Phe Gly
    130                 135                 140

Ser Leu Ala Phe Leu Pro Glu Ser Phe Asp Gly Asp Pro Ala Ser Asn
145                 150                 155                 160

Thr Ala Pro Leu Gln Pro Glu Gln Leu Gln Val Phe Glu Thr Leu Glu
                165                 170                 175

Glu Ile Thr Gly Tyr Leu Tyr Ile Ser Ala Trp Pro Asp Ser Leu Pro
            180                 185                 190

Asp Leu Ser Val Phe Gln Asn Leu Gln Val Ile Arg Gly Arg Ile Leu
        195                 200                 205
```

His Asn Gly Ala Tyr Ser Leu Thr Leu Gln Gly Leu Gly Ile Ser Trp
    210                 215                 220

Leu Gly Leu Arg Ser Leu Arg Glu Leu Gly Ser Gly Leu Ala Leu Ile
225                 230                 235                 240

His His Asn Thr His Leu Cys Phe Val His Thr Val Pro Trp Asp Gln
                245                 250                 255

Leu Phe Arg Asn Pro His Gln Ala Leu Leu His Thr Ala Asn Arg Pro
                260                 265                 270

Glu Asp Glu Cys Val Gly Glu Gly Leu Ala Cys His Gln Leu Cys Ala
            275                 280                 285

Arg Gly Gln Gln Lys Ile Arg Lys Tyr Thr Met Arg Arg Leu Leu Gln
290                 295                 300

Glu Thr Glu Leu Val Glu Pro Leu Thr Pro Ser Gly Ala Met Pro Asn
305                 310                 315                 320

Gln Ala Gln Met Arg Ile Leu Lys Glu Thr Glu Leu Arg Lys Val Lys
                325                 330                 335

Val Leu Gly Ser Gly Ala Phe Gly Thr Val Tyr Lys Gly Ile Trp Ile
            340                 345                 350

Pro Asp Gly Glu Asn Val Lys Ile Pro Val Ala Ile Lys Val Leu Arg
        355                 360                 365

Glu Asn Thr Ser Pro Lys Ala Asn Lys Glu Ile Leu Asp Glu Ala Tyr
370                 375                 380

Val Met Ala Gly Val Gly Ser Pro Tyr Val Ser Arg Leu Leu Gly Ile
385                 390                 395                 400

Cys Leu Thr Ser Thr Val Gln Leu Val Thr Gln Leu Met Pro Tyr Gly
                405                 410                 415

Cys Leu Leu Asp
        420

<210> SEQ ID NO 3
<211> LENGTH: 1323
<212> TYPE: DNA
<213> ORGANISM: Listeria monocytogenes

<400> SEQUENCE: 3
atgaaaaaaa taatgctagt ttttattaca cttatattag ttagtctacc aattgcgcaa      60
caaactgaag caaggatgc atctgcattc aataaagaaa attcaatttc atccatggca     120
ccaccagcat ctccgcctgc aagtcctaag acgccaatcg aaagaaaca cgcggatgaa     180 atcgataagt atatacaagg attggattac aataaaaaca atgtattagt ataccacgga     240
gatgcagtga caaatgtgcc gccaagaaaa ggttacaaag atggaaatga atatattgtt     300
gtggagaaaa agaagaaatc catcaatcaa ataatgcag acattcaagt tgtgaatgca     360
atttcgagcc taacctatcc aggtgctctc gtaaaagcga attcggaatt agtagaaaat     420
caaccagatg ttctccctgt aaaacgtgat tcattaacac tcagcattga tttgccaggt     480
atgactaatc aagacaataa aatagttgta aaaaatgcca ctaaatcaaa cgttaacaac     540
gcagtaaata cattagtgga agatggaat gaaaaatatg ctcaagctta tccaaatgta     600
agtgcaaaaa ttgattatga tgacgaaatg gcttacagtg aatcacaatt aattgcgaaa     660
tttggtacag catttaaagc tgtaaataat agcttgaatg taaacttcgg cgcaatcagt     720
gaagggaaaa tgcaagaaga agtcattagt tttaaacaaa tttactataa cgtgaatgtt     780
aatgaaccta caagaccttc cagatttttc ggcaaagctg ttactaaaga gcagttgcaa     840
gcgcttggag tgaatgcaga aaatcctcct gcatatatct caagtgtggc gtatggccgt     900

```
caagtttatt tgaaattatc aactaattcc catagtacta aagtaaaagc tgcttttgat    960
gctgccgtaa gcggaaaatc tgtctcaggt gatgtagaac taacaaatat catcaaaaat   1020
tcttccttca aagccgtaat ttacggaggt tccgcaaaag atgaagttca aatcatcgac   1080
ggcaacctcg gagacttacg cgatattttg aaaaaaggcg ctactttttaa tcgagaaaca  1140 ccaggagttc ccattgctta tacaacaaac ttcctaaaag acaatgaatt agctgttatt   1200
aaaaacaact cagaatatat tgaaacaact tcaaaagctt atacagatgg aaaaattaac   1260
atcgatcact ctggaggata cgttgctcaa ttcaacattt cttgggatga agtaaattat   1320
gat                                                                1323

<210> SEQ ID NO 4
<211> LENGTH: 441
<212> TYPE: PRT
<213> ORGANISM: Listeria monocytogenes

<400> SEQUENCE: 4

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285
```

```
Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
            435                 440

<210> SEQ ID NO 5
<211> LENGTH: 14
<212> TYPE: PRT
<213> ORGANISM: Listeria monocytogenes

<400> SEQUENCE: 5

Lys Thr Glu Glu Gln Pro Ser Glu Val Asn Thr Gly Pro Arg
1               5                   10

<210> SEQ ID NO 6
<211> LENGTH: 28
<212> TYPE: PRT
<213> ORGANISM: Listeria monocytogenes

<400> SEQUENCE: 6

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 7
<211> LENGTH: 20
<212> TYPE: PRT
<213> ORGANISM: Listeria monocytogenes

<400> SEQUENCE: 7

Lys Asn Glu Glu Val Asn Ala Ser Asp Phe Pro Pro Pro Pro Thr Asp
1               5                   10                  15

Glu Glu Leu Arg
            20

<210> SEQ ID NO 8
<211> LENGTH: 33
<212> TYPE: PRT
<213> ORGANISM: Listeria monocytogenes

<400> SEQUENCE: 8

Arg Gly Gly Ile Pro Thr Ser Glu Glu Phe Ser Ser Leu Asn Ser Gly
1               5                   10                  15
```

```
Asp Phe Thr Asp Asp Glu Asn Ser Glu Thr Thr Glu Glu Ile Asp
            20                  25                  30
Arg

<210> SEQ ID NO 9
<211> LENGTH: 17
<212> TYPE: PRT
<213> ORGANISM: Streptococcus pyogenes

<400> SEQUENCE: 9

Lys Gln Asn Thr Ala Ser Thr Glu Thr Thr Thr Thr Asn Glu Gln Pro
1               5                   10                  15
Lys

<210> SEQ ID NO 10
<211> LENGTH: 17
<212> TYPE: PRT
<213> ORGANISM: Streptococcus equisimilis

<400> SEQUENCE: 10

Lys Gln Asn Thr Ala Asn Thr Glu Thr Thr Thr Thr Asn Glu Gln Pro
1               5                   10                  15
Lys

<210> SEQ ID NO 11
<211> LENGTH: 9
<212> TYPE: PRT
<213> ORGANISM: Artificial Sequence
<220> FEATURE:
<223> OTHER INFORMATION: mapped HLA-A2 epitope located on extracellular
      domain of HER2

<400> SEQUENCE: 11

His Leu Tyr Gln Gly Cys Gln Val Val
1               5

<210> SEQ ID NO 12
<211> LENGTH: 9
<212> TYPE: PRT
<213> ORGANISM: Artificial Sequence
<220> FEATURE:
<223> OTHER INFORMATION: mapped HLA-A2 epitope located on extracellular
      domain of HER3

<400> SEQUENCE: 12

Lys Ile Phe Gly Ser Leu Ala Phe Leu
1               5

<210> SEQ ID NO 13
<211> LENGTH: 9
<212> TYPE: PRT
<213> ORGANISM: Artificial Sequence
<220> FEATURE:
<223> OTHER INFORMATION: mapped HLA-A2 epitope located on intracellular
      domain of HER2

<400> SEQUENCE: 13

Arg Leu Leu Gln Glu Thr Glu Leu Val
1               5

<210> SEQ ID NO 14
<211> LENGTH: 55
<212> TYPE: DNA
<213> ORGANISM: Artificial Sequence
```

```
<220> FEATURE:
<223> OTHER INFORMATION: Alignment of EC2 (975 -1029 bp of Her-2-neu)

<400> SEQUENCE: 14
ggtcacagct gaggacggaa cacagcgttg tgagaaatgc agcaagccct gtgct      55

<210> SEQ ID NO 15
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 15
cgagtgtgct atggtctggg catggagcac cttcgagggg cgagggccat caccagtgac  60

<210> SEQ ID NO 16
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 16
aatgtccagg agtttgatgg ctgcaagaag atctttggga gcctggcatt tttgccggag  60

<210> SEQ ID NO 17
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 17
agctttgatg gggacccctc ctccggcatt gctccgctga ggcctgagca gctccaagtg  60

<210> SEQ ID NO 18
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 18
ttcgaaaccc tggaggagat cacaggttac ctgtacatct cagcatggcc agacagtctc  60

<210> SEQ ID NO 19
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 19
cgtgacctca gtgtcttcca gaaccttcga atcattcggg acggattct ccacgatggc   60

<210> SEQ ID NO 20
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 20
gcgtactcat tgacactgca aggcctgggg atccactcgc tggggctgcg ctcactgcgg  60
```

<210> SEQ ID NO 21
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 21
gagctgggca gtggattggc tctgattcac cgcaacgccc atctctgctt tgtacacact    60

<210> SEQ ID NO 22
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 22
gtaccttggg accagctctt ccggaaccca catcaggccc tgctccacag tgggaaccgg    60

<210> SEQ ID NO 23
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 23
ccggaagagg attgtggtct cgagggcttg gtctgtaact cactgtgtgc ccacgggcac    60

<210> SEQ ID NO 24
<211> LENGTH: 60
<212> TYPE: DNA
<213> ORGANISM: Artificial Sequence
<220> FEATURE:
<223> OTHER INFORMATION: Alignment of EC2 (975 -1029 bp of Her-2-neu)

<400> SEQUENCE: 24 tgctggggc cagggcccac ccagtgtgtc aactgcagtc atttccttcg gggccaggag    60

<210> SEQ ID NO 25
<211> LENGTH: 57
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 25
cgcccagcgg agcaatgccc aaccaggctc agatgcggat cctaaaagag acggagc    57

<210> SEQ ID NO 26
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 26
taaggaaggt gaaggtgctt ggatcaggag cttttggcac tgtctacaag ggcatctgga    60

<210> SEQ ID NO 27
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 27
tcccagatgg ggagaatgtg aaaatccccg tggctatcaa ggtgttgaga gaaaacacat    60

<210> SEQ ID NO 28
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 28
ctcctaaagc caacaaagaa attctagatg aagcgtatgt gatggctggt gtgggttctc    60

<210> SEQ ID NO 29
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 29
cgtatgtgtc ccgcctcctg ggcatctgcc tgacatccac agtacagctg gtgacacagc    60

<210> SEQ ID NO 30
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 30
ttatgcccta cggctgcctt ctggaccatg tccgagaaca ccgaggtcgc ctaggctccc    60

<210> SEQ ID NO 31
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 31
aggacctgct caactggtgt gttcagattg ccaaggggat gagctacctg gaggacgtgc    60

<210> SEQ ID NO 32
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 32
ggcttgtaca cagggacctg gctgcccgga atgtgctagt caagagtccc aaccacgtca    60

<210> SEQ ID NO 33
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 33
agattacaga tttcgggctg gctcggctgc tggacattga tgagacagag taccatgcag    60

<210> SEQ ID NO 34

<210> SEQ ID NO 34
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 34
atgggggcaa ggtgcccatc aaatggatgg cattggaatc tattctcaga cgccggttca    60

<210> SEQ ID NO 35
<211> LENGTH: 60
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 35
cccatcagag tgatgtgtgg agctatggag tgactgtgtg ggagctgatg acttttgggg    60

<210> SEQ ID NO 36
<211> LENGTH: 59
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 36
ccaaacctta cgatggaatc ccagcccggg agatccctga tttgctggag aagggagaa     59

<210> SEQ ID NO 37
<211> LENGTH: 58
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 37
cgcctacctc agcctccaat ctgcaccatt gatgtctaca tgattatggt caaatgtt      58

<210> SEQ ID NO 38
<211> LENGTH: 54
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 38
ggatgattga ctctgaatgt cgcccgagat tccgggagtt ggtgtcagaa tttt          54

<210> SEQ ID NO 39
<211> LENGTH: 52
<212> TYPE: DNA
<213> ORGANISM: Artificial Sequence
<220> FEATURE:
<223> OTHER INFORMATION: Alignment of IC1 (2114-3042 bp of Her-2-neu)

<400> SEQUENCE: 39
cacgtatggc gagggacccc cagcgttttg tggtcatcca gaacgaggac tt            52

<210> SEQ ID NO 40
<211> LENGTH: 60
<212> TYPE: DNA
<213> ORGANISM: Artificial Sequence
<220> FEATURE:
<223> OTHER INFORMATION: Alignment of EC1 (399-758 bp of Her-2-neu)

<400> SEQUENCE: 40

```
cccaggcaga accccagagg ggctgcggga gctgcagctt cgaagtctca cagagatcct        60
```

<210> SEQ ID NO 41
<211> LENGTH: 60
<212> TYPE: DNA
<213> ORGANISM: Artificial Sequence
<220> FEATURE:
<223> OTHER INFORMATION: Alignment of EC1 (399-758 bp of Her-2-neu)

<400> SEQUENCE: 41

```
gaagggagga gttttgatcc gtgggaaccc tcagctctgc taccaggaca tggttttgtg        60
```

<210> SEQ ID NO 42
<211> LENGTH: 60
<212> TYPE: DNA
<213> ORGANISM: Artificial Sequence
<220> FEATURE:
<223> OTHER INFORMATION: Alignment of EC1 (399-758 bp of Her-2-neu)

<400> SEQUENCE: 42

```
ccgggcctgt ccaccttgtg cccccgcctg caaagacaat cactgttggg gtgagagtcc        60
```

<210> SEQ ID NO 43
<211> LENGTH: 60
<212> TYPE: DNA
<213> ORGANISM: Artificial Sequence
<220> FEATURE:
<223> OTHER INFORMATION: Alignment of EC1 (399-758 bp of Her-2-neu)

<400> SEQUENCE: 43

```
ggaagactgt cagatcttga ctggcaccat ctgtaccagt ggttgtgccc ggtgcaaggg        60
```

<210> SEQ ID NO 44
<211> LENGTH: 60
<212> TYPE: DNA
<213> ORGANISM: Artificial Sequence
<220> FEATURE:
<223> OTHER INFORMATION: Alignment of EC1 (399-758 bp of Her-2-neu)

<400> SEQUENCE: 44

```
ccggctgccc actgactgct gccatgagca gtgtgccgca ggctgcacgg gccccaagca        60
```

<210> SEQ ID NO 45
<211> LENGTH: 3716
<212> TYPE: DNA
<213> ORGANISM: Rattus norvegicus

<400> SEQUENCE: 45

```
ccggaatcgc gggcacccaa gtgtgtaccg gcacagacat gaagttgcgg ctccctgcca        60
gtcctgagac ccacctggac atgctccgcc acctgtacca gggctgtcag gtagtgcagg       120
gcaacttgga gcttacctac gtgcctgcca atgccagcct ctcattcctg caggacatcc       180
aggaagttca gggttacatg ctcatcgctc acaaccaggt gaagcgcgtc ccactgcaaa       240
ggctgcgcat cgtgagaggg acccagctct ttgaggacaa gtatgccctg gctgtgctag       300
acaaccgaga tcctcaggac aatgtcgccg cctccacccc aggcagaacc ccagggggc       360
tgcgggagct gcagcttcga agtctcacag agatcctgaa ggaggagtt ttgatccgtg       420
ggaaccctca gctctgctac caggacatgg ttttgtggaa ggacgtcttc cgcaagaata       480
accaactggc tcctgtcgat atagacacca atcgttcccg ggcctgtcca ccttgtgccc       540
ccgcctgcaa agacaatcac tgttggggtg agagtccgga agactgtcag atcttgactg       600
```

```
gcaccatctg taccagtggt tgtgcccggt gcaagggccg gctgcccact gactgctgcc      660
atgagcagtg tgccgcaggc tgcacgggcc ccaagcattc tgactgcctg gcctgcctcc      720
acttcaatca tagtggtatc tgtgagctgc actgcccagc cctcgtcacc tacaacacag      780
acacctttga gtccatgcac aaccctgagg gtcgctacac cttttggtgcc agctgcgtga      840
ccacctgccc ctacaactac ctgtctacgg aagtgggatc ctgcactctg gtgtgtcccc      900
cgaataacca agaggtcaca gctgaggacg aaacacagcg ttgtgagaaa tgcagcaagc      960
cctgtgctcg agtgtgctat ggtctgggca tggagcacct tcgaggggcg agggccatca     1020
ccagtgacaa tgtccaggag tttgatggct gcaagaagat ctttgggagc ctggcatttt     1080
tgccggagag ctttgatggg gacccctcct ccggcattgc tccgctgagg cctgagcagc     1140
tccaagtgtt cgaaaccctg aggagatca caggttacct gtacatctca gcatggccag     1200
acagtctccg tgacctcagt gtcttccaga accttcgaat cattcgggga cggattctcc     1260
acgatggcgc gtactcattg acactgcaag gcctggggat ccactcgctg gggctgcgct     1320
cactgcggga gctgggcagt ggattggctc tgattcaccg caacgccat ctctgctttg     1380
tacacactgt accttgggac cagctcttcc ggaacccaca tcaggccctg ctccacagtg     1440
ggaaccggcc ggaagaggat tgtggtctcg agggcttggt ctgtaactca ctgtgtgccc     1500
acgggcactg ctgggggcca gggcccaccc agtgtgtcaa ctgcagtcat ttccttcggg     1560
gccaggagtg tgtggaggag tgccgagtat ggaaggggct ccccgggag tatgtgagtg     1620
acaagcgctg tctgccgtgt caccccgagt gtcagcctca aaacagctca gagacctgct     1680
ttggatcgga ggctgatcag tgtgcagcct gcgcccacta caaggactcg tcctcctgtg     1740
tggctcgctg ccccagtggt gtgaaaccgg acctctccta catgcccatc tggaagtacc     1800
cggatgagga gggcatatgc cagccgtgcc ccatcaactg cacccactcc tgtgtggatc     1860
tggatgaacg aggctgccca gcagagcaga gagccagccc ggtgacattc atcattgcaa     1920
ctgtagtggg cgtcctgctg ttcctgatct tagtggtggt cgttggaatc ctaatcaaac     1980
gaaggagaca gaagatccgg aagtatacga tgcgtaggct gctgcaggaa actgagttag     2040
tggagccgct gacgcccagc ggagcaatgc ccaaccaggc tcagatgcgg atcctaaaag     2100
agacggagct aaggaaggtg aaggtgcttg gatcaggagc ttttggcact gtctacaagg     2160
gcatctggat cccagatggg gagaatgtga aaatccccgt ggctatcaag gtgttgagag     2220
aaaacacatc tcctaaagcc aacaaagaaa ttctagatga agcgtatgtg atggctggtg     2280
tgggttctcc gtatgtgtcc cgcctcctgg gcatctgcct gacatccaca gtacagctgg     2340
tgacacagct tatgccctac ggctgccttc tggaccatgt ccgagaacac cgaggtcgcc     2400
taggctccca ggacctgctc aactggtgtg ttcagattgc caaggggatg agctacctgg     2460
aggacgtgcg gcttgtacac agggacctgg ctgcccggaa tgtgctagtc aagagtccca     2520
accacgtcaa gattacagat ttcgggctgg ctcggctgct ggacattgat gagacagagt     2580
accatgcaga tgggggcaag gtgcccatca aatggatggc attggaatct attctcagac     2640
gccggttcac ccatcagagt gatgtgtgga gctatggagt gactgtgtgg gagctgatga     2700
cttttgggc caaaccttac gatggaatcc cagcccggga gatccctgat ttgctggaga     2760
gggagaacg cctacctcag cctccaatct gcaccattga tgtctacatg attatggtca     2820
aatgttggat gattgactct gaatgtcgcc cgagattccg ggagttggtg tcagaattt     2880
cacgtatggc gagggacccc cagcgttttg tggtcatcca gaacgaggac ttgggcccat     2940
ccagccccat ggacagtacc ttctaccgtt cactgctgga agatgatgac atgggtgacc     3000
```

```
tggtagacgc tgaagagtat ctggtgcccc agcagggatt cttctcccg gaccctaccc      3060 caggcactgg gagcacagcc catagaaggc accgcagctc gtccaccagg agtggaggtg      3120
gtgagctgac actgggcctg gagccctcgg aagaagggcc ccccagatct ccactggctc      3180
cctcggaagg ggctggctcc gatgtgtttg atggtgacct ggcaatgggg gtaaccaaag      3240
ggctgcagag cctctctcca catgacctca gccctctaca gcggtacagc gaggacccca      3300
cattacctct gcccccgag actgatggct atgttgctcc cctggcctgc agccccagc       3360 ccgagtatgt gaaccaatca gaggttcagc tcagcctcc tttaacccca gagggtcctc       3420
tgcctcctgt ccggcctgct ggtgctactc tagaaagacc caagactctc tctcctggga      3480
agaatggggt tgtcaaagac gttttgcct tcggggtgc tgtggagaac cctgaatact        3540
tagtaccgag agaaggcact gcctctccgc cccaccttc tcctgccttc agcccagcct       3600
ttgacaacct ctattactgg gaccagaact catcggagca ggggcctcca ccaagtaact      3660
ttgaagggac ccccactgca gagaaccctg agtacctagg cctggatgta cctgta          3716
```

<210> SEQ ID NO 46
<211> LENGTH: 360
<212> TYPE: DNA
<213> ORGANISM: Rattus norvegicus

<400> SEQUENCE: 46

```
cccaggcaga accccagagg ggctgcggga gctgcagctt cgaagtctca cagagatcct       60
gaagggagga gttttgatcc gtgggaaccc tcagctctgc taccaggaca tggttttgtg      120
gaaggacgtc ttccgcaaga ataaccaact ggctcctgtc gatatagaca ccaatcgttc      180
ccgggcctgt ccaccttgtg cccccgcctg caaagacaat cactgttggg gtgagagtcc      240
ggaagactgt cagatcttga ctggcaccat ctgtaccagt ggttgtgccc ggtgcaaggg      300
ccggctgccc actgactgct gccatgagca gtgtgccgca ggctgcacgg gccccaagca      360
```

<210> SEQ ID NO 47
<211> LENGTH: 618
<212> TYPE: DNA
<213> ORGANISM: Rattus norvegicus

<400> SEQUENCE: 47

```
ggtcacagct gaggacggaa cacagcgttg tgagaaatgc agcaagccct gtgctcgagt       60
gtgctatggt ctgggcatgg agcaccttcg aggggcgagg ccatcacca gtgacaatgt      120 ccaggagttt gatggctgca agaagatctt tgggagcctg cattttgc cggagagctt       180 tgatggggac ccctcctccg gcattgctcc gctgaggcct gagcagctcc aagtgttcga      240
aaccctggag gagatcacag gttacctgta catctcagca tggccagaca gtctccgtga      300
cctcagtgtc ttccagaacc ttcgaatcat tcggggacgg attctccacg atggcgcgta      360
ctcattgaca ctgcaaggcc tggggatcca ctcgctgggg ctgcgctcac tgcgggagct      420
gggcagtgga ttggctctga ttcaccgcaa cgcccatctc tgctttgtac acactgtacc      480
ttgggaccag ctcttccgga acccacatca ggccctgctc cacagtggga accggccgga      540
agaggattgt ggtctcgagg gcttggtctg taactcactg tgtgcccacg gcactgctg       600 ggggccaggg cccaccca                                                     618
```

<210> SEQ ID NO 48
<211> LENGTH: 929
<212> TYPE: DNA

<213> ORGANISM: Rattus norvegicus

<400> SEQUENCE: 48

| | | | | | |
|---|---|---|---|---|---|
| cgcccagcgg | agcaatgccc | aaccaggctc | agatgcggat | cctaaaagag | acggagctaa | 60 |
| ggaaggtgaa | ggtgcttgga | tcaggagctt | ttggcactgt | ctacaagggc | atctggatcc | 120 |
| cagatgggga | gaatgtgaaa | atccccgtgg | ctatcaaggt | gttgagagaa | aacacatctc | 180 |
| ctaaagccaa | caaagaaatt | ctagatgaag | cgtatgtgat | ggctggtgtg | ggttctccgt | 240 |
| atgtgtcccg | cctcctgggc | atctgcctga | catccacagt | acagctggtg | acacagctta | 300 |
| tgccctacgg | ctgccttctg | gaccatgtcc | gagaacaccg | aggtcgccta | ggctcccagg | 360 |
| acctgctcaa | ctggtgtgtt | cagattgcca | aggggatgag | ctacctggag | gacgtgcggc | 420 |
| ttgtacacag | ggacctggct | gcccggaatg | tgctagtcaa | gagtcccaac | cacgtcaaga | 480 |
| ttacagattt | cgggctggct | cggctgctgg | acattgatga | gacagagtac | catgcagatg | 540 |
| ggggcaaggt | gcccatcaaa | tggatggcat | tggaatctat | tctcagacgc | cggttcaccc | 600 |
| atcagagtga | tgtgtggagc | tatggagtga | ctgtgtggga | gctgatgact | ttggggccaa | 660 |
| aaccttacga | tggaatccca | gcccgggaga | tccctgattt | gctggagaag | ggagaacgcc | 720 |
| tacctcagcc | tccaatctgc | accattgatg | tctacatgat | tatggtcaaa | tgttggatga | 780 |
| ttgactctga | atgtcgcccg | agattccggg | agttggtgtc | agaattttca | cgtatggcga | 840 |
| gggacccccca | gcgttttgtg | gtcatccaga | acgaggactt | gggcccatcc | agccccatgg | 900 |
| acagtacctt | ctaccgttca | ctgctggaa | | | | 929 |

<210> SEQ ID NO 49
<211> LENGTH: 3798
<212> TYPE: DNA
<213> ORGANISM: Homo sapiens

<400> SEQUENCE: 49

| | | | | | |
|---|---|---|---|---|---|
| atggagctgg | cggccttgtg | ccgctggggg | ctcctcctcg | ccctcttgcc | ccccggagcc | 60 |
| gcgagcaccc | aagtgtgcac | cggcacagac | atgaagctgc | ggctccctgc | cagtcccgag | 120 |
| acccacctgg | acatgctccg | ccacctctac | cagggctgcc | aggtggtgca | gggaaacctg | 180 |
| gaactcacct | acctgcccac | caatgccagc | ctgtccttcc | tgcaggatat | ccaggaggtg | 240 |
| cagggctacg | tgctcatcgc | tcacaaccaa | gtgaggcagg | tcccactgca | gaggctgcgg | 300 |
| attgtgcgag | gcacccagct | ctttgaggac | aactatgccc | tggccgtgct | agacaatgga | 360 |
| gacccgctga | caataccac | ccctgtcaca | ggggcctccc | caggaggcct | gcgggagctg | 420 |
| cagcttcgaa | gcctcacaga | gatcttgaaa | ggaggggtct | tgatccagcg | gaaccccag | 480 |
| ctctgctacc | aggacacgat | tttgtggaag | gacatcttcc | acaagaacaa | ccagctggct | 540 |
| ctcacactga | tagacaccaa | ccgctctcgg | gcctgccacc | cctgttctcc | gatgtgtaag | 600 |
| ggctcccgct | gctggggaga | gagttctgag | gattgtcaga | gcctgacgcg | cactgtctgt | 660 |
| gccggtggct | gtgcccgctg | caaggggcca | ctgcccactg | actgctgcca | tgagcagtgt | 720 |
| gctgccggct | gcacgggccc | caagcactct | gactgcctgg | cctgcctcca | cttcaaccac | 780 |
| agtggcatct | gtgagctgca | ctgcccagcc | ctggtcacct | acaacacaga | cacgtttgag | 840 |
| tccatgccca | atcccgaggg | ccggtataca | ttcggcgcca | gctgtgtgac | tgcctgtccc | 900 |
| tacaactacc | tttctacgga | cgtgggatcc | tgcaccctcg | tctgccccct | gcacaaccaa | 960 |
| gaggtgacag | cagaggatgg | aacacagcgg | tgtgagaagt | gcagcaagcc | ctgtgcccga | 1020 |
| gtgtgctatg | gtctgggcat | ggagcacttg | cgagaggtga | gggcagttac | cagtgccaat | 1080 |

```
atccaggagt tgctggctg caagaagatc tttgggagcc tggcatttct gccggagagc    1140
tttgatgggg acccagcctc caacactgcc ccgctccagc cagagcagct ccaagtgttt    1200
gagactctgg aagagatcac aggttaccta tacatctcag catggccgga cagcctgcct    1260
gacctcagcg tcttccagaa cctgcaagta atccggggac gaattctgca caatggcgcc    1320
tactcgctga ccctgcaagg gctgggcatc agctggctgg ggctgcgctc actgagggaa    1380
ctgggcagtg gactggccct catccaccat aacacccacc tctgcttcgt gcacacggtg    1440
ccctgggacc agctctttcg gaacccgcac caagctctgc tccacactgc caaccggcca    1500
gaggacgagt gtgtgggcga gggcctggcc tgccaccagc tgtgcgcccg agggcactgc    1560
tggggtccag ggcccaccca gtgtgtcaac tgcagccagt ccttcggggg ccaggagtgc    1620
gtggaggaat gccgagtact gcaggggctc ccagggagt atgtgaatgc caggcactgt    1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagttcc agatgaggag    1860 ggcgcatgcc agccttgccc catcaactgc acccactcct gtgtggacct ggatgacaag    1920
ggctgccccg ccgagcagag agccagccct ctgacgtcca tcgtctctgc ggtggttggc    1980
attctgctgg tcgtggtctt gggggtggtc tttgggatcc tcatcaagcg acggcagcag    2040
aagatccgga gtacacgat gcggagactg ctgcaggaaa cggagctggt ggagccgctg    2100
acacctagcg gagcgatgcc caaccaggcg cagatgcgga tcctgaaaga cggagctg    2160 aggaaggtga aggtgcttgg atctggcgct tttggcacag tctacaaggg catctggatc    2220
cctgatgggg agaatgtgaa aattccagtg gccatcaaag tgttgaggga aaacacatcc    2280
cccaaagcca acaaagaaat cttagacgaa gcatacgtga tggctggtgt gggctcccca    2340
tatgtctccc gccttctggg catctgcctg acatccacgg tgcagctggt gacacagctt    2400 atgcctatg gctgcctctt agaccatgtc cgggaaaacc gcggacgcct gggctcccag    2460
gacctgctga actggtgtat gcagattgcc aagggatga gctacctgga ggatgtgcgg    2520
ctcgtacaca gggacttggc cgctcggaac gtgctggtca agagtcccaa ccatgtcaaa    2580
attacagact cgggctggc tcggctgctg gacattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac tttgggcc    2760 aaaccttacg atgggatccc agcccgggag atccctgacc tgctggaaaa gggggagcgg    2820
ctgccccagc cccccatctg caccattgat gtctacatga tcatggtcaa atgttggatg    2880
attgactctg aatgtcggcc aagattccgg gagttggtgt ctgaattctc ccgcatggcc    2940
agggaccccc agcgctttgt ggtcatccag aatgaggact gggcccagc cagtcccttg    3000 gacagcacct tctaccgctc actgctggag gacgatgaca tggggacct ggtggatgct    3060 gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggaccccac agtacccctg    3360
ccctctgaga ctgatggcta cgttgccccc ctgacctgca gccccagcc tgaatatgtg    3420
```

```
aaccagccag atgttcggcc ccagccccct tcgccccgag agggccctct gcctgctgcc    3480
cgacctgctg gtgccactct ggaaagggcc aagactctct ccccagggaa gaatgggtc     3540 gtcaaagacg tttttgcctt tggggtgcc  gtggagaacc ccgagtactt gacaccccag    3600
ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtgaac cagaaggcca    3780
agtccgcaga agccctga                                                 3798

<210> SEQ ID NO 50
<211> LENGTH: 393
<212> TYPE: DNA
<213> ORGANISM: Homo sapiens

<400> SEQUENCE: 50
gagacccacc tggacatgct ccgccacctc taccagggct gccaggtggt gcagggaaac     60
ctggaactca cctacctgcc caccaatgcc agcctgtcct tcctgcagga tatccaggag    120
gtgcagggct acgtgctcat cgctcacaac caagtgaggc aggtcccact gcagaggctg    180
cggattgtgc gaggcaccca gctctttgag gacaactatg ccctggccgt gctagacaat    240
ggagacccgc tgaacaatac caccccctgtc acagggcct  ccccaggagg cctgcgggag    300
ctgcagcttc gaagcctcac agagatcttg aaaggagggg tcttgatcca gcggaaccccc   360 cagctctgct accaggacac gattttgtgg aag                                 393

<210> SEQ ID NO 51
<211> LENGTH: 477
<212> TYPE: DNA
<213> ORGANISM: Homo sapiens

<400> SEQUENCE: 51
aatatccagg agtttgctgg ctgcaagaag atctttggga gcctggcatt tctgccggag     60
agctttgatg gggacccagc ctccaacact gccccgctcc agccagagca gctccaagtg    120
tttgagactc tggaagagat cacaggttac ctatacatct cagcatggcc ggacagcctg    180
cctgacctca gcgtcttcca gaacctgcaa gtaatccggg gacgaattct gcacaatggc    240
gcctactcgc tgaccctgca agggctgggc atcagctggc tggggctgcg ctcactgagg    300
gaactgggca gtggactggc cctcatccac cataacaccc acctctgctt cgtgcacacg    360
gtgccctggg accagctctt tcggaacccg caccaagctc tgctccacac tgccaaccgg    420
ccagaggacg agtgtgtggg cgagggcctg gcctgccacc agctgtgcgc ccgaggg       477

<210> SEQ ID NO 52
<211> LENGTH: 391
<212> TYPE: DNA
<213> ORGANISM: Homo sapiens

<400> SEQUENCE: 52
cagcagaaga tccggaagta cacgatgcgg agactgctgc aggaaacgga gctggtggag     60
ccgctgacac ctagcggagc gatgcccaac caggcgcaga tgcggatcct gaaagagacg    120
gagctgagga aggtgaaggt gcttggatct ggcgcttttg gcacagtcta caagggcatc    180
tggatccctg atggggagaa tgtgaaaatt ccagtggcca tcaaagtgtt gagggaaaac    240 acatcccccaa agccaacaa agaaatctta gacgaagcat acgtgatggc tggtgtgggc    300
tccccatatg tctcccgcct tctgggcatc tgcctgacat ccacggtgca gctggtgaca    360
```
cagcttatgc cctatggctg cctcttagac t                                      391

<210> SEQ ID NO 53
<211> LENGTH: 7075
<212> TYPE: DNA
<213> ORGANISM: Artificial Sequence
<220> FEATURE:
<223> OTHER INFORMATION: pAdv164 sequence (7075 base pairs)

<400> SEQUENCE: 53
cggagtgtat actggcttac tatgttggca ctgatgaggg tgtcagtgaa gtgcttcatg    60
tggcaggaga aaaaggctg caccggtgcg tcagcagaat atgtgataca ggatatattc   120
cgcttcctcg ctcactgact cgctacgctc ggtcgttcga ctgcggcgag cggaaatggc   180
ttacgaacgg ggcggagatt tcctggaaga tgccaggaag atacttaaca gggaagtgag   240
agggccgcgg caaagccgtt tttccatagg ctccgccccc ctgacaagca tcacgaaatc   300
tgacgctcaa atcagtggtg cgaaacccg acaggactat aaagatacca ggcgtttccc   360
cctggcggct ccctcgtgcg ctctcctgtt cctgcctttc ggtttaccgg tgtcattccg   420
ctgttatggc cgcgtttgtc tcattccacg cctgacactc agttccgggt aggcagttcg   480
ctccaagctg gactgtatgc acgaaccccc cgttcagtcc gaccgctgcg ccttatccgg   540
taactatcgt cttgagtcca acccggaaag acatgcaaaa gcaccactgg cagcagccac   600
tggtaattga tttagaggag ttagtcttga agtcatgcgc cggttaaggc taaactgaaa   660
ggacaagttt tggtgactgc gctcctccaa gccagttacc tcggttcaaa gagttggtag   720
ctcagagaac cttcgaaaaa ccgccctgca aggcggtttt ttcgttttca gagcaagaga   780
ttacgcgcag accaaaacga tctcaagaag atcatcttat taatcagata aaatatttct   840
agccctcctt tgattagtat attcctatct taaagttact tttatgtgga ggcattaaca   900
tttgttaatg acgtcaaaag gatagcaaga ctagaataaa gctataaagc aagcatataa   960
tattgcgttt catctttaga agcgaatttc gccaatatta taattatcaa aagagagggg  1020
tggcaaacgg tatttggcat tattaggtta aaaaatgtag aaggagagtg aaacccatga  1080
aaaaataat gctagttttt attacactta tattagttag tctaccaatt gcgcaacaaa  1140
ctgaagcaaa ggatgcatct gcattcaata agaaaattc aatttcatcc atggcaccac  1200
cagcatctcc gcctgcaagt cctaagacgc caatcgaaaa gaaacacgcg gatgaaatcg  1260
ataagtatat acaaggattg gattacaata aaaacaatgt attagtatac cacggagatg  1320
cagtgacaaa tgtgccgcca agaaaaggtt acaaagatgg aaatgaatat attgttgtgg  1380
agaaaaagaa gaaatccatc aatcaaaata tgcagacat tcaagttgtg aatgcaattt  1440
cgagcctaac ctatccaggt gctctcgtaa agcgaattc ggaattagta gaaaatcaac  1500
cagatgttct ccctgtaaaa cgtgattcat taacactcag cattgatttg ccaggtatga  1560
ctaatcaaga cataaaata gttgtaaaaa atgccactaa atcaaacgtt aacaacgcag  1620
taaatacatt agtggaaaga tggaatgaaa atatgctca agcttatcca aatgtaagtg  1680
caaaaattga ttatgatgac gaaatggctt acagtgaatc acaattaatt gcgaaatttg  1740
gtacagcatt taaagctgta aataatagct tgaatgtaaa cttcggcgca atcagtgaag  1800
ggaaaatgca agaagaagtc attagtttta aacaaattta ctataacgtg aatgttaatg  1860
aacctacaag accttccaga ttttcggca agctgttac taaagagcag ttgcaagcgc  1920
ttggagtgaa tgcagaaaat cctcctgcat atatctcaag tgtggcgtat ggccgtcaag  1980

```
tttatttgaa attatcaact aattcccata gtactaaagt aaaagctgct tttgatgctg    2040
ccgtaagcgg aaaatctgtc tcaggtgatg tagaactaac aaatatcatc aaaaattctt    2100
ccttcaaagc cgtaatttac ggaggttccg caaaagatga agttcaaatc atcgacggca    2160
acctcggaga cttacgcgat attttgaaaa aaggcgctac ttttaatcga gaaacaccag    2220
gagttcccat tgcttataca acaaacttcc taaaagacaa tgaattagct gttattaaaa    2280
acaactcaga atatattgaa acaacttcaa aagcttatac agatggaaaa attaacatcg    2340
atcactctgg aggatacgtt gctcaattca acatttcttg ggatgaagta aattatgatc    2400
tcgagaccca cctggacatg ctccgccacc tctaccaggg ctgccaggtg gtgcagggaa    2460
acctggaact cacctacctg cccaccaatg ccagcctgtc cttcctgcag gatatccagg    2520
aggtgcaggg ctacgtgctc atcgctcaca accaagtgag gcaggtccca ctgcagaggc    2580
tgcggattgt gcgaggcacc cagctctttg aggacaacta tgccctggcc gtgctagaca    2640
atggagaccc gctgaacaat accacccctg tcacagggc ctccccagga ggcctgcggg    2700
agctgcagct tcgaagcctc acagagatct tgaaggagg ggtcttgatc cagcggaacc    2760
cccagctctg ctaccaggac acgatttttgt ggaagaatat ccaggagttt gctggctgca    2820
agaagatctt tgggagcctg gcatttctgc cggagagctt tgatgggggac ccagcctcca    2880 acactgcccc gctccagcca gagcagctcc aagtgtttga gactctggaa gagatcacag    2940
gttacctata catctcagca tggccggaca gcctgcctga cctcagcgtc ttccagaacc    3000
tgcaagtaat ccggggacga attctgcaca tggcgcctga ctcgctgacc ctgcaagggc    3060
tgggcatcag ctggctgggg ctgcgctcac tgagggaact gggcagtgga ctggccctca    3120
tccaccataa cacccacctc tgcttcgtgc acacggtgcc ctgggaccag ctctttcgga    3180
acccgcacca agctctgctc cacactgcca accggccaga ggacgagtgt gtgggcgagg    3240
gcctggcctg ccaccagctg tgcgcccgag ggcagcagaa gatccggaag tacacgatgc    3300
ggagactgct gcaggaaacg gagctggtgg agccgctgac acctagcgga gcgatgccca    3360
accaggcgca gatgcggatc ctgaaagaga cggagctgag gaaggtgaag gtgcttggat    3420
ctggcgcttt tggcacagtc tacaagggca tctggatccc tgatggggag aatgtgaaaa    3480
ttccagtggc catcaaagtg ttgagggaaa acacatcccc caaagccaac aaagaaatct    3540
tagacgaagc atacgtgatg gctggtgtgg gctcccccata tgtctcccgc cttctgggca    3600
tctgcctgac atccacggtg cagctggtga cacagcttat gcccctatggc tgcctcttag    3660
```

```
acatttacgc attggacacc aaacgtttat cgttatggta cgtatgcaga cgaaaaccgt   4440
tcatacacta aaggacattc tgaaaacaat ttaagacaaa tcaatacctt ctttattgat   4500
tttgatattc acacggaaaa agaaactatt tcagcaagcg atattttaac aacagctatt   4560
gatttaggtt ttatgcctac gttaattatc aaatctgata aaggttatca agcatatttt   4620
gttttagaaa cgccagtcta tgtgacttca aaatcagaat ttaaatctgt caaagcagcc   4680
aaaataatct cgcaaaatat ccgagaatat tttggaaagt ctttgccagt tgatctaacg   4740
tgcaatcatt ttgggattgc tcgtatacca agaacggaca atgtagaatt ttttgatccc   4800
aattaccgtt attctttcaa agaatggcaa gattggtctt tcaaacaaac agataataag   4860
ggctttactc gttcaagtct aacggtttta agcggtacag aaggcaaaaa acaagtagat   4920
gaaccctggt ttaatctctt attgcacgaa acgaaatttt caggagaaaa gggtttagta   4980
gggcgcaata gcgttatgtt taccctctct ttagcctact ttagttcagg ctattcaatc   5040
gaaacgtgcg aatataatat gtttgagttt aataatcgat tagatcaacc cttagaagaa   5100
aaagaagtaa tcaaaattgt tagaagtgcc tattcagaaa actatcaagg ggctaatagg   5160
gaatacatta ccattctttg caaagcttgg gtatcaagtg atttaaccag taaagattta   5220
tttgtccgtc aagggtggtt taaattcaag aaaaaaagaa gcgaacgtca acgtgttcat   5280
ttgtcagaat ggaaagaaga tttaatggct tatattagcg aaaaaagcga tgtatacaag   5340
ccttatttag cgacgaccaa aaaagagatt agagaagtgc taggcattcc tgaacggaca   5400
ttagataaat tgctgaaggt actgaaggcg aatcaggaaa ttttctttaa gattaaacca   5460
ggaagaaatg gtggcattca acttgctagt gttaaatcat tgttgctatc gatcattaaa   5520
ttaaaaaaag aagaacgaga aagctatata aaggcgctga cagcttcgtt taatttagaa   5580 cgtacatttta ttcaagaaac tctaaacaaa ttggcagaac gccccaaaac ggacccacaa   5640
ctcgatttgt ttagctacga tacaggctga aaataaaacc cgcactatgc cattacattt   5700
atatctatga tacgtgtttg ttttttcttg ctggctagct taattgctta tatttacctg   5760
caataaagga tttcttactt ccattatact cccattttcc aaaaacatac ggggaacacg   5820
ggaacttatt gtacaggcca cctcatagtt aatggtttcg agccttcctg caatctcatc   5880
catgaaaata tattcatccc cctgccggcc tattaatgtg acttttgtgc ccggcggata   5940
ttcctgatcc agctccacca taaattggtc catgcaaatt cggccggcaa ttttcaggcg   6000
ttttcccttc acaaggatgt cggtcccttt caattttcgg agccagccgt ccgcatagcc   6060
tacaggcacc gtcccgatcc atgtgtcttt ttccgctgtg tactcggctc cgtagctgac   6120
gctctcgcct tttctgatca gtttgacatg tgacagtgtc gaatgcaggg taaatgccgg   6180
acgcagctga aacggtatct cgtccgacat gtcagcagac gggcgaaggc catacatgcc   6240
gatgccgaat ctgactgcat taaaaaagcc ttttttcagc cggagtccag cggcgctgtt   6300
cgcgcagtgg accattagat tctttaacgg cagcggagca atcagctctt taagcgctc    6360 aaactgcatt aagaaatagc ctctttcttt ttcatccgct gtcgcaaaat gggtaaatac   6420
ccctttgcac tttaaacgag ggttgcggtc aagaattgcc atcacgttct gaacttcttc   6480
ctctgttttt acaccaagtc tgttcatccc cgtatcgacc ttcagatgaa aatgaagaga   6540 acctttttc gtgtggcggg ctgcctcctg aagccattca acagaataac ctgttaaggt    6600
cacgtcatac tcagcagcga ttgccacata tccgggggga accgcgccaa gcaccaatat   6660
aggcgccttc aatccctttt tgcgcagtga aatcgcttca tccaaaatgg ccacggccaa   6720
```

| | |
|---|---|
| gcatgaagca cctgcgtcaa gagcagcctt tgctgtttct gcatcaccat gcccgtaggc | 6780 |
| gtttgctttc acaactgcca tcaagtggac atgttcaccg atatgttttt tcatattgct | 6840 |
| gacatttcc tttatcgcgg acaagtcaat ttccgcccac gtatctctgt aaaaaggttt | 6900 |
| tgtgctcatg gaaaactcct ctcttttttc agaaaatccc agtacgtaat taagtatttg | 6960 |
| agaattaatt ttatattgat taatactaag tttacccagt tttcacctaa aaaacaaatg | 7020 |
| atgagataat agctccaaag gctaagagg actataccaa ctatttgtta attaa | 7075 |

<210> SEQ ID NO 54
<211> LENGTH: 921
<212> TYPE: DNA
<213> ORGANISM: Homo sapiens

<400> SEQUENCE: 54

| | |
|---|---|
| gccgcgagca cccaagtgtg caccggcaca gacatgaagc tgcggctccc tgccagtccc | 60 |
| gagacccacc tggacatgct ccgccacctc taccagggct gccaggtggt gcagggaaac | 120 |
| ctggaactca cctacctgcc caccaatgcc agcctgtcct tcctgcagga tatccaggag | 180 |
| gtgcagggct acgtgctcat cgctcacaac caagtgaggc aggtcccact gcagaggctg | 240 |
| cggattgtgc gaggcaccca gctctttgag gacaactatg ccctgccgt gctagacaat | 300 |
| ggagacccgc tgaacaatac caccctgtc acaggggcct ccccaggagg cctgcgggag | 360 |
| ctgcagcttc gaagcctcac agagatcttg aaggagggg tcttgatcca gcggaacccc | 420 |
| cagctctgct accaggacac gattttgtgg aaggacatct ccacaagaa caaccagctg | 480 |
| gctctcacac tgatagacac caaccgctct cgggcctgcc accctgttc tccgatgtgt | 540 |
| aagggctccc gctgctgggg agagagttct gaggattgtc agagcctgac gcgcactgtc | 600 |
| tgtgccggtg gctgtgcccg ctgcaagggg ccactgccca ctgactgctg ccatgagcag | 660 |
| tgtgctgccg gctgcacggg ccccaagcac tctgactgcc tggcctgcct ccacttcaac | 720 |
| cacagtggca tctgtgagct gcactgccca gccctggtca cctacaacac agacacgttt | 780 |
| gagtccatgc caatcccga gggccggtat acattcggcg ccagctgtgt gactgcctgt | 840 |
| ccctacaact acctttctac ggacgtggga tcctgcaccc tcgtctgccc cctgcacaac | 900 |
| caagaggtga cagcagagga t | 921 |

<210> SEQ ID NO 55
<211> LENGTH: 597
<212> TYPE: DNA
<213> ORGANISM: Homo sapiens

<400> SEQUENCE: 55

| | |
|---|---|
| tacctttcta cggacgtggg atcctgcacc ctcgtctgcc cctgcacaa ccaagaggtg | 60 |
| acagcagagg atggaacaca gcggtgtgag aagtgcagca gccctgtgc ccgagtgtgc | 120 |
| tatggtctgg gcatggagca cttgcgagag gtgagggcag ttaccagtgc caatatccag | 180 |
| gagtttgctg gctgcaagaa gatctttggg agcctggcat ttctgccgga gagctttgat | 240 |
| ggggacccag cctccaacac tgccccgctc agccagagc agctccaagt gtttgagact | 300 |
| ctggaagaga tcacaggtta cctatacatc tcagcatggc cggacagcct gcctgacctc | 360 |
| agcgtcttcc agaacctgca gtaatccgg ggacgaattc tgcacaatgg cgcctactcg | 420 |
| ctgaccctgc aagggctggg catcagctgg ctggggctgc gctcactgag ggaactgggc | 480 |
| agtggactgg ccctcatcca ccataacacc cacctctgct tcgtgcacac ggtgccctgg | 540 |
| gaccagctct ttcggaaccc gcaccaagct ctgctccaca ctgccaaccg gccagag | 597 |

<210> SEQ ID NO 56
<211> LENGTH: 1209
<212> TYPE: DNA
<213> ORGANISM: Homo sapiens

<400> SEQUENCE: 56
cagcagaaga tccggaagta cacgatgcgg agactgctgc aggaaacgga gctggtggag      60
ccgctgacac ctagcggagc gatgcccaac caggcgcaga tgcggatcct gaaagagacg     120
gagctgagga aggtgaaggt gcttggatct ggcgcttttg cacagtctac aagggcatc     180 tggatccctg atggggagaa tgtgaaaatt ccagtggcca tcaaagtgtt gagggaaaac     240
acatccccca aagccaacaa agaaatctta gacgaagcat acgtgatggc tggtgtgggc     300
tccccatatg tctcccgcct tctgggcatc tgcctgacat ccacggtgca gctggtgaca     360
cagcttatgc cctatggctg cctcttagac catgtccggg aaaaccgcgg acgcctgggc     420
tcccaggacc tgctgaactg gtgtatgcag attgccaagg ggatgagcta cctggaggat     480
gtgcggctcg tacacaggga cttggccgct cggaacgtgc tggtcaagag tcccaaccat     540
gtcaaaatta cagacttcgg gctggctcgg ctgctggaca ttgacgagac agagtaccat     600
gcagatgggg gcaaggtgcc catcaagtgg atggcgctgg agtccattct ccgccggcgg     660
ttcacccacc agagtgatgt gtggagttat ggtgtgactg tgtgggagct gatgactttt     720
ggggccaaac cttacgatgg gatcccagcc cgggagatcc ctgacctgct ggaaaagggg     780
gagcggctgc cccagccccc catctgcacc attgatgtct acatgatcat ggtcaaatgt     840
tggatgattg actctgaatg tcggccaaga ttccgggagt tggtgtctga attctcccgc     900
atggccaggg accccagcg ctttgtggtc atccagaatg aggacttggg cccagccagt     960
cccttggaca gcaccttcta ccgctcactg ctggaggacg atgacatggg ggacctggtg    1020
gatgctgagg agtatctggt accccagcag ggcttcttct gtccagaccc tgccccgggc    1080
gctgggggca tggtccacca caggcaccgc agctcatcta ccaggagtgg cggtgggac    1140 ctgacactag gctggagcc ctctgaagag gaggccccca ggtctccact ggcaccctcc    1200
gaaggggct                                                          1209

<210> SEQ ID NO 57
<211> LENGTH: 28
<212> TYPE: DNA
<213> ORGANISM: Artificial Sequence
<220> FEATURE:
<223> OTHER INFORMATION: Her-2-Chimera (F)

<400> SEQUENCE: 57
tgatctcgag acccacctgg acatgctc                                         28

<210> SEQ ID NO 58
<211> LENGTH: 49
<212> TYPE: DNA
<213> ORGANISM: Artificial Sequence
<220> FEATURE:
<223> OTHER INFORMATION: HerEC1-EC2F (Junction)

<400> SEQUENCE: 58
ctaccaggac acgattttgt ggaagaatat ccaggagttt gctggctgc                  49

<210> SEQ ID NO 59
<211> LENGTH: 49
<212> TYPE: DNA

```
<213> ORGANISM: Artificial Sequence
<220> FEATURE:
<223> OTHER INFORMATION: HerEC1-EC2R (Junction)

<400> SEQUENCE: 59
gcagccagca aactcctgga tattcttcca caaaatcgtg tcctggtag          49

<210> SEQ ID NO 60
<211> LENGTH: 50
<212> TYPE: DNA
<213> ORGANISM: Artificial Sequence
<220> FEATURE:
<223> OTHER INFORMATION: HerEC2-ICIF (Junction)

<400> SEQUENCE: 60
ctgccaccag ctgtgcgccc gagggcagca gaagatccgg aagtacacga         50

<210> SEQ ID NO 61
<211> LENGTH: 50
<212> TYPE: DNA
<213> ORGANISM: Artificial Sequence
<220> FEATURE:
<223> OTHER INFORMATION: HerEC2-ICIR (Junction)

<400> SEQUENCE: 61
tcgtgtactt ccggatcttc tgctgccctc gggcgcacag ctggtggcag         50

<210> SEQ ID NO 62
<211> LENGTH: 39
<212> TYPE: DNA
<213> ORGANISM: Artificial Sequence
<220> FEATURE:
<223> OTHER INFORMATION: Her-2-Chimera (R)

<400> SEQUENCE: 62
gtggcccggg tctagattag tctaagaggc agccatagg                    39

<210> SEQ ID NO 63
<211> LENGTH: 28
<212> TYPE: DNA
<213> ORGANISM: Artificial Sequence
<220> FEATURE:
<223> OTHER INFORMATION: Her-2-EC1(F)

<400> SEQUENCE: 63
ccgcctcgag gccgcgagca cccaagtg                                28

<210> SEQ ID NO 64
<211> LENGTH: 31
<212> TYPE: DNA
<213> ORGANISM: Artificial Sequence
<220> FEATURE:
<223> OTHER INFORMATION: Her-2-EC1(R)

<400> SEQUENCE: 64
cgcgactagt ttaatcctct gctgtcacct c                            31

<210> SEQ ID NO 65
<211> LENGTH: 28
<212> TYPE: DNA
<213> ORGANISM: Artificial Sequence
<220> FEATURE:
<223> OTHER INFORMATION: Her-2-EC2(F)

<400> SEQUENCE: 65
ccgcctcgag tacctttcta cggacgtg                                28
```

-continued

<210> SEQ ID NO 66
<211> LENGTH: 30
<212> TYPE: DNA
<213> ORGANISM: Artificial Sequence
<220> FEATURE:
<223> OTHER INFORMATION: Her- 2- EC2(R)

<400> SEQUENCE: 66
cgcgactagt ttactctggc cggttggcag                                    30

<210> SEQ ID NO 67
<211> LENGTH: 31
<212> TYPE: DNA
<213> ORGANISM: Artificial Sequence
<220> FEATURE:
<223> OTHER INFORMATION: Her-2-Her-2-IC1(F)

<400> SEQUENCE: 67
ccgcctcgag cagcagaaga tccggaagta c                                  31

<210> SEQ ID NO 68
<211> LENGTH: 30
<212> TYPE: DNA
<213> ORGANISM: Artificial Sequence
<220> FEATURE:
<223> OTHER INFORMATION: Her-2-IC1(R)

<400> SEQUENCE: 68
cgcgactagt ttaagcccct tcggagggtg                                    30

<210> SEQ ID NO 69
<211> LENGTH: 131
<212> TYPE: PRT
<213> ORGANISM: Homo sapiens

<400> SEQUENCE: 69

Ser Leu Ser Phe Leu Gln Asp Ile Gln Glu Val Gln Gly Tyr Val Leu
1               5                   10                  15

Ile Ala His Asn Gln Val Arg Gln Val Pro Leu Gln Arg Leu Arg Ile
            20                  25                  30

Val Arg Gly Thr Gln Leu Phe Glu Asp Asn Tyr Ala Leu Ala Val Leu
        35                  40                  45

Asp Asn Gly Asp Pro Leu Asn Asn Thr Thr Pro Val Thr Gly Ala Ser
    50                  55                  60

Pro Gly Gly Leu Arg Glu Leu Gln Leu Arg Ser Leu Thr Glu Ile Leu
65                  70                  75                  80

Lys Gly Gly Val Leu Ile Gln Arg Asn Pro Gln Leu Cys Tyr Gln Asp
                85                  90                  95

Thr Ile Leu Trp Lys Asp Ile Phe His Lys Asn Asn Gln Leu Ala Leu
            100                 105                 110

Thr Leu Ile Asp Thr Asn Arg Ser Arg Ala Cys His Pro Cys Ser Pro
        115                 120                 125

Met Cys Lys
    130

<210> SEQ ID NO 70
<211> LENGTH: 131
<212> TYPE: PRT
<213> ORGANISM: Canis familiaris

<400> SEQUENCE: 70

```
Ser Leu Ser Phe Leu Gln Asp Ile Gln Glu Val Gln Gly Tyr Val Leu
1               5                   10                  15

Ile Ala His Ser Gln Val Arg Gln Ile Pro Leu Gln Arg Leu Arg Ile
            20                  25                  30

Val Arg Gly Thr Gln Leu Phe Glu Asp Asn Tyr Ala Leu Ala Val Leu
            35                  40                  45

Asp Asn Gly Asp Pro Leu Glu Gly Gly Ile Pro Ala Pro Gly Ala Ala
        50                  55                  60

Pro Gly Gly Leu Arg Glu Leu Gln Leu Arg Ser Leu Thr Glu Ile Leu
65              70                  75                  80

Lys Gly Gly Val Leu Ile Gln Arg Ser Pro Gln Leu Cys His Gln Asp
                85                  90                  95

Thr Ile Leu Trp Lys Asp Val Phe His Lys Asn Asn Gln Leu Ala Leu
            100                 105                 110

Thr Leu Ile Asp Thr Asn Arg Ser Arg Ala Cys Pro Pro Cys Ser Pro
            115                 120                 125

Ala Cys Lys
    130
```

<210> SEQ ID NO 71
<211> LENGTH: 75
<212> TYPE: PRT
<213> ORGANISM: Homo sapiens

<400> SEQUENCE: 71

```
Thr Ala Pro Leu Gln Pro Glu Gln Leu Gln Val Phe Glu Thr Leu Glu
1               5                   10                  15

Glu Ile Thr Gly Tyr Leu Tyr Ile Ser Ala Trp Pro Asp Ser Leu Pro
            20                  25                  30

Asp Leu Ser Val Phe Gln Asn Leu Gln Val Ile Arg Gly Arg Ile Leu
            35                  40                  45

His Asn Gly Ala Tyr Ser Leu Thr Leu Gln Gly Leu Gly Ile Ser Trp
        50                  55                  60

Leu Gly Leu Arg Ser Leu Arg Glu Leu Gly Ser
65                  70                  75
```

<210> SEQ ID NO 72
<211> LENGTH: 75
<212> TYPE: PRT
<213> ORGANISM: Canis familiaris

<400> SEQUENCE: 72

```
Thr Ala Pro Leu Gln Pro Glu Gln Leu Arg Val Phe Glu Ala Leu Glu
1               5                   10                  15

Glu Ile Thr Gly Tyr Leu Tyr Ile Ser Ala Trp Pro Asp Ser Leu Pro
            20                  25                  30

Asn Leu Ser Val Phe Gln Asn Leu Arg Val Ile Arg Gly Arg Val Leu
            35                  40                  45

His Asp Gly Ala Tyr Ser Leu Thr Leu Gln Gly Leu Gly Ile Ser Trp
        50                  55                  60

Leu Gly Leu Arg Ser Leu Arg Glu Leu Gly Ser
65                  70                  75
```

<210> SEQ ID NO 73
<211> LENGTH: 131
<212> TYPE: PRT
<213> ORGANISM: Homo sapiens

```
<400> SEQUENCE: 73

Asn Gln Ala Gln Met Arg Ile Leu Lys Glu Thr Glu Leu Arg Lys Val
1               5                   10                  15

Lys Val Leu Gly Ser Gly Ala Phe Gly Thr Val Tyr Lys Gly Ile Trp
            20                  25                  30

Ile Pro Asp Gly Glu Asn Val Lys Ile Pro Val Ala Ile Lys Val Leu
        35                  40                  45

Arg Glu Asn Thr Ser Pro Lys Ala Asn Lys Glu Ile Leu Asp Glu Ala
50                  55                  60

Tyr Val Met Ala Gly Val Gly Ser Pro Tyr Val Ser Arg Leu Leu Gly
65                  70                  75                  80

Ile Cys Leu Thr Ser Thr Val Gln Leu Val Thr Gln Leu Met Pro Tyr
                85                  90                  95

Gly Cys Leu Leu Asp His Val Arg Glu Asn Arg Gly Arg Leu Gly Ser
            100                 105                 110

Gln Asp Leu Leu Asn Trp Cys Met Gln Ile Ala Lys Gly Met Ser Tyr
        115                 120                 125

Leu Glu Asp
    130

<210> SEQ ID NO 74
<211> LENGTH: 131
<212> TYPE: PRT
<213> ORGANISM: Canis familiaris

<400> SEQUENCE: 74

Asn Gln Ala Gln Met Arg Ile Leu Lys Glu Thr Glu Leu Arg Lys Val
1               5                   10                  15

Lys Val Leu Gly Ser Gly Ala Phe Gly Thr Val Tyr Lys Gly Ile Trp
            20                  25                  30

Ile Pro Asp Gly Glu Asn Val Lys Ile Pro Val Ala Ile Lys Val Leu
        35                  40                  45

Arg Glu Asn Thr Ser Pro Lys Ala Asn Lys Glu Ile Leu Asp Glu Ala
50                  55                  60

Tyr Val Met Ala Gly Val Gly Ser Pro Tyr Val Ser Arg Leu Leu Gly
65                  70                  75                  80

Ile Cys Leu Thr Ser Thr Val Gln Leu Val Thr Gln Leu Met Pro Tyr
                85                  90                  95

Gly Cys Leu Leu Asp His Val Arg Glu Asn Arg Gly Arg Leu Gly Ser
            100                 105                 110

Gln Asp Leu Leu Asn Trp Cys Met Gln Ile Ala Lys Gly Met Ser Tyr
        115                 120                 125

Leu Glu Asp
    130
```

COMBINATION IMMUNO THERAPY AND RADIOTHERAPY FOR THE TREATMENT OF HER-2-POSITIVE CANCERS

CROSS REFERENCE TO RELATED APPLICATIONS

This application is a Continuation-In-Part of U.S. patent application Ser. No. 14/268,436, filed on May 2, 2014, which is a Continuation-In-Part of U.S. patent application Ser. No. 14/189,008, filed on Feb. 25, 2014, which is a Continuation-In-Part of U.S. patent application Ser. No. 13/210,696, filed on Aug. 16, 2011, which is a Continuation-In-Part of U.S. patent application Ser. No. 12/945,386, filed Nov. 12, 2010, which claims the benefit of U.S. Provisional Application Ser. No. 61/260,277, filed Nov. 12, 2009. This application is also a Continuation-In-Part of International Application Serial Number PCT/US15/17559, filed on Feb. 25, 2015, which claims the benefit of U.S. Provisional Application Ser. No. 62/076,411, filed Nov. 6, 2014. These applications are hereby incorporated in their entirety by reference herein.

FIELD OF INVENTION

This invention provides methods for inducing an immune response against a Her-2/neu antigen-expressing tumor and for treating the same and vaccinating against the same in human and canine subjects using a combination of radiation therapy and a recombinant attenuated *Listeria* strain vaccine.

BACKGROUND OF THE INVENTION

Her-2/neu (referred to henceforth as "Her-2") is a 185 kDa glycoprotein that is a member of the epidermal growth factor receptor (EGFR) family of tyrosine kinases, and is overexpressed in 25 to 40% of all breast cancers and in many cancers of the bone (osteosarcoma—OSA), ovaries, lung, pancreas, brain, and gastrointestinal tract. Patients with cancers that overexpress Her-2 exhibit tolerance even with detectable humoral, CD8$^+$ T cell, and CD4$^+$ T cell responses directed against Her-2.

Large breed dogs spontaneously develop OSA that recapitulates many aspects of human pediatric OSA including histologic heterogeneity, aggressive local disease and early metastases. At diagnosis, 95% of dogs have micrometastatic disease and despite amputation and chemotherapy, the median survival time is 10 months with most dogs euthanized due to progressive metastatic disease. The overall survival of human patients with metastatic osteosarcoma ranges from 10-50%, depending on the location and the number of metastatic foci.

Radiation therapy (RT), which is used to destroy tumor cells or to alter tumor/stroma architecture, is an integral part of treatment of many types of cancer. However, because OSA is radioresistant to standard dose of radiotherapy, it is not used for treating OSA.

Recently there has been evidence that RT may synergize with targeted immune therapy. For example, RT induces immunogenic cell death wherein tumor cells die slowly over time from apoptosis, necrosis and/or mitotic catastrophe, leading to the clearance of the dying cells by the immune system. This in turn serves as a potential source of tumor antigens for immune therapy. RT also modulates tumor cell surface expression of cell death receptors, tumor-associated antigens and adhesion molecules, which render the tumor cells more susceptible to immune-mediated killing.

The present invention meets the needs of subjects suffering from OSA with surprising findings that radiation therapy when combined with a recombinant *Listeria*-Her-2/neu vaccine (ADXS31-164) that was generated using the LmddA vaccine vector which has a well-defined attenuation mechanism and is devoid of antibiotic selection markers is particularly effective against osteosarcoma and pulmonary metastasis.

SUMMARY OF THE INVENTION

In one embodiment, the present invention provides a method of treating a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of eliciting an enhanced immune response against a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of prolonging survival in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of delaying metastatic disease in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of breaking tolerance to Her-2/neu in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional adjuvant and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In one embodiment, the subject is a human. In one embodiment, the human subject is a child. In another embodiment, the human subject is an adult. In another embodiment, the subject is a canine.

In another embodiment, administering said fusion polypeptide to said subject prevents escape mutations within said tumor.

In another embodiment, said Her-2/neu chimeric antigen comprises at least 5, 9, 13, 14, or 17 of the mapped human MHC-class I epitopes. In another embodiment, said Her-2/neu chimeric antigen comprises at least 5, 9, 13, 14, or 17 of the canine MHC-class I epitopes.

In one embodiment, the nucleic acid molecule is integrated into the *Listeria* genome. In another embodiment, the nucleic acid molecule is in a plasmid in said recombinant *Listeria* vaccine strain and the plasmid is stably maintained in the recombinant *Listeria* vaccine strain in the absence of antibiotic selection.

In one embodiment, the recombinant *Listeria* lacks the actA virulence gene. In one embodiment, the additional polypeptide is selected from the group consisting of: a) non-hemolytic LLO protein or N-terminal fragment, b) a PEST sequence, or c) an ActA fragment. In one embodiment, the metabolic enzyme encoded by said second open reading frame is an alanine racemase enzyme or a D-amino acid transferase enzyme. In some embodiments of this invention, a recombinant attenuated *Listeria* strain is ADXS31-164.

In one embodiment, the recombinant attenuated *Listeria* strain is administered with an independent adjuvant, which, in one embodiment, comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

In one embodiment, the cancer is osteosarcoma (OSA). In another embodiment, the cancer or tumor is pulmonary metastatic disease. In one embodiment, administration comprises at least two administrations of said recombinant attenuated *Listeria* strain. In one embodiment, the administration of said radiation therapy comprises at least two administrations of said radiation therapy. In one embodiment, provided herein is a combination therapy comprising a radiation therapy and administration of ADXS31-164 provided herein. In one embodiment, the radiation therapy is administered prior to administration of the recombinant attenuated *Listeria* strain.

In another embodiment, the subject does not undergo amputation prior to administration of said radiation therapy and said recombinant attenuated *Listeria* strain. In another embodiment, the method further comprises administering said radiation therapy and said recombinant attenuated *Listeria* strain following a relapse or metastasis in said subject, which in one embodiment, is pulmonary metastatic disease.

In one embodiment, the method results in increased overall survival of said subject. In another embodiment, the method results in a delay of metastatic disease in a subject. In another embodiment, the method results in an increased Her-2/neu specific T cell response. In another embodiment, said elicitation of an enhanced immune response results in increased overall survival of said subject. In another embodiment, said elicitation of an enhanced immune response results in a delay of metastatic disease in a subject. In one embodiment, the metastatic disease is pulmonary metastatic disease. In another embodiment, said elicitation of an enhanced immune response results in an increased Her-2/neu specific T cell response.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3. Tumor Prevention Studies for *Listeria*-ChHER2/neu Vaccines HER2/neu transgenic mice were injected six times with each recombinant *Listeria*-ChHer2 or a control *Listeria* vaccine. Immunizations started at 6 weeks of age and continued every three weeks until week 21. Appearance of tumors was monitored on a weekly basis and expressed as percentage of tumor free mice. *p<0.05, N=9 per group.

FIG. 4. Effect of immunization with ADXS31-164 on the % of Tregs in Spleens. FVB/N mice were inoculated s.c. with $1\times10^6$ NT-2 cells and immunized three times with each vaccine at one week intervals. Spleens were harvested 7 days after the second immunization. After isolation of the immune cells, they were stained for detection of Tregs by anti CD3, CD4, CD25 and FoxP3 antibodies. dot-plots of the Tregs from a representative experiment showing the frequency of $CD25^+/FoxP3^+$ T cells, expressed as percentages of the total $CD3^+$ or $CD3^+CD4^+$ T cells across the different treatment groups.

FIG. 5. Effect of immunization with ADXS31-164 on the % of tumor infiltrating Tregs in NT-2 tumors. FVB/N mice were inoculated s.c. with $1\times10^6$ NT-2 cells and immunized three times with each vaccine at one week intervals. Tumors were harvested 7 days after the second immunization. After isolation of the immune cells, they were stained for detection of Tregs by anti CD3, CD4, CD25 and FoxP3 antibodies. (A). dot-plots of the Tregs from a representative experiment. (B). Frequency of $CD25^+/FoxP3^+$ T cells, expressed as percentages of the total $CD3^+$ or $CD3^+CD4^+$ T cells (left panel) and intratumoral CD8/Tregs ratio (right panel) across the different treatment groups. Data is shown as mean±SEM obtained from 2 independent experiments.

FIG. 6. Vaccination with ADXS31-164 can delay the growth of a breast cancer cell line in the brain. Balb/c mice were immunized thrice with ADXS31-164 or a control *Listeria* vaccine. EMT6-Luc cells (5,000) were injected intracranially in anesthetized mice. (A) Ex vivo imaging of the mice was performed on the indicated days using a Xenogen X-100 CCD camera. (B) Pixel intensity was graphed as number of photons per second per cm2 of surface area; this is shown as average radiance. (C) Expression of HER2/neu by EMT6-Luc cells, 4T1-Luc and NT-2 cell lines was detected by Western blots, using an anti-HER2/neu antibody. J774.A2 cells, a murine macrophage like cell line was used as a negative control.

FIG. 7. Shows the first 18 canine osteosarcoma patients vaccinated with ADXS31-164, following amputation and chemotherapy.

FIG. 8. Shows that ADXS31-164 administration does not cause A) early evidence of dilated cardiomyopathy. B) Sequential cardiac troponin I levels evaluated over the course of the study showing that the levels stay within the normal range throughout the study period for the majority of dogs. It should be noted that the one dog with a temporarily increased cardiac troponin I level had unremarkable echocardiograms at the time these values were mildly increased (see also FIG. 26D).

FIG. 13 A-B. Treatment-related adverse events and survival curves following ADXS-31-164 administration. FIG. 13A shows treatment-related adverse events. FIG. 13B shows all dogs without metastatic disease at the time of trial enrollment. Dogs in the control group underwent limb amputation followed by either carboplatin alone or carboplatin plus Adriamycin. 2 dogs have been censored from the vaccine arm as they died of unrelated causes (1 dog died from aspiration pneumonia, the other died from nephroblastoma). Vaccinated group Red line; Control group Black line.

FIG. 14. Radiographic images of primary and metastatic osteosarcoma (OSA) in a human (A) and canine (B) patient. In both species, primary lesions are characterized by areas of proliferation and lysis in the bone metaphysis (arrows in A).

FIG. 15. Schematic of the phase I, 3+3 clinical trial to evaluate the safety and efficacy of ADXS31-164 in dogs with HER2+ osteosarcoma (OSA). Privately owned dogs with spontaneous HER2+ appendicular OSA underwent standard of care amputation and follow up carboplatin chemotherapy. Three weeks after the last carboplatin dose, dogs were vaccinated with either $2\times10^8$, $5\times10^8$, $1\times10^9$ or $3.3\times10^9$ CFU of ADXS31-164 intravenously (three vaccinations given three weeks apart). Dogs were re-staged every 2 months until death to determine vaccine efficacy in preventing metastatic disease.

FIG. 21. Kaplan Meier estimates for (A) Time To Metastasis (TTM) and (B) OSA Specific Survival.

FIG. 28 A-C. Shows the results of a pain questionnaire in subjects with pain interfering with general activity (FIG. 28A), in subjects with pain interfering with the ability to walk (FIG. 28B), and in subjects with pain interfering with the enjoyment of life (FIG. 28C).

FIG. 31. Shows the HER2/neu specific immune responses for the eighteen dogs enrolled in the Phase I clinical trial. Immunological responses against the human EC1, EC2 and IC1 domains of HER2/neu were measured at baseline, 3 weeks after the third ADXS31-164 vaccination, 2 months later, and 4 months later.

Figure 1:
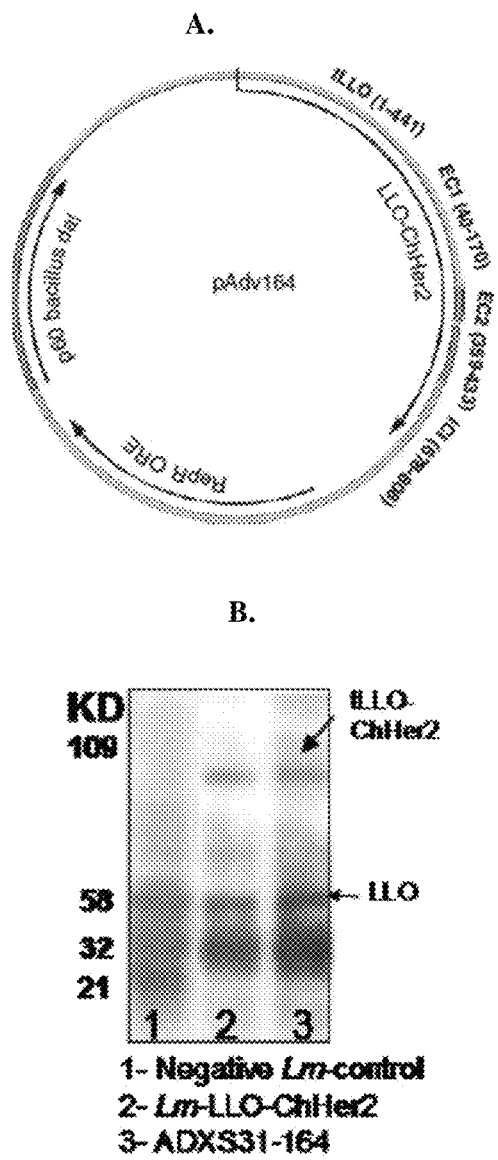
FIG. 1. Construction of ADXS31-164. (A) Plasmid map of pAdv164, which harbors *bacillus subtilis* dal gene under the control of constitutive *Listeria* p60 promoter for complementation of the chromosomal dal-dat deletion in LmddA strain. It also contains the fusion of truncated $LLO_{(1-441)}$ to the chimeric human HER2/neu gene, which was constructed by the direct fusion of 3 fragments the HER2/neu: EC1 (aa 40-170), EC2 (aa 359-518) and ICI (aa 679-808). The vector schematic on the right shows details pAdv164 expressing a chimeric HER2/neu fusion protein consisting of 2 extracellular domains and one intracellular domain of human HER2/neu fused to truncated LLO. The plasmid is maintained within the recombinant dal/dat/actA⁻ *listeria* strain (LmddA) by means of auxotrophic complementation of the dal gene (See Examples). (B) Expression and secretion of tLLO-ChHer2 was detected in Lm-LLO-ChHer2 (Lm-LLO-138) and LmddA-LLO-ChHer2 (ADXS31-164) by western blot analysis of the TCA precipitated cell culture supernatants blotted with anti-LLO antibody. A differential band of ~104 KD corresponds to tLLO-ChHer2. The endogenous LLO is detected as a 58 KD band. *Listeria* control lacked ChHer2 expression.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the present invention provides a method of treating a tumor growth or cancer in a subject comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In one embodiment, the present invention provides a method of preventing a tumor growth or cancer in a subject comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In one embodiment, the present invention provides a method of eliciting an enhanced immune response against a tumor growth or cancer in a subject comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In one embodiment, the present invention provides a method of prolonging survival in a subject suffering from a tumor growth or cancer comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In one embodiment, the present invention provides a method of delaying metastatic disease in a subject suffering from a tumor growth or cancer comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In one embodiment, the present invention provides a method of breaking tolerance to a tumor specific antigen in a subject suffering from a tumor growth or cancer expressing said tumor specific antigen comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In one embodiment, the tumor specific antigen is Her-2/neu.

In one embodiment, the present invention provides a method of treating a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide.

In one embodiment, the present invention provides a method of preventing a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide.

In another embodiment, the present invention provides a method of eliciting an enhanced immune response against a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide.

In another embodiment, the present invention provides a method of prolonging survival in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide.

In another embodiment, the present invention provides a method of delaying metastatic disease in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide.

In another embodiment, the present invention provides a method of breaking tolerance to Her-2/neu in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional adjuvant.

In one embodiment, the recombinant attenuated *Listeria* strain further comprises a second open reading frame encoding a metabolic enzyme, wherein said metabolic enzyme complements an endogenous gene that is mutated in the chromosome of said recombinant attenuated *Listeria* strain.

In one embodiment, the present invention provides a method of treating a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In one embodiment, the present invention provides a method of preventing a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In another embodiment, the present invention provides a method of eliciting an enhanced immune response against a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain.

In another embodiment, the present invention provides a method of prolonging survival in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In another embodiment, the present invention provides a method of delaying metastatic disease in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain.

In another embodiment, the present invention provides a method of breaking tolerance to Her-2/neu in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional adjuvant and a second open reading frame encoding a metabolic enzyme, wherein said metabolic enzyme complements an endogenous gene that is mutated in the chromosome of said recombinant attenuated *Listeria* strain.

In one embodiment, the administration of said radiation therapy comprises at least two administrations of said radiation therapy.

In one embodiment, the present invention provides a method of treating a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of eliciting an enhanced immune response against a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of prolonging survival in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of delaying metastatic disease in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In another embodiment, the present invention provides a method of breaking tolerance to Her-2/neu in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional adjuvant and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

In one embodiment, the subject is a human. In one embodiment, the human subject is a child. In another embodiment, the human subject is an adult.

In one embodiment, the present invention provides a method of treating a Her-2/neu-expressing tumor growth or cancer in a human subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In one embodiment, the present invention provides a method of preventing a Her-2/neu-expressing tumor growth or cancer in a human subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In another embodiment, the present invention provides a method of eliciting an enhanced immune response against a Her-2/neu-expressing tumor growth or cancer in a human subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain.

In another embodiment, the present invention provides a method of prolonging survival in a human subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In another embodiment, the present invention provides a method of delaying metastatic disease in a human subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain.

In another embodiment, the present invention provides a method of breaking tolerance to Her-2/neu in a human subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional adjuvant and a second open reading frame encoding a metabolic enzyme, wherein said metabolic enzyme complements an endogenous gene that is mutated in the chromosome of said recombinant attenuated *Listeria* strain.

In another embodiment, the subject is a canine. In one embodiment, the canine is a dog.

In one embodiment, the present invention provides a method of treating a Her-2/neu-expressing tumor growth or cancer in a canine subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In one embodiment, the present invention provides a method of preventing a Her-2/neu-expressing tumor growth or cancer in a canine subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In another embodiment, the present invention provides a method of eliciting an enhanced immune response against a Her-2/neu-expressing tumor growth or cancer in a canine subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain.

In another embodiment, the present invention provides a method of prolonging survival in a canine subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, and a second open reading frame encoding a metabolic enzyme, wherein said metabolic enzyme complements an endogenous gene that is mutated in the chromosome of said recombinant attenuated *Listeria* strain.

In another embodiment, the present invention provides a method of delaying metastatic disease in a canine subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide and a second open reading frame encoding a metabolic enzyme, wherein said metabolic enzyme complements an endogenous gene that is mutated in the chromosome of said recombinant attenuated *Listeria* strain.

In another embodiment, the present invention provides a method of breaking tolerance to Her-2/neu in a canine subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional adjuvant and a second open reading frame encoding a metabolic enzyme, wherein said metabolic enzyme complements an endogenous gene that is mutated in the chromosome of said recombinant attenuated *Listeria* strain.

In one embodiment, the present invention provides a method of delaying metastatic disease or treating metastatic disease in a subject. In one embodiment, the metastatic disease is pulmonary metastatic disease.

Thus, in one embodiment, the present invention provides a method of delaying pulmonary metastatic disease in a subject suffering from a tumor growth or cancer comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In another embodiment, the present invention provides a method of treating pulmonary metastatic disease in a subject suffering from a tumor growth or cancer comprising the step of administering a combination of radiation therapy and a recombinant attenuated *Listeria* strain comprising a nucleic acid comprising a first open reading frame encoding a fusion polypeptide comprising a tumor specific antigen fused to an additional polypeptide.

In one embodiment, provided herein are methods for preventing, treating, prolonging survival, delaying metastatic disease, breaking tolerance to Her-2/neu, vaccinating against a Her2-neu antigen-expressing tumor, inducing an immune response, eliciting an enhanced immune response against sub-dominant epitopes of the Her2-neu antigen, while circumventing mutation avoidance. In another embodiment, the administration of the fusion polypeptide of the present invention to the subject prevents escape mutations within said tumor. In another embodiment, circumventing mutation avoidance is due to epitope spreading. In yet another embodiment, mutation avoidance is due to the chimeric nature of the antigen.

In another embodiment, provided herein is an immunogenic composition for use in the claimed methods comprising a fusion polypeptide, wherein said fusion polypeptide comprises a Her-2/neu chimeric antigen fused to an additional polypeptide, and wherein administering the fusion protein to a subject having an Her-2/neu-expressing tumor prevents escape mutations within said tumor. In another embodiment, provided herein is a recombinant *Listeria* vaccine strain for use in the claimed methods comprising the immunogenic composition.

In one embodiment, the recombinant attenuated *Listeria* strain is a vaccine strain. In one embodiment, the nucleic acid referred to herein is a nucleic acid molecule.

In one embodiment, the recombinant attenuated *Listeria* strain for use in the methods of the present invention further comprises a nucleic acid molecule comprising a third open reading frame encoding a metabolic enzyme, and wherein the metabolic enzyme complements an endogenous gene that is mutated in the chromosome of the recombinant *Listeria* strain.

In another embodiment, provided herein is a recombinant attenuated *Listeria* strain comprising a nucleic acid molecule, wherein the nucleic acid molecule comprises a first open reading frame encoding a polypeptide, wherein the polypeptide comprises a Her-2/neu chimeric antigen, wherein the nucleic acid molecule further comprises a second and a third open reading frame, each encoding a metabolic enzyme, and wherein the metabolic enzyme complements an endogenous gene that is mutated in the chromosome of said recombinant *Listeria* strain.

In one embodiment, the nucleic acid molecule is integrated into the *Listeria* genome. In another embodiment, the nucleic acid molecule is in a plasmid in the recombinant *Listeria* vaccine strain. In yet another embodiment, the plasmid is stably maintained in the recombinant *Listeria* vaccine strain in the absence of antibiotic selection. In another embodiment, the plasmid does not confer antibiotic resistance upon the recombinant *Listeria*. In another embodiment, the recombinant *Listeria* strain is attenuated. In another embodiment, the recombinant *Listeria* is an attenuated auxotrophic strain. In another embodiment, the high metabolic burden that the expression of a foreign antigen exerts on a bacterium such as one of the present invention is also an important mechanism of attenuation.

In one embodiment the attenuated strain is LmddA. In another embodiment, this strain exerts a strong adjuvant effect, which is an inherent property of *Listeria*-based vaccines. One manifestation of this adjuvant effect is the 5-fold decrease in the number of the intratumoral Tregs caused by either *Listeria* expressing an antigen other than a human chimeric Her-2/neu or the ADXS-31-164 (expressing a human chimeric Her-2/neu) vaccines (see FIG. 5 herein). In another embodiment, the LmddA vector expressing a different antigen (HPV16 E7) is also associated with a significant decrease in the frequency of Tregs in the tumors, likely as a consequence of innate immunity responses. In another embodiment, the LmddA vector expresses a prostate-specific antigen (PSA), a human papilloma virus (HPV) antigen (E6, E7). In another embodiment, the HPV strain is HPV16, HPV18, or any strain known in the art.

In one embodiment, the attenuated auxotrophic *Listeria* vaccine strain is the ADXS-31-164 strain. ADXS-31-164 is based on a *Listeria* vaccine vector which is attenuated due to the deletion of virulence gene actA and retains the plasmid for Her-2/neu expression in vivo and in vitro by complementation of dal gene. In one embodiment, ADXS31-164 expresses and secretes the chimeric Her-2/neu protein fused to the first 441 amino acids of listeriolysin O (LLO). In another embodiment, ADXS31-164 exerts strong and antigen specific anti-tumor responses with ability to break tolerance toward Her-2/neu in transgenic animals (see Examples). In another embodiment, the ADXS31-164 strain is highly attenuated and has a better safety profile than previous *Listeria* vaccine generations, as it is more rapidly cleared from the spleens of the immunized mice. In another embodiment, the ADXS31-164 results in a longer delay of tumor onset in transgenic animals than Lm-LLO-ChHer2, the antibiotic resistant and more virulent version of this vaccine (see FIG. 3). In one embodiment, the Lm-LLO-ChHer2 strain is Lm-LLO-138.

In another embodiment, ADXS31-164 strain is highly immunogenic, able to break tolerance toward the Her-2/neu self-antigen and prevent tumor formation in Her-2/neu transgenic animals. In another embodiment, ADXS31-164 causes a significant decrease in intra-tumoral T regulatory cells (Tregs). In another embodiment, the lower frequency of Tregs in tumors treated with LmddA vaccines resulted in an increased intratumoral CD8/Tregs ratio, suggesting that a more favorable tumor microenvironment can be obtained after immunization with LmddA vaccines. In another embodiment, the use of this chimeric antigen does not result in escape mutations indicating that tumors do not mutate away from a therapeutic efficacious response to treatment with this novel antigen (see Example 6). In another embodiment, peripheral immunization with ADXS31-164 delays the growth of a metastatic breast cancer cell line in the brain (see Example 7).

In another embodiment, canine subjects suffering from osteosarcoma and provided treatment including amputation, chemotherapy, and vaccination with ADXS31-164, have prolonged survival compared with control subjects not receiving the vaccination with ADXS31-164 (see Examples 9 and 10). In another embodiment, canine subjects suffering from osteosarcoma and provided treatment including amputation, chemotherapy, and vaccination with ADXS31-164, show reduced metastasis compared with control subjects not receiving the vaccination with ADXS31-164 (see Example 10). In another embodiment, canine subjects suffering from osteosarcoma and provided treatment including amputation, chemotherapy, and vaccination with ADXS31-164, show increased specific T cell response induced compared with control subjects not receiving the vaccination with ADXS31-164 (see Example 10). In another embodiment, canine subjects suffering from osteosarcoma and provided radiation therapy prior to vaccination with ADXS31-164, have prolonged survival compared with control subjects receiving either only radiation therapy or only vaccination with ADXS31-164 (see Example 11). In another embodiment, canine subjects suffering from osteosarcoma and provided radiation therapy prior to vaccination with ADXS31-164 show reduced metastasis compared with control subjects receiving either only radiation therapy or only vaccination with ADXS31-164 (see Example 11).

In another embodiment, the terms "ADXS31-164," "Lm-human chimeric Her-2/neu," "Lm-huHer2-neu," and "Lm-hucHer-2/neu," are used interchangeably herein.

In one embodiment, osteosarcoma cells are not easily killed by radiation, so radiation therapy is rarely used to treat osteosarcoma. In one embodiment, recombinant attenuated, antibiotic-free *Listeria*-expressing chimeric antigens are useful for preventing, and treating a cancer or solid tumors, as exemplified herein. In another embodiment, the tumor is a Her-2/neu positive tumor. In another embodiment, the cancer is a Her-2/neu-expressing cancer. In another embodiment, the cancer is breast cancer, a central nervous system (CNS) cancer, a head and neck cancer, an osteosarcoma (OSA), a canine OSA, Ewing's sarcoma (ES), or any Her-2/neu-expressing cancer known in the art. In another embodiment, a canine osteosarcoma is an appendicular osteosarcoma. In another embodiment, the tumor is an osteosarcoma tumor, a breast tumor, a head and neck tumor, or any other antigen-expressing tumor known in the art. In another embodiment, said cancer or solid tumor is a result of relapse or metastatic disease. In one embodiment, the metastatic disease is pulmonary metastatic disease.

In one embodiment, the present invention provides methods of treating, preventing, or delaying metastases. In one embodiment, the present invention provides methods of treating, preventing, or delaying metastases of OSA. In one embodiment, the metastases are in the lung. In another embodiment, the metastases are in another tissue. In another embodiment, the metastases are in bone, which in one embodiment is proximal to the site of the initial OSA, and in another embodiment, is distal to the site of the initial OSA. In another embodiment, the metastases are in the kidney. In another embodiment, the metastases are in the heart. In another embodiment, the metastases are isolated. In another embodiment, the metastases are an isolated local recurrence. In another embodiment, the metastases are multi-site metastases.

In another embodiment, recombinant *Listeria* expressing a chimeric Her-2/neu are useful as a therapeutic vaccine for the treatment of Her-2/neu overexpressing solid tumors. In another embodiment, the Her-2/neu chimeric antigen provided herein is useful for treating Her-2/neu-expressing tumors and preventing escape mutations of the same. In another embodiment, the term "escape mutation" refers to a tumor mutating away from a therapeutic efficacious response to treatment.

In one embodiment, provided herein is a nucleic acid molecule comprising a first open reading frame encoding a recombinant polypeptide provided herein, wherein the nucleic acid molecule resides within the recombinant *Listeria* vaccine strain. In another embodiment, the nucleic acid molecule provided herein is used to transform the *Listeria* in order to arrive at a recombinant *Listeria*. In another embodiment, the nucleic acid provided herein lacks a virulence gene. In another embodiment, the nucleic acid molecule integrated into the *Listeria* genome carries a non-functional virulence gene. In another embodiment, the virulence gene is mutated in the genome of the recombinant *Listeria*. In yet another embodiment, the nucleic acid molecule is used to inactivate the endogenous gene present in the *Listeria* genome. In yet another embodiment, the virulence gene is an actA gene. In another embodiment, the virulence gene is a prfA gene. In another embodiment, the virulence gene is an inlB gene. As will be understood by a skilled artisan, the virulence gene can be any gene known in the art to be associated with virulence in the recombinant *Listeria*.

In one embodiment, the metabolic gene, the virulence gene, or both is lacking in a chromosome of the *Listeria* strain. In another embodiment, the metabolic gene, the virulence gene, or both is lacking in the chromosome and in any episomal genetic element of the *Listeria* strain. It will be appreciated by a skilled artisan that the term "episome," "episomal," etc. refer to a plasmid vector or use thereof that does not integrate into the chromosome of the *Listeria* provided herein. In another embodiment, the term refers to plasmid vectors that integrate into the chromosome of the *Listeria* provided herein. In another embodiment, the metabolic gene, the virulence gene, or both is lacking in the genome of the *Listeria* strain. In one embodiment, the metabolic gene, the virulence gene, or both is mutated in the chromosome. In another embodiment, the metabolic gene, the virulence gene, or both is deleted from the chromosome. In another embodiment, the metabolic gene, the virulence gene, or both is inactivated in the chromosome.

In another embodiment, the nucleic acids and plasmids provided herein do not confer antibiotic resistance upon the recombinant *Listeria*.

"Nucleic acid molecule" refers, in one embodiment, to a plasmid. In another embodiment, the term refers to an integration vector. In another embodiment, the term refers to a non-integration vector. In another embodiment, the term refers to a plasmid comprising an integration vector. In another embodiment, the integration vector is a site-specific integration vector. In another embodiment, a nucleic acid molecule of methods and compositions of the present invention are composed of any type of nucleotide known in the art. Each possibility represents a separate embodiment of the present invention.

"Metabolic enzyme" refers, in another embodiment, to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient. Each possibility represents a separate embodiment of the present invention.

"Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations.

In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than 500 generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the present invention.

In one embodiment, the present invention provides a recombinant *Listeria* strain expressing the antigen. The present invention also provides recombinant polypeptides comprising a listeriolysin (LLO) protein fragment fused to a Her-2 chimeric protein or fragment thereof, vaccines and immunogenic compositions comprising same, and methods of inducing an anti-Her-2 immune response and treating and vaccinating against a Her-2-expressing tumor, comprising the same.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed by any other method known in the art.

In one embodiment, the polypeptide provided herein is a fusion protein comprising an additional polypeptide selected from the group consisting of: a) non-hemolytic LLO protein or N-terminal fragment, b) a PEST sequence, or c) an ActA fragment, and further wherein said additional polypeptide is fused to the Her-2/neu chimeric antigen. In another embodiment, the additional polypeptide is functional. In another embodiment, a fragment of the additional polypeptide is immunogenic. In another embodiment, the additional polypeptide is immunogenic.

In another embodiment, the polypeptide provided herein is a fusion protein comprising a non-hemolytic LLO protein or N-terminal fragment fused to the Her-2/neu chimeric antigen. In another embodiment, a fusion protein of methods and compositions of the present invention comprises an ActA sequence from a *Listeria* organism. In one embodiment, ActA proteins and fragments thereof augment antigen presentation and immunity in a similar fashion to LLO.

In one embodiment of methods and compositions of the present invention, the fusion protein comprises the Her-2/neu antigen and an additional polypeptide. In another embodiment, the additional polypeptide fused to Her-2/neu antigen is referred to as an additional adjuvant polypeptide. In one embodiment, the additional polypeptide is a non-hemolytic LLO protein or fragment thereof (Examples herein). In another embodiment, the additional polypeptide is a PEST sequence. In another embodiment, the additional polypeptide is an ActA protein or a fragment thereof.

The additional polypeptide of methods and compositions of the present invention is, in another embodiment, a listeriolysin (LLO) peptide. In another embodiment, the additional polypeptide is an ActA peptide. In another embodiment, the additional polypeptide is a PEST sequence peptide. In another embodiment, the additional polypeptide is any other peptide capable of enhancing the immunogenicity of an antigen peptide. Each possibility represents a separate embodiment of the present invention.

Fusion proteins comprising the Her-2/neu chimeric antigen may be prepared by any suitable method, including, for example, cloning and restriction of appropriate sequences or direct chemical synthesis by methods discussed below. Alternatively, subsequences may be cloned and the appropriate subsequences cleaved using appropriate restriction enzymes. The fragments may then be ligated to produce the desired DNA sequence. In one embodiment, DNA encoding the antigen can be produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

The results of the present invention demonstrate that administration of compositions of the present invention has utility for inducing formation of antigen-specific T cells (e.g. cytotoxic T cells) that recognize and kill tumor cells (Examples herein).

In one embodiment, the present invention provides a recombinant polypeptide comprising an N-terminal fragment of an LLO protein fused to a Her-2 chimeric protein or fused to a fragment thereof. In one embodiment, the present invention provides a recombinant polypeptide consisting of an N-terminal fragment of an LLO protein fused to a Her-2 chimeric protein or fused to a fragment thereof.

In another embodiment, the Her-2 chimeric protein of the methods and compositions of the present invention is a human Her-2 chimeric protein. In another embodiment, the Her-2 protein is a mouse Her-2 chimeric protein. In another embodiment, the Her-2 protein is a rat Her-2 chimeric protein. In another embodiment, the Her-2 protein is a primate Her-2 chimeric protein. In another embodiment, the Her-2 protein is a canine Her-2 chimeric protein. In another embodiment, the Her-2 protein is a Her-2 chimeric protein of human or any other animal species or combinations thereof known in the art. Each possibility represents a separate embodiment of the present invention.

In another embodiment, a Her-2 protein is a protein referred to as "Her-2/neu," "Erbb2," "v-erb-b2," "c-erb-b2," "neu," or "cNeu." In another embodiment, the term Her2/neu, or grammatical equivalents thereof, is also referred to herein as "Her-2," "Her-2 protein," "HER2 protein," or "HER2"). Each possibility represents a separate embodiment of the present invention.

In one embodiment, the Her2-neu chimeric protein, harbors two of the extracellular and one intracellular fragments of Her-2/neu antigen showing clusters of MHC-class I epitopes of the oncogene, where, in another embodiment, the chimeric protein, harbors 3 H2Dq and at least 17 of the mapped human MHC-class I epitopes of the Her-2/neu antigen (fragments EC1, EC2, and IC1) (See FIG. 1A). In another embodiment, the chimeric protein harbors at least 13 of the mapped human MHC-class I epitopes (fragments EC2 and IC1). In another embodiment, the chimeric protein harbors at least 14 of the mapped human MHC-class I epitopes (fragments EC1 and IC1). In another embodiment, the chimeric protein harbors at least 9 of the mapped human MHC-class I epitopes (fragments EC1 and IC2). In another embodiment, the Her2-neu chimeric protein is fused to a non-hemolytic listeriolysin O (LLO). In another embodiment, the Her2-neu chimeric protein is fused to truncated listeriolysin O (tLLO). In another embodiment, the Her2-neu chimeric protein is fused to the first 441 amino acids of the *Listeria-monocytogenes* listeriolysin O (LLO) protein and expressed and secreted by the *Listeria monocytogenes* attenuated auxotrophic strain LmddA. In another embodiment, the expression and secretion of the fusion protein tLLO-ChHer2 from the attenuated auxotrophic strain provided herein that expresses a chimeric Her-2/neu antigen/LLO fusion protein is comparable to that of the Lm-LLO-ChHer2 in TCA precipitated cell culture supernatants after 8 hours of in vitro growth (See FIG. 1B).

Figure 2:
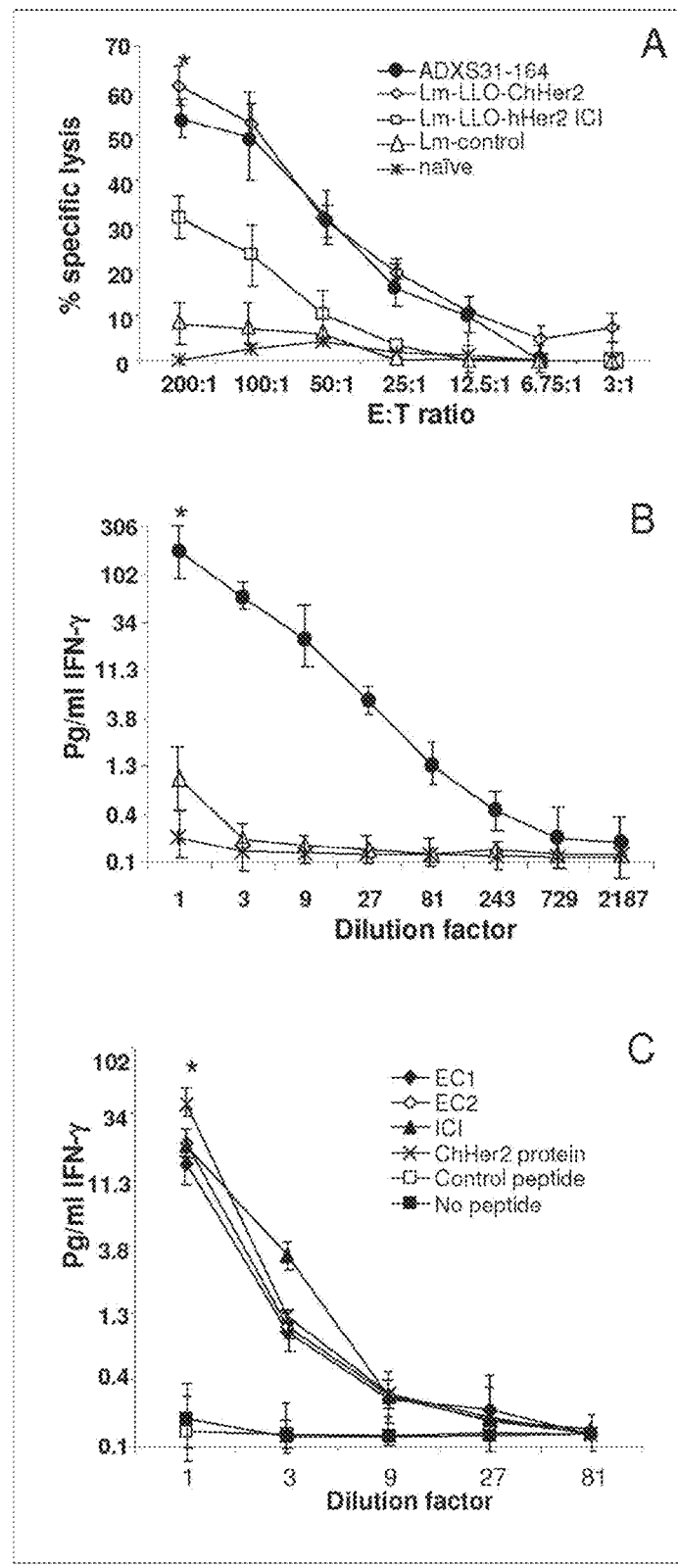
FIG. 2. Immunogenic properties of ADXS31-164 (A) Cytotoxic T cell responses elicited by HER2/neu *Listeria*-based vaccines in splenocytes from immunized mice were tested using NT-2 cells as stimulators and 3T3/neu cells as targets. Lm-control was based on the LmddA background that was identical in all ways but expressed an irrelevant antigen (HPV16-E7). (B) IFN-γ secreted by the splenocytes from immunized FVB/N mice into the cell culture medium, measured by ELISA, after 24 hours of in vitro stimulation with mitomycin C treated NT-2 cells. (C) IFN-γ secretion by splenocytes from HLA-A2 transgenic mice immunized with the chimeric vaccine, in response to in vitro incubation with peptides from different regions of the protein. A recombinant ChHer2 protein was used as positive control and an irrelevant peptide or no peptide groups constituted the negative controls as listed in the figure legend. IFN-γ secretion was detected by an ELISA assay using cell culture supernatants harvested after 72 hours of co-incubation. Each data point was an average of triplicate data +/− standard error. *P value<0.001.

In one embodiment, no CTL activity is detected in naïve animals or mice injected with an irrelevant *Listeria* vaccine stimulate the secretion of IFN-γ by the splenocytes from wild type FVB/N mice (FIG. 2B).

In another embodiment, the metabolic enzyme of the methods and compositions provided herein is an amino acid metabolism enzyme, where, in another embodiment, the metabolic enzyme is an alanine racemase enzyme. In another embodiment, the metabolic enzyme is a D-amino acid transferase enzyme. In another embodiment, the metabolic enzyme catalyzes a formation of an amino acid used for a cell wall synthesis in the recombinant *Listeria* strain, where in another embodiment, the metabolic enzyme is an alanine racemase enzyme.

In another embodiment, the gene encoding the metabolic enzyme is expressed under the control of the *Listeria* p60 promoter. In another embodiment, the inlA (encodes internalin) promoter is used. In another embodiment, the hly promoter is used. In another embodiment, the ActA promoter is used. In another embodiment, the integrase gene is expressed under the control of any other gram positive promoter. In another embodiment, the gene encoding the metabolic enzyme is expressed under the control of any other promoter that functions in *Listeria*. The skilled artisan will appreciate that other promoters or polycistronic expression cassettes may be used to drive the expression of the gene. Each possibility represents a separate embodiment of the present invention.

In another embodiment, the Her-2 chimeric protein is encoded by the following nucleic acid sequence set forth in SEQ ID NO:1

(SEQ ID NO: 1)
```
gagacccacctggacatgctccgccacctctaccagggctgccaggtggtgcagggaaacctggaactcacctacct gcccaccaatgccagcctgtccacctgcaggatatccaggaggtgcagggctacgtgctcatcgctcacaaccaagtgaggcaggt cccactgcagaggctgcggattgtgcgaggcacccagctcatgaggacaactatgccctggccgtgctagacaatggagacccgc tgaacaataccaccctgtcacaggggcctccccaggaggcctgcgggagctgcagcttcgaagcctcacagagatcttgaaagga ggggtcttgatccagcggaacccccagctctgctaccaggacacgattagtggaagaatatccaggagtagctggctgcaagaaga tctagggagcctggcatactgccggagagctttgatggggacccagcctccaacactgccccgctccagccagagcagctccaag tgatgagactctggaagagatcacaggttacctatacatctcagcatggccggacagcctgcctgacctcagcgtcaccagaacctg caagtaatccggggacgaattctgcacaatggcgcctactcgctgaccctgcaagggctgggcatcagctggctggggctgcgctc actgagggaactgggcagtggactggccctcatccaccataacacccacctctgcttcgtgcacacggtgccctgggaccagctcttt cggaacccgcaccaagctctgctccacactgccaaccggccagaggacgagtgtgtgggcgagggcctggcctgccaccagctg tgcgcccgagggcagcagaagatccggaagtacacgatgcggagactgctgcaggaaacggagctggtggagccgctgacacc tagcggagcgatgcccaaccaggcgcagatgcggatcctgaaagagacggagctgaggaaggtgaaggtgcaggatctggcgc ttaggcacagtctacaagggcatctggatccctgatggggagaatgtgaaaattccagtggccatcaaagtgagagggaaaacaca tcccccaaagccaacaaagaaatcttagacgaagcatacgtgatggctggtgtgggctccccatatgtctcccgccactgggcatctg cctgacatccacggtgcagctggtgacacagcttatgccctatggctgcctcttagactaa.
```

(See FIG. 2A). While in another embodiment, the attenuated auxotrophic strain (ADXS31-164) provided herein is able to In another embodiment, the Her-2 chimeric protein has the sequence:

(SEQ ID NO: 2)
E T H L D M L R H L Y Q G C Q V V Q G N L E L T Y L P T N

A S L S F L Q D I Q E V Q G Y V L I A H N Q V R Q V P L Q R L R I

VRGTQLFEDNYALAVLDNGDPLNNTTPVTGAS

PGGLRELQLRSLTEILKGGVLIQRNPQLCYQDTI

LWKNIQEFAGCKKIFGSLAFLPESFDGDPASNT

APLQPEQLQVFETLEEITGYLYISAWPDSLPDL

SVFQNLQVIRGRILHNGAYSLTLQGLGISWLGL

RSLRELGSGLALIHHNTHLCFVHTVPWDQLFRN

PHQALLHTANRPEDECVGEGLACHQLCARGQQ

KIRKYTMRRLLQETELVEPLTPSGAMPNQAQM

RILKETELRKVKVLGSGAFGTVYKGIWIPDGEN

VKIPVAIKVLRENTSPKANKEILDEAYVMAGVGS

PYVSRLLGICLTSTVQLVTQLMPYGCLLD.

Table 1 below shows the percent (%) identity between the amino acid sequences of human and canine Her-2 EC and IC fragments, respectively.

TABLE 1

```
Human    SLSFLQDIQEVQCYVLIAHNQVRQVPLQRLRIVRGTQLFEDNYALAVLDNGDPLNNTTPV  60
Canine   SLSYLQDIQEVQGYVLIAHSQVRQIPLQRLNIVRGTQLFEDNYALAVLDNGDPLEGGIPA  60
         *** ************* **** ************************** *   *

Human    TGASPCGLRELQLRSLTEILKGGVLIQRNPQLCYQDTILWKDIFNKNNQLALTLIDTNRS  120
Canine   PGAAPCGLRELQLRSLTEILKGGVLIQRSPQLCHQDTILWKDVFHKNNQLALTLIDTNRS  120
          ** ************************ **** ******** * **************

Human    RACMPCSPMCK  131  SEQ ID NO: 69  89% identity EC1
Canine   RACPPCSPACK  131  SEQ ID NO: 70
         ***  ****  **

Human    TAPLQPEQLQVFETLEEITGYLYISAWPDSLPDLSVTQNLQVIRGRILHNGAYSLTLQGL  60
Canine   TAPLQPEQLRVFEALEEITGYLYISAWPDSLPNLSVYQNLRVIRGRVLHDGAYSLTLQGL  60
         ********* *** ***************** ** **** ***** ** **********

Human    GISWLGLRSLRELGS  75  SEQ ID NO: 71  93% identity EC2
Canine   GISWLGLRSLRELGS  75  SEQ ID NO: 72
         ***************

Human    NQAQMRILKETELRKVKVLGSGAFGTVYKGIWIPDGENVKIPVAIKVLRENTSPKANKEI  60
Canine   NQAQMRILKETELRKVKVLGSGAFGTVYKGIWIPDGENVKIPVAIKVLRENTSPKANKEI  60
         ************************************************************

Human    LDKAYVMAGVGSPYVSRLLCICLTSTVQLVTQLMPYCCLLDNVRKNRCRLGSQDLLNWCM  120
Canine   LDKAYVMAGVGSPYVSRLLCICLTSTVQLVTQLMPYCCLLDHVREHRCRLCSQDLLNWCV  120
         ***************************************** *** **** *******

Human    QIAKCMSYLED  131  SEQ ID NO: 70  98% identity IC1
Canine   QIAKCMSYLED  131  SEQ ID NO: 74
         ***********
```

In another embodiment, an amino acid sequence encoding a human Her-2/neu EC1 fragment is set forth in (SEQ ID NO: 69):

(SEQ ID NO: 69)
SLSFLQDIQEVQGYVLIAHNQVRQVPLQRLRIVRGTQLFEDNYALAVLDN

GDPLNNTTPVTGASPGGLRELQLRSLTEILKGGVLIQRNPQLCYQDTILW

KDIFHKNNQLALTLIDTNRSRACHPCSPMCK.

In another embodiment, an amino acid sequence encoding a canine Her-2/neu EC1 fragment is set forth in (SEQ ID NO: 70):

(SEQ ID NO: 70)
SLSFLQDIQEVQGYVLIAHSQVRQIPLQRLRIVRGTQLFEDNYALAVLDN

GDPLEGGIPAPGAAPGGLRELQLRSLTEILKGGVLIQRSPQLCHQDTILW

KDVFHKNNQLALTLIDTNRSRACPPCSPACK.

In another embodiment, an amino acid sequence encoding a human Her-2/neu EC2 fragment is set forth in (SEQ ID NO: 71):

(SEQ ID NO: 71)
TAPLQPEQLQVFETLEEITGYLYISAWPDSLPDLSVFQNLQVIRGRILHN

GAYSLTLQGLGISWLGLRSLRELGS.

fragment is set forth in (SEQ ID NO: 72):

(SEQ ID NO: 72)
TAPLQPEQLRVFEALEEITGYLYISAWPDSLPNLSVFQNLRVIRGRVLHD

GAYSLTLQGLGISWLGLRSLRELGS.

In another embodiment, an amino acid sequence encoding a human Her-2/neu IC1 fragment is set forth in (SEQ ID NO: 73):

(SEQ ID NO: 73)
NQAQMRILKETELRKVKVLGSGAFGTVYKGIWIPDGENVKIPVAIKVLRE

NTSPKANKEILDEAYVMAGVGSPYVSRLLGICLTSTVQLVTQLMPYGCLL

DHVRENRGRLGSQDLLNWCMQIAKGMSYLED.

In another embodiment, an amino acid sequence encoding a canine Her-2/neu IC1 fragment is set forth in (SEQ ID NO: 74):

(SEQ ID NO: 74)
NQAQMRILKETELRKVKVLGSGAFGTVYKGIWIPDGENVKIPVAIKVLRE

NTSPKANKEILDEAYVMAGVGSPYVSRLLGICLTSTVQLVTQLMPYGCLL

DHVRENRGRLGSQDLLNWCMQIAKGMSYLED.

In one embodiment, the human amino acid sequence of Her-2 EC1 fragment (SEQ ID NO: 69) has 89% identity with that of a canine Her-2 EC1 fragment (SEQ ID NO: 70). In another embodiment, the human amino acid sequence of Her-2 EC2 fragment (SEQ ID NO: 71) has 93% identity with that of a canine Her-2 EC2 fragment (SEQ ID NO: 72). In another embodiment, the human amino acid sequence of Her-2 IC1 fragment (SEQ ID NO: 73) has 98% identity with that of a canine Her-2 IC1 fragment (SEQ ID NO: 74).

In one embodiment, the Her2 chimeric protein or fragment thereof of the methods and compositions provided herein does not include a signal sequence thereof. In another embodiment, omission of the signal sequence enables the Her2 fragment to be successfully expressed in *Listeria*, due the high hydrophobicity of the signal sequence. Each possibility represents a separate embodiment of the present invention.

In another embodiment, the fragment of a Her2 chimeric protein of methods and compositions of the present invention does not include a transmembrane domain (TM) thereof. In one embodiment, omission of the TM enables the Her-2 fragment to be successfully expressed in *Listeria*, due the high hydrophobicity of the TM. Each possibility represents a separate embodiment of the present invention.

In one embodiment, the nucleic acid sequence of rat-Her-2/neu gene is (SEQ ID NO: 45)
CCGGAATCGCGGGCACCCAAGTGTGTACCGGCACAGACATGAAGTTGCGG

CTCCCTGCCAGTCCTGAGACCCACCTGGACATGCTCCGCCACCTGTACCA

GGGCTGTCAGGTAGTGCAGGGCAACTTGGAGCTTACCTACGTGCCTGCCA

ATGCCAGCCTCTCATTCCTGCAGGACATCCAGGAAGTTCAGGGTTACATG

CTCATCGCTCACAACCAGGTGAAGCGCGTCCCACTGCAAAGGCTGCGCAT

CGTGAGAGGGACCCAGCTCTTTGAGGACAAGTATGCCCTGGCTGTGCTAG

ACAACCGAGATCCTCAGGACAATGTCGCCGCCTCCACCCCAGGCAGAACC

-continued
CCAGAGGGGCTGCGGGAGCTGCAGCTTCGAAGTCTCACAGAGATCCTGAA

GGGAGGAGTTTTGATCCGTGGGAACCCTCAGCTCTGCTACCAGGACATGG

TTTTGTGGAAGGACGTCTTCCGCAAGAATAACCAACTGGCTCCTGTCGAT

ATAGACACCAATCGTTCCCGGGCCTGTCCACCTTGTGCCCCCGCCTGCAA

AGACAATCACTGTTGGGGTGAGAGTCCGGAAGACTGTCAGATCTTGACTG

GCACCATCTGTACCAGTGGTTGTGCCCGGTGCAAGGGCCGGCTGCCCACT

GACTGCTGCCATGAGCAGTGTGCCGCAGGCTGCACGGGCCCCAAGCATTC

TGACTGCCTGGCCTGCCTCCACTTCAATCATAGTGGTATCTGTGAGCTGC

ACTGCCCAGCCCTCGTCACCTACAACACAGACACCTTTGAGTCCATGCAC

AACCCTGAGGGTCGCTACACCTTTGGTGCCAGCTGCGTGACCACCTGCCC

CTACAACTACCTGTCTACGGAAGTGGGATCCTGCACTCTGGTGTGTCCCC

CGAATAACCAAGAGGTCACAGCTGAGGACGGAACACAGCGTTGTGAGAAA

TGCAGCAAGCCCTGTGCTCGAGTGTGCTATGGTCTGGGCATGGAGCACCT

TCGAGGGGCGAGGGCCATCACCAGTGACAATGTCCAGGAGTTTGATGGCT

GCAAGAAGATCTTTGGGAGCCTGGCATTTTTGCCGGAGAGCTTTGATGGG

GACCCCTCCTCCGGCATTGCTCCGCTGAGGCCTGAGCAGCTCCAAGTGTT

CGAAACCCTGGAGGAGATCACAGGTTACCTGTACATCTCAGCATGGCCAG

ACAGTCTCCGTGACCTCAGTGTCTTCCAGAACCTTCGAATCATTCGGGGA

CGGATTCTCCACGATGGCGCGTACTCATTGACACTGCAAGGCCTGGGGAT

CCACTCGCTGGGGCTGCGCTCACTGCGGGAGCTGGGCAGTGGATTGGCTC

TGATTCACCGCAACGCCCATCTCTGCTTTGTACACACTGTACCTTGGGAC

CAGCTCTTCCGGAACCCACATCAGGCCCTGCTCCACAGTGGGAACCGGCC

GGAAGAGGATTGTGGTCTCGAGGGCTTGGTCTGTAACTCACTGTGTGCCC

ACGGGCACTGCTGGGGGCCAGGGCCCACCCAGTGTGTCAACTGCAGTCAT

TTCCTTCGGGGCCAGGAGTGTGTGGAGGAGTGCCGAGTATGGAAGGGGCT

CCCCCGGGAGTATGTGAGTGACAAGCGCTGTCTGCCGTGTCACCCCGAGT

GTCAGCCTCAAAACAGCTCAGAGACCTGCTTTGGATCGGAGGCTGATCAG

TGTGCAGCCTGCGCCCACTACAAGGACTCGTCCTCCTGTGTGGCTCGCTG

CCCCAGTGGTGTGAAACCGGACCTCTCCTACATGCCCATCTGGAAGTACC

CGGATGAGGAGGGCATATGCCAGCCGTGCCCCATCAACTGCACCCACTCC

TGTGTGGATCTGGATGAACGAGGCTGCCCAGCAGAGCAGAGAGCCAGCCC

GGTGACATTCATCATTGCAACTGTAGTGGGCGTCCTGCTGTTCCTGATCT

TAGTGGTGGTCGTTGGAATCCTAATCAAACGAAGGAGACAGAAGATCCGG

AAGTATACGATGCGTAGGCTGCTGCAGGAAACTGAGTTAGTGGAGCCGCT

GACGCCCAGCGGAGCAATGCCCAACCAGGCTCAGATGCGGATCCTAAAAG

AGACGGAGCTAAGGAAGGTGAAGGTGCTTGGATCAGGAGCTTTTGGCACT

GTCTACAAGGGCATCTGGATCCCAGATGGGGAGAATGTGAAAATCCCCGT

GGCTATCAAGGTGTTGAGAGAAAACACATCTCCTAAAGCCAACAAAGAAA

TTCTAGATGAAGCGTATGTGATGGCTGGTGTGGGTTCTCCGTATGTGTCC

CGCCTCCTGGGCATCTGCCTGACATCCACAGTACAGCTGGTGACACAGCT

TATGCCCTACGGCTGCCTTCTGGACCATGTCCGAGAACACCGAGGTCGCC

TAGGCTCCCAGGACCTGCTCAACTGGTGTGTTCAGATTGCCAAGGGGATG

AGCTACCTGGAGGACGTGCGGCTTGTACACAGGGACCTGGCTGCCCGGAA

TGTGCTAGTCAAGAGTCCCAACCACGTCAAGATTACAGATTTCGGGCTGG

CTCGGCTGCTGGACATTGATGAGACAGAGTACCATGCAGATGGGGCAAG

GTGCCCATCAAATGGATGGCATTGGAATCTATTCTCAGACGCCGGTTCAC

CCATCAGAGTGATGTGTGGAGCTATGGAGTGACTGTGTGGGAGCTGATGA

CTTTTGGGGCCAAACCTTACGATGGAATCCCAGCCCGGGAGATCCCTGAT

TTGCTGGAGAAGGGAGAACGCCTACCTCAGCCTCCAATCTGCACCATTGA

TGTCTACATGATTATGGTCAAATGTTGGATGATTGACTCTGAATGTCGCC

CGAGATTCCGGGAGTTGGTGTCAGAATTTTCACGTATGGCGAGGGACCCC

CAGCGTTTTGTGGTCATCCAGAACGAGGACTTGGGCCCATCCAGCCCCAT

GGACAGTACCTTCTACCGTTCACTGCTGGAAGATGATGACATGGGTGACC

TGGTAGACGCTGAAGAGTATCTGGTGCCCCAGCAGGGATTCTTCTCCCCG

GACCCTACCCCAGGCACTGGGAGCACAGCCCATAGAAGGCACCGCAGCTC

GTCCACCAGGAGTGGAGGTGGTGAGCTGACACTGGGCCTGGAGCCCTCGG

AAGAAGGGCCCCCAGATCTCCACTGGCTCCCTCGGAAGGGGCTGGCTCC

GATGTGTTTGATGGTGACCTGGCAATGGGGGTAACCAAAGGGCTGCAGAG

CCTCTCTCCACATGACCTCAGCCCTCTACAGCGGTACAGCGAGGACCCCA

CATTACCTCTGCCCCCCGAGACTGATGGCTATGTTGCTCCCCTGGCCTGC

AGCCCCCAGCCCGAGTATGTGAACCAATCAGAGGTTCAGCCTCAGCCTCC

TTTAACCCCAGAGGGTCCTCTGCCTCCTGTCCGGCCTGCTGGTGCTACTC

TAGAAAGACCCAAGACTCTCTCTCCTGGGAAGAATGGGGTTGTCAAAGAC

GTTTTTGCCTTCGGGGGTGCTGTGGAGAACCCTGAATACTTAGTACCGAG

AGAAGGCACTGCCTCTCCGCCCCACCCTTCTCCTGCCTTCAGCCCAGCCT

TTGACAACCTCTATTACTGGGACCAGAACTCATCGGAGCAGGGGCCTCCA

CCAAGTAACTTTGAAGGGACCCCCACTGCAGAGAACCCTGAGTACCTAGG

CCTGGATGTACCTGTA.

In one embodiment, the nucleic acid sequence encoding the rat/Her-2/neu EC1 fragment is (SEQ ID NO: 46)
CCCAGGCAGAACCCCAGAGGGGCTGCGGGAGCTGCAGCTTCGAAGTCTCA

CAGAGATCCTGAAGGGAGGAGTTTTGATCCGTGGGAACCCTCAGCTCTGC

TACCAGGACATGGTTTTGTGGAAGGACGTCTTCCGCAAGAATAACCAACT

GGCTCCTGTCGATATAGACACCAATCGTTCCCGGGCCTGTCCACCTTGTG

CCCCCGCCTGCAAAGACAATCACTGTTGGGGTGAGAGTCCGGAAGACTGT

CAGATCTTGACTGGCACCATCTGTACCAGTGGTTGTGCCCGGTGCAAGGG

CCGGCTGCCCACTGACTGCTGCCATGAGCAGTGTGCCGCAGGCTGCACGG

GCCCCAAGCA.

In another embodiment, the nucleic acid sequence encoding the rat Her-2/neu EC2 fragment is:

(SEQ ID NO: 47)
GGTCACAGCTGAGGACGGAACACAGCGTTGTGAGAAATGCAGCAAGCCCT

GTGCTCGAGTGTGCTATGGTCTGGGCATGGAGCACCTTCGAGGGGCGAGG

GCCATCACCAGTGACAATGTCCAGGAGTTTGATGGCTGCAAGAAGATCTT

TGGGAGCCTGGCATTTTTGCCGGAGAGCTTTGATGGGGACCCCTCCTCCG

GCATTGCTCCGCTGAGGCCTGAGCAGCTCCAAGTGTTCGAAACCCTGGAG

GAGATCACAGGTTACCTGTACATCTCAGCATGGCCAGACAGTCTCCGTGA

CCTCAGTGTCTTCCAGAACCTTCGAATCATTCGGGGACGGATTCTCCACG

ATGGCGCGTACTCATTGACACTGCAAGGCCTGGGGATCCACTCGCTGGGG

CTGCGCTCACTGCGGGAGCTGGGCAGTGGATTGGCTCTGATTCACCGCAA

CGCCCATCTCTGCTTTGTACACACTGTACCTTGGGACCAGCTCTTCCGGA

ACCCACATCAGGCCCTGCTCCACAGTGGGAACCGGCCGGAAGAGGATTGT

GGTCTCGAGGGCTTGGTCTGTAACTCACTGTGTGCCCACGGGCACTGCTG

GGGGCCAGGGCCCACCCA.

In another embodiment, the nucleic acid sequence encoding the rat Her-2/neu IC1 fragment is:

(SEQ ID NO: 48)
CGCCCAGCGGAGCAATGCCCAACCAGGCTCAGATGCGGATCCTAAAAG

AGACGGAGCTAAGGAAGGTGAAGGTGCTTGGATCAGGAGCTTTTGGCACT

GTCTACAAGGGCATCTGGATCCCAGATGGGGAGAATGTGAAAATCCCCGT

GGCTATCAAGGTGTTGAGAGAAAACACATCTCCTAAAGCCAACAAAGAAA

TTCTAGATGAAGCGTATGTGATGGCTGGTGTGGGTTCTCCGTATGTGTCC

CGCCTCCTGGGCATCTGCCTGACATCCACAGTACAGCTGGTGACACAGCT

TATGCCCTACGGCTGCCTTCTGGACCATGTCCGAGAACACCGAGGTCGCC

TAGGCTCCCAGGACCTGCTCAACTGGTGTGTTCAGATTGCCAAGGGGATG

AGCTACCTGGAGGACGTGCGGCTTGTACACAGGGACCTGGCTGCCCGGAA

TGTGCTAGTCAAGAGTCCCAACCACGTCAAGATTACAGATTTCGGGCTGG

CTCGGCTGCTGGACATTGATGAGACAGAGTACCATGCAGATGGGGCAAG

GTGCCCATCAAATGGATGGCATTGGAATCTATTCTCAGACGCCGGTTCAC

CCATCAGAGTGATGTGTGGAGCTATGGAGTGACTGTGTGGGAGCTGATGA

CTTTTGGGGCCAAACCTTACGATGGAATCCCAGCCCGGGAGATCCCTGAT

TTGCTGGAGAAGGGAGAACGCCTACCTCAGCCTCCAATCTGCACCATTGA

TGTCTACATGATTATGGTCAAATGTTGGATGATTGACTCTGAATGTCGCC

CGAGATTCCGGGAGTTGGTGTCAGAATTTTCACGTATGGCGAGGGACCCC

CAGCGTTTTGTGGTCATCCAGAACGAGGACTTGGGCCCATCCAGCCCCAT

GGACAGTACCTTCTACCGTTCACTGCTGGAA.

In one embodiment, the nucleic acid sequence of human-Her-2/neu gene is:

(SEQ ID NO: 49)
ATGGAGCTGGCGGCCTTGTGCCGCTGGGGGCTCCTCCTCGCCCTCTTGC

CCCCCGGAGCCGCGAGCACCCAAGTGTGCACCGGCACAGACATGAAGCTG

-continued
CGGCTCCCTGCCAGTCCCGAGACCCACCTGGACATGCTCCGCCACCTCTA
CCAGGGCTGCCAGGTGGTGCAGGGAAACCTGGAACTCACCTACCTGCCCA
CCAATGCCAGCCTGTCCTTCCTGCAGGATATCCAGGAGGTGCAGGGCTAC
GTGCTCATCGCTCACAACCAAGTGAGGCAGGTCCCACTGCAGAGGCTGCG
GATTGTGCGAGGCACCCAGCTCTTTGAGGACAACTATGCCCTGGCCGTGC
TAGACAATGGAGACCCGCTGAACAATACCACCCCTGTCACAGGGGCCTCC
CCAGGAGGCCTGCGGGAGCTGCAGCTTCGAAGCCTCACAGAGATCTTGAA
AGGAGGGGTCTTGATCCAGCGGAACCCCCAGCTCTGCTACCAGGACACGA
TTTTGTGGAAGGACATCTTCCACAAGAACAACCAGCTGGCTCTCACACTG
ATAGACACCAACCGCTCTCGGGCCTGCCACCCCTGTTCTCCGATGTGTAA
GGGCTCCCGCTGCTGGGGAGAGAGTTCTGAGGATTGTCAGAGCCTGACGC
GCACTGTCTGTGCCGGTGGCTGTGCCCGCTGCAAGGGGCCACTGCCCACT
GACTGCTGCCATGAGCAGTGTGCTGCCGGCTGCACGGGCCCCAAGCACTC
TGACTGCCTGGCCTGCCTCCACTTCAACCACAGTGGCATCTGTGAGCTGC
ACTGCCCAGCCCTGGTCACCTACAACACAGACACGTTTGAGTCCATGCCC
AATCCCGAGGGCCGGTATACATTCGGCGCCAGCTGTGTGACTGCCTGTCC
CTACAACTACCTTTCTACGACGTGGGATCCTGCACCCTCGTCTGCCCCC
TGCACAACCAAGAGGTGACAGCAGAGGATGGAACACAGCGGTGTGAGAAG
TGCAGCAAGCCCTGTGCCCGAGTGTGCTATGGTCTGGGCATGGAGCACTT
GCGAGAGGTGAGGGCAGTTACCAGTGCCAATATCCAGGAGTTTGCTGGCT
GCAAGAAGATCTTTGGGAGCCTGGCATTTCTGCCGGAGAGCTTTGATGGG
GACCCAGCCTCCAACACTGCCCCGCTCCAGCCAGAGCAGCTCCAAGTGTT
TGAGACTCTGGAAGAGATCACAGGTTACCTATACATCTCAGCATGGCCGG
ACAGCCTGCCTGACCTCAGCGTCTTCCAGAACCTGCAAGTAATCCGGGGA
CGAATTCTGCACAATGGCGCCTACTCGCTGACCCTGCAAGGGCTGGGCAT
CAGCTGGCTGGGGCTGCGCTCACTGAGGGAACTGGGCAGTGGACTGGCCC
TCATCCACCATAACACCCACCTCTGCTTCGTGCACACGGTGCCCTGGGAC
CAGCTCTTTCGGAACCCGCACCAAGCTCTGCTCCACACTGCCAACCGGCC
AGAGGACGAGTGTGTGGGCGAGGGCCTGGCCTGCCACCAGCTGTGCGCCC
GAGGGCACTGCTGGGGTCCAGGGCCCACCCAGTGTGTCAACTGCAGCCAG
TTCCTTCGGGGCCAGGAGTGCGTGGAGGAATGCCGAGTACTGCAGGGGCT
CCCCAGGGAGTATGTGAATGCCAGGCACTGTTTGCCGTGCCACCCTGAGT
GTCAGCCCCAGAATGGCTCAGTGACCTGTTTTGGACCGGAGGCTGACCAG
TGTGTGGCCTGTGCCCACTATAAGGACCCTCCCTTCTGCGTGGCCCGCTG
CCCCAGCGGTGTGAAACCTGACCTCTCCTACATGCCCATCTGGAAGTTTC
CAGATGAGGAGGGCGCATGCCAGCCTTGCCCCATCAACTGCACCCACTCC
TGTGTGGACCTGGATGACAAGGGCTGCCCCGCCGAGCAGAGAGCCAGCCC
TCTGACGTCCATCGTCTCTGCGGTGGTTGGCATTCTGCTGGTCGTGGTCT
TGGGGGTGGTCTTTGGGATCCTCATCAAGCGACGGCAGCAGAAGATCCGG
AAGTACACGATGCGGAGACTGCTGCAGGAAACGGAGCTGGTGGAGCCGCT
GACACCTAGCGGAGCGATGCCCAACCAGGCGCAGATGCGGATCCTGAAAG -continued
AGACGGAGCTGAGGAAGGTGAAGGTGCTTGGATCTGGCGCTTTTGGCACA
GTCTACAAGGGCATCTGGATCCCTGATGGGGAGAATGTGAAAATTCCAGT
GGCCATCAAAGTGTTGAGGGAAAACACATCCCCCAAAGCCAACAAAGAAA
TCTTAGACGAAGCATACGTGATGGCTGGTGTGGGCTCCCCATATGTCTCC
CGCCTTCTGGGCATCTGCCTGACATCCACGGTGCAGCTGGTGACACAGCT
TATGCCCTATGGCTGCCTCTTAGACCATGTCCGGGAAAACCGCGGACGCC
TGGGCTCCCAGGACCTGCTGAACTGGTGTATGCAGATTGCCAAGGGGATG
AGCTACCTGGAGGATGTGCGGCTCGTACACAGGGACTTGGCCGCTCGGAA
CGTGCTGGTCAAGAGTCCCAACCATGTCAAAATTACAGACTTCGGGCTGG
CTCGGCTGCTGGACATTGACGAGACAGAGTACCATGCAGATGGGGGCAAG
GTGCCCATCAAGTGGATGGCGCTGGAGTCCATTCTCCGCCGGCGGTTCAC
CCACCAGAGTGATGTGTGGAGTTATGGTGTGACTGTGTGGGAGCTGATGA
CTTTTGGGGCCAAACCTTACGATGGGATCCCAGCCCGGGAGATCCCTGAC
CTGCTGGAAAAGGGGGAGCGGCTGCCCCAGCCCCCCATCTGCACCATTGA
TGTCTACATGATCATGGTCAAATGTTGGATGATTGACTCTGAATGTCGGC
CAAGATTCCGGGAGTTGGTGTCTGAATTCTCCCGCATGGCCAGGGACCCC
CAGCGCTTTGTGGTCATCCAGAATGAGGACTTGGGCCCAGCCAGTCCCTT
GGACAGCACCTTCTACCGCTCACTGCTGGAGGACGATGACATGGGGGACC
TGGTGGATGCTGAGGAGTATCTGGTACCCCAGCAGGGCTTCTTCTGTCCA
GACCCTGCCCCGGGCGCTGGGGGCATGGTCCACCACAGGCACCGCAGCTC
ATCTACCAGGAGTGGCGGTGGGGACCTGACACTAGGGCTGGAGCCCTCTG
AAGAGGAGGCCCCCAGGTCTCCACTGGCACCCTCCGAAGGGGCTGGCTCC
GATGTATTTGATGGTGACCTGGGAATGGGGGCAGCCAAGGGGCTGCAAAG
CCTCCCCACACATGACCCCAGCCCTCTACAGCGGTACAGTGAGGACCCCA
CAGTACCCCTGCCCTCTGAGACTGATGGCTACGTTGCCCCCCTGACCTGC
AGCCCCAGCCTGAATATGTGAACCAGCCAGATGTTCGGCCCCAGCCCCC
TTCGCCCCGAGAGGGCCCTCTGCCTGCTGCCCGACCTGCTGGTGCCACTC
TGGAAAGGGCCAAGACTCTCTCCCCAGGGAAGAATGGGGTCGTCAAAGAC
GTTTTTGCCTTTGGGGGTGCCGTGGAGAACCCCGAGTACTTGACACCCCA
GGGAGGAGCTGCCCCTCAGCCCCACCCTCCTCCTGCCTTCAGCCCAGCCT
TCGACAACCTCTATTACTGGGACCAGGACCCACCAGAGCGGGGGCTCCA
CCCAGCACCTTCAAAGGGACACCTACGGCAGAGAACCCAGAGTACCTGGG
TCTGGACGTGCCAGTGTGAACCAGAAGGCCAAGTCCGCAGAAGCCCTGA.

In another embodiment, the nucleic acid sequence encoding the human Her-2/neu EC1 fragment implemented into the chimera spans from 120-510 bp of the human EC1 region and is set forth in (SEQ ID NO: 50).

(SEQ ID NO: 50)
GAGACCCACCTGGACATGCTCCGCCACCTCTACCAGGGCTGCCAGGTG
GTGCAGGGAAACCTGGAACTCACCTACCTGCCCACCAATGCCAGCCTGTC
CTTCCTGCAGGATATCCAGGAGGTGCAGGGCTACGTGCTCATCGCTCACA

```
ACCAAGTGAGGCAGGTCCCACTGCAGAGGCTGCGGATTGTGCGAGGCACC

CAGCTCTTTGAGGACAACTATGCCCTGGCCGTGCTAGACAATGGAGACCC

GCTGAACAATACCACCCCTGTCACAGGGGCCTCCCCAGGAGGCCTGCGGG

AGCTGCAGCTTCGAAGCCTCACAGAGATCTTGAAAGGAGGGGTCTTGATC

CAGCGGAACCCCCAGCTCTGCTACCAGGACACGATTTTGTGGAAG.
```

In one embodiment, the complete EC1 human Her-2/neu fragment spans from (58-979 bp of the human Her-2/neu gene and is set forth in (SEQ ID NO: 54).

```
                                          (SEQ ID NO: 54)
GCCGCGAGCACCCAAGTGTGCACCGGCACAGACATGAAGCTGCGGCTC

CCTGCCAGTCCCGAGACCCACCTGGACATGCTCCGCCACCTCTACCAGGG

CTGCCAGGTGGTGCAGGGAAACCTGGAACTCACCTACCTGCCCACCAATG

CCAGCCTGTCCTTCCTGCAGGATATCCAGGAGGTGCAGGGCTACGTGCTC

ATCGCTCACAACCAAGTGAGGCAGGTCCCACTGCAGAGGCTGCGGATTGT

GCGAGGCACCCAGCTCTTTGAGGACAACTATGCCCTGGCCGTGCTAGACA

ATACCACCCCTGTCACAGGGGCCTCCCCAGGAGGCCTGCGGGAGCTGCAG

CATGGAGACCCGCTGAACATTCGAAGCCTCACAGAGATCTTGAAAGGAGG

GGTCTTGATCCAGCGGAACCCCCAGCTCTGCTACCAGGACACGATTTTGT

GGAAGGACATCTTCCACAAGAACAACCAGCTGGCTCTCACACTGATAGAC

ACCAACCGCTCTCGGGCCTGCCACCCCTGTTCTCCGATGTGTAAGGGCTC

CCGCTGCTGGGGAGAGAGTTCTGAGGATTGTCAGAGCCTGACGCGCACTG

TCTGTGCCGGTGGCTGTGCCCGCTGCAAGGGGCCACTGCCCACTGACTGC

TGCCATGAGCAGTGTGCTGCCGGCTGCACGGGCCCCAAGCACTCTGACTG

CCTGGCCTGCCTCCACTTCAACCACAGTGGCATCTGTGAGCTGCACTGCC

CAGCCCTGGTCACCTACAACACAGACACGTTTGAGTCCATGCCCAATCCC

GAGGGCCGGTATACATTCGGCGCCAGCTGTGTGACTGCCTGTCCCTACAA

CTACCTTTCTACGGACGTGGGATCCTGCACCCTCGTCTGCCCCCTGCACA

ACCAAGAGGTGACAGCAGAGGAT.
```

In another embodiment, the nucleic acid sequence encoding the human Her-2/neu EC2 fragment implemented into the chimera spans from 1077-1554 bp of the human Her-2/neu EC2 fragment and includes a 50 bp extension, and is set forth in (SEQ ID NO: 51).

```
                                          (SEQ ID NO: 51)
AATATCCAGGAGTTTGCTGGCTGCAAGAAGATCTTTGGGAGCCTGGCA

TTTCTGCCGGAGAGCTTTGATGGGGACCCAGCCTCCAACACTGCCCCGCT

CCAGCCAGAGCAGCTCCAAGTGTTTGAGACTCTGGAAGAGATCACAGGTT

ACCTATACATCTCAGCATGGCCGGACAGCCTGCCTGACCTCAGCGTCTTC

CAGAACCTGCAAGTAATCCGGGACGAATTCTGCACAATGGCGCCTACTC

GCTGACCCTGCAAGGGCTGGGCATCAGCTGGCTGGGGCTGCGCTCACTGA

GGGAACTGGGCAGTGGACTGGCCCTCATCCACCATAACACCCACCTCTGC

TTCGTGCACACGGTGCCCTGGGACCAGCTCTTTCGGAACCCGCACCAAGC
```

```
TCTGCTCCACACTGCCAACCGGCCAGAGGACGAGTGTGTGGGCGAGGGCC

TGGCCTGCCACCAGCTGTGCGCCCGAGGG.
```

In one embodiment, complete EC2 human Her-2/neu fragment spans from 907-1504 bp of the human Her-2/neu gene and is set forth in (SEQ ID NO: 55).

```
                                          (SEQ ID NO: 55)
TACCTTTCTACGGACGTGGGATCCTGCACCCTCGTCTGCCCCCTGCACA

ACCAAGAGGTGACAGCAGAGGATGGAACACAGCGGTGTGAGAAGTGCAGC

AAGCCCTGTGCCCGAGTGTGCTATGGTCTGGGCATGGAGCACTTGCGAGA

GGTGAGGGCAGTTACCAGTGCCAATATCCAGGAGTTTGCTGGCTGCAAGA

AGATCTTTGGGAGCCTGGCATTTCTGCCGGAGAGCTTTGATGGGGACCCA

GCCTCCAACACTGCCCCGCTCCAGCCAGAGCAGCTCCAAGTGTTTGAGAC

TCTGGAAGAGATCACAGGTTACCTATACATCTCAGCATGGCCGGACAGCC

TGCCTGACCTCAGCGTCTTCCAGAACCTGCAAGTAATCCGGGGACGAATT

CTGCACAATGGCGCCTACTCGCTGACCCTGCAAGGGCTGGGCATCAGCTG

GCTGGGGCTGCGCTCACTGAGGGAACTGGGCAGTGGACTGGCCCTCATCC

ACCATAACACCCACCTCTGCTTCGTGCACACGGTGCCCTGGGACCAGCTC

TTTCGGAACCCGCACCAAGCTCTGCTCCACACTGCCAACCGGCCAGAG.
```

In another embodiment, the nucleic acid sequence encoding the human Her-2/neu IC1 fragment implemented into the chimera is set forth in (SEQ ID NO: 52).

```
                                          (SEQ ID NO: 52)
CAGCAGAAGATCCGGAAGTACACGATGCGGAGACTGCTGCAGGAAAC

GGAGCTGGTGGAGCCGCTGACACCTAGCGGAGCGATGCCCAACCAGGCGC

AGATGCGGATCCTGAAAGAGACGGAGCTGAGGAAGGTGAAGGTGCTTGGA

TCTGGCGCTTTTGGCACAGTCTACAAGGGCATCTGGATCCCTGATGGGGA

GAATGTGAAAATTCCAGTGGCCATCAAAGTGTTGAGGGAAAACACATCCC

CCAAAGCCAACAAAGAAATCTTAGACGAAGCATACGTGATGGCTGGTGTG

GGCTCCCCATATGTCTCCCGCCTTCTGGGCATCTGCCTGACATCCACGGT

GCAGCTGGTGACACAGCTTATGCCCTATGGCTGCCTCTTAGACT.
```

In another embodiment, the nucleic acid sequence encoding the complete human Her-2/neu IC1 fragment spans from 2034-3243 of the human Her-2/neu gene and is set forth in (SEQ ID NO: 56).

```
                                          (SEQ ID NO: 56)
CAGCAGAAGATCCGGAAGTACACGATGCGGAGACTGCTGCAGGAAAC

GGAGCTGGTGGAGCCGCTGACACCTAGCGGAGCGATGCCCAACCAGGCGC

AGATGCGGATCCTGAAAGAGACGGAGCTGAGGAAGGTGAAGGTGCTTGGA

TCTGGCGCTTTTGGCACAGTCTACAAGGGCATCTGGATCCCTGATGGGGA

GAATGTGAAAATTCCAGTGGCCATCAAAGTGTTGAGGGAAAACACATCCC

CCAAAGCCAACAAAGAAATCTTAGACGAAGCATACGTGATGGCTGGTGTG

GGCTCCCCATATGTCTCCCGCCTTCTGGGCATCTGCCTGACATCCACGGT

GCAGCTGGTGACACAGCTTATGCCCTATGGCTGCCTCTTAGACCATGTCC
```

-continued
```
GGGAAAACCGCGGACGCCTGGGCTCCCAGGACCTGCTGAACTGGTGTATG
CAGATTGCCAAGGGGATGAGCTACCTGGAGGATGTGCGGCTCGTACACAG
GGACTTGGCCGCTCGGAACGTGCTGGTCAAGAGTCCCAACCATGTCAAAA
TTACAGACTTCGGGCTGGCTCGGCTGCTGGACATTGACGAGACAGAGTAC
CATGCAGATGGGGCAAGGTGCCCATCAAGTGGATGGCGCTGGAGTCCAT
TCTCCGCCGGCGGTTCACCCACCAGAGTGATGTGTGGAGTTATGGTGTGA
CTGTGTGGGAGCTGATGACTTTTGGGGCCAAACCTTACGATGGGATCCCA
GCCCGGGAGATCCCTGACCTGCTGGAAAAGGGGGAGCGGCTGCCCCAGCC
CCCCATCTGCACCATTGATGTCTACATGATCATGGTCAAATGTTGGATGA
TTGACTCTGAATGTCGGCCAAGATTCCGGGAGTTGGTGTCTGAATTCTCC
CGCATGGCCAGGGACCCCCAGCGCTTTGTGGTCATCCAGAATGAGGACTT
GGGCCCAGCCAGTCCCTTGGACAGCACCTTCTACCGCTCACTGCTGGAGG
```

-continued
```
ACGATGACATGGGGGACCTGGTGGATGCTGAGGAGTATCTGGTACCCCAG
CAGGGCTTCTTCTGTCCAGACCCTGCCCCGGGCGCTGGGGGCATGGTCCA
CCACAGGCACCGCAGCTCATCTACCAGGAGTGGCGGTGGGGACCTGACAC
TAGGGCTGGAGCCCTCTGAAGAGGAGGCCCCCAGGTCTCCACTGGCACCC
TCCGAAGGGGCT.
```

The LLO utilized in the methods and compositions provided herein is, in one embodiment, a *Listeria* LLO. In one embodiment, the *Listeria* from which the LLO is derived is *Listeria monocytogenes* (LM). In another embodiment, the *Listeria* is *Listeria ivanovii*. In another embodiment, the *Listeria* is *Listeria welshimeri*. In another embodiment, the *Listeria* is *Listeria seeligeri*. In another embodiment, the LLO protein is a non-Listerial LLO protein. In another embodiment, the LLO protein is a synthetic LLO protein. In another embodiment it is a recombinant LLO protein.

In one embodiment, the LLO protein is encoded by the following nucleic acid sequence set forth in (SEQ ID NO: 3)

```
(SEQ ID NO: 3)
atgaaaaaaataatgctagtattattacacttatattagttagtctaccaattgcgcaacaaactgaagcaaaggatgcatct
gcattcaataaagaaaattcaatttcatccatggcaccaccagcatctccgcctgcaagtcctaagacgccaatcgaaagaaacacg
cggatgaaatcgataagtatatacaaggattggattacaataaaaacaatgtattagtataccacggagatgcagtgacaaatgtgccg
ccaagaaaaggttacaaagatggaaatgaatatattgttgtggagaaaaagaagaaatccatcaatcaaaataatgcagacattcaagt
tgtgaatgcaatttcgagcctaacctatccaggtgctctcgtaaaagcgaattcggaattagtagaaaatcaaccagatgttctccctgta
aaacgtgattcattaacactcagcattgatttgccaggtatgactaatcaagacaataaaatagagtaaaaaatgccactaaatcaaacg
ttaacaacgcagtaaatacattagtggaaagatggaatgaaaaatatgctcaagcttatccaaatgtaagtgcaaaaattgattatgatga
cgaaatggcttacagtgaatcacaattaattgcgaaatttggtacagcatttaaagctgtaaataatagcttgaatgtaaacttcggcgca
atcagtgaagggaaatgcaagaagaagtcattagttttaaacaaatttactataacgtgaatgttaatgaacctacaagaccaccagat
ttacggcaaagctgttactaaagagcagagcaagcgcttggagtgaatgcagaaaatcctcctgcatatatctcaagtgtggcgtatg
gccgtcaagatatttgaaattatcaactaattcccatagtactaaagtaaaagctgctatgatgctgccgtaagcggaaaatctgtctcag
gtgatgtagaactaacaaatatcatcaaaaattcaccttcaaagccgtaatttacggaggaccgcaaaagatgaagttcaaatcatcga
cggcaacctcggagacttacgcgatattttgaaaaaaggcgctactataatcgagaaacaccaggagacccattgcttatacaacaaa
cttcctaaaagacaatgaattagctgttattaaaaacaactcagaatatattgaaacaacttcaaaagcttatacagatggaaaaattaaca
tcgatcactctggaggatacgttgctcaattcaacatttcttgggatgaagtaaattatgat.
```

In another embodiment, the LLO protein comprises the sequence SEQ ID NO: 4

```
(SEQ ID NO: 4)
M K K I M L V F I T L I L V S L P I A Q Q T E A K D A S A F
N K E N S I S S M A P P A S P P A S P K T P I E K K H A D E I D K
Y I Q G L D Y N K N N V L V Y H G D A V T N V P P R K G Y K D
G N E Y I V V E K K K S I N Q N N A D I Q V V N A I S S L T Y P
G A L V K A N S E L V E N Q P D V L P V K R D S L T L S I D L P G
M T N Q D N K I V V K N A T K S N V N N A V N T L V E R W N E
K Y A Q A Y P N V S A K I D Y D D E M A Y S E S Q L I A K F G T
A F K A V N N S L N V N F G A I S E G K M Q E E V I S F K Q I Y Y
```

-continued

```
N V N V N E P T R P S R F F G K A V T K E Q L Q A L G V N A E N

P P A Y I S S V A Y G R Q V Y L K L S T N S H S T K V K A A F D

A A V S G K S V S G D V E L T N I I K N S S F K A V I Y G G S A K

D E V Q I I D G N L G D L R D I L K K G A T F N R E T P G V P I A

Y T T N F L K D N E L A V I K N N S E Y I E T T S K A Y T D G K I

N I D H S G G Y V A Q F N I S W D E V N Y D
```

The first 25 amino acids of the proprotein corresponding to this sequence are the signal sequence and are cleaved from LLO when it is secreted by the bacterium. Thus, in this embodiment, the full length active LLO protein is 504 residues long. In another embodiment, the LLO protein has a sequence set forth in GenBank Accession No. DQ054588, DQ054589, AY878649, U25452, or U25452. In another embodiment, the LLO protein is a variant of an LLO protein. In another embodiment, the LLO protein is a homologue of an LLO protein. Each possibility represents a separate embodiment of the present invention.

In another embodiment, "truncated LLO" or "tLLO" refers to a fragment of LLO that comprises the PEST domain. In another embodiment, the terms refer to an LLO fragment that does not contain the activation domain at the amino terminus and does not include cystine 484. In another embodiment, the LLO fragment consists of a PEST sequence. In another embodiment, the LLO fragment comprises a PEST sequence. In another embodiment, the LLO fragment consists of about the first 400 to 441 amino acids of the 529 amino acid full-length LLO protein. In another embodiment, the LLO fragment is a non-hemolytic form of the LLO protein.

In another embodiment of methods and compositions of the present invention, a polypeptide encoded by a nucleic acid sequence of methods and compositions of the present invention is a fusion protein comprising the chimeric Her-2/neu antigen and an additional polypeptide, where in another embodiment, the fusion protein comprises, inter alia, a *Listeria Monocytogenes* non-hemolytic LLO protein (Examples herein).

In one embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425. Each possibility represents a separate embodiment of the present invention.

In another embodiment, a fusion protein of methods and compositions of the present invention comprises a PEST sequence, either from an LLO protein or from another organism, e.g. a prokaryotic organism.

The PEST amino acid sequence has, in another embodiment, a sequence selected from SEQ ID NO: 5-9. In another embodiment, the PEST sequence is a PEST sequence from the *Listeria Monocytogenes* ActA protein. In another embodiment, the PEST sequence is KTEEQPSEVNTGPR (SEQ ID NO: 5), KASVTDTSEGDLDSSMQSADESTPQ-PLK (SEQ ID NO: 6), KNEEVNASDFPPPPTDEELR (SEQ ID NO: 7), or RGGIPTSEEFSSLNSGDFTDDENS-ETTEEEIDR (SEQ ID NO: 8). In another embodiment, the PEST sequence is from Streptolysin O protein of *Streptococcus* sp. In another embodiment, the PEST sequence is from *Streptococcus pyogenes* Streptolysin O, e.g. KQN-TASTETTTTNEQPK (SEQ ID NO: 9) at amino acids 35-51. In another embodiment, the PEST sequence is from *Streptococcus equisimilis* Streptolysin O, e.g. KQNTAN-TETTTTNEQPK (SEQ ID NO: 10) at amino acids 38-54. In another embodiment, the PEST sequence is another PEST amino acid sequence derived from a prokaryotic organism. In another embodiment, the PEST sequence is any other PEST sequence known in the art. Each possibility represents a separate embodiment of the present invention.

In one embodiment, fusion of an antigen to the PEST sequence of *Listeria Monocytogenes* enhanced cell mediated and anti-tumor immunity of the antigen. Thus, fusion of an antigen to other PEST sequences derived from other prokaryotic organisms will also enhance immunogenicity of the antigen. PEST sequence of other prokaryotic organism can be identified in accordance with methods such as described by, for example Rechsteiner and Rogers (1996, Trends Biochem. Sci. 21:267-271) for *Listeria Monocytogenes*. Alternatively, PEST amino acid sequences from other prokaryotic organisms can also be identified based by this method. Other prokaryotic organisms wherein PEST amino acid sequences would be expected to include, but are not limited to, other *Listeria* species. In another embodiment, the PEST sequence is embedded within the antigenic protein. Thus, in another embodiment, "fusion" refers to an antigenic protein comprising both the antigen and the PEST amino acid sequence either linked at one end of the antigen or embedded within the antigen.

In another embodiment, provided herein is a vaccine comprising a recombinant polypeptide of the present invention. In another embodiment, provided herein is a vaccine consisting of a recombinant polypeptide of the present invention.

In another embodiment, provided herein is a nucleotide molecule encoding a recombinant polypeptide of the present invention. In another embodiment, provided herein is a vaccine comprising the nucleotide molecule.

In another embodiment, provided herein is a nucleotide molecule encoding a recombinant polypeptide of the present invention.

In another embodiment, provided herein is a recombinant polypeptide encoded by the nucleotide molecule of the present invention.

In another embodiment, provided herein is a vaccine comprising a nucleotide molecule or recombinant polypeptide of the present invention.

In another embodiment, provided herein is an immunogenic composition comprising a nucleotide molecule or recombinant polypeptide of the present invention.

In another embodiment, provided herein is a vector comprising a nucleotide molecule or recombinant polypeptide of the present invention.

In another embodiment, provided herein is a recombinant form of *Listeria* comprising a nucleotide molecule of the present invention.

In another embodiment, provided herein is a vaccine comprising a recombinant form of *Listeria* of the present invention.

In another embodiment, provided herein is a culture of a recombinant form of *Listeria* of the present invention.

In one embodiment, a vaccine or composition for use in the methods of the present invention comprises a recombinant *Listeria monocytogenes*, in any form or embodiment as described herein. In one embodiment, the vaccine or composition for use in the present invention consists of a recombinant *Listeria monocytogenes* of the present invention, in any form or embodiment as described herein. In another embodiment, the vaccine or composition for use in the methods of the present invention consists essentially of a recombinant *Listeria monocytogenes* of the present invention, in any form or embodiment as described herein. In one embodiment, the term "comprise" refers to the inclusion of a recombinant *Listeria monocytogenes* in the vaccine or composition, as well as inclusion of other vaccines, compositions or treatments that may be known in the art. In another embodiment, the term "consisting essentially of" refers to a vaccine, whose functional component is the recombinant *Listeria monocytogenes*, however, other components of the vaccine may be included that are not involved directly in the therapeutic effect of the vaccine and may, for example, refer to components which facilitate the effect of the recombinant *Listeria monocytogenes* (e.g. stabilizing, preserving, etc.). In another embodiment, the term "consisting" refers to a vaccine, which contains the recombinant *Listeria monocytogenes*.

In another embodiment, provided herein is a method of impeding or delaying metastatic disease origination from a HER2-expressing tumor in a subject, wherein and in another embodiment, the method comprises the step of administering to the subject a composition comprising the recombinant *Listeria* vaccine strain described herein.

In another embodiment, the methods of the present invention comprise the step of administering a recombinant *Listeria monocytogenes*, in any form or embodiment as described herein. In one embodiment, the methods of the present invention consist of the step of administering a recombinant *Listeria monocytogenes* of the present invention, in any form or embodiment as described herein. In another embodiment, the methods of the present invention consist essentially of the step of administering a recombinant *Listeria monocytogenes* of the present invention, in any form or embodiment as described herein. In one embodiment, the term "comprise" refers to the inclusion of the step of administering a recombinant *Listeria monocytogenes* in the methods, as well as inclusion of other methods or treatments that may be known in the art. In another embodiment, the term "consisting essentially of" refers to a methods, whose functional component is the administration of recombinant *Listeria monocytogenes*, however, other steps of the methods may be included that are not involved directly in the therapeutic effect of the methods and may, for example, refer to steps which facilitate the effect of the administration of recombinant *Listeria monocytogenes*. In one embodiment, the term "consisting" refers to a method of administering recombinant *Listeria monocytogenes* with no additional steps.

In another embodiment, the *Listeria* of methods and compositions of the present invention is *Listeria monocytogenes*. In another embodiment, the *Listeria* is *Listeria ivanovii*. In another embodiment, the *Listeria* is *Listeria welshimeri*. In another embodiment, the *Listeria* is *Listeria seeligeri*. Each type of *Listeria* represents a separate embodiment of the present invention.

In one embodiment, the *Listeria* strain of the methods and compositions of the present invention is the ADXS31-164 strain. In another embodiment, ADXS31-164 stimulates the secretion of IFN-γ by the splenocytes from wild type FVB/N mice. Further, the data presented herein show that ADXS31-164 is able to elicit anti-Her-2/neu specific immune responses to human epitopes that are located at different domains of the targeted antigen.

In another embodiment, the present invention provides a recombinant form of *Listeria* comprising a nucleotide molecule encoding a Her-2 chimeric protein or a fragment thereof.

In one embodiment, the two molecules of the fusion protein (the LLO, ActA fragment or PEST sequence and the antigen) are joined directly. In another embodiment, the two molecules are joined by a short spacer peptide, consisting of one or more amino acids. In one embodiment, the spacer has no specific biological activity other than to join the proteins or to preserve some minimum distance or other spatial relationship between them. In another embodiment, the constituent amino acids of the spacer are selected to influence some property of the molecule such as the folding, net charge, or hydrophobicity. In another embodiment, the two molecules of the protein (the LLO fragment and the antigen) are synthesized separately or unfused. In another embodiment, the two molecules of the protein are synthesized separately from the same nucleic acid. In yet another embodiment, the two molecules are individually synthesized from separate nucleic acids. Each possibility represents a separate embodiment of the present invention.

In one embodiment, nucleic acids encoding the recombinant polypeptides provided herein also encode a signal peptide or sequence. In another embodiment, the fusion protein of methods and compositions of the present invention comprises an LLO signal sequence from LLO. In one embodiment, a heterologous antigen may be expressed through the use of a signal sequence, such as a Listerial signal sequence, for example, the hemolysin signal sequence or the actA signal sequence. Alternatively, for example, foreign genes can be expressed downstream from a *L. monocytogenes* promoter without creating a fusion protein. In another embodiment, the signal peptide is bacterial (Listerial or non-Listerial). In one embodiment, the signal peptide is native to the bacterium. In another embodiment, the signal peptide is foreign to the bacterium. In another embodiment, the signal peptide is a signal peptide from *Listeria monocytogenes*, such as a secA1 signal peptide. In another embodiment, the signal peptide is a Usp45 signal peptide from *Lactococcus lactis*, or a Protective Antigen signal peptide from *Bacillus anthracis*. In another embodiment, the signal peptide is a secA2 signal peptide, such the p60 signal peptide from *Listeria monocytogenes*. In addition, the recombinant nucleic acid molecule optionally comprises a third polynucleotide sequence encoding p60, or a fragment thereof. In another embodiment, the signal peptide is a Tat signal peptide, such as a *B. subtilis* Tat signal peptide (e.g., PhoD). In one embodiment, the signal peptide is in the same translational reading frame encoding the recombinant polypeptide.

In another embodiment, provided herein is a method of inducing an anti-Her-2 immune response in a subject, comprising administering to the subject a recombinant nucleotide encoding a recombinant polypeptide comprising an N-terminal fragment of a LLO protein fused to a Her-2 chimeric protein or fused to a fragment thereof, thereby inducing an anti-Her-2 immune response in a subject.

In one embodiment, provided herein is a method of eliciting an enhanced immune response to a Her-2/neu-expressing tumor in a subject, where in another embodiment, the method comprises administering to the subject a composition comprising the recombinant *Listeria* vaccine strain provided herein. In another embodiment, the immune response against the Her-2-expressing tumor comprises an immune response to a subdominant epitope of the Her-2 protein. In another embodiment, the immune response against the Her-2-expressing tumor comprises an immune response to several subdominant epitopes of the Her-2 protein. In another embodiment, the immune response against the Her-2-expressing tumor comprises an immune response to at least 1-5 subdominant epitopes of the Her-2 protein. In another embodiment, the immune response against the Her-2-expressing tumor comprises an immune response to at least 1-10 subdominant epitopes of the Her-2 protein. In another embodiment, the immune response against the Her-2-expressing tumor comprises an immune response to at least 1-17 subdominant epitopes of the Her-2 protein. In another embodiment, the immune response against the Her-2-expressing tumor comprises an immune response to at least 17 subdominant epitopes of the Her-2 protein.

Point mutations or amino-acid deletions in the oncogenic protein Her-2/neu, have been reported to mediate treatment of resistant tumor cells, when these tumors have been targeted by small fragment *Listeria*-based vaccines or trastuzumab (a monoclonal antibody against an epitope located at the extracellular domain of the Her-2/neu antigen). Described herein is a chimeric Her-2/neu based composition which harbors two of the extracellular and one intracellular fragments of Her-2/neu antigen showing clusters of MHC-class I epitopes of the oncogene. This chimeric protein, which harbors 3 H2Dq and at least 17 of the mapped human MHC-class I epitopes of the Her-2/neu antigen was fused to the first 441 amino acids of the *Listeria-monocytogenes* listeriolysin O protein and expressed and secreted by the *Listeria monocytogenes* attenuated strain LmddA.

Previous reports have shown that when Her-2/neu transgenic mice were immunized with *Listeria*-based vaccines expressing and secreting small fragments of the Her-2/neu antigen separately (each of which harbored only one H2Dq epitope of the Her-2/neu oncogene), Her-2/neu over-expressing tumors could escape due to mutations in those epitopes of the Her-2/neu antigen targeted by each vaccine (see Singh R, Paterson Y. Immunoediting sculpts tumor epitopes during immunotherapy. Cancer Res 2007; 67: 1887-92). Demonstrated herein is the unexpected result that when three or more epitopes of the Her-2/neu protein are incorporated in a chimeric vaccine, it can eliminate the selection and escape of these tumors by escape mutations Immunization with the novel Her-2/neu chimeric *Listeria* vaccines did not result in any escape mutations that could be associated with point mutations or amino acid deletions in the Her-2/neu antigen (see Example 4 herein).

In one embodiment, provided herein is a method of engineering a *Listeria* vaccine strain to express a Her-2 chimeric protein or recombinant polypeptide expressing the chimeric protein, the method comprising transforming a *Listeria* strain with a nucleic acid molecule. In another embodiment, the nucleic acid molecule comprises a first open reading frame encoding a polypeptide, wherein the polypeptide comprises a Her-2/neu chimeric antigen. In another embodiment, the nucleic acid molecule further comprises a second open reading frame encoding a metabolic enzyme, and wherein said metabolic enzyme complements an endogenous gene that is mutated in the chromosome of the recombinant *Listeria* strain, thereby engineering a *Listeria* vaccine strain to express a Her-2 chimeric protein.

In one embodiment, the methods and compositions provided herein further comprise an adjuvant, which in one embodiment, is an independent adjuvant, where in another embodiment, the adjuvant or independent adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide. In another embodiment, the adjuvant is an aluminum adjuvant, Freund's adjuvant, MPL, emulsion, SBAS2, a nucleotide molecule encoding an immune-stimulating cytokine, a bacterial mitogen, or a bacterial toxin.

In one embodiment, an "adjuvant" is a component that potentiates the immune responses to an antigen and/or modulates it towards the desired immune responses. In one embodiment, the adjuvant is an immunologic adjuvant which in one embodiment is a substance that acts to accelerate, prolong, or enhance antigen-specific immune responses when used in combination with specific vaccine antigens.

In one embodiment, an "independent" adjuvant is an adjuvant that is independent, which in one embodiment, is not identical to the "additional adjuvant polypeptide" of the present invention which is present in a fusion polypeptide with a tumor specific antigen, which in one embodiment, is Her-2/neu.

In one embodiment, attenuated *Listeria* strains, such as *Listeria Monocytogenes* delta-actA mutant (Brundage et al, 1993, Proc. Natl. Acad. Sci., USA, 90:11890-11894), *L. monocytogenes* delta-plcA (Camilli et al, 1991, J. Exp. Med., 173:751-754), or delta-ActA, delta INL-b (Brockstedt et 5 al, 2004, PNAS, 101:13832-13837) are used in the present invention. In another embodiment, attenuated *Listeria* strains are constructed by introducing one or more attenuating mutations, as will be understood by one of ordinary skill in the art when equipped with the disclosure herein. Examples of such strains include, but are not limited to *Listeria* strains auxotrophic for aromatic amino acids (Alexander et al, 1993, Infection and Immunity 10 61:2245-2248) and mutant for the formation of lipoteichoic acids (Abachin et al, 2002, Mol. Microbiol. 43:1-14) and those attenuated by a lack of a virulence gene (see examples herein).

In another embodiment, the nucleic acid molecule of methods and compositions of the present invention is operably linked to a promoter/regulatory sequence. In another embodiment, the first open reading frame of methods and compositions of the present invention is operably linked to a promoter/regulatory sequence. In another embodiment, the second open reading frame of methods and compositions of the present invention is operably linked to a promoter/regulatory sequence. In another embodiment, the third open reading frame of methods and compositions of the present invention is operably linked to a promoter/regulatory sequence. In another embodiment, each of the open reading frames are operably linked to a promoter/regulatory sequence. Each possibility represents a separate embodiment of the present invention.

The skilled artisan, when equipped with the present disclosure and the methods provided herein, will readily understand that different transcriptional promoters, terminators, carrier vectors or specific gene sequences (e.g. those in commercially available cloning vectors) can be used successfully in methods and compositions of the present invention. As is contemplated in the present invention, these functionalities are provided in, for example, the commercially available vectors known as the pUC series. In another embodiment, non-essential DNA sequences (e.g. antibiotic resistance genes) are removed. Each possibility represents a separate embodiment of the present invention. In another embodiment, a commercially available plasmid is used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art.

In another embodiment, a plasmid such as pCR2.1 (Invitrogen, La Jolla, Calif.), which is a prokaryotic expression vector with a prokaryotic origin of replication and promoter/regulatory elements is used to facilitate expression of a polypeptide of the present invention in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

Antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, streptomycin, erythromycin, kanamycin, tetracycline, cloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the *Listeria* vaccine strain of the present invention is transformed by electroporation. Each method represents a separate embodiment of the present invention.

In another embodiment, conjugation is used to introduce genetic material and/or plasmids into bacteria. Methods for conjugation are well known in the art, and are described, for example, in Nikodinovic J et al. (A second generation snp-derived *Escherichia coli-Streptomyces* shuttle expression vector that is generally transferable by conjugation. Plasmid. 2006 November; 56(3):223-7) and Auchtung J M et al (Regulation of a *Bacillus subtilis* mobile genetic element by intercellular signaling and the global DNA damage response. Proc Natl Acad Sci USA. 2005 Aug. 30; 102 (35):12554-9). Each method represents a separate embodiment of the present invention.

"Transforming," in one embodiment, is used identically with the term "transfecting," and refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the present invention.

Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of 5 bacteriophage lambda (PL and PR), the trp, recA, lacZ, lad, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann Rev. Genet. 18:415-442). Further examples of promoter/regulatory elements contemplated in the present invention include, but are not limited to the Listerial prfA promoter, the Listerial hly promoter, the Listerial p60 promoter and the Listerial ActA promoter (GenBank Acc. No. NC_003210) or fragments thereof.

In another embodiment, a plasmid of methods and compositions of the present invention comprises a gene encoding a fusion protein. In another embodiment, subsequences are cloned and the appropriate subsequences cleaved using appropriate restriction enzymes. The fragments are then, in another embodiment, ligated to produce the desired DNA sequence. In another embodiment, DNA encoding the antigen is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

In another embodiment, the present invention further comprises a phage based chromosomal integration system for clinical applications. A host strain that is auxotrophic for essential enzymes, including, but not limited to, d-alanine racemase will be used, for example Lmdal(−)dat(−). In another embodiment, in order to avoid a "phage curing step," a phage integration system based on PSA is used (Lauer, et al., 2002 J Bacteriol, 184:4177-4186). This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain will be complemented.

The recombinant proteins of the present invention are synthesized, in another embodiment, using recombinant DNA methodology. This involves, in one embodiment, creating a DNA sequence that encodes the fusion protein, placing the DNA in an expression cassette, such as the plasmid of the present invention, under the control of a particular promoter/regulatory element, and expressing the protein. DNA encoding the fusion protein (e.g. non-hemolytic LLO/antigen) of the present invention is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 15 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then ligated to produce the desired DNA sequence.

In another embodiment, DNA encoding the fusion protein or the recombinant protein of the present invention is cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning. The same is repeated for the isolated nucleic acid encoding an antigen. Ligation of the non-hemolytic LLO and antigen sequences and insertion into a plasmid or vector produces a vector encoding non-hemolytic LLO joined to a terminus of the antigen. The two molecules are joined either directly or by a short spacer introduced by the restriction site.

In another embodiment, the molecules are separated by a peptide spacer consisting of one or more amino acids, generally the spacer will have no specific biological activity other than to join the proteins or to preserve some minimum distance or other spatial relationship between them. In another embodiment, the constituent amino acids of the spacer are selected to influence some property of the molecule such as the folding, net charge, or hydrophobicity. In another embodiment, the nucleic acid sequences encoding the fusion or recombinant proteins are transformed into a variety of host cells, including E. coli, other bacterial hosts, such as Listeria, yeast, and various higher eukaryotic cells such as the COS, CHO and HeLa cells lines and myeloma cell lines. The recombinant fusion protein gene will be operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e g immunoglobulin genes, SV40, cytomegalovirus, etc., and a polyadenylation sequence. In another embodiment, the sequences include splice donor and acceptor sequences.

In one embodiment, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In another embodiment, in order to select for an auxotrophic bacterium comprising the plasmid, transformed auxotrophic bacteria are grown on a media that will select for expression of the amino acid metabolism gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the *Listeria* vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, provided herein is a method of impeding the growth of a Her-2-expressing tumor in a subject, wherein and in another embodiment, the method comprises the step of administering to the subject a composition comprising the recombinant *Listeria* vaccine strain described herein.

In another embodiment, provided herein is a method of eliciting an enhanced immune response to a Her-2/neu-expressing tumor in a subject, wherein and in another embodiment, the method comprises the step of administering to the subject a composition comprising the recombinant *Listeria* vaccine strain described herein. In yet another embodiment, the immune response against the Her-2/neu-expressing tumor comprises an immune response to at least one subdominant epitope of the Her-2/neu protein.

In one embodiment, provided herein is a method of preventing an escape mutation in the treatment of Her-2/neu over-expressing tumors, wherein and in another embodiment, the method comprises the step of administering to said subject a composition comprising the recombinant *Listeria* vaccine strain provided herein.

In another embodiment, provided herein is a method of preventing the onset of a Her-2/neu antigen-expressing tumor in a subject, wherein and in another embodiment, the method comprises the step of administering to the subject a composition comprising the recombinant *Listeria* vaccine strain provided herein.

In one embodiment, provided herein is a method of decreasing the frequency of intra-tumoral T regulatory cells, wherein and in another embodiment, the method comprises the step of administering to the subject a composition comprising the recombinant *Listeria* vaccine strain provided herein.

In one embodiment, provided herein is a method of decreasing the frequency of intra-tumoral myeloid derived suppressor cells, wherein and in another embodiment, the method comprises the step of administering to the subject a composition comprising the recombinant *Listeria* vaccine strain provided herein.

In another embodiment, provided herein is a method of decreasing the frequency of myeloid derived suppressor cells, wherein and in another embodiment, the method comprises the step of administering to the subject a composition comprising the recombinant *Listeria* vaccine strain provided herein.

In one embodiment, provided herein a method of preventing the development of a Her-2/neu-expressing tumor in a subject, wherein and in another embodiment, the method comprises the step of administering to the subject a composition comprising the recombinant *Listeria* vaccine strain provided herein.

In another embodiment, provided herein is a method of preventing the formation of a metastatic disease coming from an Her-2/neu-expressing tumor in a subject, wherein and in another embodiment, the method comprises the step of administering to the subject a composition comprising the recombinant *Listeria* vaccine strain the provided herein.

In another embodiment, provided herein is a method of treating a metastatic disease originating from a Her-2/neu-expressing tumor in a subject, wherein and in another embodiment, the method comprises the step of administering to the subject a composition comprising the recombinant *Listeria* vaccine strain provided herein.

In one embodiment, provided herein is a method of administering the composition of the present invention. In another embodiment, provided herein is a method of administering the vaccine of the present invention. In another embodiment, provided herein is a method of administering the recombinant polypeptide or recombinant nucleotide of the present invention. In another embodiment, the step of administering the composition, vaccine, recombinant polypeptide or recombinant nucleotide of the present invention is performed with an attenuated recombinant form of *Listeria* comprising the composition, vaccine, recombinant nucleotide or expressing the recombinant polypeptide, each in its own discrete embodiment. In another embodiment, the administering is performed with a different attenuated bacterial vector. In another embodiment, the administering is performed with a DNA vaccine (e.g. a naked DNA vaccine). In another embodiment, administration of a recombinant polypeptide of the present invention is performed by producing the protein recombinantly, then administering the recombinant protein to a subject. Each possibility represents a separate embodiment of the present invention.

In another embodiment, the immune response elicited by methods and compositions of the present invention comprises a $CD8^+$ T cell-mediated response. In another embodiment, the immune response consists primarily of a $CD8^+$ T cell-mediated response. In another embodiment, the only detectable component of the immune response is a $CD8^+$ T cell-mediated response.

In another embodiment, the immune response elicited by methods and compositions provided herein comprises a $CD4^+$ T cell-mediated response. In another embodiment, the immune response consists primarily of a $CD4^+$ T cell-mediated response. In another embodiment, the only detectable component of the immune response is a $CD4^+$ T cell-mediated response. In another embodiment, the $CD4^+$ T cell-mediated response is accompanied by a measurable antibody response against the antigen. In another embodiment, the $CD4^+$ T cell-mediated response is not accompanied by a measurable antibody response against the antigen.

In another embodiment, the present invention provides a method of inducing a $CD8^+$ T cell-mediated immune response in a subject against a subdominant $CD8^+$ T cell epitope of an antigen, comprising the steps of (a) fusing a nucleotide molecule encoding the Her2-neu chimeric antigen or a fragment thereof to a nucleotide molecule encoding an N-terminal fragment of a LLO protein, thereby creating a recombinant nucleotide encoding an LLO-antigen fusion protein; and (b) administering the recombinant nucleotide or the LLO-antigen fusion to the subject; thereby inducing a $CD8^+$ T cell-mediated immune response against a subdominant $CD8^+$ T cell epitope of an antigen.

In one embodiment, provided herein is a method of increasing intratumoral ratio of CD8+/T regulatory cells, wherein and in another embodiment, the method comprises the step of administering to the subject a composition comprising the recombinant polypeptide, recombinant *Listeria*, or recombinant vector of the present invention.

In another embodiment, provided herein is a method of decreasing the frequency of intra-tumoral T regulatory cells, wherein and in another embodiment, the method comprises the step of administering to the subject a composition comprising the recombinant *Listeria* vaccine strain provided herein.

In another embodiment, the immune response elicited by the methods and compositions provided herein comprises an immune response to at least one subdominant epitope of the antigen. In another embodiment, the immune response does not comprise an immune response to a subdominant epitope. In another embodiment, the immune response consists primarily of an immune response to at least one subdominant epitope. In another embodiment, the only measurable component of the immune response is an immune response to at least one subdominant epitope. Each type of immune response represents a separate embodiment of the present invention.

In one embodiment, methods of this invention break tolerance in a subject to a Her-2/neu expressing tumor or cancer in said subject, wherein and in another embodiment, the method comprises the step of administering to the subject a composition comprising the recombinant *Listeria* vaccine strain provided herein.

Methods of measuring immune responses are well known in the art, and include, e.g. measuring suppression of tumor growth, flow cytometry, target cell lysis assays (e.g. chromium release assay), the use of tetramers, and others. Each method represents a separate embodiment of the present invention.

In another embodiment, the present invention provides a method of impeding the growth of a Her-2-expressing tumor in a subject, wherein and in another embodiment, the method comprises administering to the subject a combination of radiation therapy and a recombinant polypeptide comprising an N-terminal fragment of a LLO protein fused to the Her-2 chimeric protein or a fragment thereof or a recombinant nucleotide encoding the recombinant polypeptide, wherein the subject mounts an immune response against the Her-2-expressing tumor, thereby impeding the growth of a Her-2-expressing tumor in a subject.

In another embodiment, the present invention provides a method of delaying or inhibiting a metastatic disease emanating from a Her-2-expressing tumor in a subject, wherein and in another embodiment, the method comprises administering to the subject a combination of radiation therapy and a recombinant polypeptide comprising an N-terminal fragment of a LLO protein fused to the Her-2 chimeric protein or a fragment thereof or a recombinant nucleotide encoding the recombinant polypeptide, wherein the subject mounts an immune response against the Her-2-expressing tumor, thereby delaying or inhibiting the metastatic disease emanating from a Her-2-expressing tumor in a subject.

In another embodiment, the present invention provides a method of improving the antigenicity of a Her-2 chimeric protein, wherein and in another embodiment, the method comprises the step of fusing a nucleotide encoding an N-terminal fragment of a LLO protein to a nucleotide encoding the Her-2 protein or a fragment thereof to create a recombinant nucleotide, thereby improving the antigenicity of a Her-2 chimeric protein.

In another embodiment, provided herein is a method of improving the antigenicity of a Her-2 chimeric protein, wherein and in another embodiment, the method comprises engineering a *Listeria* strain to express the recombinant nucleotide. In another embodiment, a different bacterial vector is used to express the recombinant nucleotide. In another embodiment, the bacterial vector is attenuated. In another embodiment, a DNA vaccine (e.g. a naked DNA vaccine) is used to express the recombinant nucleotide. In another embodiment, administration of the LLO-Her-2 chimera fusion peptide encoded by the nucleotide is performed by producing the protein recombinantly, then administering the recombinant protein to a subject. Each possibility represents a separate embodiment of the present invention.

In one embodiment, the present invention provides a method that induces "epitope spreading" of a tumor. In another embodiment, the immunization using the compositions and methods provided herein induce epitope spreading onto other tumors bearing antigens other than the antigen carried in the vaccine of the present invention.

In another embodiment, the dominant epitope or subdominant epitope is dominant or subdominant, respectively, in the subject being treated. In another embodiment, the dominant epitope or subdominant epitope is dominant or subdominant in a population being treated.

In one embodiment, provided herein is a method of preventing, treating, suppressing, inhibiting, inducing an immune response against, or eliciting an enhanced immune response against sub-dominant epitopes against a cancer or a tumor growth in a subject by epitope spreading wherein and in another embodiment, said cancer is associated with expression of an antigen or fragment thereof comprised in the composition of the present invention. In another embodiment, the method comprises administering to said subject a composition comprising the recombinant polypeptide, recombinant *Listeria*, or recombinant vector of the present invention. In yet another embodiment, the subject mounts an immune response against the antigen-expressing cancer or the antigen-expressing tumor, thereby treating, suppressing, or inhibiting a cancer or a tumor growth in a subject.

"Dominant $CD8^+$ T cell epitope," in one embodiment, refers to an epitope that is recognized by over 30% of the antigen-specific $CD8^+$ T cells that are elicited by vaccination, infection, or a malignant growth with a protein or a pathogen or cancer cell containing the protein. In another embodiment, the term refers to an epitope recognized by over 35% of the antigen-specific $CD8^+$ T cells that are elicited thereby. In another embodiment, the term refers to an epitope recognized by over 40% of the antigen-specific $CD8^+$ T cells. In another embodiment, the term refers to an epitope recognized by over 45% of the antigen-specific $CD8^+$ T cells. In another embodiment, the term refers to an epitope recognized by over 50% of the antigen-specific $CD8^+$ T cells. In another embodiment, the term refers to an epitope recognized by over 55% of the antigen-specific $CD8^+$ T cells. In another embodiment, the term refers to an epitope recognized by over 60% of the antigen-specific $CD8^+$ T cells. In another embodiment, the term refers to an epitope recognized by over 65% of the antigen-specific $CD8^+$ T cells. In another embodiment, the term refers to an epitope recognized by over 70% of the antigen-specific $CD8^+$ T cells. In another embodiment, the term refers to an epitope recognized by over 75% of the antigen-specific $CD8^+$ T cells. In another embodiment, the term refers to an epitope recognized by over 80% of the antigen-specific $CD8^+$ T cells. In another embodiment, the term refers to an epitope recognized by over 85% of the antigen-specific $CD8^+$ T cells. In another embodiment, the term refers to an epitope recognized by over 90% of the antigen-specific $CD8^+$ T cells. In another embodiment, the term refers to an epitope recognized by over 95% of the antigen-specific $CD8^+$ T cells. In another embodiment, the term refers to an epitope recognized by over 96% of the antigen-specific $CD8^+$ T cells. In another embodiment, the term refers to an epitope recognized by over 97% of the antigen-specific $CD8^+$ T cells. In another embodiment, the term refers to an epitope recognized by over 98% of the antigen-specific $CD8^+$ T cells.

"Subdominant CD8+ T cell epitope," in one embodiment, refers to an epitope recognized by fewer than 30% of the antigen-specific CD8+ T cells that are elicited by vaccination, infection, or a malignant growth with a protein or a pathogen or cancer cell containing the protein. In another embodiment, the term refers to an epitope recognized by fewer than 28% of the antigen-specific CD8+ T cells. In another embodiment, the term refers to an epitope recognized by over 26% of the antigen-specific CD8+ T cells. In another embodiment, the term refers to an epitope recognized by fewer than 24% of the antigen-specific CD8+ T cells. In another embodiment, the term refers to an epitope recognized by over 22% of the antigen-specific CD8+ T cells. In another embodiment, the term refers to an epitope recognized by fewer than 20% of the antigen-specific CD8+ T cells. In another embodiment, the term refers to an epitope recognized by over 18% of the antigen-specific CD8+ T cells. In another embodiment, the term refers to an epitope recognized by fewer than 16% of the antigen-specific CD8+ T cells. In another embodiment, the term refers to an epitope recognized by over 14% of the antigen-specific CD8+ T cells. In another embodiment, the term refers to an epitope recognized by over 12% of the antigen-specific CD8+ T cells. In another embodiment, the term refers to an epitope recognized by fewer than 10% of the antigen-specific CD8+ T cells. In another embodiment, the term refers to an epitope recognized by over 8% of the antigen-specific CD8+ T cells. In another embodiment, the term refers to an epitope recognized by fewer than 6% of the antigen-specific CD8+ T cells. In another embodiment, the term refers to an epitope recognized by fewer than 5% of the antigen-specific CD8+ T cells. In another embodiment, the term refers to an epitope recognized by over 4% of the antigen-specific CD8+ T cells. In another embodiment, the term refers to an epitope recognized by fewer than 3% of the antigen-specific CD8+ T cells. In another embodiment, the term refers to an epitope recognized by fewer than 2% of the antigen-specific CD8+ T cells. In another embodiment, the term refers to an epitope recognized by fewer than 1% of the antigen-specific CD8+ T cells. In another embodiment, the term refers to an epitope recognized by fewer than 0.5% of the antigen-specific CD8+ T cells.

Each type of the dominant epitope and subdominant epitope represents a separate embodiment of the present invention.

The antigen in methods and compositions of the present invention is, in one embodiment, expressed at a detectable level on a non-tumor cell of the subject. In another embodiment, the antigen is expressed at a detectable level on at least a certain percentage (e.g. 0.01%, 0.03%, 0.1%, 0.3%, 1%, 2%, 3%, or 5%) of non-tumor cells of the subject. In one embodiment, "non-tumor cell" refers to a cell outside the body of the tumor. In another embodiment, "non-tumor cell" refers to a non-malignant cell. In another embodiment, "non-tumor cell" refers to a non-transformed cell. In another embodiment, the non-tumor cell is a somatic cell. In another embodiment, the non-tumor cell is a germ cell. Each possibility represents a separate embodiment of the present invention.

"Detectable level" refers, in one embodiment, to a level that is detectable when using a standard assay. In one embodiment, the assay is an immunological assay. In one embodiment, the assay is enzyme-linked immunoassay (ELISA). In another embodiment, the assay is Western blot. In another embodiment, the assay is FACS. It is to be understood by a skilled artisan that any other assay available in the art can be used in the methods provided herein. In another embodiment, a detectable level is determined relative to the background level of a particular assay. Methods for performing each of these techniques are well known to those skilled in the art, and each technique represents a separate embodiment of the present invention.

In one embodiment, vaccination with recombinant antigen-expressing *Listeria Monocytogenes* induces epitope spreading. In another embodiment, vaccination with LLO-antigen fusions, even outside the context of Her2, induces epitope spreading as well. Each possibility represents a separate embodiment of the present invention.

In another embodiment, the present invention provides a method of impeding the growth of an Her-2-expressing tumor in a subject, comprising administering to the subject a recombinant polypeptide comprising an N-terminal fragment of a LLO protein fused to a Her-2 chimeric antigen, wherein the antigen has one or more subdominant CD8+ T cell epitopes, wherein the subject mounts an immune response against the antigen-expressing tumor, thereby impeding the growth of an Her-2-expressing tumor in a subject. In another embodiment, the antigen does not contain any of the dominant CD8+ T cell epitopes. In another embodiment, provided herein is a method of impeding the growth on a Her-2-expressing tumor in a subject, comprising administering to the subject a recombinant form of *Listeria* comprising a recombinant nucleotide encoding the recombinant polypeptide provided herein.

In another embodiment, the present invention provides a method for inducing formation of cytotoxic T cells in a host having cancer, comprising administering to the host a composition of the present invention, thereby inducing formation of cytotoxic T cells in a host having cancer.

In another embodiment, the present invention provides a method of reducing an incidence of cancer, comprising administering a composition of the present invention. In another embodiment, the present invention provides a method of ameliorating cancer, comprising administering a composition of the present invention. Each possibility represents a separate embodiment of the present invention.

In one embodiment, the composition is administered to the cells of the subject ex vivo; in another embodiment, the composition is administered to the cells of a donor ex vivo; in another embodiment, the composition is administered to the cells of a donor in vivo, then is transferred to the subject. Each possibility represents a separate embodiment of the present invention.

In one embodiment, the cancer treated by a method of the present invention is breast cancer. In another embodiment, the cancer is a Her2 containing cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is a CNS carcinoma. In another embodiment, the cancer is an endometrial carcinoma. In another embodiment, the cancer is a bladder cancer. In another embodiment, the cancer is mesothelioma. In another embodiment, the cancer is malignant mesothelioma (MM). In another embodiment, the cancer is a head and neck cancer. In another embodiment, the cancer is a prostate carcinoma.

In one embodiment, the cancer is an osteosarcoma, which in one embodiment is a cancerous bone tumor. In one embodiment, the osteosarcoma is any one of the following subtypes: osteoblastic, chondroblastic, fibroblastic OSA, telangiectatic OSA, small cell OSA, low-grade central OSA, periosteal OSA, paraosteal OSA, secondary OSA, high-grade periosteal OSA, or extraskeletal OSA.

In another embodiment, the cancer is a Her-2/neu expressing osteosarcoma. In one embodiment, the osteosarcoma is canine osteosarcoma. In another embodiment, the osteosarcoma is localized osteosarcoma. In another embodiment, the osteosarcoma is metastatic osteosarcoma. In another embodiment, the osteosarcoma is high grade osteosarcoma. In another embodiment, the osteosarcoma is canine appendicular osteosarcoma. In another embodiment, the cancer is pulmonary metastatic disease. Each possibility represents a separate embodiment of the present invention.

In another embodiment of the methods of the present invention, the subject mounts an immune response against the antigen-expressing tumor or target antigen, thereby mediating the anti-tumor effects.

In another embodiment, the present invention provides an immunogenic composition for treating cancer, the composition comprising a fusion of a truncated LLO to a Her-2 chimeric protein. In another embodiment, the immunogenic composition further comprises a *Listeria* strain expressing the fusion. Each possibility represents a separate embodiment of the present invention. In another embodiment, the present invention provides an immunogenic composition for treating cancer, the composition comprising a *Listeria* strain expressing a Her-2 chimeric protein.

In another embodiment, provided herein is an immunogenic composition comprising a recombinant form of *Listeria* of the present invention.

In one embodiment, a treatment protocol of the present invention is therapeutic. In another embodiment, the protocol is prophylactic. In another embodiment, the vaccines of the present invention are used to protect people at risk for cancer such as breast cancer or other types of Her2-containing tumors because of familial genetics or other circumstances that predispose them to these types of ailments as will be understood by a skilled artisan. In another embodiment, the vaccines are used as a cancer immunotherapy after debulking of tumor growth by surgery, conventional chemotherapy or radiation treatment. In another embodiment, the vaccines are combined with radiation treatment and either surgery, conventional chemotherapy or both. Following such treatments, the vaccines of the present invention are administered so that the CTL response to the tumor antigen of the vaccine destroys remaining metastases and prolongs remission from the cancer. In another embodiment, vaccines are used as a cancer immunotherapy in combination with surgery, conventional chemotherapy, radiation treatment, or any combination thereof. In another embodiment, such combination treatment is used in subjects that cannot undergo amputation. In another embodiment, such combination treatment is used in subjects with primary osteosarcoma that cannot undergo amputation. In another embodiment, vaccines of the present invention are used to affect the growth of previously established tumors and to kill existing tumor cells. Each possibility represents a separate embodiment of the present invention.

In another embodiment, the vaccines and immunogenic compositions utilized in any of the methods described above have any of the characteristics of vaccines and immunogenic compositions of the present invention. Each characteristic represents a separate embodiment of the present invention. It is to be understood that compositions described in the context of the compositions and uses of the present invention may be referred to as immunogenic compositions and vice versa.

Various embodiments of dosage ranges are contemplated by this invention. In one embodiment, in the case of vaccine vectors, the dosage is in the range of 0.4 $LD_{50}$/dose. In another embodiment, the dosage is from about 0.4-4.9 $LD_{50}$/dose. In another embodiment the dosage is from about 0.5-0.59 $LD_{50}$/dose. In another embodiment the dosage is from about 0.6-0.69 $LD_{50}$/dose. In another embodiment the dosage is from about 0.7-0.79 $LD_{50}$/dose. In another embodiment the dosage is about 0.8 $LD_{50}$/dose. In another embodiment, the dosage is 0.4 $LD_{50}$/dose to 0.8 of the $LD_{50}$/dose.

In another embodiment, the dosage is $10^7$ bacteria/dose. In another embodiment, the dosage is $1.5 \times 10^7$ bacteria/dose. In another embodiment, the dosage is $2 \times 10^7$ bacteria/dose. In another embodiment, the dosage is $3 \times 10^7$ bacteria/dose. In another embodiment, the dosage is $4 \times 10^7$ bacteria/dose. In another embodiment, the dosage is $6 \times 10^7$ bacteria/dose. In another embodiment, the dosage is $8 \times 10^7$ bacteria/dose. In another embodiment, the dosage is $1 \times 10^8$ bacteria/dose. In another embodiment, the dosage is $1.5 \times 10^8$ bacteria/dose. In another embodiment, the dosage is $2 \times 10^8$ bacteria/dose. In another embodiment, the dosage is $3 \times 10^8$ bacteria/dose. In another embodiment, the dosage is $4 \times 10^8$ bacteria/dose. In another embodiment, the dosage is $6 \times 10^8$ bacteria/dose. In another embodiment, the dosage is $8 \times 10^8$ bacteria/dose. In another embodiment, the dosage is $1 \times 10^9$ bacteria/dose. In another embodiment, the dosage is $1.5 \times 10^9$ bacteria/dose. In another embodiment, the dosage is $2 \times 10^9$ bacteria/dose. In another embodiment, the dosage is $3 \times 10^9$ bacteria/dose. In another embodiment, the dosage is $5 \times 10^9$ bacteria/dose. In another embodiment, the dosage is $6 \times 10^9$ bacteria/dose. In another embodiment, the dosage is $8 \times 10^9$ bacteria/dose. In another embodiment, the dosage is $1 \times 10^{10}$ bacteria/dose. In another embodiment, the dosage is $1.5 \times 10^{10}$ bacteria/dose. In another embodiment, the dosage is $2 \times 10^{10}$ bacteria/dose. In another embodiment, the dosage is $3 \times 10^{10}$ bacteria/dose. In another embodiment, the dosage is $5 \times 10^{10}$ bacteria/dose. In another embodiment, the dosage is $6 \times 10^{10}$ bacteria/dose. In another embodiment, the dosage is $8 \times 10^{10}$ bacteria/dose. In another embodiment, the dosage is $8 \times 10^9$ bacteria/dose. In another embodiment, the dosage is $1 \times 10^{11}$ bacteria/dose. In another embodiment, the dosage is $1.5 \times 10^{11}$ bacteria/dose. In another embodiment, the dosage is $2 \times 10^{11}$ bacteria/dose. In another embodiment, the dosage is $3 \times 10^{11}$ bacteria/dose. In another embodiment, the dosage is $5 \times 10^{11}$ bacteria/dose. In another embodiment, the dosage is $6 \times 10^{11}$ bacteria/dose. In another embodiment, the dosage is $8 \times 10^{11}$ bacteria/dose. In another embodiment, the dosage is $5.0 \times 10^8$ bacteria/dose. In another embodiment, the dosage is $3.3 \times 10^9$ bacteria/dose. In another embodiment, a composition for the use in the methods provided herein comprises $3.3 \times 10^9$ *Listeria*/dose. Each possibility represents a separate embodiment of the present invention.

In one embodiment, a vaccine or immunogenic composition of the present invention is administered alone to a subject. In another embodiment, the vaccine or immunogenic composition is administered together with another cancer therapy, which in one embodiment is radiation therapy. Each possibility represents a separate embodiment of the present invention.

The recombinant *Listeria* of methods and compositions of the present invention is, in one embodiment, stably transformed with a construct encoding a Her-2 chimeric antigen or an LLO-Her-2 chimeric antigen fusion. In one embodiment, the construct contains a polylinker to facilitate further subcloning. Several techniques for producing recombinant *Listeria* are known.

In one embodiment, the construct or nucleic acid molecule is integrated into the Listerial chromosome using homologous recombination. Techniques for homologous recombination are well known in the art, and are described, for example, in Baloglu S, Boyle S M, et al (Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7); and Jiang L L, Song H H, et al., (Characterization of a mutant *Listeria monocytogenes* strain expressing green fluorescent protein. Acta Biochim Biophys Sin (Shanghai) 2005, 37(1): 19-24). In another embodiment, homologous recombination is performed as described in U.S. Pat. No. 6,855,320. In this case, a recombinant *Listeria Monocytogenes* strain that expresses E7 was made by chromosomal integration of the E7 gene under the control of the hly promoter and with the inclusion of the hly signal sequence to ensure secretion of the gene product, yielding the recombinant referred to as Lm-AZ/E7. In another embodiment, a temperature sensitive plasmid is used to select the recombinants. Each technique represents a separate embodiment of the present invention.

In another embodiment, the construct or nucleic acid molecule is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or nucleic acid molecule is integrated into the Listerial chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. Each possibility represents a separate embodiment of the present invention.

In another embodiment, one of various promoters is used to express the antigen or fusion protein containing same. In one embodiment, a *Listeria monocytogenes* promoter is used, e.g. promoters for the genes hly, actA, plea, plcB and mpl, which encode the Listerial proteins hemolysin, actA, phosphotidylinositol-specific phospholipase, phospholipase C, and metalloprotease, respectively. Each possibility represents a separate embodiment of the present invention.

In another embodiment, methods and compositions of the present invention utilize a homologue of a Her-2 chimeric protein or LLO sequence of the present invention. In another embodiment, the methods and compositions of the present invention utilize a Her-2 chimeric protein from a non-human mammal. The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

In another embodiment, the present invention provides an isolated nucleic acid encoding a signal peptide or a recombinant polypeptide or fusion protein of the present invention. In one embodiment, the isolated nucleic acid comprises a sequence sharing at least 65% homology with a nucleic acid encoding the signal peptide or the recombinant polypeptide or the fusion protein of the present invention. In another embodiment, the isolated nucleic acid comprises a sequence sharing at least 75% homology with a nucleic acid encoding the signal peptide or the recombinant polypeptide or the fusion protein of the present invention. In another embodiment, the isolated nucleic acid comprises a sequence sharing at least 85% homology with a nucleic acid encoding the signal peptide or the recombinant polypeptide or the fusion protein of the present invention. In another embodiment, the isolated nucleic acid comprises a sequence sharing at least 90% homology with a nucleic acid encoding the signal peptide or the recombinant polypeptide or the fusion protein of the present invention. In another embodiment, the isolated nucleic acid comprises a sequence sharing at least 95% homology with a nucleic acid encoding the signal peptide or the recombinant polypeptide or the fusion protein of the present invention. In another embodiment, the isolated nucleic acid comprises a sequence sharing at least 97% homology with a nucleic acid encoding the signal peptide or the recombinant polypeptide or the fusion protein of the present invention. In another embodiment, the isolated nucleic acid comprises a sequence sharing at least 99% homology with a nucleic acid encoding the signal peptide or the recombinant polypeptide or the fusion protein of the present invention.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from a sequence (nucleic acid or amino acid sequence) provided herein of greater than 65%. In another embodiment, "homology" refers to identity to a sequence selected from a sequence provided herein of greater than 70%. In another embodiment, the identity is greater than 75%. In another embodiment, the identity is greater than 78%. In another embodiment, the identity is greater than 80%. In another embodiment, the identity is greater than 82%. In another embodiment, the identity is greater than 83%. In another embodiment, the identity is greater than 85%. In another embodiment, the identity is greater than 87%. In another embodiment, the identity is greater than 88%. In another embodiment, the identity is greater than 90%. In another embodiment, the identity is greater than 92%. In another embodiment, the identity is greater than 93%. In another embodiment, the identity is greater than 95%. In another embodiment, the identity is greater than 96%. In another embodiment, the identity is greater than 97%. In another embodiment, the identity is greater than 98%. In another embodiment, the identity is greater than 99%. In another embodiment, the identity is 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example, methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA.

In one embodiment of the present invention, "nucleic acids" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

The terms "contacting" or "administering," in one embodiment, refer to directly contacting the cancer cell or tumor with a composition of the present invention. In another embodiment, the terms refer to indirectly contacting the cancer cell or tumor with a composition of the present invention. In another embodiment, methods of the present invention include methods in which the subject is contacted with a composition of the present invention after which the composition is brought in contact with the cancer cell or tumor by diffusion or any other active transport or passive transport process known in the art by which compounds circulate within the body.

In another embodiment, methods of this invention may include at least a single administration of a composition of this invention, wherein in another embodiment, methods of this invention may include multiple administrations of a composition of this invention. Each possibility represents a separate embodiment of the present invention.

In one embodiment, the present invention provides methods in which recombinant *Listeria* is administered only once. In another embodiment, *Listeria* is administered twice. In another embodiment, *Listeria* is administered three times. In another embodiment, *Listeria* is administered four times. In another embodiment, *Listeria* is administered more than four times. In another embodiment, *Listeria* is administered multiple times. In another embodiment, *Listeria* is administered at regular intervals, which in one embodiment, may be daily, weekly, every two weeks, every three weeks, or every month. Each possibility represents a separate embodiment of the present invention.

In one embodiment, the present invention provides methods in which radiation therapy is administered only once. In another embodiment, radiation therapy is administered twice. In another embodiment, radiation therapy is administered three times. In another embodiment, radiation therapy is administered four times. In another embodiment, radiation therapy is administered more than four times. In another embodiment, radiation therapy is administered multiple times. In another embodiment, radiation therapy is administered at regular intervals, which in one embodiment, may be daily, weekly, every two weeks, every three weeks, or every month. Each possibility represents a separate embodiment of the present invention.

In one embodiment, the radiation therapy is administered prior to the administration of the recombinant attenuated *Listeria*. In another embodiment, the radiation therapy is administered twice prior to the first administration of the recombinant attenuated *Listeria*. In another embodiment, the radiation therapy is administered three times prior to the first administration of the recombinant attenuated *Listeria*.

In another embodiment, the recombinant attenuated *Listeria* is administered prior to the administration of the radiation therapy. In another embodiment, the recombinant attenuated *Listeria* is administered twice prior to the first administration of the radiation therapy. In another embodiment, the recombinant attenuated *Listeria* is administered three times prior to the first administration of the radiation therapy.

In another embodiment, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

Pharmaceutical Compositions

It will be appreciated by a skilled artisan that the terms "immunogenic composition", "composition" and "pharmaceutical composition" may be used interchangeably. It is also to be understood that administration of such compositions enhances an immune response, or increase a T effector cell to regulatory T cell ratio or elicit an anti-tumor immune response, as further provided herein.

In one embodiment, the immunogenic composition provided herein comprises a recombinant *Listeria* provided herein.

In one embodiment, a "combination therapy" refers to the combination of radiation therapy described herein administered in conjunction with, or prior to administration of a composition comprising the recombinant *Listeria* provided herein.

The pharmaceutical compositions containing vaccines and compositions of the present invention are, in another embodiment, administered to a subject by any method known to a person skilled in the art, such as parenterally, paracancerally, transmucosally, transdermally, intramuscularly, intravenously, intra-dermally, subcutaneously, intra-peritoneally, intra-ventricularly, intra-cranially, intra-vaginally or intra-tumorally.

In another embodiment of the methods and compositions provided herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like.

In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In one embodiment, repeat administrations (booster doses) of compositions of this invention may be undertaken immediately following the first course of treatment or after an interval of days, weeks or months to achieve tumor regression. In another embodiment, repeat doses may be undertaken immediately following the first course of treatment or after an interval of days, weeks or months to achieve suppression of tumor growth. Assessment may be determined by any of the techniques known in the art, including diagnostic methods such as imaging techniques, analysis of serum tumor markers, biopsy, or the presence, absence or amelioration of tumor associated symptoms.

In one embodiment, a subject is administered a booster dose every 1-2 weeks, every 2-3 weeks, every 3-4 weeks, every 4-5 weeks, every 6-7 weeks, every 7-8 weeks, or every 9-10 weeks in order to achieve the intended anti-tumor response. In one embodiment, a subject is administered a booster dose every 1-2 months, every 2-3 months, every 3-4 months, every 4-5 months, every 6-7 months, every 7-8 months, or every 9-10 months in order to achieve the intended anti-tumor response.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to increasing performance free survival or overall survival of a patient. In another embodiment, "treating" refers to stabilizing the progression of a disease. In another embodiment, "treating" refers to inducing remission. In another embodiment, "treating" refers to slowing the progression of a disease. The terms "reducing", "suppressing" and "inhibiting" refer in another embodiment to lessening or decreasing. Each possibility represents a separate embodiment of the present invention.

The term "about" as used herein means in quantitative terms plus or minus 5%, or in another embodiment plus or minus 10%, or in another embodiment plus or minus 15%, or in another embodiment plus or minus 20%.

It is to be understood by the skilled artisan that the term "subject" can encompass a mammal including an adult human or a human child, teenager or adolescent in need of therapy for, or susceptible to, a condition or its sequelae, and also may include non-human mammals such as dogs, cats, pigs, cows, sheep, goats, horses, rats, and mice. It will also be appreciated that the term may encompass livestock. The term "subject" does not exclude an individual that is normal in all respects.

In one embodiment, the term "subject" also encompasses dogs that cannot undergo amputation. In another embodiment, the term "subject" also encompasses humans that cannot undergo surgery. In another embodiment, the term "subject" also encompasses humans that cannot undergo amputation.

It will be appreciated by the skilled artisan that the term "mammal" for purposes of treatment refers to any animal classified as a mammal, including, but not limited to, humans, domestic and farm animals, and zoo, sports, or pet animals, such as canines, including dogs, and horses, cats, cattle, pigs, sheep, etc.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a vaccine provided herein for purposes of treatment of tumor may be determined empirically and in a routine manner.

In one embodiment, compositions for use in the methods of the present invention comprise a second open reading frame encoding a metabolic enzyme, wherein said metabolic enzyme complements an endogenous gene that is mutated in the chromosome of said recombinant attenuated *Listeria* strain. In another embodiment, the metabolic enzyme complements an endogenous gene that is lacking in the chromosome of said recombinant attenuated *Listeria* strain.

In one embodiment, "mutated" or "mutant" describes a deletion. In another embodiment, "mutated" or "mutant" describes an inactivation. In another embodiment, "mutated" or "mutant" describes a truncation. In another embodiment, "mutated" or "mutant" describes an addition. In another embodiment, "mutated" or "mutant" describes a substitution. In another embodiment, "mutated" or "mutant" describes insertion of a premature stop codon. In another embodiment, "mutated" or "mutant" describes a change to one or more nucleic acids within a gene which disrupts expression of the gene.

In one embodiment, "radiation therapy" or "radiotherapy" refers to the medical use of ionizing radiation as part of cancer treatment to control or eradicate malignant cells. Radiotherapy may be used for curative, adjuvant, or palliative treatment. Suitable types of radiotherapy include conventional external beam radiotherapy, stereotactic radiation therapy (e.g., Axesse, Cyberknife, Gamma Knife, Novalis, Primatom, Synergy, X-Knife, TomoTherapy or Trilogy), Intensity-Modulated Radiation Therapy, particle therapy (e.g., proton therapy), brachytherapy, delivery of radioisotopes, intraoperative radiotherapy, Auger therapy, Volumetric modulated arc therapy (VMAT), Virtual simulation, 3-dimensional conformal radiation therapy, and intensity-modulated radiation therapy, etc. It is to be understood that this list is not meant to be limiting.

In one embodiment, radiation therapy uses high-energy radiation to shrink tumors and kill cancer cells. In one embodiment, X-rays, gamma rays, and charged particles are types of radiation that may be used for cancer treatment. In one embodiment, radiation therapy kills cancer cells by damaging their DNA either directly or by creating free radicals within the cells that can in turn damage the DNA.

In one embodiment, the radiation may be delivered by a machine outside the body (external-beam radiation therapy), or in another embodiment, it may come from radioactive material placed in the body near cancer cells (internal radiation therapy, also called brachytherapy).

In one embodiment, systemic radiation therapy uses radioactive substances, such as radioactive iodine, that travel in the blood to kill cancer cells.

In one embodiment, the present invention provides a method for concomitantly treating radiation insensitive cancers such as osteosarcomas with standard radiation in combination with immunotherapy, such as administration of recombinant *Listeria* in a regimen which requires shorter radiation treatment times, thus ameliorating side effects ordinarily associated with radiation treatment.

In one embodiment, the radiation is administered according to this invention by standard techniques with standard megavoltage equipment, such as AECL Theratron 80, Varian Clinac 4 or Varian Clinac. In one embodiment, the maximum size of the radiation portal should be no greater than 300 cm2. In one embodiment, a suitable does is between about 15 Gy and 35 Gy, with the specific dose dependent on the area of the body treated. Thus, a dose to the spinal cord would be about 35 Gy, whereas a dose to the bilateral kidneys would be about 15 Gy and to the whole liver 20 Gy. Breaks in the therapy are at the discretion of the clinician taking into consideration the patients tolerance for radiation therapy.

In one embodiment, radiation doses range from 70-80 Gy. In another embodiment, radiation doses ranging from 10-26 GY are administered. In another embodiment, radiation doses are approximately $\alpha/\beta=5.4$ Gy and $\mu=1.73$ Gy-1 for an adult male.

In one embodiment, the radiation therapy described in the present invention is palliative radiation therapy. In one embodiment, radiation therapy may be given with palliative intent. In one embodiment, palliative treatments are intended to relieve symptoms and reduce the suffering caused by cancer or a tumor or tumors rather than to cure the cancer or tumor.

The following examples are presented in order to more fully illustrate the preferred embodiments of the invention. They should in no way be construed, however, as limiting the broad scope of the invention.

EXAMPLES

Materials and Methods

Oligonucleotides were synthesized by Invitrogen (Carlsbad, Calif.) and DNA sequencing was done by Genewiz Inc, South Plainfield, N.J. Flow cytometry reagents were purchased from Becton Dickinson Biosciences (BD, San Diego, Calif.). Cell culture media, supplements and all other reagents, unless indicated, were from Sigma (St. Louise, Mo.). Her-2/neu HLA-A2 peptides were synthesized by EZbiolabs (Westfield, Ind.). Complete RPMI 1640 (C-RPMI) medium contained 2 mM glutamine, 0.1 mM non-essential amino acids, and 1 mM sodium pyruvate, 10% fetal bovine serum, penicillin/streptomycin, Hepes (25 mM). The polyclonal anti-LLO antibody was described previously and anti-Her-2/neu antibody was purchased from Sigma.

Mice and Cell Lines

All animal experiments were performed according to approved protocols by IACUC at the University of Pennsylvania or Rutgers University. FVB/N mice were purchased from Jackson laboratories (Bar Harbor, Me.). The FVB/N Her-2/neu transgenic mice, which overexpress the rat Her-2/neu onco-protein were housed and bred at the animal core facility at the University of Pennsylvania. The NT-2 tumor cell line expresses high levels of rat Her-2/neu protein, was derived from a spontaneous mammary tumor in these mice and grown as described previously. DHFR-G8 (3T3/neu)

cells were obtained from ATCC and were grown according to the ATCC recommendations. The EMT6-Luc cell line was a generous gift from Dr. John Ohlfest (University of Minnesota, Minn.) and was grown in complete C-RPMI medium. Bioluminescent work was conducted under guidance by the Small Animal Imaging Facility (SAIF) at the University of Pennsylvania (Philadelphia, Pa.).

Listeria Constructs and Antigen Expression

Her-2/neu-pGEM7Z was kindly provided by Dr. Mark Greene at the University of Pennsylvania and contained the full-length human Her-2/neu (hHer2) gene cloned into the pGEM7Z plasmid (Promega, Madison Wis.). This plasmid was used as a template to amplify three segments of hHer-2/neu, namely, EC1, EC2, and IC1, by PCR using pfx DNA polymerase (Invitrogen) and the oligos indicated in Table 1.

vector, pAdv134. The sequences of the insert, LLO and hly promoter were confirmed by DNA sequencing analysis. This plasmid was electroporated into electro-competent actA, dal, dat mutant *Listeria monocytogenes* strain, LmddA and positive clones were selected on Brain Heart infusion (BHI) agar plates containing streptomycin (250 µg/ml). In some experiments similar *Listeria* strains expressing hHer-2/neu (Lm-hHer2) fragments were used for comparative purposes. These have been previously described. In all studies, an irrelevant *Listeria* construct (Lm-control) was included to account for the antigen independent effects of *Listeria* on the immune system. Lm-controls were based on the same *Listeria* platform as ADXS31-164, but expressed a different antigen such as HPV16-E7 or NY-ESO-1. Expression and

TABLE 2

Primers for cloning of Human her-2-Chimera

| | DNA sequence | Base pair region | Amino acid region or junctions |
|---|---|---|---|
| Her-2-Chimera (F) | TGAT<u>CTCGAG</u>ACCCACCTGGACATGCTC (SEQ ID NO: 57) | 120-510 | 40-170 |
| HerEC1-EC2F (Junction) | CTACCAGGACACGATTTTGTGGAAG-AATATCCA GGAGTTTGCTGGCTGC (SEQ ID NO: 58) | 510/1077 | 170/359 |
| HerEC1-EC2R (Junction) | GCAGCCAGCAAACTCCTGGATATT-CTTCCACAA AATCGTGTCCTGGTAG (SEQ ID NO: 59) | | |
| HerEC2-IC1F (Junction) | CTGCCACCAGCTGTGCGCCCGAGGG-CAGCAGAAGATCCGGAAGTACACGA (SEQ ID NO: 60) | 1554/2034 | 518/679 |
| HerEC2-IC1R (Junction) | TCGTGTACTTCCGGATCTTCTGCTG CCCTCGGGC GCACAGCTGGTGGCAG (SEQ ID NO: 61) | | |
| Her-2-Chimera (R) | GTGG<u>CCCGGG</u>TCTAGATTAGTCTAAGAGGCAGCCATAGG (SEQ ID NO: 62) | 2034-2424 | 679-808 |

The Her-2/neu chimera construct was generated by direct fusion by the SOEing PCR method and each separate hHer-2/neu segment as templates. Primers are shown in Table 3.

Sequence of primers for amplification of different segments human Her2 regions.

secretion of fusion proteins from *Listeria* were tested. Each construct was passaged twice in vivo.

Cytotoxicity Assay

Groups of 3-5 FVB/N mice were immunized three times with one week intervals with $1 \times 10^8$ colony forming units (CFU) of Lm-LLO-ChHer2, ADXS31-164, Lm-hHer2 IC1

TABLE 3

| | DNA sequence | Base pair region | Amino acid region |
|---|---|---|---|
| Her-2-EC1(F) | CCGC<u>CTCGAG</u>GCCGCGAGCACCCAAGTG (SEQ ID NO: 63) | 58-979 | 20-326 |
| Her-2-EC1(R) | CGCG<u>ACTAGT</u>TTAATCCTCTGCTGTCACCTC (SEQ ID NO: 64) | | |
| Her-2-EC2(F) | CCGC<u>CTCGAG</u>TACCTTTCTACGGACGTG (SEQ ID NO: 65) | 907-1504 | 303-501 |
| Her-2-EC2(R) | CGCG<u>ACTAGT</u>TTACTCTGGCCGGTTGGCAG (SEQ ID NO: 66) | | |
| Her-2-Her-2-IC1(F) | CCGC<u>CTCGAG</u>CAGCAGAAGATCCGGAAGTAC (SEQ ID NO: 67) | 2034-3243 | 679-1081 |
| Her-2-IC1(R) | CGCG<u>ACTAGT</u>TTAAGCCCCTTCGGAGGGTG (SEQ ID NO: 68) | | |

ChHer2 gene was excised from pAdv138 using XhoI and SpeI restriction enzymes, and cloned in frame with a truncated, non-hemolytic fragment of LLO in the Lmdd shuttle or Lm-control (expressing an irrelevant antigen) or were left naïve. NT-2 cells were grown in vitro, detached by trypsin and treated with mitomycin C (250 µg/ml in serum free C-RPMI medium) at 37° C. for 45 minutes. After 5 washes, they were co-incubated with splenocytes harvested from immunized or naïve animals at a ratio of 1:5 (Stimulator: Responder) for 5 days at 37° C. and 5% $CO_2$. A standard cytotoxicity assay was performed using europium labeled 3T3/neu (DHFR-G8) cells as targets according to the method previously described. Released europium from killed target cells was measured after 4 hour incubation using a spectrophotometer (Perkin Elmer, Victor$^2$) at 590 nm Percent specific lysis was defined as (lysis in experimental group-spontaneous lysis)/(Maximum lysis-spontaneous lysis).

Interferon-γ Secretion by Splenocytes from Immunized Mice

Groups of 3-5 FVB/N or HLA-A2 transgenic mice were immunized three times with one week intervals with $1 \times 10^8$ CFU of ADXS31-164, a negative *Listeria* control (expressing an irrelevant antigen) or were left naïve. Splenocytes from FVB/N mice were isolated one week after the last immunization and co-cultured in 24 well plates at $5 \times 10^6$ cells/well in the presence of mitomycin C treated NT-2 cells in C-RPMI medium. Splenocytes from the HLA-A2 transgenic mice were incubated in the presence of 1 μM of HLA-A2 specific peptides or 1 μg/ml of a recombinant His-tagged ChHer2 protein, produced in *E. coli* and purified by a nickel based affinity chromatography system. Samples from supernatants were obtained 24 or 72 hours later and tested for the presence of interferon-γ (IFN-γ) using mouse IFN-γ Enzyme-linked immunosorbent assay (ELISA) kit according to manufacturer's recommendations.

INF-γ ELISpot Assay

Cryopreserved PBMC from each indicated time point were thawed, rested overnight at 37° C. and then counted. Cells were stimulated with 2.5 uM pools of overlapping human Her-2/neu peptides (11mers overlapping by 5 amino acids) that represent the EC1, EC2 and IC1 domains of Her-2/neu present in the chimeric vaccine, and recombinant human IL-2 (Invitrogen, Fredrick, Md.) for 5 days. Cells were harvested, washed twice in 1xPBS and counted. IFN-γ ELISpot assays were performed according to the manufacturer's protocol using a commercial canine IFN-γ ELISpot assay kit (R&D Systems, Minneapolis, Minn.). Briefly, 0.8-2×105 stimulated cells were incubated with 2.5 uM of EC1, EC2 or IC1 peptide pools plus IL-2 or IL-2 alone (to determine background counts). All assays were performed in duplicates. Plates were developed according to the manufacturer's instructions. Spots were counted using a CTL-Immunospot analyzer (C.T.L, Shaker Heights, Ohio). Number of spots were normalized by subtracting twice the number of spots counted in non-stimulated wells.

Tumor Studies in Her2 Transgenic Animals

Six weeks old FVB/N rat Her-2/neu transgenic mice (9-14/group) were immunized 6 times with $5 \times 10^8$ CFU of Lm-LLO-ChHer2, ADXS31-164 or Lm-control. They were observed twice a week for the emergence of spontaneous mammary tumors, which were measured using an electronic caliper, for up to 52 weeks. Escaped tumors were excised when they reached a size 1 cm$^2$ in average diameter and preserved in RNAlater at −20° C. In order to determine the effect of mutations in the Her-2/neu protein on the escape of these tumors, genomic DNA was extracted using a genomic DNA isolation kit, and sequenced.

Effect of ADXS31-164 on Regulatory T Cells in Spleens and Tumors

Mice were implanted subcutaneously (s.c.) with $1 \times 10^6$ NT-2 cells. On days 7, 14 and 21, they were immunized with $1 \times 10^8$ CFUs of ADXS31-164, LmddA-control or left naïve. Tumors and spleens were extracted on day 28 and tested for the presence of CD3$^+$/CD4$^+$/FoxP3$^+$ Tregs by FACS analysis. Briefly, splenocytes were isolated by homogenizing the spleens between two glass slides in C-RPMI medium. Tumors were minced using a sterile razor blade and digested with a buffer containing DNase (12 U/ml), and collagenase (2 mg/ml) in PBS. After 60 min incubation at RT with agitation, cells were separated by vigorous pipetting. Red blood cells were lysed by RBC lysis buffer followed by several washes with complete RPMI-1640 medium containing 10% FBS. After filtration through a nylon mesh, tumor cells and splenocytes were resuspended in FACS buffer (2% FBS/PBS) and stained with anti-CD3-PerCP-Cy5.5, CD4-FITC, CD25-APC antibodies followed by permeabilization and staining with anti-Foxp3-PE. Flow cytometry analysis was performed using 4-color FACS calibur (BD) and data were analyzed using cell quest software (BD).

Statistical Analysis

The log-rank Chi-Squared test was used for survival data and student's t-test for the CTL and ELISA assays, which were done in triplicates. A p-value of less than 0.05 (marked as *) was considered statistically significant in these analyzes. All statistical analysis was done with either Prism software, V.4.0a (2006) or SPSS software, V.15.0 (2006). For all FVB/N rat Her-2/neu transgenic studies we used 8-14 mice per group, for all wild-type FVB/N studies we used at least 8 mice per group unless otherwise stated. All studies were repeated at least once except for the long term tumor study in Her-2/neu transgenic mouse model.

Example 1

Generation of L. *Monocytogenes* Strains that Secrete LLO Fragments Fused to her-2 Fragments: Construction of ADXS31-164

Construction of the chimeric Her-2/neu gene (ChHer2) was described previously. Briefly, ChHer2 gene was generated by direct fusion of two extracellular (aa 40-170 and aa 359-433) and one intracellular fragment (aa 678-808) of the Her-2/neu protein by SOEing PCR method. The chimeric protein harbors most of the known human MHC class I epitopes of the protein. ChHer2 gene was excised from the plasmid, pAdv138 (which was used to construct Lm-LLO-ChHer2) and cloned into LmddA shuttle plasmid, resulting in the plasmid pAdv164 (FIG. 1A). There are two major differences between these two plasmid backbones. 1) Whereas pAdv138 uses the chloramphenicol resistance marker (cat) for in vitro selection of recombinant bacteria, pAdv164 harbors the D-alanine racemase gene (dal) from *bacillus subtilis*, which uses a metabolic complementation pathway for in vitro selection and in vivo plasmid retention in LmddA strain which lacks the dal-dat genes. This vaccine platform was designed and developed to address FDA concerns about the antibiotic resistance of the engineered *Listeria* vaccine strains. 2) Unlike pAdv138, pAdv164 does not harbor a copy of the prfA gene in the plasmid (see sequence below and FIG. 1A), as this is not necessary for in vivo complementation of the Lmdd strain. The LmddA vaccine strain also lacks the actA gene (responsible for the intracellular movement and cell-to-cell spread of *Listeria*) so the recombinant vaccine strains derived from this backbone are 100 times less virulent than those derived from the Lmdd, its parent strain. LmddA-based vaccines are also cleared much faster (in less than 48 hours) than the Lmdd-based vaccines from the spleens of the immunized mice. The expression and secretion of the fusion protein tLLO-ChHer2 from this strain was comparable to that of the Lm-LLO-ChHer2 in TCA precipitated cell culture supernatants after 8 hours of in vitro growth (FIG. 1B) as a band of ~104 KD was detected by an anti-LLO antibody using Western Blot analysis. The *Listeria* backbone strain expressing only tLLO was used as negative control.

pAdv164 sequence (7075 base pairs) (see FIG. 1):

(SED ID NO: 53)

cggagtgtatactggcttactatgaggcactgatgagggtgtcagtgaagtgcttcatgtggcaggagaaaaaaggctg caccggtgcgtcagcagaatatgtgatacaggatatattccgcacctcgctcactgactcgctacgctcggtcgttcgactgcggcga gcggaaatggcttacgaacggggcggagatttcctggaagatgccaggaagatacttaacagggaagtgagagggccgcggcaa agccgtattccataggctccgccccctgacaagcatcacgaaatctgacgctcaaatcagtggtggcgaaacccgacaggactata aagataccaggcgatcccctggcggctccctcgtgcgctctcctgttcctgccatcggataccggtgtcattccgctgttatggccg cgtagtctcattccacgcctgacactcagaccgggtaggcagttcgctccaagctggactgtatgcacgaaccccccgttcagtccg accgctgcgccttatccggtaactatcgtcttgagtccaacccggaaagacatgcaaaagcaccactggcagcagccactggtaattg atttagaggagttagtcttgaagtcatgcgccggttaaggctaaactgaaaggacaagtatggtgactgcgctcctccaagccagttac ctcggttcaaagagaggtagctcagagaaccttcgaaaaaccgcctgcaaggcggattacgattcagagcaagagattacgcgc agaccaaaacgatctcaagaagatcatcttattaatcagataaaatatactagccctcctagattagtatattcctatcttaaagttactata tgtggaggcattaacatttgttaatgacgtcaaaaggatagcaagactagaataaagctataaagcaagcatataatattgcgtttcatctt tagaagcgaatttcgccaatattataattatcaaaagagagggtggcaaacggtatttggcattattaggttaaaaaatgtagaaggag agtgaaacccatgaaaaaaataatgctagtattattacacttatattagttagtctaccaattgcgcaacaaactgaagcaaaggatgcat ctgcattcaataaagaaaattcaatttcatccatggcaccaccagcatctccgcctgcaagtcctaagacgccaatcgaaaagaaacac gcggatgaaatcgataagtatatacaaggattggattacaataaaaacaatgtattagtataccacggagatgcagtgacaaatgtgcc gccaagaaaaggttacaaagatggaaatgaatatattgagtggagaaaagaagaaatccatcaatcaaaataatgcagacattcaa gttgtgaatgcaatttcgagcctaacctatccaggtgctctcgtaaaagcgaattcggaattagtagaaaatcaaccagatgactccctg taaaacgtgattcattaacactcagcattgatttgccaggtatgactaatcaagacaataaaatagagtaaaaaatgccactaaatcaaa cgttaacaacgcagtaaatacattagtggaaagatggaatgaaaaatatgctcaagcttatccaaatgtaagtgcaaaaattgattatgat gacgaaatggcttacagtgaatcacaattaattgcgaaataggtacagcattttaaagctgtaaataatagcttgaatgtaaacttcggcg caatcagtgaagggaaatgcaagaagaagtcattagattaaacaaatttactataacgtgaatgttaatgaacctacaagaccacca gatattcggcaaagctgttactaaagagcagttgcaagcgcaggagtgaatgcagaaaatcctcctgcatatatctcaagtgtggcgt atggccgtcaagatatttgaaattatcaactaattcccatagtactaaagtaaaagctgcttagatgctgccgtaagcggaaaatctgtct caggtgatgtagaactaacaaatatcatcaaaaattcaccttcaaagccgtaatttacggaggaccgcaaaagatgaagttcaaatcat cgacggcaacctcggagacttacgcgatattagaaaaaaggcgctacattaatcgagaaacaccaggagacccattgcttatacaa caaacttcctaaaagacaatgaattagctgttattaaaaacaactcagaatatattgaaacaacttcaaaagcttatacagatggaaaaatt aacatcgatcactctggaggatacgagctcaattcaacatttcagggatgaagtaaattatgatctcgagacccacctggacatgctcc gccacctctaccagggctgccaggtggtgcagggaaacctggaactcacctacctgcccaccaatgccagcctgtccacctgcagg atatccaggaggtgcagggctacgtgctcatcgctcacaaccaagtgaggcaggtcccactgcagaggctgcggattgtgcgaggc acccagctcatgaggacaactatgccctggccgtgctagacaatggagaccgctgaacaataccaccctgtcacaggggcctcc ccaggaggcctgcgggagctgcagcttcgaagcctcacagagatcttgaaaggaggggtcttgatccagcggaaccccagctct gctaccaggacacgattagtggaagaatatccaggagtagctggctgcaagaagatctagggagcctggcatactgccgagag catgatggggacccagcctccaacactgccccgctccagccagagcagctccaagtgatgagactctggaagagatcacaggtta cctatacatctcagcatggccggacagcctgcctgacctcagcgtcaccagaacctgcaagtaatccggggacgaattctgcacaat ggcgcctactcgctgaccctgcaagggctgggcatcagctggctggggctgcgctcactgagggaactgggcagtggactggccc tcatccaccataacacccacctctgcttcgtgcacacggtgcccctgggaccagctcatcggaacccgcaccaagctctgctccacact gccaaccggccagaggacgagtgtgtgggcgagggcctggcctgccaccagctgtgcgcccgagggcagcagaagatccgga agtacacgatgcggagactgctgcaggaaacggagctggtggagccgctgacacctagcggagcgatgcccaaccaggcgcag atgcggatcctgaaagagacggagctgaggaaggtgaaggtgcaggatctggcgcttaggcacagtctacaagggcatctggatc -continued

```
cctgatggggagaatgtgaaaattccagtggccatcaaagtgagagggaaaacacatcccccaaagccaacaaagaaatcttagac
gaagcatacgtgatggctggtgtgggctcccatatgtctcccgccactgggcatctgcctgacatccacggtgcagctggtgacac
agcttatgccctatggctgcctcttagactaatctagacccgggccactaactcaacgctagtagtggatttaatcccaaatgagccaac
agaaccagaaccagaaacagaacaagtaacattggagttagaaatggaagaagaaaaaagcaatgatttcgtgtgaataatgcacg
aaatcattgcttattatttaaaaagcgatatactagatataacgaaacaacgaactgaataaagaatacaaaaaaagagccacgaccag
ttaaagcctgagaaactttaactgcgagccttaattgattaccaccaatcaattaaagaagtcgagacccaaaataggtaaagtatttaat
tactttattaatcagatacttaaatatctgtaaaccattatatcgggatttgaggggatttcaagtcataagaagataccaggcaatcaatt
aagaaaaacttagttgattgccattagagtgattcaactagatcgtagcttctaactaattaattacgtaagaaaggagaacagctgaat
gaatatcccattgagtagaaactgtgcttcatgacggcagttaaagtacaaatttaaaaatagtaaaattcgctcaatcactaccaagcc
aggtaaaagtaaaggggctatattgcgtatcgctcaaaaaaaagcatgattggcggacgtggcgttgactgacttccgaagaagcga
ttcacgaaaatcaagatacatttacgcattggacaccaaacgatatcgttatggtacgtatgcagacgaaaaccgttcatacactaaag
gacattctgaaaacaatttaagacaaatcaataccactttattgattagatattcacacggaaaagaaactatttcagcaagcgatatat
aacaacagctattgatttaggattatgcctacgttaattatcaaatctgataaaggttatcaagcatattagattagaaacgccagtctatgt
gacttcaaaatcagaatttaaatctgtcaaagcagccaaaataatctcgcaaaatatccgagaatattaggaaagtcatgccagttgatc
taacgtgcaatcattagggattgctcgtataccaagaacggacaatgtagaattattgatcccaattaccgttattcatcaaagaatggc
aagattggtcatcaaacaaacagataataagggcatactcgttcaagtctaacggattaagcggtacagaaggcaaaaaacaagtag
atgaaccctggataatctcttattgcacgaaacgaaattacaggagaaaaggggatagtagggcgcaatagcgttatgatccctctctt
tagcctactttagttcaggctattcaatcgaaacgtgcgaatataatatgatgagataataatcgattagatcaaccctttagaagaaaaag
aagtaatcaaaattgttagaagtgcctattcagaaaactatcaagggctaatagggaatacattaccattcatgcaaagcagggtatc
aagtgatttaaccagtaaagatttatagtccgtcaagggtggataaattcaagaaaaaagaagcgaacgtcaacgtgacatagtca
gaatggaaagaagatttaatggcttatattagcgaaaaagcgatgtatacaagccttatttagcgacgaccaaaaaagagattagaga
agtgctaggcattcctgaacggacattagataaattgctgaaggtactgaaggcgaatcaggaaattactttaagattaaaccaggaag
aaatggtggcattcaacttgctagtgttaaatcattgagctatcgatcattaaattaaaaaagaagaacgagaaagctatataaaggcg
ctgacagcttcgataatttagaacgtacatttattcaagaaactctaaacaaattggcagaacgccccaaaacggacccacaactcgat
ttgatagctacgatacaggctgaaaataaaacccgcactatgccattacatttatatctatgatacgtgatgatactagctggctagctta
attgctatatttacctgcaataaaggatacttacttccattatactcccattaccaaaaacatacggggaacacgggaacttattgtacag
gccacctcatagttaatggatcgagccacctgcaatctcatccatggaaatatattcatcccctgccggcctattaatgtgacttagtg
cccggcggatattcctgatccagctccaccataaaattggtccatgcaaattcggccggcaattacaggcgattcccacacaaggatgt
cggtcccatcaattacggagccagccgtccgcatagcctacaggcaccgtcccgatccatgtgtctattccgctgtgtactcggctcc
gtagctgacgctctcgccattctgatcagatgacatgtgacagtgtcgaatgcagggtaaatgccggacgcagctgaaacggtatctc
gtccgacatgtcagcagacgggcgaaggccatacatgccgatgccgaatctgactgcattaaaaaagccattacagccggagtcca
gcggcgctgacgcgcagtggaccattagattcataacggcagcggagcaatcagctcataaagcgctcaaactgcattaagaaata
gcctctactattcatccgctgtcgcaaaatgggtaaatacccccatgcactttaaacgagggagcggtcaagaattgccatcacgactg
aacttcacctctgatttacaccaagtctgacatccccgtatcgaccacagatgaaaatgaagagaaccattacgtgtggcgggctgc
ctcctgaagccattcaacagaataacctgttaaggtcacgtcatactcagcagcgattgccacatactccggggaaccgcgccaag
caccaatataggcgccacaatcccatttgcgcagtgaaatcgcttcatccaaaatggccacggccaagcatgaagcacctgcgtcaa
gagcagccatgctgatctgcatcaccatgcccgtaggcgtagcatcacaactgccatcaagtggacatgacaccgatatgattaca
tattgctgacattaccatatcgcggacaagtcaataccgcccacgtatctctgtaaaaaggattgtgctcatggaaaactcctctcatat
cagaaaatcccagtacgtaattaagtatttgagaattaatatatattgattaatactaagatacccagattcacctaaaaaacaaatgatga
gataatagctccaaaggctaaagaggactataccaactatttgttaattaa.
```

Example 2

ADXS31-164 is as Immunogenic as
Lm-LLO-ChHer2

Immunogenic properties of ADXS31-164 in generating anti-Her-2/neu specific cytotoxic T cells were compared to those of the Lm-LLO-ChHer2 vaccine in a standard CTL assay. Both vaccines elicited strong but comparable cytotoxic T cell responses toward Her-2/neu antigen expressed by 3T3/neu target cells. Accordingly, mice immunized with a Listeria expressing only an intracellular fragment of Her2-fused to LLO showed lower lytic activity than the chimeras which contain more MHC class I epitopes. No CTL activity was detected in naïve animals or mice injected with the irrelevant Listeria vaccine (FIG. 2A). ADXS31-164 was also able to stimulate the secretion of IFN-γ by the splenocytes from wild type FVB/N mice (FIG. 2B). This was detected in the culture supernatants of these cells that were co-cultured with mitomycin C treated NT-2 cells, which express high levels of Her-2/neu antigen (FIG. 5C).

Proper processing and presentation of the human MHC class I epitopes after immunizations with ADXS31-164 was tested in HLA-A2 mice. Splenocytes from immunized HLA-A2 transgenics were co-incubated for 72 hours with peptides corresponding to mapped HLA-A2 restricted epitopes located at the extracellular (HLYQGCQVV SEQ ID NO: 11 or KIFGSLAFL SEQ ID NO: 12) or intracellular (RLLQETELV SEQ ID NO: 13) domains of the Her-2/neu molecule (FIG. 2C). A recombinant ChHer2 protein was used as positive control and an irrelevant peptide or no peptide as negative controls. The data from this experiment show that ADXS31-164 is able to elicit anti-Her-2/neu specific immune responses to human epitopes that are located at different domains of the targeted antigen.

Example 3

ADXS31-164 was More Efficacious than
Lm-LLO-ChHer2 in Preventing the Onset of
Spontaneous Mammary Tumors Anti-tumor effects of ADXS31-164 were compared to those of Lm-LLO-ChHer2 in Her-2/neu transgenic animals which develop slow growing, spontaneous mammary tumors at 20-25 weeks of age. All animals immunized with the irrelevant Listeria-control vaccine developed breast tumors within weeks 21-25 and were sacrificed before week 33. In contrast, Listeria-Her-2/neu recombinant vaccines caused a significant delay in the formation of the mammary tumors. On week 45, more than 50% of ADXS31-164 vaccinated mice (5 out of 9) were still tumor free, as compared to 25% of mice immunized with Lm-LLO-ChHer2. At week 52, 2 out of 8 mice immunized with ADXS31-164 still remained tumor free, whereas all mice from other experimental groups had already succumbed to their disease (FIG. 3). These results indicate that despite being more attenuated, ADXS31-164 is more efficacious than Lm-LLO-ChHer2 in preventing the onset of spontaneous mammary tumors in Her-2/neu transgenic animals.

Example 4

Mutations in Her-2/Neu Gene Upon Immunization
with ADXS31-164

Mutations in the MHC class I epitopes of Her-2/neu have been considered responsible for tumor escape upon immunization with small fragment vaccines or trastuzumab (Herceptin), a monoclonal antibody that targets an epitope in the extracellular domain of Her-2/neu. To assess this, genomic material was extracted from the escaped tumors in the transgenic animals and sequenced the corresponding fragments of the neu gene in tumors immunized with the chimeric or control vaccines. Mutations were not observed within the Her-2/neu gene of any vaccinated tumor samples suggesting alternative escape mechanisms (data not shown).

Example 5

ADXS31-164 Causes a Significant Decrease in
Intra-Tumoral T Regulatory Cells

To elucidate the effect of ADXS31-164 on the frequency of regulatory T cells in spleens and tumors, mice were implanted with NT-2 tumor cells. Splenocytes and intra-tumoral lymphocytes were isolated after three immunizations and stained for Tregs, which were defined as $CD3^+$/$CD4^+$/$CD25^+$/$FoxP3^+$ cells, although comparable results were obtained with either FoxP3 or CD25 markers when analyzed separately. The results indicated that immunization with ADXS31-164 had no effect on the frequency of Tregs in the spleens, as compared to an irrelevant Listeria vaccine or the naïve animals (See FIG. 4). In contrast, immunization with the Listeria vaccines caused a considerable impact on the presence of Tregs in the tumors (FIG. 5A). Whereas in average 19.0% of all $CD3^+$ T cells in untreated tumors were Tregs, this frequency was reduced to 4.2% for the irrelevant vaccine and 3.4% for ADXS31-164, a 5-fold reduction in the frequency of intra-tumoral Tregs (FIG. 5B). The decrease in the frequency of intra-tumoral Tregs in mice treated with either of the LmddA vaccines could not be attributed to differences in the sizes of the tumors. In a representative experiment, the tumors from mice immunized with ADXS31-164 were significantly smaller [mean diameter (mm)±SD, 6.71±0.43, n=5] than the tumors from untreated mice (8.69±0.98, n=5, p<0.01) or treated with the irrelevant vaccine (8.41±1.47, n=5, p=0.04), whereas comparison of these last two groups showed no statistically significant difference in tumor size (p=0.73). The lower frequency of Tregs in tumors treated with LmddA vaccines resulted in an increased intratumoral CD8/Tregs ratio, suggesting that a more favorable tumor microenvironment can be obtained after immunization with LmddA vaccines. However, only the vaccine expressing the target antigen Her-2/neu (ADXS31-164) was able to reduce tumor growth, indicating that the decrease in Tregs has an effect only in the presence of antigen-specific responses in the tumor.

Example 6

No Escape Mutations were Introduced by Listeria
Vaccine Expressing Her-2 Chimera Tumor samples of the mice immunized with different vaccines such as Lm-LLO-138, LmddA164 and irrelevant vaccine Lm-LLO-NY were harvested. The DNA was purified from these samples and the DNA fragments corresponding to Her-2/neu regions IC1, EC1 and EC2 were amplified and were sequenced to determine if there were any immune escape mutations. The alignment of sequence from each DNA was performed using CLUSTALW. The results of the analysis indicated that there were no mutations in the DNA sequences harvested from tumors. The reference sequences are listed below:

Alignment of EC2 (975-1029 bp of Her-2-neu)

(SEQ ID NO: 14)
GGTCACAGCTGAGGACGGAACACAGCGTTGTGAGAAATGCAGCAAGC
CCTGTGCT (SEQ ID NO: 15)
CGAGTGTGCTATGGTCTGGGCATGGAGCACCTTCGAGGGGCGAGGGCC
ATCACCAGTGAC (SEQ ID No: 16)
AATGTCCAGGAGTTTGATGGCTGCAAGAAGATCTTTGGGAGCCTGGCA
TTTTTGCCGGAG (SEQ ID No: 17)
AGCTTTGATGGGACCCCTCCTCCGGCATTGCTCCGCTGAGGCCTGAGC
AGCTCCAAGTG (SEQ ID NO: 18)
TTCGAAACCCTGGAGGAGATCACAGGTTACCTGTACATCTCAGCATGG
CCAGACAGTCTC (SEQ ID NO: 19)
CGTGACCTCAGTGTCTTCCAGAACCTTCGAATCATTCGGGGACGGATTC
TCCACGATGGC (SEQ ID NO: 20)
GCGTACTCATTGACACTGCAAGGCCTGGGGATCCACTCGCTGGGGCTG
CGCTCACTGCGG (SEQ ID NO: 21)
GAGCTGGGCAGTGGATTGGCTCTGATTCACCGCAACGCCCATCTCTGCT
TTGTACACACT (SEQ ID NO: 22)
GTACCTTGGGACCAGCTCTTCCGGAACCCACATCAGGCCCTGCTCCAC
AGTGGGAACCGG (SEQ ID NO: 23)
CCGGAAGAGGATTGTGGTCTCGAGGGCTTGGTCTGTAACTCACTGTGT
GCCCACGGGCAC (SEQ ID NO: 24)
TGCTGGGGGCCAGGGCCCACCCAGTGTGTCAACTGCAGTCATTTCCTTC
GGGGCCAGGAG

Alignment of IC1 (2114-3042 bp of Her-2-neu)

(SEQ ID NO: 25)
CGCCCAGCGGAGCAATGCCCAACCAGGCTCAGATGCGGATCCTAAAAG
AGACGGAGC (SEQ ID NO: 26)
TAAGGAAGGTGAAGGTGCTTGGATCAGGAGCTTTTGGCACTGTCTACA
AGGGCATCTGGA (SEQ ID NO: 27)
TCCCAGATGGGGAGAATGTGAAAATCCCCGTGGCTATCAAGGTGTTGA
GAGAAAACACAT (SEQ ID NO: 28)
CTCCTAAAGCCAACAAAGAAATTCTAGATGAAGCGTATGTGATGGCTG
GTGTGGGTTCTC (SEQ ID NO: 29)
CGTATGTGTCCCGCCTCCTGGGCATCTGCCTGACATCCACAGTACAGCT
GGTGACACAGC (SEQ ID NO: 30)
TTATGCCCTACGGCTGCCTTCTGGACCATGTCCGAGAACACCGAGGTC
GCCTAG (SEQ ID NO: 31)
AGGACCTGCTCAACTGGTGTGTTCAGATTGCCAAGGGGATGAGCTACC
TGGAGGACGTGC (SEQ ID NO: 32)
GGCTTGTACACAGGGACCTGGCTGCCCGGAATGTGCTAGTCAAGAGTC
CCAACCACGTCA (SEQ ID NO: 33)
AGATTACAGATTTCGGGCTGGCTCGGCTGCTGGACATTGATGAGACAG
AGTACCATGCAG (SEQ ID NO: 34)
ATGGGGCAAGGTGCCCATCAAATGGATGGCATTGGAATCTATTCTCA
GACGCCGGTTCA (SEQ ID NO: 35)
CCCATCAGAGTGATGTGTGGAGCTATGGAGTGACTGTGTGGGAGCTGA
TGACTTTTGGGG (SEQ ID NO: 36)
CCAAACCTTACGATGGAATCCCAGCCCGGGAGATCCCTGATTTGCTGG
AGAAGGGAGAA (SEQ ID NO: 37)
CGCCTACCTCAGCCTCCAATCTGCACCATTGATGTCTACATGATTATGG
TCAAATGTT (SEQ ID NO: 38)
GGATGATTGACTCTGAATGTCGCCCGAGATTCCGGGAGTTGGTGTCAG
AATTTT (SEQ ID NO: 39)
CACGTATGGCGAGGGACCCCCAGCGTTTTGTGGTCATCCAGAACGAGG
ACTT

Alignment of EC1 (399-758 bp of Her-2-neu)

(SEQ ID NO: 40)
CCCAGGCAGAACCCCAGAGGGGCTGCGGGAGCTGCAGCTTCGAAGTCT
CACAGAGATCCT (SEQ ID NO: 41)
GAAGGGAGGAGTTTTGATCCGTGGGAACCCTCAGCTCTGCTACCAGGA
CATGGTTTTGTG (SEQ ID NO: 42)
CCGGGCCTGTCCACCTTGTGCCCCCGCCTGCAAAGACAATCACTGTTGG
GGTGAGAGTCC (SEQ ID NO: 43)
GGAAGACTGTCAGATCTTGACTGGCACCATCTGTACCAGTGGTTGTGC
CCGGTGCAAGGG (SEQ ID NO: 44)
CCGGCTGCCCACTGACTGCTGCCATGAGCAGTGTGCCGCAGGCTGCAC
GGGCCCCAAGCA

Example 7

Peripheral Immunization with ADXS31-164 can Delay the Growth of a Metastatic Breast Cancer Cell Line in the Brain Mice were immunized IP with ADXS31-164 or irrelevant Lm-control vaccines and then implanted intra-cranially with 5,000 EMT6-Luc tumor cells, expressing luciferase and low levels of Her-2/neu (FIG. 6C). Tumors were monitored at different times post-inoculation by ex vivo imaging of anesthetized mice. On day 8 post-tumor inoculation, tumors were detected in all control animals, but none of the mice in ADXS31-164 group showed any detectable tumors (FIGS. 6A and B). ADXS31-164 could clearly delay the onset of these tumors, as on day 11 post-tumor inoculation, all mice in the negative control group had already succumbed to their tumors, but all mice in ADXS31-164 group were still alive and only showed small signs of tumor growth. These results strongly suggest that the immune responses obtained with the peripheral administration of ADXS31-164 could possibly reach the central nervous system and that LmddA-based vaccines might have a potential use for treatment of CNS tumors.

Example 8

Treatment of Canine Osteasarcoma by Immunization with ADXS31-164

Canine Osteosarcoma is a cancer of long (leg) bones that is a leading killer of large dogs over the age of 10 years. Standard treatment is amputation immediately after diagnosis, followed by chemotherapy. Invariably, however, the cancer metastasizes to the lungs. With chemotherapy, dogs survive about 18 months compared to 6-12 months, without treatment. The HER2 antigen is believed to be present in up to 50% of osteosarcoma. ADXS31-164 creates an immune attack on cells expressing this antigen and has been developed to treat human breast cancer.

Dogs with a histological diagnosis of osteosarcoma and evidence of expression of HER2/neu by malignant cells are eligible for enrollment.

Canine Osteosarcoma Trial

In the first regiment the limbs are amputated, followed by round of chemotherapy treatment. 3 doses of Her-2 vaccine are subsequently administered with or without a 6 month interval booster.

All dogs are to receive 4 weeks of carboplatin therapy. Four weeks after the last carboplatin dose, dogs are to receive ADXS-HER2 once every three weeks for a total of 3 doses. Group 1 (3 dogs) receive $1 \times 10^8$ CFU per dose, Group 2 (3 dogs) each receive $5 \times 10^8$ CFU per dose and Group 3 (3 dogs) receives $1 \times 10^9$ CFU per dose. Additional dogs are added to a Group to gather more data should if a potentially dose limiting toxicities, be observed. Therefore 9-18 dogs may be treated in the initial study.

In the second regiment, the same as the first regiment is repeated with the exception that only a single dose of vaccine is administered before chemotherapy (1 month before) for a total of 4 doses.

Further, in both regiments a single dose is administered a month after chemotherapy.

Example 9

Phase 1 Dose Escalation Study Evaluating the Safety of ADXS-cHer2 in Companion Dogs with Her-2/Neu Overexpressing Canine Osteosarcoma A pilot phase I dose escalation study was performed to determine the dose of a *L. monocytogenes* expressing human Her-2/neu recombinant vaccine that can safely and effectively stimulate tumor-specific immunity in dogs with osteosarcoma. The tumors of all dogs presenting to PennVet for limb amputation due to suspected or confirmed OSA were routinely harvested and evaluated histopathologically to confirm the diagnosis of OSA. In addition, tumor sections from all dogs were evaluated by IHC and Western blot analysis to determine whether the tumor expresses Her-2/neu. Only dogs with a histological diagnosis of OSA and evidence of expression of Her-2/neu by malignant cells were eligible for enrollment. Single cell suspensions of tumor tissue taken at surgery were cryopreserved and used as autologous tumor targets in chromium release assays to determine anti-tumor immunity.

Up to 18 privately owned dogs with appendicular OSA and confirmed expression of Her2-neu were enrolled (FIG. 7). At enrollment (3 weeks post last carboplatin treatment), all dogs received basic clinical laboratory tests including a Complete Blood Count (CBC), Chemistry Screen (CS) and urinalysis (UA) and a baseline evaluation of cardiac function by echocardiography and measurement of cardiac-specific Troponin I (cTnI) levels. Thoracic radiographs were taken to determine whether pulmonary metastases are present. Only dogs with no evidence of pulmonary metastases were eligible for inclusion in the study. At the time of enrollment, peripheral blood mononuclear cells (PBMCs) are collected to assess baseline levels of anti-tumor immunity (see Assessment of anti-tumor immunity). Furthermore, blood was taken to evaluate baseline immune function to ensure they were no longer immune suppressed by carboplatin. Only dogs with functionally intact immune systems were eligible to receive the *Listeria* vaccine.

Lm Recombinant Dosing and Data Capture

All dogs were vaccinated using a single Lm-huHer-2/neu recombinant vaccine. The first Lm-huHer2-neu vaccine were given three weeks after the last carboplatin dose and were given once every three weeks after this for a total of 3 doses (FIG. 7).

Group 1 (3 dogs) received the ADXS31-164 (Lm-hucHer-2/neu) vaccine at $1 \times 10^8$ CFU per dose, Group 2 (3 dogs) each received $5 \times 10^8$ CFU per dose, Group 3 (3 dogs) receive $1 \times 10^9$ CFU per dose, and $3.3 \times 10^9$ CFU per dose (1 dog). Recombinant Lm was administered as a slow intravenous infusion over 30 minutes. The dose chosen for Group 1 is the established safe dose for the chimeric huHer-2/neu recombinant in mice. In humans, the non-toxic dose for Lm-LLO-E7 is only one log higher than that established in mice, and this dose is the dose evaluated in Group 3 in this pilot trial.

Figure 9:
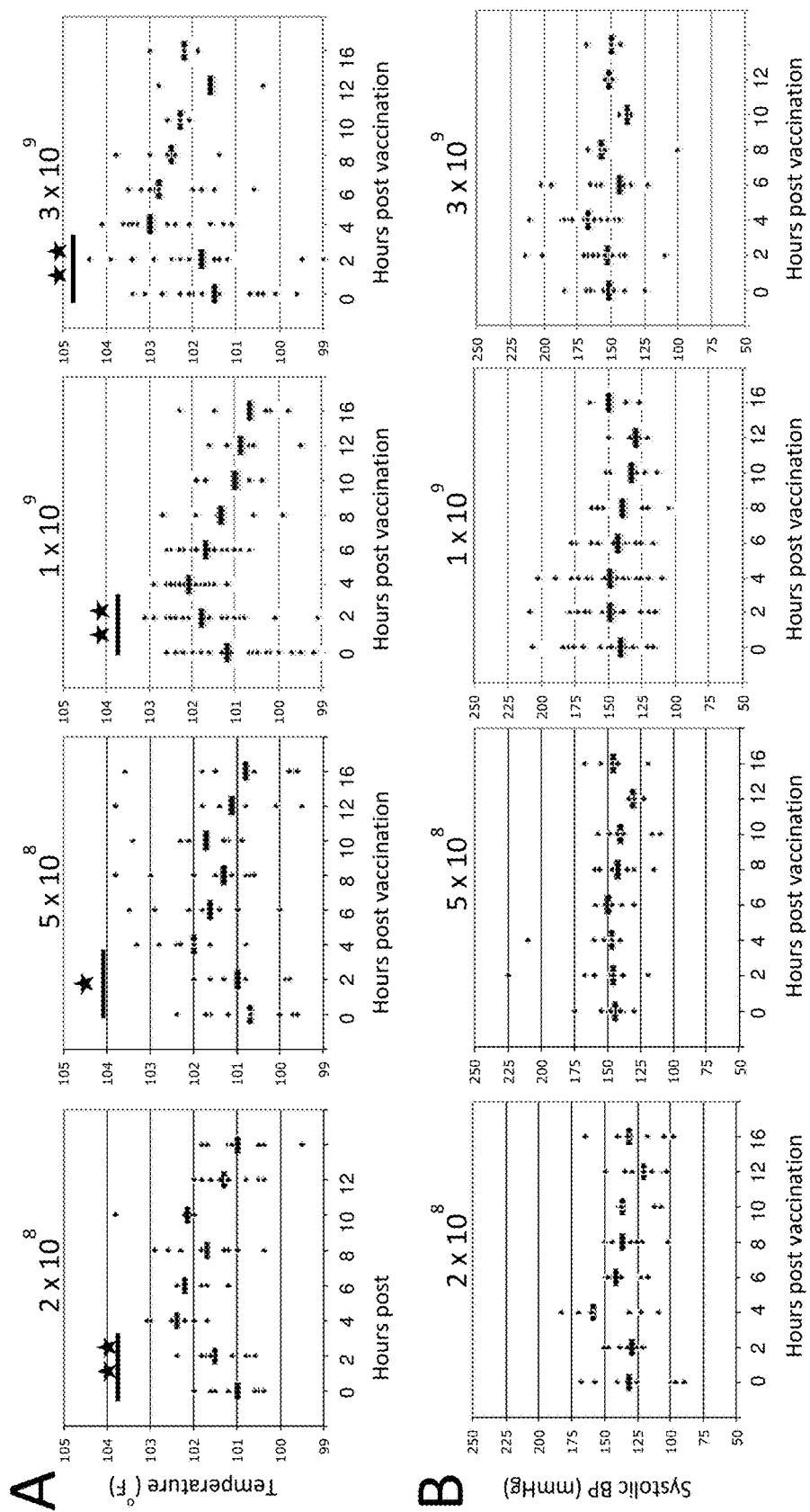
FIG. 9. Shows ADXS31-164 associated changes in A) body temperature and B) systolic blood pressure. Body temperature and systolic blood pressure were recorded at baseline and every 2 hours post ADXS31-164 administration. Parameters for each dog at each vaccination are displayed. Horizontal bars represent median values for all dogs in each dose group at each time point. *p<0.05, **p<0.005

At the time of Lm administration, dogs were monitored for evidence of systemic to adverse effects. During infusion, heart rate and rhythm was monitored by ECG and respiratory rate were recorded. Further, heart damage was monitored using ultrasound and by measuring Troponin I levels (FIG. 8). Following infusion, dogs were monitored closely for 48 hours. Core body temperature was monitored continuously for <12 hours post infusion using the Vital Sense continuous body temperature monitoring system by MiniMitter Respironics (routinely used in our Veterinary Clinical Trials Center, VCIC). Pulse rate, rhythm and quality, respiratory rate and effort, were monitored and recorded every hour for the first 6 hours then every 4 hours thereafter, as well as blood pressure and temperature (FIG. 9). All symptoms consistent with immune stimulation are noted and fluids, analgesics, anti-emetics and anti-histamines are used as necessary to control severe reactions. All dogs were observed six times a day and any signs of toxicological effects of the recombinants including discomfort, lethargy, nausea, vomiting and diarrhea were recorded. Blood samples were taken at 24, 48 and 72 hours after the first ADXS31-164 vaccine for cultures to assess the clearance of Lm after systemic administration.

Assessment of Anti-Tumor Immunity

Figure 12:
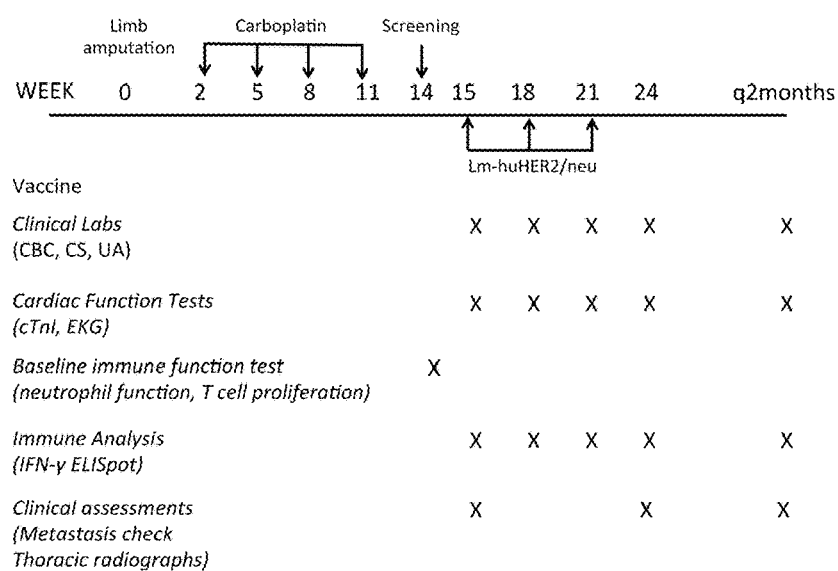
FIG. 12. Timeline of a pilot phase I clinical trial to evaluate the safety and efficacy of a *L. monocytogenes* recombinant expressing ADXS31-164 to elicit therapeutically effective anti-tumor immunity in dogs with appendicular osteosarcoma, that undergo limb amputation and follow up chemotherapy.
Figure 16:
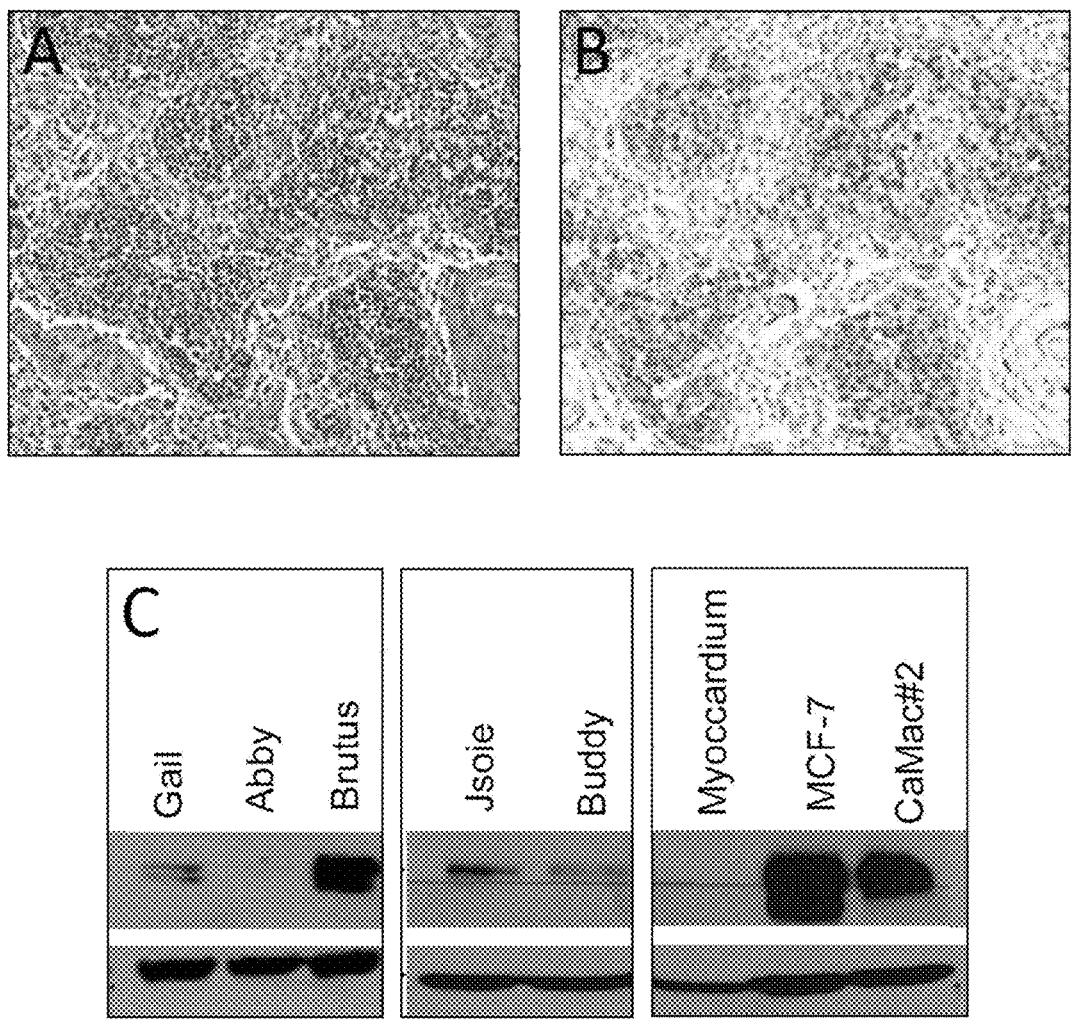
FIG. 16. HER2/neu expression in canine primary osteosarcoma. (A) H&E stain of primary OSA from a dog showing nests of malignant osteoblasts and osteoid deposition. (B) Immunohistochemical evaluation of canine primary OSA showing HER2/neu expression within malignant osteoblasts. (C) Western blot of primary OSA samples from 5 privately owned dogs showing variable expression of HER2/neu. Positive controls are: MCF-7 human mammary carcinoma cell line and CAMAC2 a canine mammary carcinoma cell line.

Three weeks following the last carboplatin dose, dogs receive a routine clinical examination and baseline blood work including CBC, CS, UA and cTnI levels. PBMCs are taken at this time for baseline evaluation of anti-tumor immunity. Repeat immune assessment is performed at the time of each vaccination and three weeks after the last vaccination. PBMCs are analyzed for Her-2/neu specific T cell responses by CFSE proliferation, cytokine production (ELISpot and qRT-PCR) and CTL assay against autologous tumor targets as outlined below (FIG. 12).

Results

To date, we have performed a total of 41 infusions of ADXS31-164 in 16 dogs.

| Number of dogs | Number of infusions | Rationale |
|---|---|---|
| 1 | 5 | Two additional infusions post priming series to treat metastatic disease |
| 4 | 4 | One additional infusion post priming series to maintain tumor free status |
| 4 | 3 | Finished scheduled priming series |
| 1 | 2 | Succumbed to metastatic disease prior to finish of priming course |
| 2 | 1 | Succumbed to metastatic disease prior to finish of priming course |
| 4 | 1 | Priming course of vaccinations underway |

ADXS31-164 dose has ranged from $1 \times 10^8$, $5 \times 10^8$, $1 \times 10^9$ and $3.3 \times 10^9$ CFU.

| Dose received | Total number of doses administered | Number of dogs | Reported side effects |
|---|---|---|---|
| $1 \times 10^8$ | 9 | 3 | Fever, nausea, vomiting, elevated liver enzymes |
| $5 \times 10^8$ | 9 | 3 | Fever, nausea, vomiting, elevated liver enzymes |
| $1 \times 10^9$ | 17 | 10 | Fever, nausea, vomiting, elevated liver enzymes, thrombocytopenia |
| $3.3 \times 10^9$ | 1 | 1 | Nausea, vomiting, |

Standard Operating Procedure for Vaccine Administration

A standard operating procedure was developed for the administration of ADXS31-164. One hour prior to vaccination, patients receive 2 mg/kg diphenhydramine via intramuscular injection and 0.2 mg/kg ondansetron as a slow intravenous push. The vaccine was kept at −80° C. and thawed patient-side. It was administered in 200 mls of 0.9% NaCl over 30 mins. The infusion line is then flushed with 30 mls of Plasmalyte. Dogs are sent home with a three day course of amoxicillin (to start 72 hours post vaccination) and a 7 day course of liver supplement (S-adenosyl-methionine) that aids in cellular growth and repair.

The primary endpoint of the study was to determine the maximum tolerated dose of ADXS31-164.

Doses up to $3.3 \times 10^9$ were well tolerated in dogs ranging in body weight from 25 kg to 67 kg. All side effects reported were grade I toxicities and the maximum tolerated dose has yet to be reached. Side effects routinely occurred within 2-4 hours of vaccine administration. High fevers usually resolved with intravenous isotonic fluids delivered at maintenance rate (4 mls/kg/hour) for 2-4 hours. In two cases where fevers reached 104.7 and above, a single subcutaneous injection of carprofen induced normothermia within 1-2 hours. Nausea and vomiting was usually self-limiting but in cases where several episodes are noted, 1 mg/kg cerenia is administered and this was very effective at preventing further nausea and vomiting. A total of 5 dogs developed mild, grade I elevations in liver enzymes within 48 hours of vaccine administration—these resolved by one week post vaccination.

Clearance of *Listeria*

After performing blood cultures on all 16 dogs vaccinated to date there was no detectable *Listeria* in the peripheral circulation of any of the dogs at 24 hours post vaccination. Shedding of *Listeria* in the urine and feces of vaccinated dogs was not assessed.

Secondary endpoints for the study are progression-free survival and overall survival. A statistically significant overall survival advantage in dogs with osteosarcoma has been observed when ADXS31-164 is administered after limb amputation and 4 doses of carboplatin. Early results from the first two dose groups (6 dogs) show a significant survival advantage in dogs that received ADXS31-164 compared to 6 dogs whose owners elected not to participate in the trial but who were followed for survival (p=0.003) (FIG. 13). The mean survival time for unvaccinated dogs is 239.5 days. The mean survival time for vaccinated dogs has not yet been reached. This remains true when all dogs within the intent to treat group are included in analysis.

In conclusion, there was no evidence of significant short or long-term side effects on the cardiovascular, hematopoietic, hepatic, or renal systems. Moreover, administration of ADXS31-164 in the presence of minimal residual disease can delay/prevent metastatic disease and prolong overall survival of dogs with Her-2/neu positive osteosarcoma.

Example 10

Phase 1 Clinical Trial Evaluating ADXS31-164 in the Spontaneous Canine Model of Osterosarcoma (OSA)

Vaccine Manufacture

Design and generation of ADXS31-164. Briefly, the dal dat actA mutant strain of *Listeria monocytogenes* (Lm) was transfected with the pADV plasmid carrying a chimeric human HER2/neu construct. The construct contains 2 extracellular domains (EC1 and EC2) and one intracellular domain (IC1) of the human HER2/neu molecule that contain the majority of HLA-A2 restricted immunodominant epitopes, fused to a truncated listeriolysin O construct. The transfer plasmid also contains the *bacillus* p60 dal gene and is maintained within the mutant Lm via auxotrophic complementation. There is no bacterial resistance cassette. Vaccines were manufactured by Vibalogics GmbH (Cuxhaven, Germany) and stored at −80° C. prior to use.

Histopathology, Staging and Immunohistochemistry

Histopathological assessment of all primary appendicular osteosarcoma tumors was performed by a board certified veterinary pathologist (J.E.). Tumors were described as osteoblastic, chondroblastic, fibroblastic and telangiectatic based on histological features. Primary tumors were scored based on mitotic index, nuclear pleomorphism and the amount of matrix and necrosis present. Histological scores were converted into a grade (I, II or III).

For HER2/neu staining, 5 micron thick serial sections of formalin fixed, decalcified, paraffin embedded tissues were mounted on negatively charged glass slides. Sections were heated at 80° C. for 20 minutes, immersed in Pro Par (clearant) and rehydrated in ethanol. Antigen retrieval was performed by boiling sections in sodium citrate buffer (pH ~9.0). Endogenous peroxidase was blocked using 3% hydrogen peroxide. Staining was performed with a rabbit anti-human HER2/neu antibody (Neu(c-18):sc-284, Santa Cruz Biotechnology) or a rabbit IgG isotype (Universal Negative Control serum, NC498, Biocare Medical). Bound antibody was detected using the Universal Streptavadin-Biotin2 System (DAKO/LSAB2, HRP). Tissues were stained with 3,3'-diaminobenzidine solution (DAKO) and counterstained with hematoxylin. Slides were viewed using a Nikon E600 infinity corrected upright microscope. Bright field images were acquired using a Nikon Digital Sight DS-Fi1 color camera and a NIS-Element BR3.0 for image analysis. Tissue sections were evaluated and scored for HER2/neu positivity by a board certified pathologist (J.E.) based on the percentage of neoplastic cells staining for HER2/neu (<10%=1, 10%-50%=2, >50%=3) and the intensity of HER2/neu staining (weak=1, moderate=2, strong=3). Scores were based on cells analyzed within 10 hpf for each tissue section. A combined HER2/neu score was obtained by multiplying the two separate scores given for percentage of tumor cells positive for HER2/neu staining and HER2/neu staining intensity. Only dogs with greater than 10% of their tumor cells staining positive for HER2/neu were eligible for trial enrollment.

Eligibility Criteria and Clinical Trial Design

Dogs with a histopathological and immunohistochemical diagnosis of HER2/neu positive OSA that had undergone primary tumor removal either by limb amputation or limb-sparing surgery and had received 4 doses of 300 mg/m$^2$ carboplatin given once every 3 weeks (or once every 4 weeks if myelosuppression occurred) as adjuvant chemotherapy were eligible for screening. Dogs were screened three weeks after their last carboplatin treatment. A thorough physical examination, Complete Blood Count (CBC), Chemistry Screen (CS) and Urinalysis (UA) were performed to determine general health status. Basic innate and adaptive immune function was tested using a flow cytometric neutrophil oxidative burst assay and mitogen-induced lymphocyte proliferation assay respectively. Baseline cardiac status was evaluated by electrocardiography, echocardiography and serum cardiac troponin I levels. Thoracic radiographs were performed to determine the presence of pulmonary metastatic disease (see FIG. 14B). Only those dogs found to be systemically healthy with intact innate and adaptive immune function, no evidence of underlying cardiac disease and no evidence of pulmonary metastatic disease were eligible for enrollment. Dogs that died during the course of the study underwent necropsy. The presence and location of metastatic disease was recorded and histopathology and immunohistochemistry to evaluate HER2/neu expression in metastatic lesions were performed.

Immune Analysis

Neutrophil Oxidative Burst Assay.

Red blood cells in sodium heparin anti-coagulated blood were lysed using 0.83% $NH_4Cl$ and the remaining white blood cells were washed twice in 1×PBS. Cells were labeled with 15 ug/ml of dihydrorhodamine 123 (DHR-123; Molecular Probes, Grand Island, N.Y.) and activated with 3 nM phorbol 12-myristate 13-acetate (PMA, Sigma, St. Louis, Mo.) for 30 minutes at 37° C. Cells were placed on ice for 15 minutes prior to flow cytometric analysis. Cells were acquired on a FACS Canto cytometer (BD Biosciences, San Jose, Calif.) and analyzed using FloJo software (Treestar, San Carlos, Calif.).

Lymphocyte Proliferation Assay.

Peripheral Blood Mononuclear Cells (PBMCs) were isolated from sodium heparin anti-coagulated whole blood by density centrifugation. PBMCs were washed twice in 1×PBS and counted. Cells were labeled with 5 uM CFSE and stimulated with 1.25 uM Concanavalin A at 37° C. for 5 days. Cells were harvested, washed twice in FACS buffer, labeled with APC-conjugated rat anti-canine CD4 and PE conjugated rat anti-canine CD8 antibodies (Serotec, Raleigh, N.C.) and analyzed by flow cytometry. For immune function analysis, peripheral blood taken from healthy colony dogs (IACUC #804197) was used as a positive control.

T Cell Subset Analysis.

PBMCs taken at baseline, prior to each vaccination, at re-stage and at every 2 months thereafter were analyzed for CD4 and CD8 T cell subsets. Briefly, cryopreserved cells were thawed and washed twice in FACS buffer (1×PBS, 0.2% BSA fraction V, and 4 mM sodium azide) prior to surface staining with mouse anti-canine CD3, PE-labeled rat anti-dog CD8 or Alexa-labeled rat anti-dog CD4 (Serotec, Raleigh, N.C.). Cells were incubated with the vital dye 7-ADD immediately prior to flow cytometric acquisition. Total $CD4^+$ and $CD8^+$ T cell numbers were calculated from the flow cytometric percentages and total lymphocyte counts determined using a Cell Dyn 3700CS Hematology analyzer.

Vaccine Administration

Prior to vaccination, dogs received the 5HT3 antagonist ondansetron (0.2 mg/kg) intravenously and the H1 receptor blocker, diphenhydramine (2 mg/kg) intramuscularly to prevent nausea and anaphylaxis respectively. A standard 3+3 clinical trial design was employed. ADXS31-164 was administered at the following doses; Group 1 ($2\times10^8$ CFU), Group 2 ($5\times10^8$ CFU), Group 3 ($1\times10^9$ CFU) and Group 4 ($3.3\times10^9$ CFU). ADXS31-164 was diluted in 100 mls 0.9% NaCl (Groups 1 and 2) and 200 mls 0.9% NaCl (Groups 3 and 4) and administered intravenously over 30 minutes. Temperature, pulse, respiratory rate, heart rate and rhythm (by EKG) and blood pressure were monitored every hour following infusion. In cases where body temperature exceeded 103° F., dogs were placed on intravenous Plasmalyte at 4 mls/kg/hr until their temperature fell below 103° F. Dogs were monitored every hour for signs of lethargy, nausea or vomiting. Blood samples were drawn 24 hours and one week post vaccination to assess for any changes in hematological or biochemical parameters and blood cultures were performed at 24 hours post vaccination to determine persistence of live bacteria in the blood stream. All dogs received a short course of amoxycillin and S-Adenosylmethionine (SAMe) 72 hours after vaccination to kill any remaining *listeria* and provide anti-oxidant support to the liver.

Owners with dogs that were free of metastatic disease at least 5 months after receiving the last vaccine in the initial series were offered the option to receive a booster vaccine at a standard dose of $1\times10^9$ CFU. Booster vaccines were administered as described and dogs were monitored after infusion as described above.

Toxicity

Toxicity was graded according to the Veterinary Cooperative Oncology Group-Common Terminology Criteria for Adverse Events (VCOG-CTCAE). Assessment of cardiac toxicity was performed through serial electrocardiograms, echocardiograms and serum cardiac troponin I levels at baseline, at the time of each vaccination, 3 weeks after the last vaccination and every 2 months thereafter until death. Parameters assessed included Left Ventricular Fractional Shortening (LVFS) and Left Ventricular Internal Dimension in diastole (LVIDd) and Left Ventricular Internal Dimension in systole (LVIDs). LVIDd and LVIDs were normalized to body weight to account for the wide range of body size amongst dogs.

ELISpot Analysis

Cryopreserved PBMC from each indicated time point were thawed, rested overnight at 37° C. and then counted. Cells were stimulated with 2.5 uM pools of overlapping human HER2/Neu peptides (11mers overlapping by 5 amino acids) that represent the EC1, EC2 and IC1 domains of HER2/Neu present in the chimeric vaccine, and recombinant human IL-2 (Invitrogen, Fredrick, Md.) for 5 days. Cells were harvested, washed twice in 1×PBS and counted. IFN-γ ELISpot assays were performed according to the manufacturer's protocol using a commercial canine IFN-γ ELISpot assay kit (R&D Systems, Minneapolis, Minn.). Briefly, $0.8$-$2\times10^5$ stimulated cells were incubated with 2.5 uM of EC1, EC2 or IC1 peptide pools plus IL-2 or IL-2 alone (to determine background counts). All assays were performed in duplicates. Plates were developed according to the manufacturer's instructions. Spots were counted using a CTL-Immunospot analyzer (C.T.L, Shaker Heights, Ohio).

Primary and Secondary Outcome Measures

Time To Metastasis (TTM) was calculated as the time between amputation and development of metastatic disease. OSA Specific Survival was calculated as the time between amputation and death. Patients that died of unrelated causes were censored at the time of their death.

Results

Eighteen dogs that fulfilled the eligibility criteria were enrolled in this phase I clinical trial. The age, breed, sex, tumor location, subtype, grade and HER2/neu status were recorded (Table 4). A standard 3+3 clinical trial design was employed. ADXS31-164 was administered at the following doses; Group 1: $2\times10^8$ CFU (n=3), Group 2: $5\times10^8$ CFU (n=3), Group 3: $1\times10^9$ CFU (n=9), and Group 4: $3\times10^9$ CFU (n=3). Five additional dogs with pre-existing pulmonary metastatic disease, identified at the time of screening also received ADXS31-164 on a compassionate care basis (Table 4). Four of these dogs had strong HER2/neu staining in >50% of neoplastic cells from their primary tumor. Three of these dogs had multiple pulmonary metastatic nodules and two dogs had a single metastatic nodule at screening. Dogs with multiple pulmonary nodules received one vaccine each before disease progression and withdrawal from the study for alternative treatments. The two dogs with single nodules received the full course of three vaccines each. Dogs with pre-existing metastatic disease received either $1\times10^9$ CFU (n=3) or $3\times10^9$ CFU (n=2) ADXS31-164 (Table 5).

FIG. 15 shows a schematic of the time-line of the phase 1 clinical trial, wherein three vaccinations were administered following amputation and follow-up chemotherapy.

TABLE 4

Signalment and tumor characteristics of enrolled dogs

| AGE | BREED | SEX | TUMOR LOCATION | SUBTYPE | GRADE | HER2 SCORE | DOSE | OVERALL SURVIVAL (days) |
|---|---|---|---|---|---|---|---|---|
| Group 1 | | | | | | | | |
| 12.5 | American Pit Bull | FS | Proximal humerus | Osteoblastic | II | 2 | $2 \times 10^8$ | 738 |
| 11.5 | Mixbreed | FS | Distal radius | Osteoblastic | I | 5 | $2 \times 10^8$ | 267 |
| 9 | Labrador | MC | Proximal humerus | Fibroblastic | II | 7.5 | $2 \times 10^8$ | 977+ |
| Group 2 | | | | | | | | |
| 6 | Mixbreed | FS | Distal tibia | Osteoblastic | I | 4.5 | $5 \times 10^8$ | 943+ |
| 7 | Rottweiler | MC | Distal ulnar | Osteoblastic | III | 2.25 | $5 \times 10^8$ | 925+ |
| 4.5 | English Bulldog | MC | Proximal humerus | Osteoblastic | I | 4 | $5 \times 10^8$ | 346 |
| Group 3 | | | | | | | | |
| 6 | OES | MC | Distal femur | Osteoblastic | II | 1.5 | $1 \times 10^9$ | 744+ |
| 9 | Greyhound | MC | Proximal humerus | Osteoblastic | II | 5 | $1 \times 10^9$ | 444 |
| 8 | Golden Retriever | MC | Distal ulnar | Fibroblastic | I | 3 | $1 \times 10^9$ | 488+ |
| 2 | Labrador | FS | Proximal tibia | Fibroblastic | I | 4.5 | $1 \times 10^9$ | 438+ |
| 7.5 | Cavalier King Charles | FS | Proximal tibia | Osteoblastic | II | 7.5 | $1 \times 10^9$ | 439+ |
| 6.5 | Golden Retriever | FS | Distal radius | Osteoblastic | I | 4.5 | $1 \times 10^9$ | 430+ |
| 10 | Greyhound | MC | Distal femur | Osteoblastic | II | 2 | $1 \times 10^9$ | 276 |
| 5.5 | Labrador | MC | Distal femur | Osteoblastic | I | 9 | $1 \times 10^9$ | 312+ |
| 9 | Golden Retriever | FS | Distal femur | Osteoblastic | I | 6 | $1 \times 10^9$ | 336+ |
| Group 4 | | | | | | | | |
| 6.6 | Great Dane | MC | Distal radius | Osteoblastic | II | 7.5 | $3 \times 10^9$ | 259 |
| 7 | Mixbreed | MC | Proximal humerus | Osteoblastic | II | 9 | $3 \times 10^9$ | 345+ |
| 6.5 | Rottweiler | FS | Proximal humerus | Osteoblastic | II | 6 | $3 \times 10^9$ | 332+ |

TABLE 5

Signalment and tumor characteristics of dogs with pre-existing metastatic disease treated on a compassionate care basis.

| AGE | BREED | SEX | TUMOR LOCATION | SUBTYPE | GRADE | HER2 SCORE | DOSE | OVERALL SURVIVAL (days) |
|---|---|---|---|---|---|---|---|---|
| Vaccine group with metastatic disease | | | | | | | | |
| 5 | Neopolitan Mastiff | MC | Distal radius | Fibroblastic | I | 7.50 | $1 \times 10^9$ | 233 |
| 6.5 | Great Dane | FS | Distal radius | | | 6 | $1 \times 10^9$ | 256 |
| 2 | Labrador | F | Proximal fibula | Osteoblastic | III | 7.5 | $1 \times 10^9$ | 153 |
| 6.5 | Bernese Mountain Dog | FS | Distal ulnar | Osteoblastic | III | 8.25 | $3 \times 10^9$ | 336 |
| 7 | Rottweiler | MC | Distal radius | Osteoblastic | II | 4.00 | $3 \times 10^9$ | 231 |

Results

Figure 17:
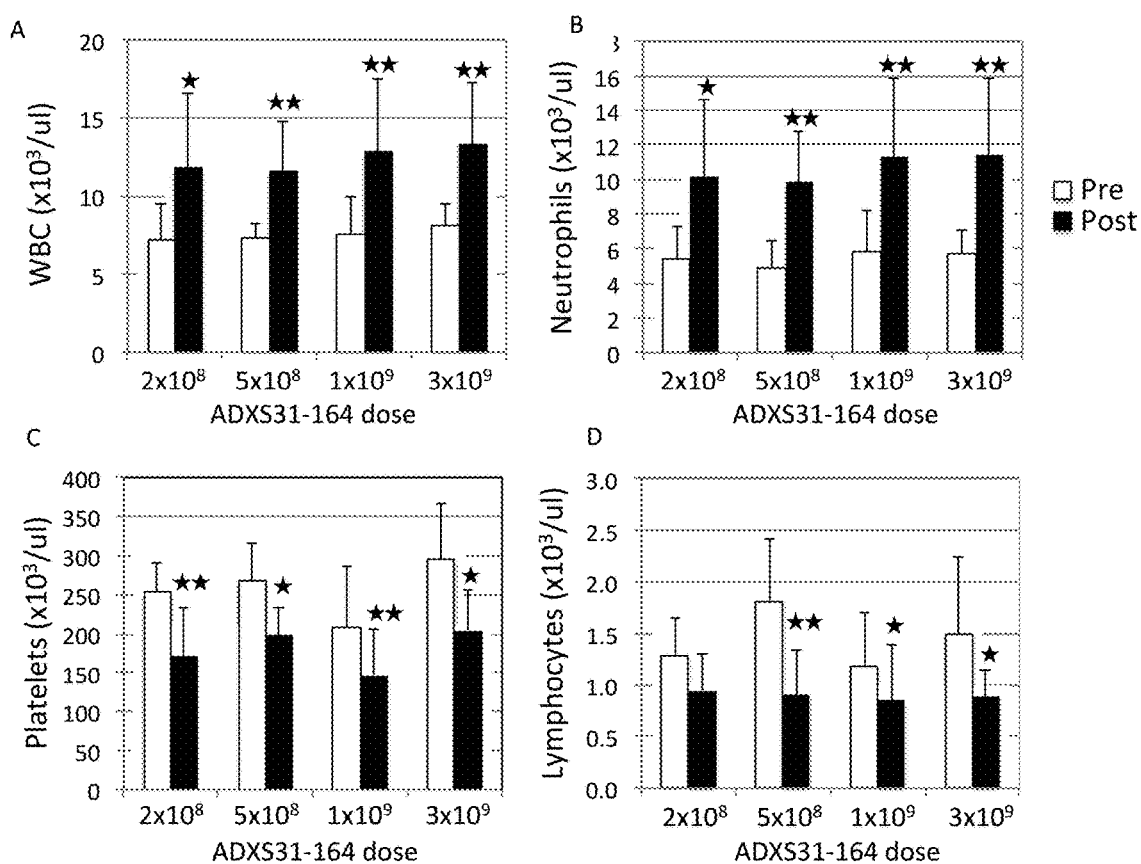
FIG. 17. Hematological values at baseline (Pre) and at 24 hours after (Post) ADXS31-164 administration. Pre and Post values from all dogs within each dose group at each vaccination were averaged. *p<0.05, **p<0.005. Shows a transient, but statistically significant increase in white blood cell and neutrophil counts (A-B) that occurred 24 hours after ADXS31-164 administration and that were accompanied by a transient decrease in platelets and lymphocytes (C-D).

Safety and Toxicity=Safety was evaluated for all 23 vaccinated dogs. All dogs tolerated ADXS31-164 administration well with only transient, low grade toxicities observed to on the day of vaccination (Table 6). A statistically significant increase in body temperature occurred 4 hours after ADXS31-164 administration in all groups irrespective of dose (FIG. 9A). Hypotension was not observed at any time point or at any dose (FIG. 9B). 8/18 dogs (without pre-existing metastatic disease) and 3/5 dogs (with pre-existing metastatic disease) developed fevers of >103° F. within 4 hours of vaccination and were given intravenous fluids at that time. Three dogs received a single dose of a non-steroid anti-inflammatory drug to reduce body temperature. In all cases, fevers resolved without further intervention. Transient lethargy, nausea and vomiting that did not require therapeutic intervention occurred within 4 hours of vaccination regardless of dose. In two dogs transient single or bigeminal ventricular premature contractions were identified shortly after vaccination. One dog with pre-existing metastatic disease developed ventricular tachycardia within 2 hours of vaccination. Treatment with lidocaine, procainamide, sotalol and corticosteroids had little effect however, the arrhythmia resolved within 72 hours. Transient, but statistically significant increases in white blood cell and neutrophil counts occurred 24 hours after ADXS31-164 and were accompanied by a transient decrease in platelets and lymphocytes (FIG. 17). Although there was no correlation between ADXS31-164 dose and magnitude of hematological change, there was a significant difference in the magnitude of white blood cell, neutrophil and monocyte responses between dogs that survived and those that died (FIG. 18A-F). Mild, transient increases in the serum concentrations of liver enzymes occurred in approximately half of the dogs, consistent with mild inflammation caused by the hepatotropic *Listeria* (Table 6). All changes identified in the peripheral blood were asymptomatic and resolved within one week of ADXS31-164 administration. No significant changes in renal function were documented in any dog. 19/23 dogs had blood cultures performed 24 hours after ADXS31-164 administration and all were negative, consistent with rapid clearance of the highly attenuated LmddA strain.

Given that HER2/neu targeted monoclonal antibodies cause cardio toxicity we evaluated biomarkers of cardiac damage and echocardiographic measures of dysfunction including cardiac troponin I, fractional shortening (%), LVIDd and LVIDs at baseline, prior to each vaccination and every 2 months thereafter. No significant, sustained changes in cardiac troponin I, fractional shortening, LVIDd or LVIDs were identified in any of the vaccinated dogs (FIG. 26A-D). One dog in Group 3 showed a stepwise increase in serum cardiac troponin I at the time of each vaccination however, this was not accompanied by echocardiographic signs of dysfunction. Values returned to baseline following the last vaccination and were not elevated on repeat assessments.

Throughout the clinical trial cardiac troponin I levels were measured along with fractional shortening, Left Ventricular Internal Diameter in systole (LVIDs) and LVID in diastole (LVIDd) as shown in FIG. 25 (A-D), there was no evidence of long or short-term cardio toxicity following administration of ADXS31-164.

Table 6 below presents data showing minimal treatment related adverse events were reported during the clinical trial.

TABLE 6

Treatment Related Adverse Events occurring at or within 48 hours of ADXS31-164 vaccination. Number of Dogs with Treatment Related Adverse Events

| ADXS31-164 dose | | $2 \times 10^8$ | $5 \times 10^8$ | $1 \times 10^9$ | $3 \times 10^9$ | Total |
|---|---|---|---|---|---|---|
| Number of dogs recruited | | 3 | 3 | 11 | 6 | 23 |
| General Disorders | | | | | | |
| Pyrexia (T > 103) | Grade 1 | 2 | 1 | 5 | 5 | 13 |
| Fatigue | Grade 1 | 1 | 0 | 7 | 2 | 10 |
| Nausea | Grade 1 | 1 | 2 | 10 | 2 | 15 |
| | Grade 2 | 1 | 0 | 0 | 0 | 1 |
| Vomiting | Grade 1 | 1 | 2 | 9 | 3 | 15 |
| | Grade 2 | 2 | 0 | 0 | 3 | 5 |
| Cardiovascular abnormalities | | | | | | |
| Arrhythmias | Grade 1 | 0 | 1 | 0 | 0 | 1 |
| | Grade 2 | 0 | 0 | 0 | 1 | 1 |
| Tachycardia | Grade 1 | 0 | 0 | 2 | 1 | 3 |
| | Grade 2 | 0 | 0 | 0 | 1 | 1 |
| Hyoptension | | 0 | 0 | 0 | 0 | 0 |
| Hypertension | Grade 1 | 2 | 3 | 8 | 5 | 18 |
| Hematological parameters | | | | | | |
| Thrombo-cytopenia | Grade 1 | 2 | 2 | 6 | 3 | 13 |
| | Grade 2 | 0 | 0 | 2 | 1 | 3 |
| Biochemical parameters (increased) | | | | | | |
| γ-GT | Grade 1 | 0 | 2 | 1 | 0 | 3 |
| ALKP | Grade 1 | 0 | 1 | 6 | 1 | 8 |
| | Grade 2 | 0 | 0 | 0 | 1 | 1 |
| | Grade 3 | 1 | 0 | 0 | 0 | 1 |
| ALT | Grade 1 | 1 | 1 | 3 | 0 | 5 |
| | Grade 2 | 0 | 0 | 0 | 1 | 1 |
| | Grade 3 | 1 | 0 | 0 | 0 | 1 |
| AST | Grade 1 | 1 | 1 | 4 | 2 | 8 |
| | Grade 2 | 0 | 0 | 2 | 0 | 2 |
| | Grade 3 | 0 | 0 | 1 | 0 | 1 |

TABLE 6-continued

Treatment Related Adverse Events occurring at or within 48 hours of ADXS31-164 vaccination.
Number of Dogs with Treatment Related Adverse Events

| ADXS31-164 dose | | $2 \times 10^8$ | $5 \times 10^8$ | $1 \times 10^9$ | $3 \times 10^9$ | Total |
|---|---|---|---|---|---|---|
| BUN | | 0 | 0 | 0 | 0 | 0 |
| CREA | | 0 | 0 | 0 | 0 | 0 |
| Cardiac Troponin I | Grade 1 | 0 | 0 | 1 | 1 | 2 |

Conclusion: ADSX31-164 toxicities were low grade and transient

Immune Response to ADXS31-164

Figure 18:
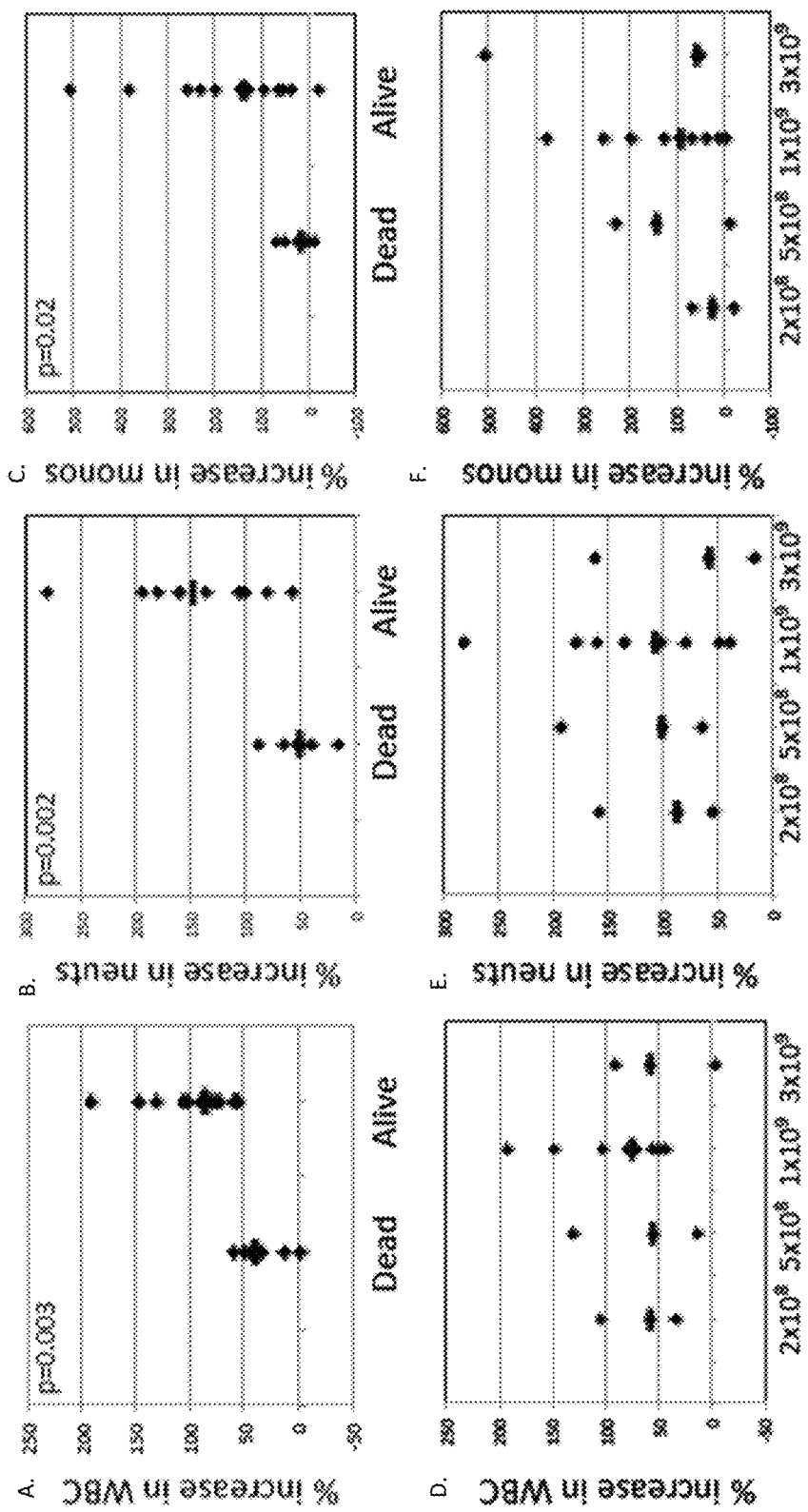
FIG. 18. ADXS31-164 induced increases in white blood cells (WBC), neutrophil and monocyte counts correlate with survival. WBC, neutrophil and monocyte counts were measured at baseline and 24 hours after vaccination. The percent increase was calculated following each vaccination and averaged for each dog. (A) Results are displayed according to survival (dead or alive). (B) Results are displayed according to ADXS31-164 dose received. Horizontal bars represent median values of the group.

The results presented in FIG. 18 demonstrate that an early immune response to ADXS31-164 in dogs receiving the vaccines predicted survival of the dogs. FIG. 18 shows that ADXS31-164 induced increases in WBC, neutrophil and monocytes counts, which correlated with survival and were accompanied by a transient decrease in platelets and lymphocytes (FIG. 17).

Figure 19:
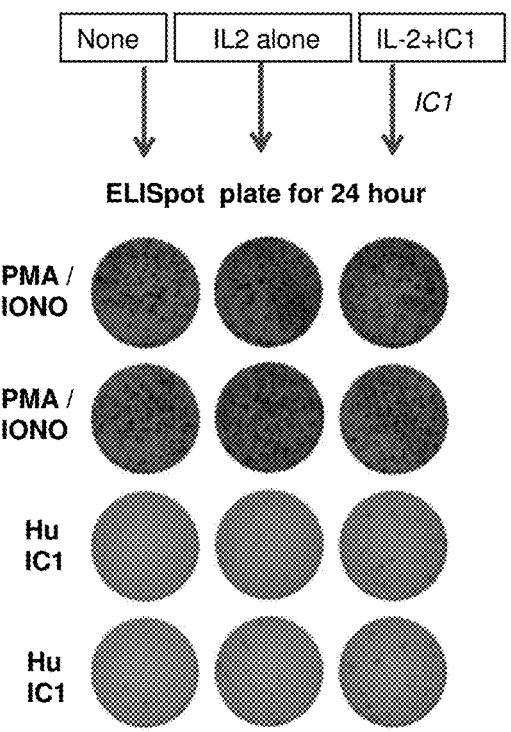
FIG. 19. Shows the results of evaluation of Her-2 specific T cell responses induced by ADXS31-164 by IFN-γ ELISpot.

The ability of ADXS31-164 to induce and maintain an immune response, and in particular to induce HER2/Neu specific T cell immunity was assessed during the clinical trial. In order to evaluate the immune response and to determine if a HER2/Neu specific T cell response was induced by ADXS31-164, HER2/Neu specific T cell numbers were assessed by IFN-γ ELISpot. Samples were taken at baseline (3 weeks post carboplatin), at every vaccination and every 2 months thereafter. FIG. 19 shows the results of the ELISpot assay.

HER2/Neu Specific Immune Responses.

Immunological responses against the human EC1, EC2 and IC1 domains of HER2/neu (sharing 89%, 93% and 98% identity with canine HER2/neu respectively) were detected at baseline in 4/18, 6/18 and 1/18 dogs respectively. Induced IFN-γ responses against one or more of the HER2/neu domains were detected in 7 dogs 3 weeks after the third ADXS31-164 vaccination (Table 7). Five of these dogs developed immune responses against the highly conserved IC1 domain. Five additional dogs developed IFN-γ responses against the IC1 domain 2 months later. Three additional dogs developed IFN-γ responses against either EC2 alone, EC2 and IC1 or EC1, EC2 and EC3 at the time of relapse (dogs 001, 002 and 017). 3 dogs that developed immunological responses against HER2/neu during their initial vaccination series were evaluated by IFN-γ ELISpot over 15 to 17 months. HER2/Neu specific IFN-γ responses were not maintained however, the dogs remained free of metastatic disease during this time. 10 dogs received additional booster vaccinations, of the 6 evaluable, 2 dogs had detectable increases in HER2/neu specific IFN-γ responses 2 months after booster vaccination. Of the 8 dogs that relapsed, 5 had no increase in HER2/neu specific IFN-γ responses 3 weeks after ADXS31-164.

Booster Vaccinations.

Ten of the 18 dogs without metastatic disease at enrollment were administered a single booster vaccine between 5 and 10 months after the initial vaccine series. Four of these dogs received additional booster vaccines given between 4 and 15 months after the first booster vaccine. Similar low grade, transient side effects were noted at the time of booster vaccination as with the initial vaccination series.

Figure 20:
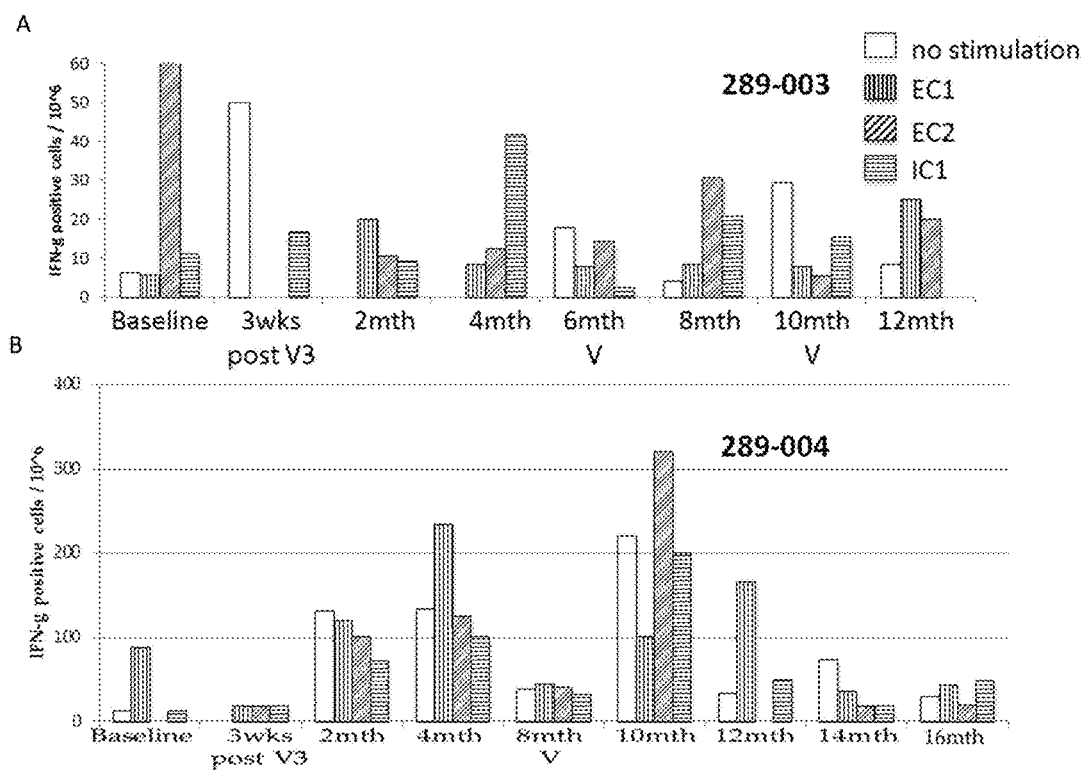
FIG. 20. Shows repeat "booster" vaccinations Stimulate Her-2 specific immunity. (A) Shows the results for patient 289-003. (B) Shows the results for patient 289-004. EC1, EC2 and IC1 represent the peptide fragments of the HER2/neu polypeptide.

FIG. 20 (A and B) show that repeat booster vaccinations also stimulated HER2 specific immunity. Repeat booster vaccinations were administered at 6 and 10 months for animal 289-003, and at 8 months for animal 289-004.

Clinical Outcomes.

8/18 dogs in the vaccinated group relapsed, 4 with pulmonary metastatic disease and 4 with bone metastases. Two dogs with bone metastases progressed to pulmonary metastases. One dog with a bone lesion in her sacrum died from aspiration pneumonia and one dog with a solitary pulmonary nodule died of nephroblastoma however, necropsy specimens from bone and lung lesions respectively were not available for histopathological confirmation of metastatic osteosarcoma. These two dogs were censored from OSA specific survival analysis. Dogs that relapsed received different rescue chemo- and radiation therapies at the discretion of the primary clinician. The 4 dogs with bone metastases were treated with analgesics only (1 dog), palliative radiation alone (1 dog) or in combination with chemotherapy (2 dogs). Two dogs received Adriamycin and 1 dog received palladia for the treatment of pulmonary metastatic disease. Median OSA specific survival for vaccinated dogs has not yet been reached. Kaplan-Meier survival curves for TTM and OSA Specific Survival are shown in FIG. 21. Overall survival rates at 1 and 2 years for vaccinated dogs are 71.4% and 57% respectively.

Figure 24:
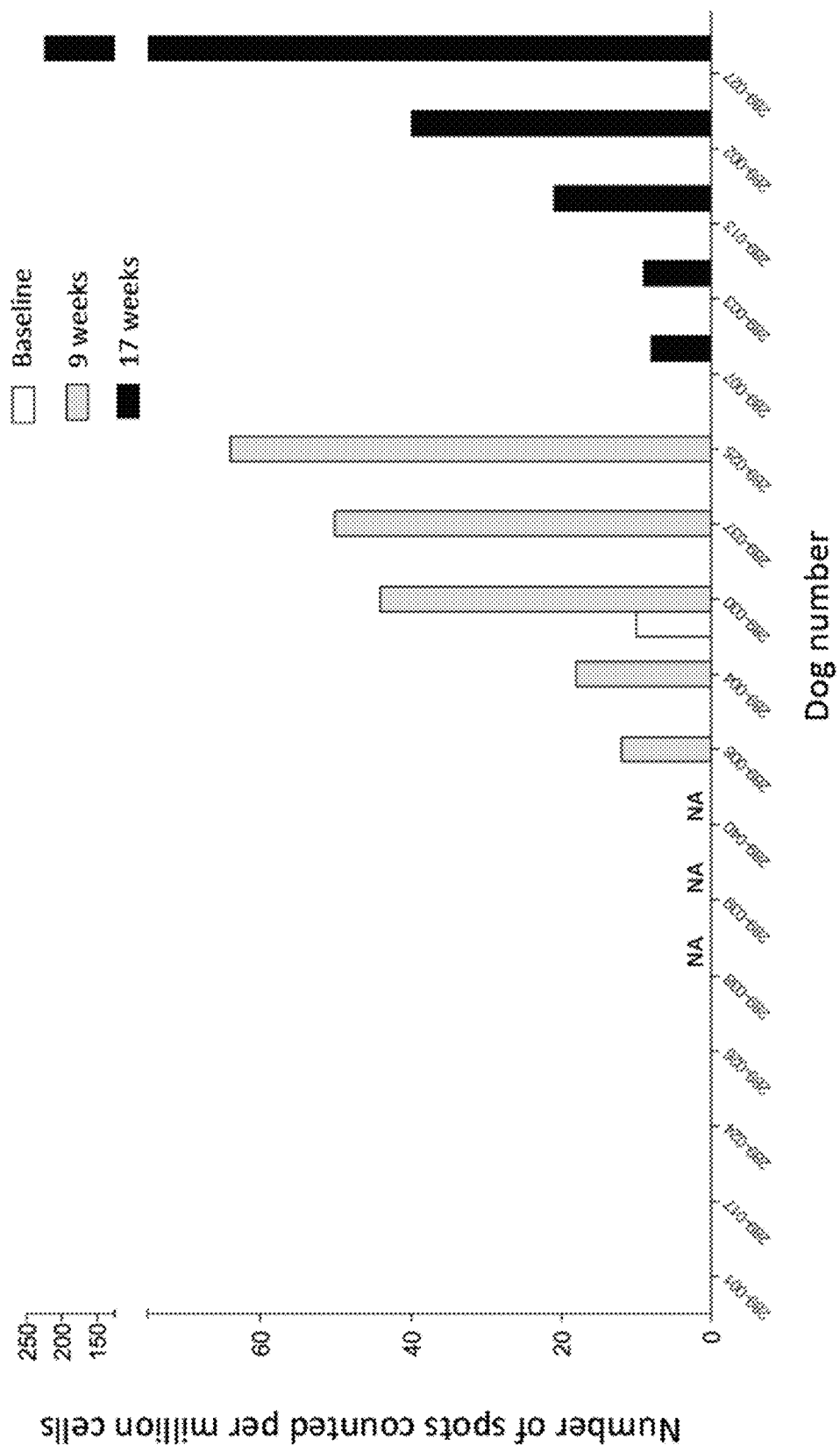
FIG. 24. Shows that ADXS31-164 breaks tolerance to HER2/neu. PBMCs were collected at baseline, 3 weeks after the $3^{rd}$ vaccine (9 weeks) and 2 months later (17 weeks) and analyzed by IFN-γ ELISpot for responses to the highly conserved IC1 domain of HER2/neu. Results presented divided dogs into early responders, late responders and apparent non-responders. NA indicates that the 17 week sample for these dogs was not yet evaluated.
Figure 25A:
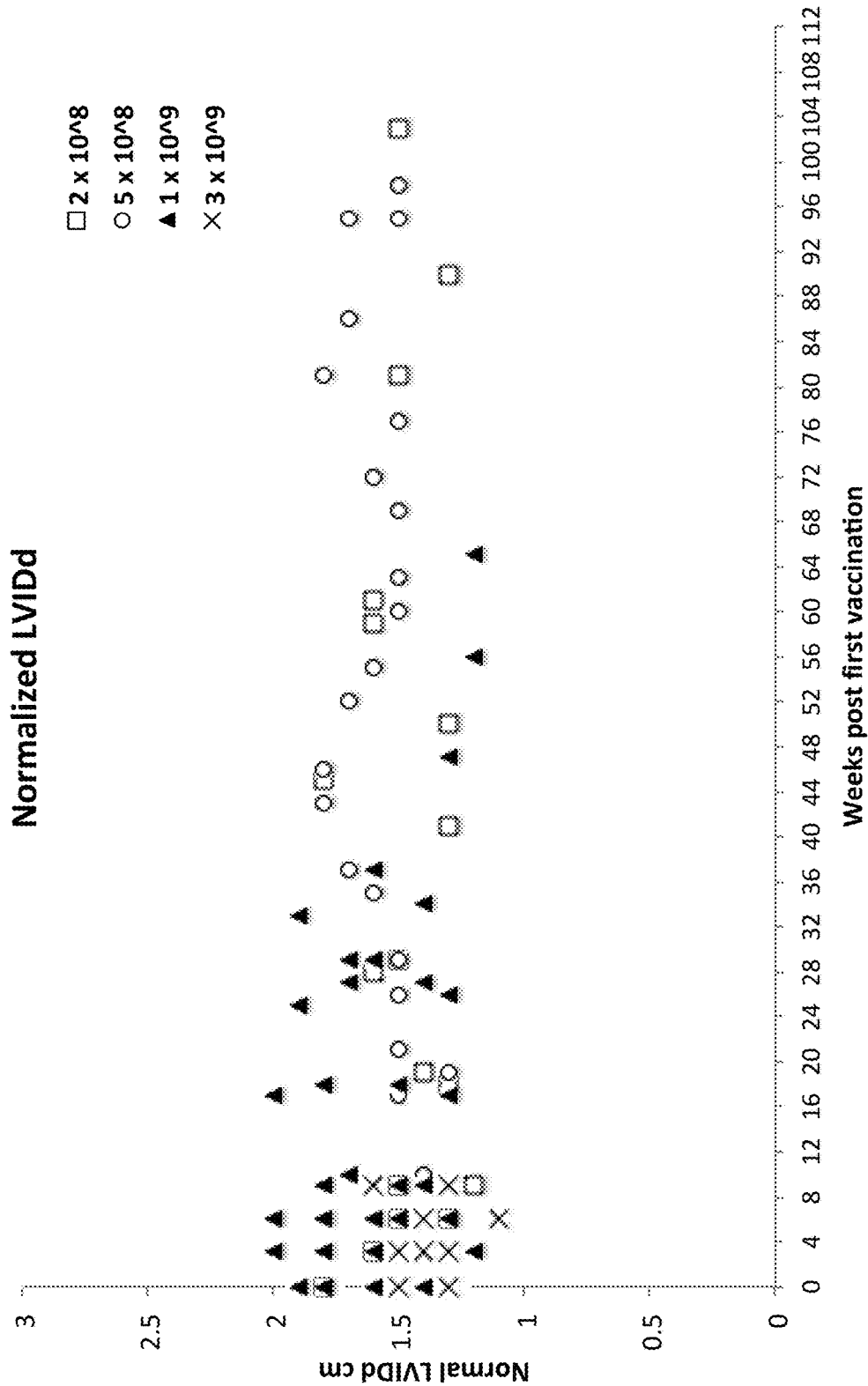
FIG. 25A-D. Shows that ADXS31-164 does not adversely affect cardiac function. Cardiac parameters LVID (diastole) (FIG. 25A), LVID (systole) (FIG. 25B) and fractional shortening (FIG. 25C) were evaluated for each dog at baseline, the time of vaccination and every 2 months thereafter. Cardiac troponin I levels were evaluated at the same time points (FIG. 25D).
Figure 25B:
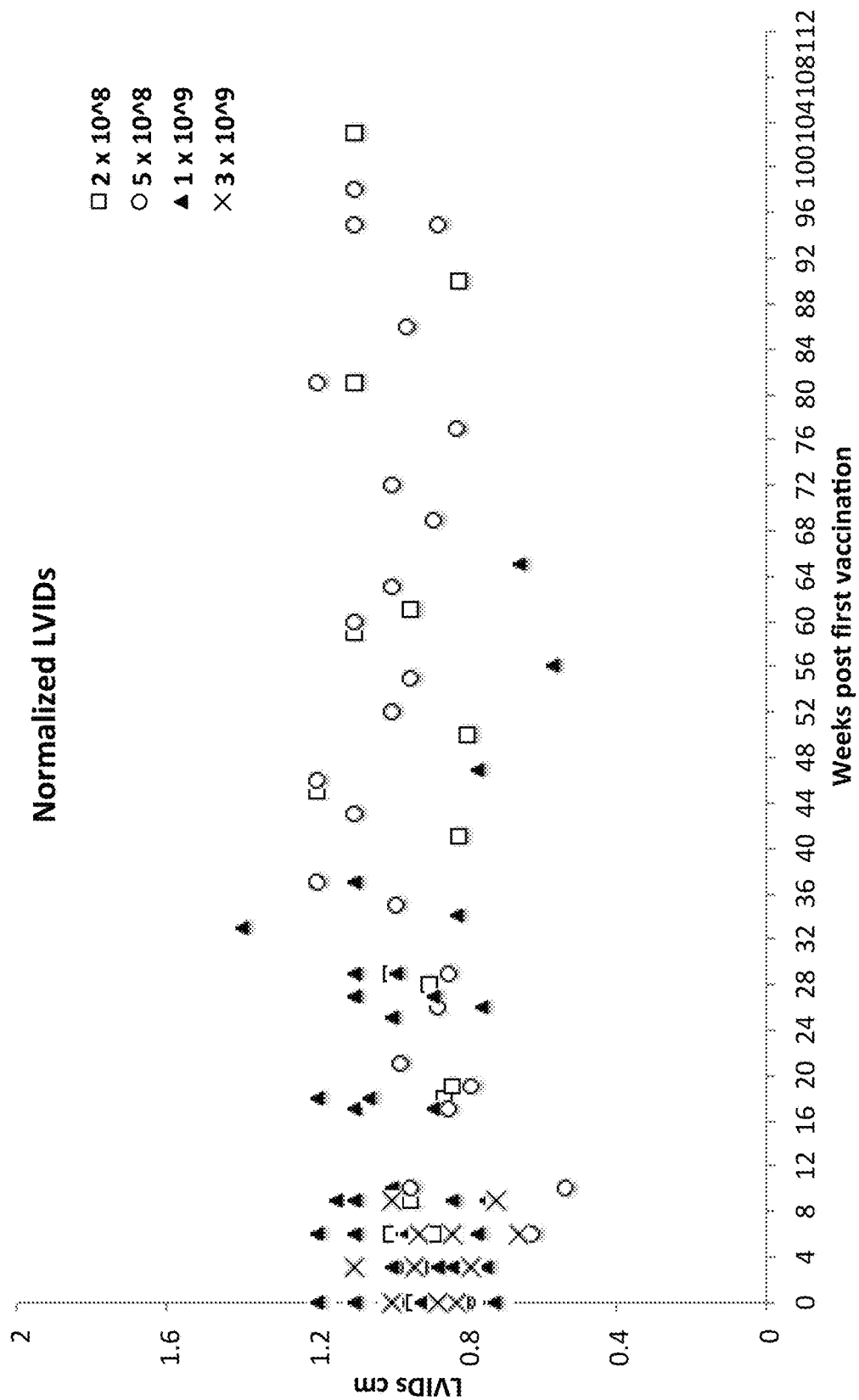
Figure 25C:
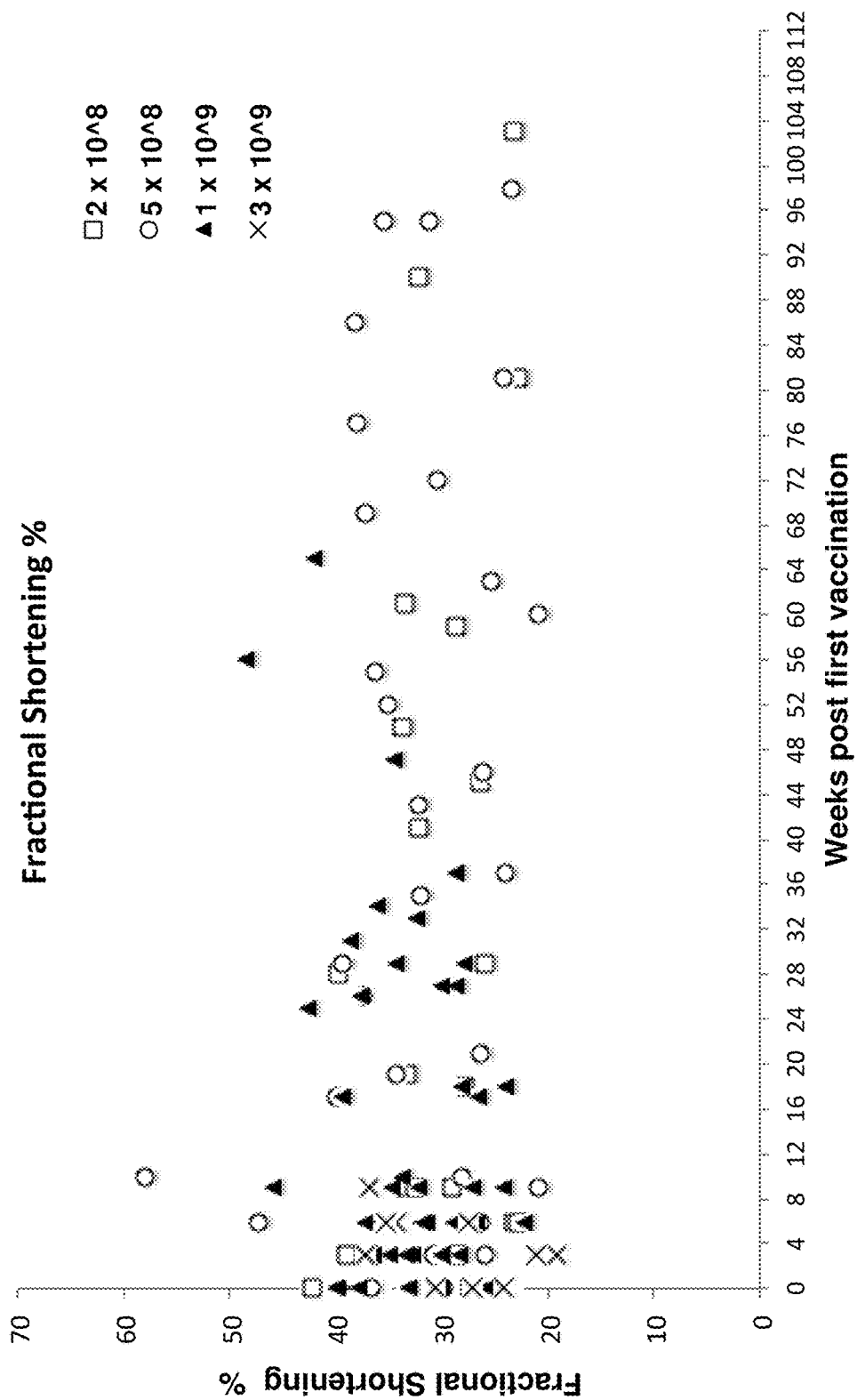
Figure 25D:
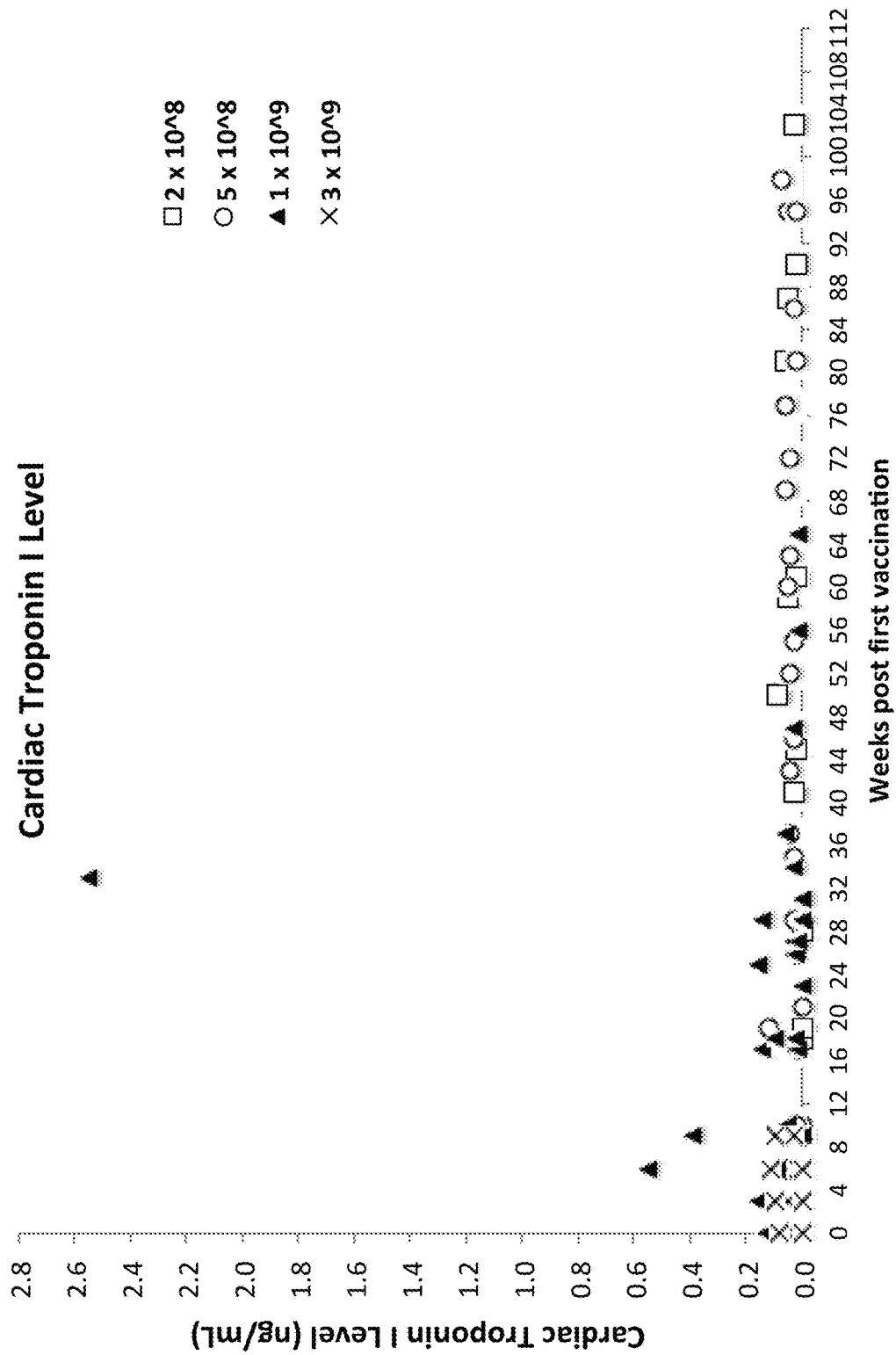
Figure 31:
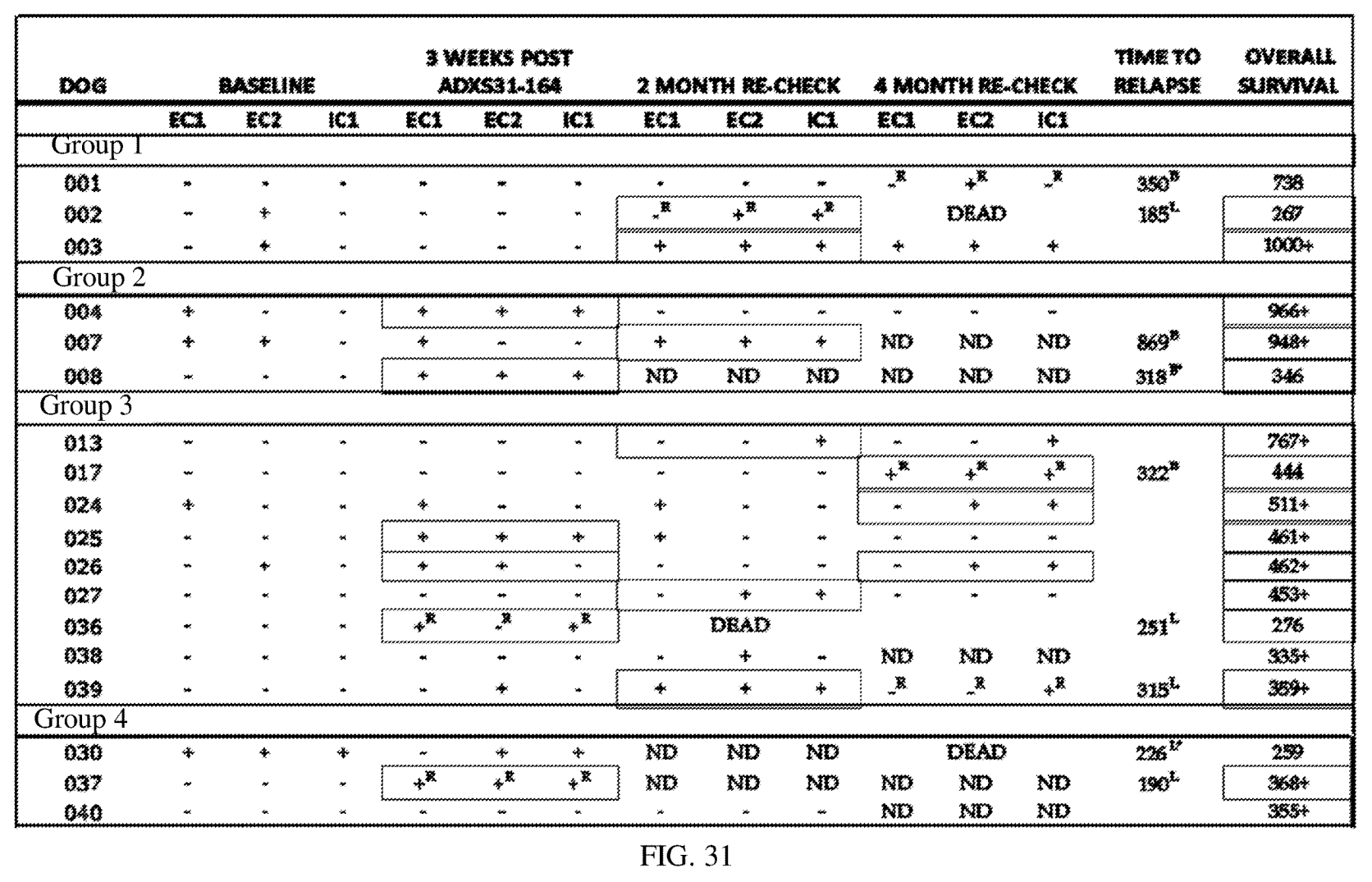

Of the 12 dogs that developed HER2/neu specific IFN-γ responses within 2 months of vaccination, 9 are still alive (3 dogs>900 days, 1 dog>700 days, 3 dogs>400 days and 2 dogs>300 days and 7 remain tumor free to date (FIG. 31)). The results presented in FIG. 24 demonstrate that ADXS31-164 breaks the tolerance to HER2/Neu. This may be significant for the treatment of OSA as well as other HER2/Neu tumors and/or cancers.

Necropsy Findings.

6/18 dogs died during the study period and necropsies were performed on 4 of these dogs. Three dogs were found to have multifocal grade II and III metastatic osteosarcoma involving the lungs (3 dogs), bone (2 dogs), mediastinum (1 dog) and kidney (1 dog). One dog, euthanized on account of a large progressive renal mass was found to have nephroblastoma. This dog also had a single pulmonary nodule but this was unfortunately not evaluated by histopathology.

Survival, Prolonged Survival, Tumor Progression Following Administration of ADXS31-164

Three dogs with multiple metastatic pulmonary nodules at screening and treated on a compassionate care basis received one vaccine each before disease progression and removal from the study. The two dogs presenting with solitary metastatic pulmonary nodules at the time of screening received all three vaccines (see Table 5 for signalment and tumor characteristics). Progressive pulmonary metastatic disease occurred in one of these dogs despite vaccination. No additional pulmonary lesions developed in the second dog despite the pre-existing pulmonary nodule doubling in size every 3 weeks (FIGS. 22A and B). CT scan one week after the last vaccination, confirmed the absence of additional metastatic lesions and the dog underwent metastatectomy. Prior to surgery, the dye indocyanine green (ICG), used to detect tumor margins and areas of inflammation, was administered intravenously and at surgery, fluorescence under near infra-red light was seen in the pulmonary nodule and several other areas of healthy appearing pulmonary parenchyma near the solitary nodule (FIGS. 22C and D). Histopathology of the pulmonary nodule revealed metastatic OSA with large areas of hemorrhage and necrosis, surrounded by a thick fibrous capsule (FIG. 22E). IHC showed an accumulation of CD3⁺ T cells around the fibrous capsule with very few T cells within the nodule itself (FIGS. 22G and H). Other areas identified by near infra-red fluorescence showed focal areas of T cell infiltrates (FIGS. 22F, 22I and 22J). T cells were seen surrounding abnormally large, vimentin positive cells with prominent mitotic figures (FIGS. 22K and 22L). These findings suggest that single metastatic sarcoma cells may be effectively targeted by tumor specific T cells within the lung and provide a possible mechanism by which ADXS31-164 prevents metastatic pulmonary disease. The dog recovered well from surgery and remained free of pulmonary metastatic disease for 5 months before developing widespread aggressive, HER2/neu+ metastatic disease in the subcutaneous tissue (osteoblastic, grade II and chondroblastic, grade III), mediastinum (osteoblastic, grade II) and diaphragm (osteoblastic, grade III). Results show that despite induction of HER2/neu specific T cell responses, off-tumor side effects were not identified, hence induction of HER2/neu specific T cells is responsible for elimination of HER2/neu positive metastatic cells and long term protection from disease recurrence. This is supported by the timing of HER2/Neu-specific T cell expansion which in 5 dogs occurred approximately 8 months post diagnosis, when many dogs will develop metastatic disease and by the histopathological findings of focal T cell responses within the pulmonary parenchyma of one dog following vaccination and metastatectomy.

Figure 22:
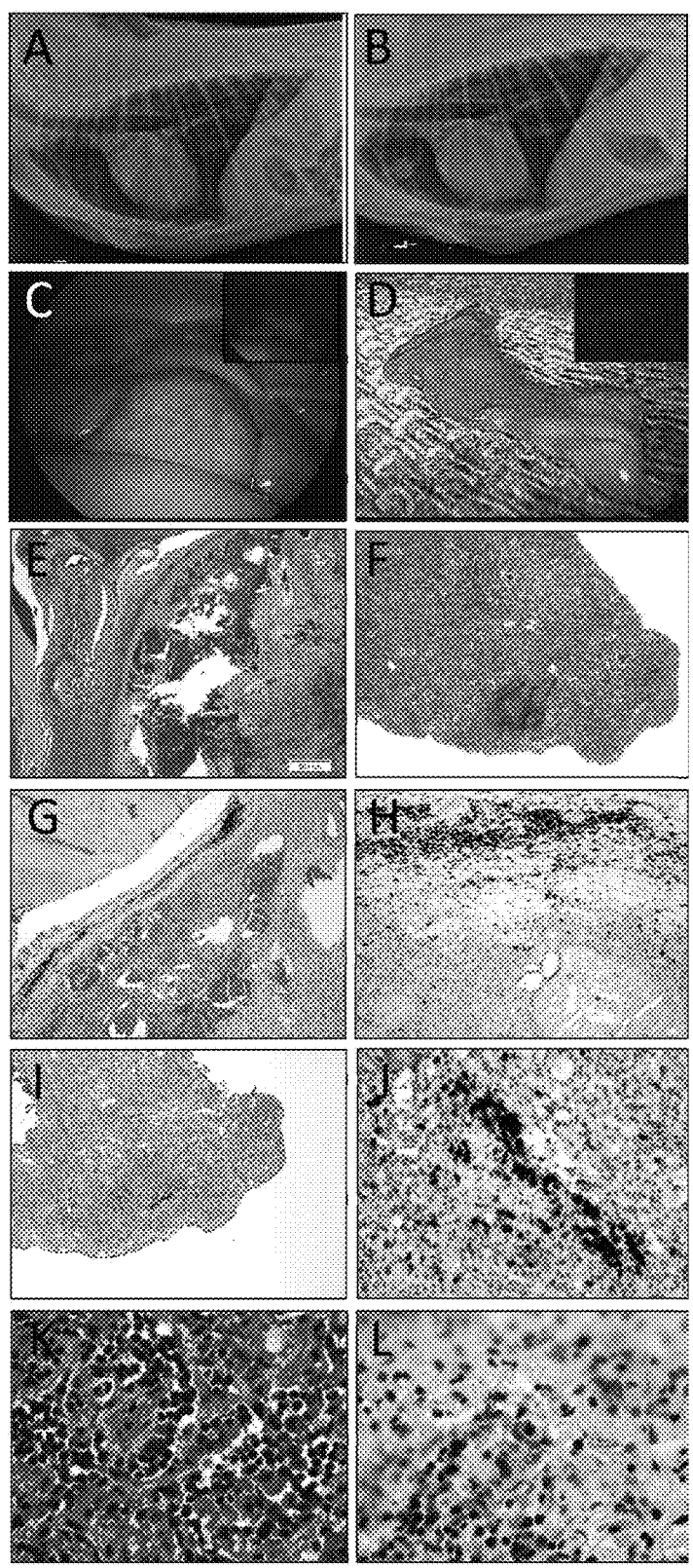
FIG. 22. Shows that ADXS31-164 prevents development of metastatic disease. (A and B) Thoracic radiographs taken 3 weeks after carboplatin therapy (A) and 3 weeks after the third ADXS31-164 vaccine (B) showing an increase in size of the pre-existing metastatic nodule in the right cranial lung lobe but lack of further metastatic disease development in remaining lung lobes. (C and D) Pulmonary nodule identified on thoracoscopy that fluoresces under near infra-red light following administration of ICG (C). Grossly normal appearing pulmonary tissue removed at the time of metastatectomy showing fluorescence under near infra-red light (inset) (D). (E and F) H&E stained histopathology of (E) pulmonary nodule and (F) fluorescing normal pulmonary tissue showing significant hemorrhage and necrosis of encapsulated pulmonary nodule (E) and focal area of inflammation in grossly normal appearing pulmonary tissue (F). (G and H) Immunohistochemistry of pulmonary nodule at low (G) and high (H) magnification showing CD3+ T cells surrounding the pulmonary nodule with minimal CD3+ T cells within the neoplastic tissue. (I and J) Immunohistochemistry of normal appearing pulmonary tissue at low (I) and high (J) magnification showing focal accumulations of CD3+ T cells. (K) High magnification H&E stain of focal pneumonia showing large abnormal cells with mitotic figures surrounded by lymphocytes. (L) Vimentin stain of pneumonic region showing a large vimentin positive cell, with prominent mitotic figures surrounded by mononuclear cells.
Figure 23:
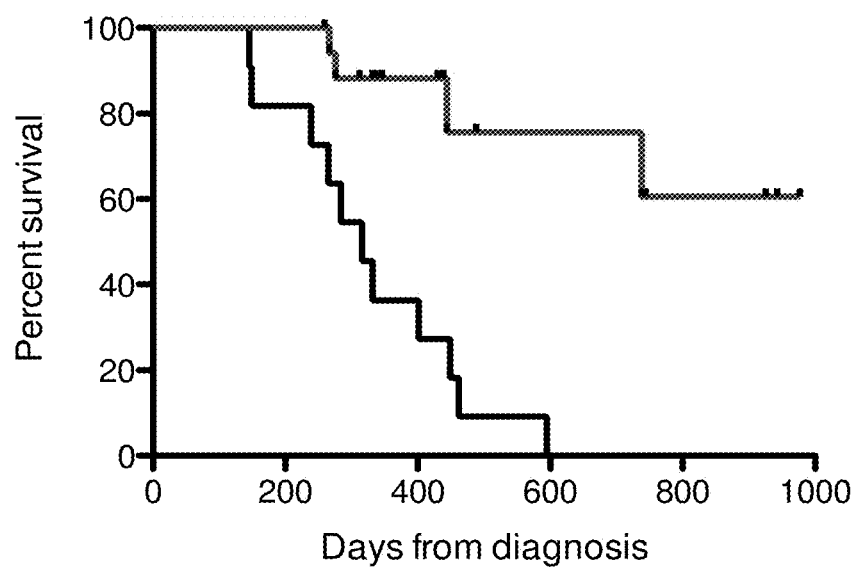
FIG. 23. ADXS31-164 delays/prevents metastatic disease and prolongs overall survival in dogs with spontaneous HER2+ osteosarcoma. Shown is a Kaplan-Meier survival curve of vaccinated dogs compared with a historical control group. The control group consisted of dogs with HER2+ appendicular OSA, treated with amputation and follow-up chemotherapy but who did not receive ADXS31-164. P<0.0001. Vaccinated group Red line; Control group Black line.

The results presented in FIG. 22 and FIG. 23 demonstrate that administration of ADXS31-164 delays and/or prevents metastatic disease and prolongs the overall survival in dogs with spontaneous HER2+ osteosarcoma. As can be seen in both figures, dogs receiving vaccine had significantly extended survival time, while the median survival for those dogs receiving vaccine has not yet been reached.

While our study demonstrates the effectiveness of this approach in preventing metastatic disease, vaccination with ADXS31-164 was unable to induce regression of pre-existing gross, pulmonary metastatic disease in 5 dogs treated on a compassionate care basis. In one dog this appeared to be associated with a failure of T cells to penetrate the fibrous capsule surrounding the metastatic lesion or for those cells to survive within the established tumor microenvironment (FIG. 22C). However, in the same dog, focal areas of T cell infiltrates surrounding large, actively dividing mesenchymal cells, purported to be metastatic OSA cells were identified in grossly normal lung parenchyma and unexpectedly, following metastatectomy this dog did not develop further pulmonary metastatic disease. Taken together, these data suggest that ADXS31-164 prevents pulmonary metastatic disease through its ability to induce potent innate immune responses that may sensitize metastatic OSA cells to FAS/FASL mediated apoptosis and adaptive immune responses in the form of HER2/Neu specific T cells that eliminate micrometastatic pulmonary disease.

Figure 26:
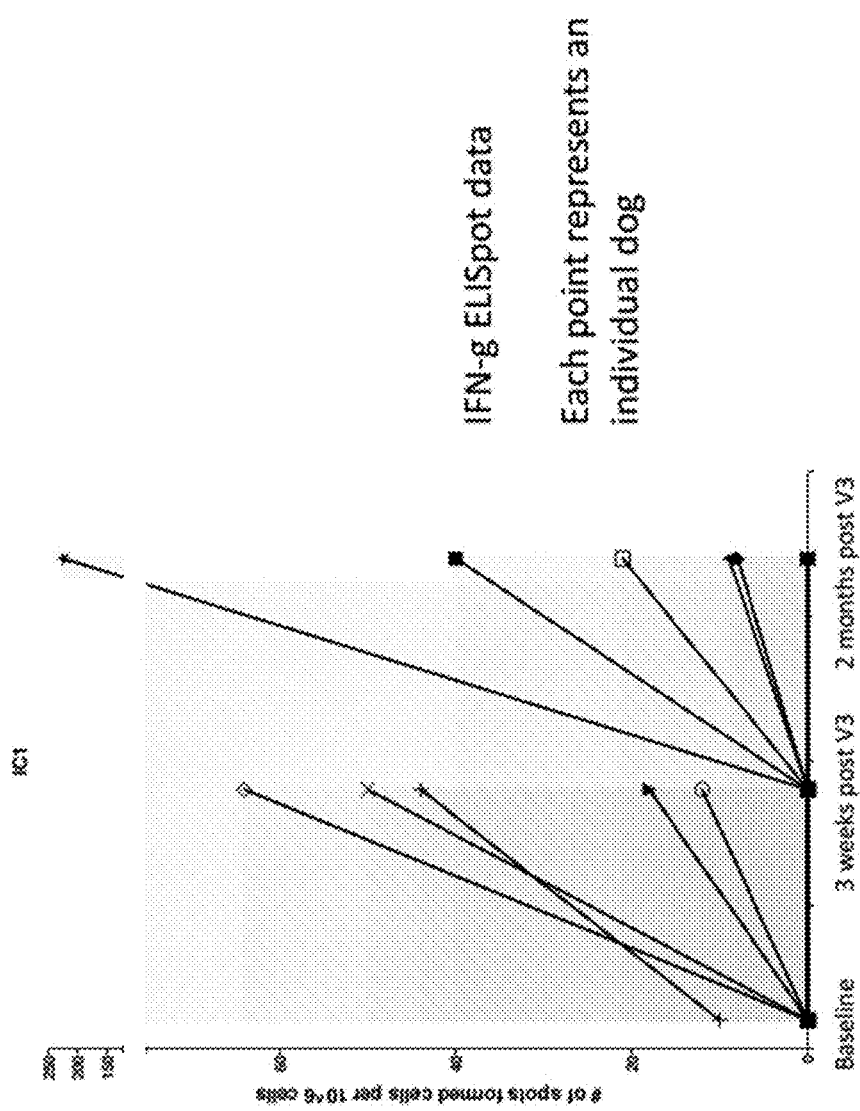
FIG. 26. Shows that ADXS31-164 breaks immune tolerance to the highly conserved intracellular domain of HER2/neu.
Figure 27A:
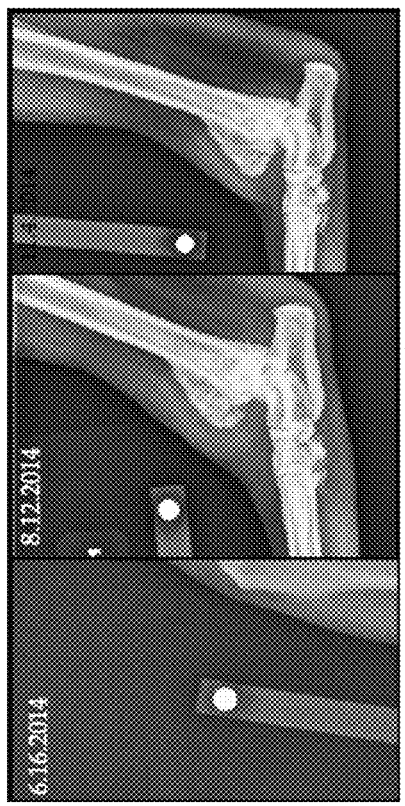
FIG. 27A-D. Shows that radiation therapy in conjunction with ADXS31-164 therapy delays progression of primary osteosarcoma (OSA) in subject 386-002 (FIG. 27A), subject 385-005 (FIG. 27B), subject 386-003 (FIG. 27C), and subject 386-007 (FIG. 27D).
Figure 27B:
Figure 27C:
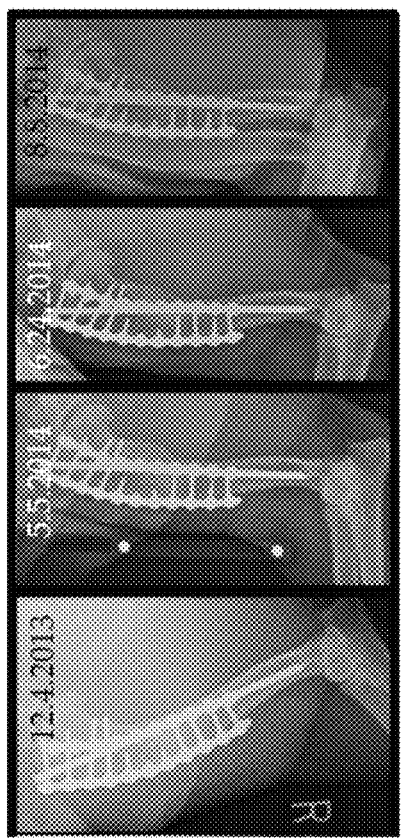
Figure 27D:
Figure 29A:
FIG. 29A-D. Shows that palliative radiation therapy in conjunction with ADXS31-164 therapy reduces lysis, promotes tumor consolidation, and prolongs survival of subjects (FIG. 29 A-D). Lateral (FIG. 29A) and AP (FIG. 29C) radiographic views of a distal tibial osteosarcoma lesion demonstrating marked cortical bone remodeling, and reduction in lysis, following 16Gy radiation (given as 8Gy on 2 consecutive days starting on Sep. 13, 2014) and 3 doses of ADXS31-164 (Nov. 25, 2014). Lateral (FIG. 29B) and AP (FIG. 29D) radiographic views of a distal radial osteosarcoma lesion treated with 16Gy radiation (given as 8Gy on 2 consecutive days starting on Jul. 16, 2014) and 3 doses of ADXS31-164 (Oct. 13, 2014). Note the significant reduction in swelling and bony lysis within the distal portion of the radius (compare radiographs dated Oct. 13, 2014 with Jul. 16, 2014 in FIG. 29B). There is increased bone density on the medial aspect of the distal tibia (compare radiographs dated Oct. 13, 2014 with Jul. 16, 2014 in FIG. 29D). There is a small minimally displaced bone fracture of the medial aspect of the distal radius seen on the Oct. 13, 2014 radiographs in FIG. 29D.
Figure 29B:
Figure 29C:
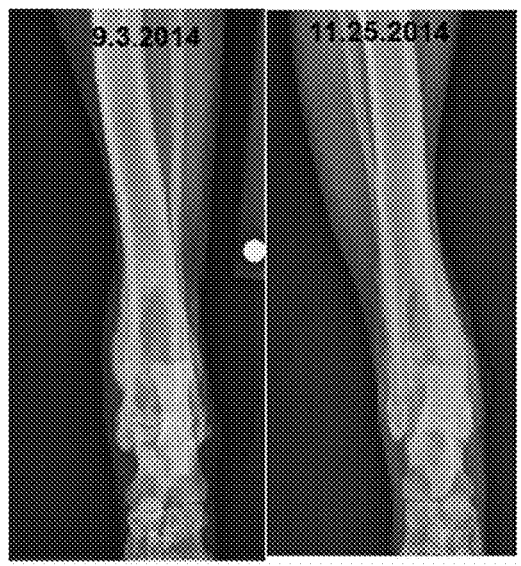
Figure 29D:
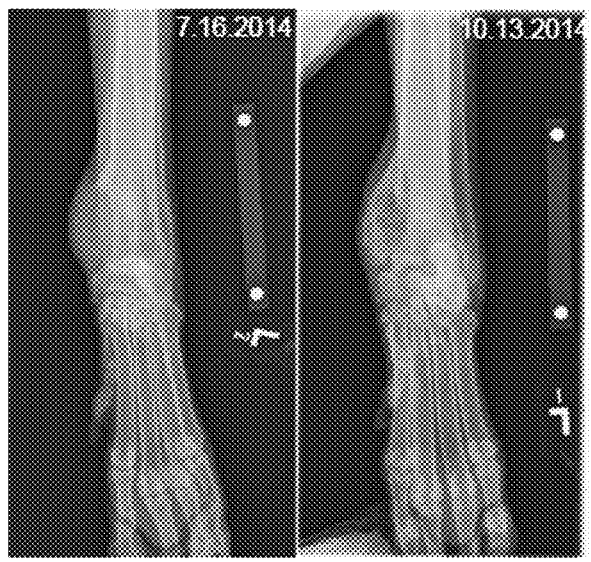
Figure 30A:
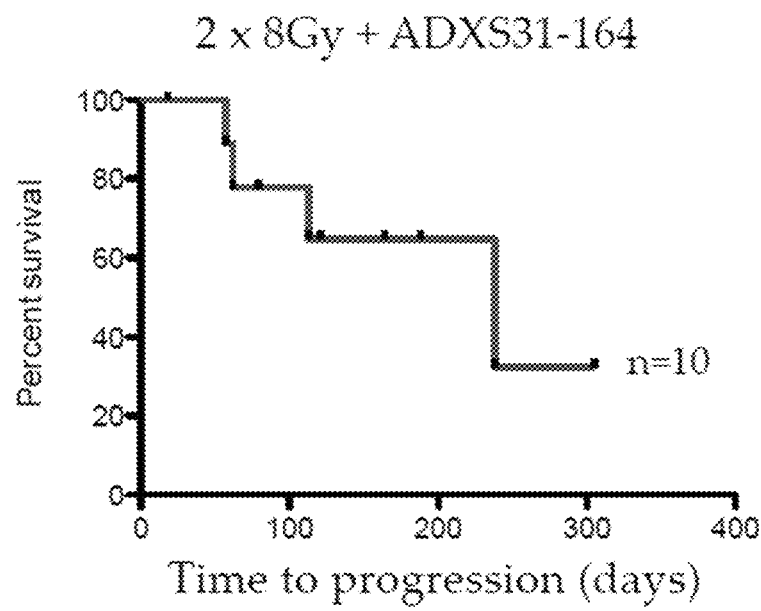
FIG. 30A-B. Shows that radiation therapy in conjunction with ADXS31-164 prolongs survival in dogs with osteosarcoma (OSA).
Figure 30B:
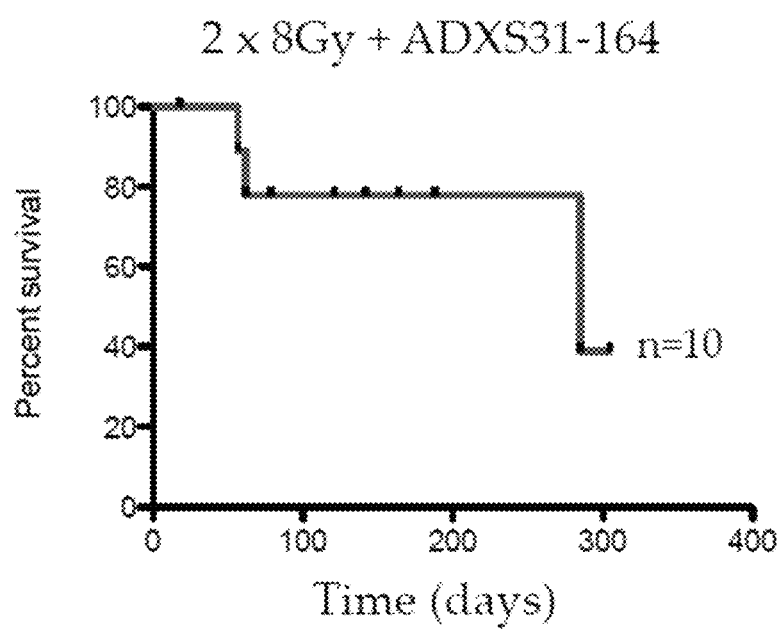

Conclusions:

At the time of filing this application 12/18 dogs have not developed pulmonary metastatic disease, demonstrating that ADXS31-164 prevents metastatic disease in a subject suffering from spontaneous HER2+ osteosarcoma when administered in the setting of minimal residual disease. Vaccinated dogs showed a statistically significant increase in overall survival compared to a historical HER2/Neu+ control group. Median survival in the HER2/Neu+ control dogs (n=11) was 316 days (p=0.032) wherein the median survival in ADSX31-164 treated dogs has not been reached. Further, the results indicate that ADXS31-164 breaks peripheral tolerance to the highly conserved IC1 domain of HER2/Neu (FIG. 26). The magnitude of the increase in leucocytes within 24 hours of ADXS31-164 administration (FIG. 18) correlates with survival, suggesting that outcome depends in part upon the ability of the dog's immune system to respond to the vaccine Importantly, this study showed that administration of up to $3\times10^9$ CFU of ADXS31-164 to dogs with spontaneous OSA is safe and causes only transient, low grade side effects at the time of administration. Moreover, prevention of pulmonary metastatic disease maybe in part associated with CD3+ T cell mediated elimination of microscopic metastatic disease in the lung. This work has important implications for pediatric OSA and other human cancers that express HER2/Neu.

Moreover, here we show that administration of ADXS31-164 in doses up to $3.3\times10^9$ CFU are safe in the dog and despite inducing HER2/neu specific immunity, do not lead to short or long term cardio toxicity. On target, off tumor side effects including cardio toxicity has been associated with the administration of large numbers of HER2/neu specific T cells or when trastuzumab has been used concurrently with anthracyclines. We employed a standard chemotherapy protocol without doxorubicin to reduce any potential risk of cardio toxicity.

Our study demonstrates that ADXS31-164 can prevent pulmonary metastatic disease in dogs with OSA. These results demonstrate safety and unprecedented survival times in dogs with OSA and pave the way to investigate the ability of ADXS31-164 to prevent metastatic disease in patients with HER2/neu expressing tumors including pediatric osteosarcoma and mammary carcinoma.

Example 11

Combination ADXS31-164 and Radiation Therapy for the Treatment of Canine and Human Osteosarcoma (OSA) and Pulmonary Metastatic Disease A recombinant *Listeria monocytogenes* expressing a human chimeric Her-2/neu construct (ADXS31-164) used in combination with palliative radiation to prevent pulmonary metastatic disease and prolong overall survival in dogs with spontaneous appendicular osteosarcoma is described. Given the similarities between canine and human osteosarcoma, we believe that this combination will be effective therapy for human disease.

Materials and Methods

Vaccine Preparation

The details of the construction of ADXS31-164 vaccine have been described above. The ADXS31-164 vaccine stocks were prepared and stored as 1 ml aliquots in freezer at −70° C. Before injection, vaccine stocks were thawed at 37° C. for 2-3 min and then washed twice with phosphate-buffer saline (PBS) and resuspended in PBS at a final concentration of $5\times10^8$ colony forming units (CFU)/ml. Each dog was immunized intraperitoneally with 200 µl of this suspension.

RT and Immunotherapy

Ten systemically healthy dogs with histopathologically confirmed, treatment naïve, HER2+ appendicular OSA, and no evidence of cardiac or metastatic disease were enrolled. All dogs received 16Gy of RT in two fractions on consecutive days, followed by the first of 8 intravenous doses of ADXS31-164 ($3.3\times10^9$ CFU per dose) given once every 3 weeks. Immunization with the *Listeria*-based vaccine was performed every 3 weeks (e.g., on days 7, 28, 49, 70, 91, 112, 133 and 154) (FIG. 10) Immune analysis was also performed on the day of immunization.

On days 4 and 5, external beam RT of 8 Gy was delivered using a Siemens 6 MV linear accelerator. The RT was given under general anesthesia. Tumors were evaluated clinically every three weeks and radiographically at baseline, at the fourth vaccine administration (day 70) and at the eighth vaccine administration (day 154). At these time points, thoracic radiographs were performed to determine the presence of pulmonary metastatic disease.

A bone biopsy to confirm the diagnosis of osteosarcoma was performed at the time of enrollment. Complete Blood Count (CBC), Chemistry Screen (CS), Urinary Analysis (UA), electrocardiogram (EKG)/Echocardiogram/serum concentration of cardiac troponin I (cTnI) and radiographs of the affected limb and the thorax were performed on Days 0, 70, and 133 and every 2 months thereafter until euthanasia. On the day of euthanasia Complete Blood Count (CBC), Chemistry Screen (CS), Urinary Analysis (UA), Immune analysis, electrocardiogram (EKG)/Echocardiogram/serum concentration of cardiac troponin I (cTnI); and necropsy were performed.

ELISpot assay Cryopreserved PBMC from each indicated time point were thawed, rested overnight at 37° C. and then counted. Cells were stimulated with 2.0 uM pools of overlapping human HER2/Neu peptides (11mers overlapping by 5 amino acids) that represent the EC1, EC2 and IC1 domains of HER2/Neu present in the chimeric vaccine, and recombinant human IL-2 (Invitrogen, Fredrick, Md.) for 5 days. Cells were harvested, washed twice in 1×PBS and counted. IFN-γ ELISpot assays were performed according to the manufacturer's protocol using a commercial canine IFN-γ ELISpot assay kit (R&D Systems, Minneapolis, Minn.). Briefly, 0.1-3×10$^5$ stimulated cells were incubated with 2.5 uM of EC1, EC2 or IC1 peptide pools or none (to determine background counts). All assays were performed in duplicates. Plates were developed according to the manufacturer's instructions. Spots were counted using a CTL-Immunospot analyzer (C.T.L, Shaker Heights, Ohio).

Results

We evaluated the use of ADXS31-164 as adjuvant therapy in dogs with spontaneous osteosarcoma as described herein above. ADXS31-164 was administered to dogs with spontaneous appendicular OSA following 16 Gy RT administered on two consecutive days. Up to 8 doses of ADXS31-164 were administered. This work showed repeat administrations of 3.3×10$^9$ CFU of ADXS31-164 to be safe.

The potential synergy between radiation therapy and ADXS31-164 to promote antitumor immunity (in particular the generation of Her-2/neu specific T cells), retard the progression of the primary tumor and prevent/delay pulmonary metastatic disease was then explored.

Figure 10:
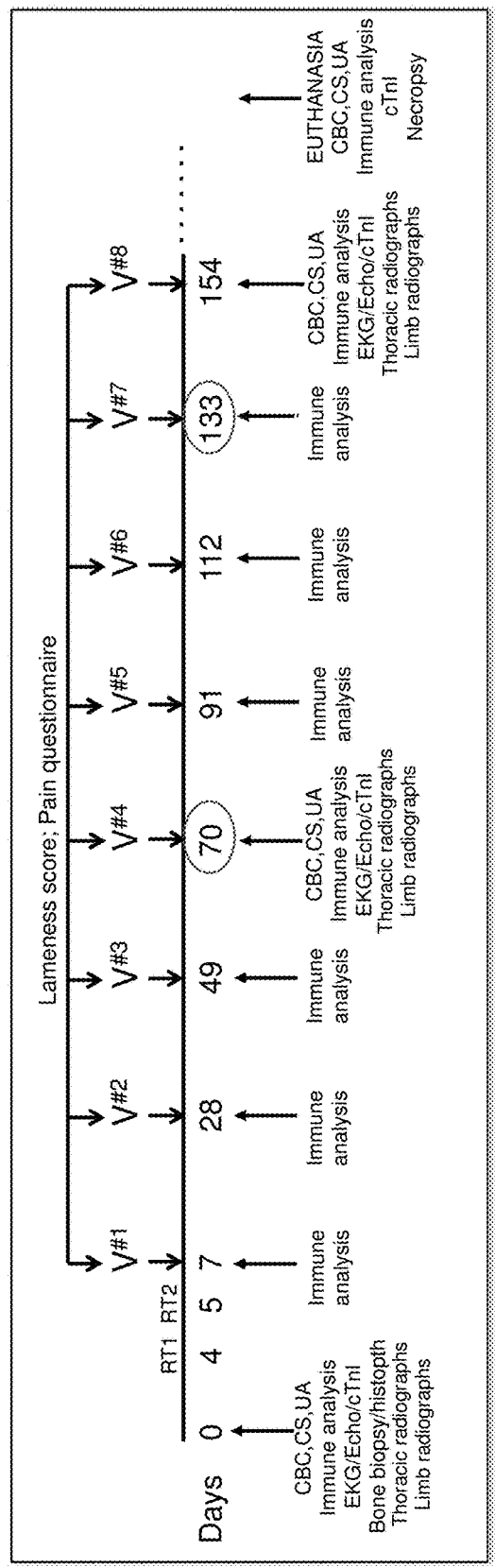
FIG. 10. Shows treatment schedule of combination ADXS31-164 and palliative radiation therapy (RT) in the context of primary appendicular osteosarcoma without amputation and chemotherapy.
Figure 11:
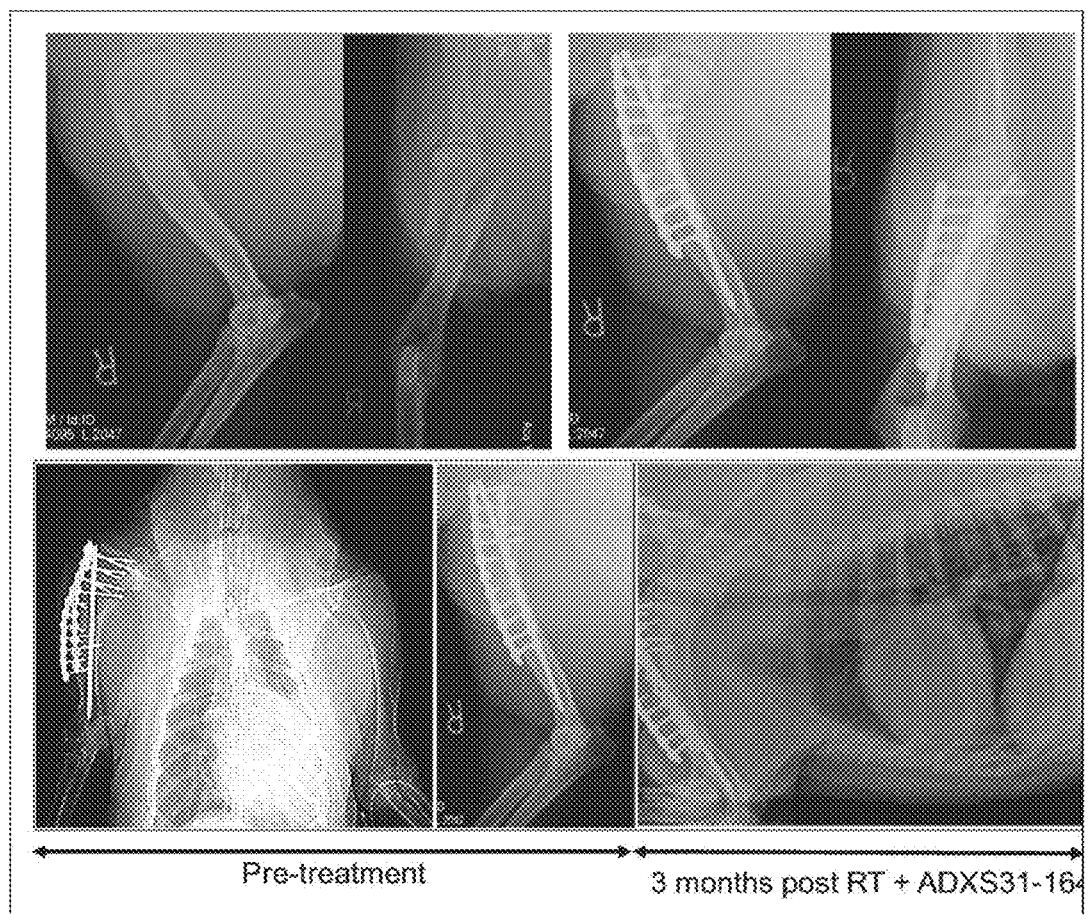
FIG. 11. Top panel: Radiographs showing the presence of a fracture of the proximal humerus associated with osteosarcoma and those taken after fracture fixation using two bone plates and an intramedullary pin. Bottom panel: A CT scan of the chest showing no evidence of metastatic disease at enrollment. Radiographs were also taken at baseline and after 8 ADXS31-164 administrations. These radiographs show no evidence of pulmonary metastatic disease and the presence of boney callus surrounding the fracture site indicating fracture healing despite the presence of osteosarcoma.

FIG. 10 describes the treatment protocol. Dogs were screened on day 0 for enrollment in the trial. Screening included evaluation of baseline blood tests, urinalysis, cardiac evaluation, thoracic and affected limb radiographs and bone biopsy to confirm the diagnosis of osteosarcoma. Palliative radiation was given on 2 consecutive days following enrollment. Multiple doses (up to 8) of ADXS31-164 were given once every 3 weeks following palliative radiation therapy with only transient, low-grade, side effects (data not shown). Thoracic and limb radiographs were repeated at day 70 and 154. Lameness scores were assigned by two board certified veterinary orthopedic surgeons to each dog at each time point based on their evaluation of videos taken of each dog at each time point. Owners also filled in a validated pain questionnaire that documented the owners perception of quality of life. 5/10 dogs are still alive, three without evidence of tumor progression or pulmonary metastatic disease. At the time of writing, median survival is 285 days which compares favorably with a historical median survival of 136 days achieved with RT alone. In one patient, presenting for trial enrollment with a pathological fracture of the proximal humerus that was stabilized by 2 bone plates and an intramedullary pin, radiographs show evidence of the fracture healing and no evidence of pulmonary metastatic disease three months after radiation therapy and ADXS31-164 administration, (FIG. 11).

Therefore, ADXS31-164 may be used without chemotherapy; in combination with radiation and potentially in the neo-adjuvant setting, prior to amputation and chemotherapy to prevent metastatic disease.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, said Her-2/neu chimeric antigen comprises amino acids as set forth in SEQ ID NO: 2, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

2. The method of claim 1, wherein said subject is a human adult or child.

3. The method of claim 1, wherein said subject is a canine.

4. The method of claim 1, wherein said Her-2/neu chimeric antigen comprises at least 5, 9, 13, 14, or 17 of the mapped human MHC-class I epitopes.

5. The method of claim 1, wherein said Her-2/neu chimeric antigen comprises at least 5, 9, 13, 14, or 17 of the canine MHC-class I epitopes.

6. The method of claim 1, wherein said nucleic acid molecule is integrated into the *Listeria* genome.

7. The method of claim 1, wherein said nucleic acid molecule is in a plasmid in said recombinant attenuated *Listeria* strain and wherein said plasmid is stably maintained in said recombinant attenuated *Listeria* strain in the absence of antibiotic selection.

8. The method of claim 1, wherein said recombinant *Listeria* comprises a deletion in the actA virulence gene.

9. The method of claim 1, wherein said additional polypeptide is selected from the group consisting of: a) non-hemolytic LLO protein or N-terminal fragment, b) a PEST sequence, or c) an ActA fragment.

10. The method of claim 1, wherein said metabolic enzyme encoded by said second open reading frame is an alanine racemase enzyme or a D-amino acid transferaseenzyme.

11. The method of claim 1, wherein said recombinant attenuated *Listeria* strain is ADXS31-164.

12. The method of claim 1, wherein said recombinant attenuated *Listeria* strain is administered with an independent adjuvant, wherein said adjuvant comprises a granulocyte/macrophage colony-stimulating factor (GM-CSP) protein, a nucleotide molecule encoding a GM-CSP protein, saponin QS21, monophosphoryl lipid A, or an unmethylated CpG-containing oligonucleotide.

13. The method of claim 1, wherein said radiation therapy is administered prior to administration of said recombinant attenuated *Listeria* strain.

14. The method of claim 1, wherein said cancer is osteosarcoma.

15. A method of eliciting an enhanced immune response against a Her-2/neu-expressing tumor growth or cancer in a subject comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, said Her-2/neu chimeric antigen comprises amino acids as set forth in SEQ ID NO: 2, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

16. The method of claim 15, wherein said subject is a human adult or child.

17. The method of claim 15, wherein said subject is a canine.

18. The method of claim 15, wherein said Her-2/neu chimeric antigen comprises at least 5, 9, 13, 14, or 17 of the mapped human MHC-class I epitopes.

19. The method of claim 15, wherein said Her-2/neu chimeric antigen comprises at least 5, 9, 13, 14, or 17 of the canine MHC-class I epitopes.

20. The method of claim 15, wherein said nucleic acid molecule is integrated into the *Listeria* genome.

21. The method of claim 15, wherein said nucleic acid molecule is in a plasmid in said recombinant attenuated *Listeria* strain and wherein said plasmid is stably maintained in said recombinant attenuated *Listeria* strain in the absence of antibiotic selection.

22. The method of claim 15, wherein said recombinant *Listeria* comprises a deletion in the actA virulence gene.

23. The method of claim 15, wherein said additional polypeptide is selected from the group consisting of: a) non-hemolytic LLO protein or N-terminal fragment, b) a PEST sequence, or c) an ActA fragment.

24. The method of claim 15, wherein said metabolic enzyme encoded by said second open reading frame is an alanine racemase enzyme or a D-amino acid transferase enzyme.

25. The method of claim 15, wherein said recombinant attenuated *Listeria* strain is ADXS31-164.

26. The method of claim 15, wherein said recombinant attenuated *Listeria* strain is administered with an independent adjuvant, wherein said adjuvant comprises a granulocyte/macrophage colony-stimulating factor (GM-CSP) protein, a nucleotide molecule encoding a GM-CSP protein, saponin QS21, monophosphoryl lipid A, or an unmethylated CpG-containing oligonucleotide.

27. The method of claim 15, wherein said radiation therapy is administered prior to administration of said recombinant attenuated *Listeria* strain.

28. The method of claim 15, wherein said cancer is osteosarcoma.

29. The method of claim 15, wherein said tumor growth or cancer is a relapse or metastasis.

30. The method of claim 29, wherein said metastasis is pulmonary metastatic disease.

31. The method of claim 15, wherein said eliciting an enhanced immune response results in an increased Her-2/neu specific T cell response.

32. A method of prolonging survival in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, said Her-2/neu chimeric antigen comprises amino acids as set forth in SEQ ID NO: 2, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

33. The method of claim 32, wherein said subject is a human adult or child.

34. The method of claim 32, wherein said subject is a canine.

35. The method of claim 32, wherein said Her-2/neu chimeric antigen comprises at least 5, 9, 13, 14, or 17 of the mapped human MHC-class I epitopes.

36. The method of claim 32, wherein said Her-2/neu chimeric antigen comprises at least 5, 9, 13, 14, or 17 of the canine MHC-class I epitopes.

37. The method of claim 32, wherein said nucleic acid molecule is integrated into the *Listeria* genome.

38. The method of claim 32, wherein said nucleic acid molecule is in a plasmid in said recombinant attenuated *Listeria* strain and wherein said plasmid is stably maintained in said recombinant attenuated *Listeria* strain in the absence of antibiotic selection.

39. The method of claim 32, wherein said recombinant *Listeria* comprises a deletion in the actA virulence gene.

40. The method of claim 32, wherein said additional polypeptide is selected from the group consisting of: a)

non-hemolytic LLO protein or N-terminal fragment, b) a PEST sequence, or c) an ActA fragment.

41. The method of claim 32, wherein said metabolic enzyme encoded by said second open reading frame is an alanine racemase enzyme or a D-amino acid transferase enzyme.

42. The method of claim 32, wherein said recombinant attenuated *Listeria* strain is ADXS31-164.

43. The method of claim 32, wherein said recombinant attenuated *Listeria* strain is administered with an independent adjuvant, wherein said adjuvant comprises a granulocyte/macrophage colony-stimulating factor (GM-CSP) protein, a nucleotide molecule encoding a GM-CSP protein, saponin QS21, monophosphoryl lipid A, or an unmethylated CpG-containing oligonucleotide.

44. The method of claim 32, wherein said radiation therapy is administered prior to administration of said recombinant attenuated *Listeria* strain.

45. The method of claim 32, wherein said cancer is osteosarcoma.

46. The method of claim 32, wherein said tumor growth or cancer is a relapse or metastasis.

47. The method of claim 46, wherein said metastasis is pulmonary metastatic disease.

48. A method of delaying metastatic disease in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional polypeptide, said Her-2/neu chimeric antigen comprises amino acids as set forth in SEQ ID NO: 2, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

49. The method of claim 48, wherein said subject is a human adult or child.

50. The method of claim 48, wherein said subject is a canine.

51. The method of claim 48, wherein said Her-2/neu chimeric antigen comprises at least 5, 9, 13, 14, or 17 of the mapped human MHC-class I epitopes.

52. The method of claim 1, wherein said Her-2/neu chimeric antigen comprises at least 5, 9, 13, 14, or 17 of the canine MHC-class I epitopes.

53. The method of claim 48, wherein said nucleic acid molecule is integrated into the *Listeria* genome.

54. The method of claim 48, wherein said nucleic acid molecule is in a plasmid in said recombinant attenuated *Listeria* strain and wherein said plasmid is stably maintained in said recombinant attenuated *Listeria* strain in the absence of antibiotic selection.

55. The method of claim 48, wherein said recombinant *Listeria* comprises a deletion in the actA virulence gene.

56. The method of claim 48, wherein said additional polypeptide is selected from the group consisting of: a) non-hemolytic LLO protein or N-terminal fragment, b) a PEST sequence, or c) an ActA fragment.

57. The method of claim 48, wherein said metabolic enzyme encoded by said second open reading frame is an alanine racemase enzyme or a D-amino acid transferaseenzyme.

58. The method of claim 48, wherein said recombinant attenuated *Listeria* strain is ADXS31-164.

59. The method of claim 48, wherein said recombinant attenuated *Listeria* strain is administered with an independent adjuvant, wherein said adjuvant comprises a granulocyte/macrophage colony-stimulating factor (GM-CSP) protein, a nucleotide molecule encoding a GM-CSP protein, saponin QS21, monophosphoryl lipid A, or an unmethylated CpG-containing oligonucleotide.

60. The method of claim 48, wherein said radiation therapy is administered prior to administration of said recombinant attenuated *Listeria* strain.

61. The method of claim 48, wherein said cancer is osteosarcoma.

62. The method of claim 48, wherein said tumor growth or cancer is a relapse or metastasis.

63. The method of claim 62, wherein said metastasis is pulmonary metastatic disease.

64. A method of breaking tolerance to Her-2/neu in a subject suffering from a Her-2/neu-expressing tumor growth or cancer comprising the step of administering a combination of radiation therapy and a recombinant attenuated *Listeria* strain comprising a nucleic acid comprising a first open reading frame encoding a fusion polypeptide comprising a Her-2/neu chimeric antigen fused to an additional adjuvant, said Her-2/neu chimeric antigen comprises amino acids as set forth in SEQ ID NO: 2, and a second open reading frame encoding a metabolic enzyme, wherein said metabolic enzyme complements an endogenous gene that is mutated in the chromosome of said recombinant attenuated *Listeria* strain, and wherein the administration of said radiation therapy comprises at least two administrations of said radiation therapy.

65. The method of claim 64, wherein said subject is a human adult or child.

66. The method of claim 64, wherein said subject is a canine.

67. The method of claim 64, wherein said Her-2/neu chimeric antigen comprises at least 5, 9, 13, 14, or 17 of the mapped human MHC-class I epitopes.

68. The method of claim 64, wherein said Her-2/neu chimeric antigen comprises at least 5, 9, 13, 14, or 17 of the canine MHC-class I epitopes.

69. The method of claim 64, wherein said nucleic acid molecule is integrated into the *Listeria* genome.

70. The method of claim 64, wherein said nucleic acid molecule is in a plasmid in said recombinant attenuated *Listeria* strain and wherein said plasmid is stably maintained in said recombinant attenuated *Listeria* strain in the absence of antibiotic selection.

71. The method of claim 64, wherein said recombinant *Listeria* comprises a deletion in the actA virulence gene.

72. The method of claim 64, wherein said additional polypeptide is selected from the group consisting of: a) non-hemolytic LLO protein or N-terminal fragment, b) a PEST sequence, or c) an ActA fragment.

73. The method of claim 64, wherein said metabolic enzyme encoded by said second open reading frame is an alanine racemase enzyme or a D-amino acid transferaseenzyme.

74. The method of claim 64, wherein said recombinant attenuated *Listeria* strain is ADXS31-164.

75. The method of claim 64, wherein said recombinant attenuated *Listeria* strain is administered with an independent adjuvant, wherein said adjuvant comprises a granulocyte/macrophage colony-stimulating factor (GM-CSP) protein, a nucleotide molecule encoding a GM-CSP protein, saponin QS21, monophosphoryl lipid A, or an unmethylated CpG-containing oligonucleotide.

76. The method of claim 64, wherein said radiation therapy is administered prior to administration of said recombinant attenuated *Listeria* strain.

77. The method of claim 64, wherein said cancer is osteosarcoma.

78. The method of claim 64, wherein said tumor growth or cancer is a relapse or metastasis.

79. The method of claim 78, wherein said metastasis is pulmonary metastatic disease.

80. The method of claim 1, wherein said tumor growth or cancer is a relapse or metastasis.

81. The method of claim 80, wherein said metastasis is pulmonary metastatic disease.

* * * * *